US007803919B2

(12) United States Patent
Seroussi et al.

(10) Patent No.: US 7,803,919 B2
(45) Date of Patent: Sep. 28, 2010

(54) **BOVINE *ABCG2* GENE MISSENSE MUTATIONS AND USES THEREOF**

(75) Inventors: Eyal Seroussi, Shaarey Tiqwa (IL); Harris A. Lewin, Champaign, IL (US); Mark R. Band, Savoy, IL (US); Miri Cohen-Zinder, Moshav Kfar Bilu (IL); James K. Drackley, Champaign, IL (US); Denis M. Larkin, Savoy, IL (US); Juan J. Loor, Urbana, IL (US); Micha Ron, Nes-Ziona (IL); Moshe Shani, Macabim (IL); Joel Ira Weller, Rehovot (IL)

(73) Assignee: The Board of Trustees of The University of Illinois, Urbana, IL (US)

( * ) Notice: Subject to any disclaimer, the term of this patent is extended or adjusted under 35 U.S.C. 154(b) by 0 days.

(21) Appl. No.: 11/427,230

(22) Filed: Jun. 28, 2006

(65) Prior Publication Data

US 2007/0118912 A1    May 24, 2007

Related U.S. Application Data

(60) Provisional application No. 60/694,430, filed on Jun. 28, 2005, provisional application No. 60/696,294, filed on Jul. 1, 2005.

(51) Int. Cl.
*C07H 21/04* (2006.01)
*C07H 21/02* (2006.01)
(52) U.S. Cl. .................... 536/23.1; 536/24.33; 536/23.5
(58) Field of Classification Search ........................ None
See application file for complete search history.

(56) References Cited

U.S. PATENT DOCUMENTS 5,474,796 A * 12/1995 Brennan ...................... 427/2.13
2002/0137160 A1* 9/2002 Byatt et al. ................... 435/183

OTHER PUBLICATIONS

Eisenblatter et al (Biochemical and Biophysical Research Communications (2002) vol. 293, pp. 1273-1278).*
ABCG2 gene card (genecards.org/cgi-bin/carddisp.pl?gene=ABCG2&search=abcg2&suff=txt, pp. 1-14, 2008).*
GenBank accession CA036005.1 GI:24334658 Oct. 24, 2002.*
Sonstegard et al (Mammalian Genome (2002) vol. 3, pp. 373-379).*
Buck et al (Biotechniques. Sep. 1999;27(3):528-36).*
Allikmets et al., "A Human Placenta-Specific ATP_Binding Cassette Involved in Multidrig Resistance," *Cancer Research, Amercian Assoc. for Cancer Research*, Baltimore, MD, 5337-5339 (1998).
Ashwell et al., "Detection of Quantitative Trait Loci Affecting Milk Production, Health, and Reproductive Traits in Holstein Cattle," *J. Dairy Sci.*, 87: 468-475 (2004).
Baily-Dell et al., "Promoter Characterization and genomic organization of the human breast cancer resistance protein (ATP-binding cassette transporteer G2) gene," *Biochimica et biophysica ACTA*, 1520(3): 234-241 (2001).

Bennewitz et al., "Top down preselection using marker assisted estimates of breeding values in dairy cattle," *J. Amin. Breed. Genet.*, 121:307-118 (2003).
Boichard et al., "Implementation of Marker-Assisted Selection in French Dairy Cattle," *Proc. 7th World Cong. Genet. Appl. Livest. Prod.*, Montpellier, France. 33:19-22 (2002).
Chenu et al., "Cloning and Sequence Analysis of Bovine Bond Sialoprotein cDNA: Conservation of Acidic Domains, Tyrosine Sulfation Consensus Repeats, and RGD Cell Attachmetn Domain," *J. Bone Miner. Res.*, 9: 417-421 (1994).
Cohen et al., "Cloning and Characterization of FAM13A1-a gene near a milk protein QTL on BTA6: evidence for population-wide linkage desequilibrium in Israeli Holsteins," *Genomics*, 84(2): 374-383 (2004).
Cohen et al., "SPP1 is a canditte gene for the QTL affecting milk protein concentration on BTA6 based on population-wide linkage desquilibrium, differential expression, and targeted inhibition," *29th Int. Conf. Ani. Gen.*, ISAG, Tokyo, Japan, F015 (2004).
Cohen-Zinder et al., "Identification of a Missense Mutation in the Bovine ABCG2 Gene with a Major Effect on the QTL on Chromosome 6 Affecting Milk Yield and Composition in Holtein Cattle," *Genome Research*, 15(7): 936-944 (2005).
Drackley et al., "Metabolic Changes in Blood and Liver of Diary Cows During Either Feed Restriction or Administration of 1,3-Butanediol1," *J. Dairy Sci.*, 74: 4254-4264 (1991).
Ejendeal et al., "Multidrug Resistance and Cancer: The Role of the Human ABC Transporter ABCG2," *Review. Curr. Protein Pept. Sci.*, 3: 503-511 (2002).
Everts-van der Wind et al., "A 1463 Gene Cattle-Human Comparative Map With Anchor Points Defined by Human Genome Sequence Coordinates," *Genome Res.*, 14: 1424-1437 (2004).
Farr et al., "An Improved Method for the Routine Biopsy of Bovine Mammary Tissue," *J Dairy Sci.*, 79: 543-549 (1996).
Fernando et al., "Marker assisted selection using best linear unbiased prediction," *Genet. Sel. Evol.*, 21:467-477 (1989).
Georges et al., "Mapping Quantitative Trait Loci Controlling Milk Production in Dairy Cattle by Exploiting Progeny Testing," *Genetics*, 139: 907-920 (1995).
Glazier et al., "Finding Genes That Underlie Complex Traits," *Science*, 298: 2345-2349 (2002).

(Continued)

*Primary Examiner*—Steven C Pohnert
(74) *Attorney, Agent, or Firm*—Judy Jarecki-Black; Chad Kitchen; Merial Limited

(57) ABSTRACT

A quantitative trait locus (QTL) affecting milk fat and protein concentration was localized to a 4cM confidence interval on chromosome 6 centered on the microsatellite BM143. The genes and sequence variation in this region were characterized, and common haplotypes spanning five polymorphic sites in the genes IBSP, SPP1, PKD2, and ABCG2 for two sires heterozygous for this QTL were localized. Expression of SPP1 and ABCG2 in the bovine mammary gland increased from parturition through lactation. SPP1 was sequenced, and all the coding exons of ABCG2 and PKD2 were sequenced for these two sires. The single nucleotide change capable of encoding a substitution of tyrosine-581 to serine (Y581S) in the ABCG2 transporter was the only polymorphism corresponding to the segregation status of all three heterozygous and 15 homozygous sires for the QTL in the Israeli and US Holstein populations.

2 Claims, 4 Drawing Sheets

OTHER PUBLICATIONS

Gottesman et al., "Multidrug Resistance in Cancer: Role of ATP-Dependent Transporters," *Nat. Rev. Cancer*, 2: 48-58 (2002).

Grisart et al., "Positional Candidate Cloning of a QTL in Dairy Cattle: Identification of a Missense Mutation in the Bovine DGAT1 Gene with Major Effect on Mile Yield and Composition," *Genome Res.*, 12: 222-231 (2002).

Grisart et al., "Genetic and functional confirmation of the causality of the DGAT1 K232A quantitative trait nucleotide in affecting mile yield and composition," *Proc. Natl. Acad. Sci.*, 101:2398-403 (2004).

Hedrick et al., "Gametic Disequilibrium Measures: Proceed With Caution," *Genetics*, 117: 331-341 (1987).

Israel et al., "Estimation of Candidate Gene Effects in Dairy Cattle Populations," *J. Dairy Sci.*, 81: 1653-1662 (1998).

Israel et al., "Effect of Misidentification on Genetic Gain and Estimation of Breeding Value in Dairy Cattle Populations," *J. Dairy Sci.*, 83:181-187 (2000).

Jonker et al., "The breast cancer resistance protein BCRP (ABCG2) concentrates drugs and carcinogenic xenotoxins into milk," *Nat Med.*, 11(2):127-129 (2005).

Kaname et al., "Isolation and Subcloning of Large Fragmetns from BACs and PACs," *Bio Techniques*, 31: 273-278 (2001).

Kashi et al., "Marker-Assisted Selection of Candidate Bulls for Progeny Testing Programmes," *Anim. Prod.*, 51:63-74 (1990).

Kaupe et al., "DGAT1 Polymorphism in Bos indicus and Bos taurus cattle breeds," *J. Dairy Res.*, 71(2): 182-187 (2004).

Kaupe et al., "Mapping of CYP11B and a putative CYHR1 paralogous gene to bovine chromosome 14 by FISH," *Animal Genetics*, 35: 462-504 (2004).

Kerr et al., "The cDNA cloning and RNA distribution of bovine osteopontin," *Gene*, 108: 237-243 (1991).

Kerr et al., "An efficient algorithm for segregation analysis in large populations," *J. Anim. Breed. Genet.*, 113: 457-469 (1996).

Kuhn et al., "Detection of QTL for milk production traits in cattle by application of a specifically developed marker map of BTA6," *Anim. Genet.*, 30: 333-340 (1999).

Litman et al., "The multidrug-resistant phenotype associated with overexpression of the new ABC half-transporter, MXR (ABCG2)," *J. Cell Sci.*, 113: 2011-2021 (2000).

Mackay et al., "The Genetic Architecture of Quantitative Traits," *Ann. Rev. Genet.*, 35: 303-339 (2001).

Mackinnon et al., "Marker-assisted preselection of yound diary sires prior to progeny-testing," *Livest. Prod. Sci.*, 54:229-250 (1998).

Meuwissen et al., "Potential Improvements in Rate of Genetic Gain from Marker-Assisted Selection of Dairy Cattle Breeding Schemes," *J. Dairy Sci.*, 75:1651-1659 (1992).

Nadesalingam et al., "Detection of QTL for mile production on Chromosomes 1 and 6 of Holstein cattle," *Mamm. Genome*, 12: 27-31 (2001).

Nakatsu et al., "Genetic polymorphisms and antiviral activity in bht ebovine MX1 gene," *Animal Genetics*, 35: 182-187 (2004).

Nauli et al., "Polycystins 1 and 2 mediate mechanosensation in the primary cilium of kidney cells," *Nat. Genet.*, 33: 129-137 (2003).

Nemir, et al., "Targeted Inhibition of Osteopontin Expression in the Mammary Gland Causes Abnormal Morphogenesis and Lactation Deficiency," *J. Biol. Chem.*, 275: 969-976 (2000).

Olsen et al., "A Genome Scan for Quantitative Trait Loci Affcting Mike Production in Norweigian Dairy Cattle," *J. Dairy Sci.*, 85: 3124-3130 (2002).

Olsen et al., "Mapping of a milk production quanttative trait locus to a 420-kp region on bovine chromosome 6," *Genetics, Genetics Society of America*, 169(1): 275-283 (2005).

Ron et al., "Multiple Quantitative Trait Locus Analysis of Bovine Chromosome 6 in the Israeli Holstein Population by a Daughter Design," *Genetics*, 159: 727-735 (2001).

Schmitz et al., "Role of ABCG1 and other ABCG family members in lipid metabolism," *J. of lipid Res.*, 49: 1513-1520 (2001).

Schnabel et al., "Fine-mapping milk production quantitative trait loci on BTA6: analysis of the bovine osteopontin gene," *PNAS*, 102(19): 6896-6901 (2005).

Seroussi et al., "Uniquely conserved Non-translated Regions are Involved in Generation of the Two Major Transcripts of Protein Phosphatase 2Cβ," *J. Mol. Biol.*, 312: 439-451 (2001).

Seroussi et al., "ShiftDetector: detection of shir mutations," *J. of BioInformatics*, 18:1137-1138 (2002).

Spelman et al., "Quantitative Trait Loci Analysis for Five Mike Production Traits on Chromosome Six in the Dutch Holstein-Friesian Population," *Genetics*, 144: 1799-1808 (1996).

Spelman et al., "Short Communication: quantitative Trait Loci Analysis on 17 Nonproduction Traits int eh new Zealand Diary Population," *J. Dairy Sci.*, 82:2514-2516 (1999).

Stekrova et al., "PKD2 mutations in a Czech population with autosomal dominant polycystic kidney disease," *Nephrol Dial Transplant.*, 19: 1116-1122 (2004).

Su et al., "Large-scale analysis of the human and mouse transcriptomes," *Proc. Natl. Acad. Sci.*, 99: 4465-4470 (2002).

Thompson et al., "Improved sensitivity of profile searches through the use of sequence weights and gap excision," *Comput. Appl. Biosci.*, 10: 1929 (1994).

To et al., "Aberrant promoter methylation of the ABCG2 gene in renal carcinoma," *Molecular and Cellular Biology*, 26(22): 8572-8585 (2006).

Veenhuizen et al., "Metabolic Changes in Blood and Liver During Development and Early Treatment of Experimental Fatty Liver and Ketosis in Cows1," *J. Dairy Sci.*, 74: 4238-4253 (1991).

Velmala et al., "A search for quantitative trait loci for milk production traits on chromosome 6 in Finnish Ayrshire cattle," *Anim. Genet.*, 30: 136-143 (1999).

Wallner et al., "Isolation of Bovine Kidney Leucine Aminopeptidase cDNA: Comparison with the Lens Enzyme and Tissue-Specific Expression of Two mRNAs," *Biochemistry*, 32: 9296-9301 (1993).

Warren et al., "Construction and characterization of a new bovine bacterial artificial chromosome library with 10 genome-equivalent coverage," *Mamm. Genome.*, 11: 662-663 (2000).

Wayne et al., "Combining mapping and arraying: An approach to candidate gene identification," *Proc. Natl. Acad. Sci.*, 99: 14903-14906 (2002).

Weichenhan et al., "Source and component genes of a 6-200 Mb gene cluster in the house mouse," *Mammalian Genome*, 12: 590-594 (2001).

Weikard et al., "A Candidate Gene for QTL on BTA6 Affecting Milk Fat Synthesis," *29th Int. Conf. Ani. Gen.*, ISAG, Tokyo, Japan. D060 (2004).

Weller et al., "Estimation of Quantitative Trait Locus Allele Frequency via a Modified Granddaughter Design," *Genetics*, 162: 841-849 (2002).

Weller et al., "Population-Wide Analysis of a QTL Affecting Milk-Fat Production in the Israeli Holstein Population," *J. Dairy Sci.*, 86: 2219-2227 (2003).

Weller et al., "Genetic Analysis of the Israeli Holstein Dairy Cattle Population for Production and Nonproduction Traits with a Multitrait Animal Model," *J. Dairy Sci.*, 87: 1519-1527 (2004).

Weller, *Quantitative Trait Loci Analysis in Animals*, CABI Publishing, London, Chaps. 2, 3, 6, & 10 (2001).

Weller, *Quantitative Trait Loci Analysis in Animals*, CABI Publishing, London, Chaps. 12-15 (2001).

Wiener et al., "Testing for the presence of previously identified QTL for milk production traits in new populations," *Anim. Genet.*, 31: 385-395 (2000).

Winter et al., "Association of a lysine-232/alanine polymorphism in a bovine gene encoding acyl-CoA:diacylglycerol acyltransferase (DGAT1) with variation at a quantitative trait locus for milk fat content," *Proc. Natl. Acad. Sci.*, 99: 9300-9305 (2002).

Zhang et al., "Mapping Quantitative Trait Loci for Milk Production and Health of Dairy Cattle in a Large Outbred Pedigree," *Genetics*, 149: 1959-1973 (1998).

International Search Report issued in corresponding patent application No. PCT/US06/25117 (2007).

\* cited by examiner

FIG. 4

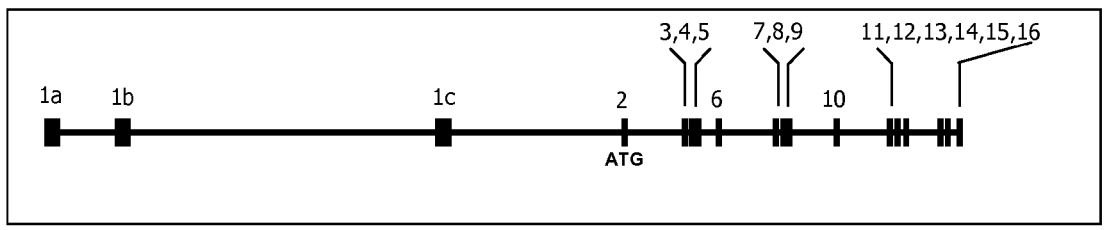
FIG. 6
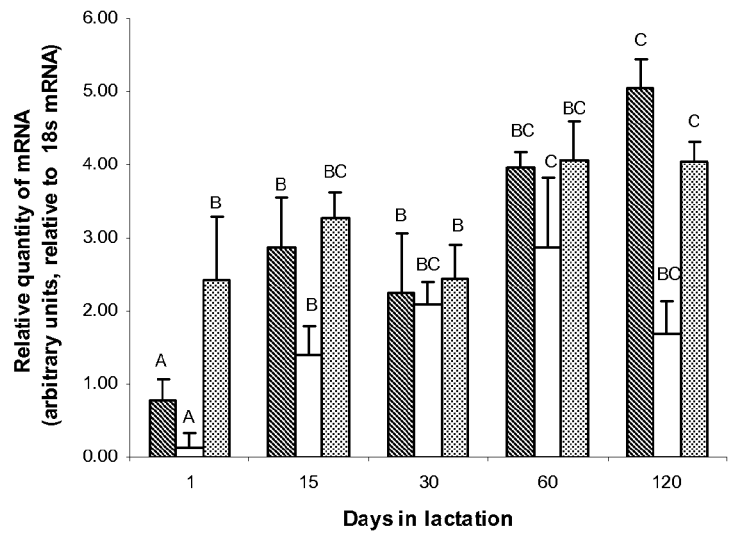
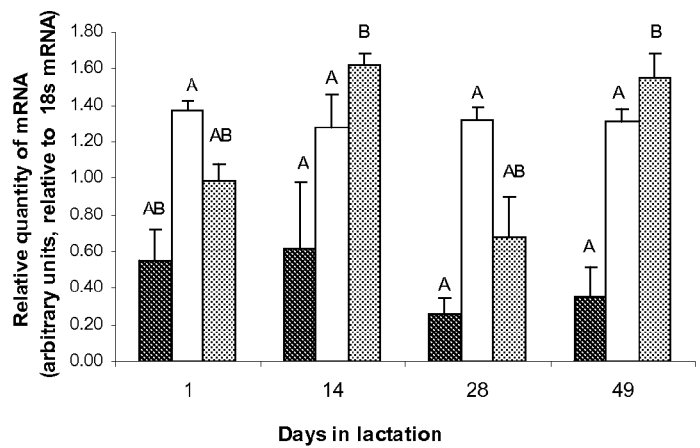
FIG. 7 (A-B)

BOVINE *ABCG2* GENE MISSENSE MUTATIONS AND USES THEREOF

This application claims priority to Application Ser. Nos. 60/694,430 filed Jun. 28, 2005 and 60/696,294 filed Jul. 1, 2005.

This invention was made with Government support under Contract No. IS-3103-99CR between the U.S. Israel Bi-national Agricultural Research and Development; and U.S. Department of Agriculture (USDA)—CSREES Livestock Genome Sequencing Initiative. The Government has certain rights in this invention.

BACKGROUND

Although many studies have demonstrated linkage between genetic markers and quantitative trait loci (QTL) in commercial animal populations, the actual DNA polymorphisms responsible for the observed effects—a quantitative trait nucleotide (QTN), has been identified in only a single case in dairy cattle (a polymorphism in exon 8 of the gene encoding acylCoA:diacyglycerol acyltransferase DGAT1) on *Bos taurus* chromosome 14 (BTA 14), which was associated with increased fat yield, fat and protein percent, as well as decreased milk and protein production. This gene was identified using bioinformatics, comparative mapping, and functional analysis.

Various studies have proposed candidate genes for the QTL on BTA6 based on their putative physiological role on the trait of interest. PPARGC1A (peroxisome proliferator activated receptor gamma, coactivator 1, alpha) was suggested as a positional and functional candidate gene for the QTL on BTA6, due to its key role in energy, fat, and glucose metabolism. The function of PKD2 corresponds with the QTL effect. This gene encodes an integral membrane protein involved in intracellular calcium homoeostasis and other signal transduction pathways. SPP1 was set forth as having an essential role in mammary gland differentiation and branching of the mammary epithelial ductal system, and is therefore a prime candidate. Furthermore, anti-sense SPP1 transgenic mice displayed abnormal mammary gland differentiation and milk secretion.

Segregating quantitive trait loci (QTL) for milk production traits on chromosome BTA6 were reported in U.S. Holsteins, British black and white cattle, Norwegian cattle, and Finnish Ayrshires. Three QTLs affecting milk, fat, and protein production, as well as fat and protein concentration are segregating on BTA6 in the Israeli Holstein population. The QTL with the greatest significance was located near the middle of the chromosome, with a confidence interval of 4 cM for protein percentage centered on microsatellite BM143. Two unrelated Israeli sires were found to be heterozygous for this QTL, whereas seven other sires were homozygous for the QTL.

The QTL confidence interval on BTA6 is orthologous to two regions on both arms of human chromosome 4 (HSA4) that contain the following annotated genes: FAM13A1, HERC3, HERC5, HERC6, PPM1K, ABCG2, PKD2, SPP1, MEPE, IBSP, LAP3, MED28, KIAA1276, HCAP-G, MLR1, and SLIT2. Physical mapping and combined linkage and linkage disequilibrium mapping determined that this QTL is located within a 420 Kbp region between genes ABCG2 and LAP3.

ABCG2, a member of the ATP binding cassette (ABC) superfamily, is a 'halftransporter," with only one ATP binding cassette in the N-terminus and one C-terminal transmembrane domain. In an ATP dependent process, ABCG2 transports various xenobiotics and cytostatic drugs across the plasma membrane. Analysis of different stages of mammary development by immunohistochemistry and western analysis revealed that ABCG2 was not expressed in virgin mice, but was greatly induced during late pregnancy and especially during lactation. ABCG2 expression is confined to the apical membrane of alveolar; but not ductal mammary epithelial cells of mice, cows, and humans; and is responsible for the active secretion of clinically and toxicologically important substrates into mouse milk. Mice homozygous for an ABCG2 knock-out mutation lack this function. However, −/−mice and their suckling progeny showed no adverse effects. ABCG2 is thought to be a drug transporter, but it is induced by estrogen. Related genes i.e. ABCG1, 5, and 8 are sterol transporters. It is therefore reasonable to propose that ABCG2 might transport cholesterol into milk.

Whereas in other tissues ABCG2 generally has a xenotoxin-protective function, transfer of xenotoxins from the mother to the suckling infant or young via milk is difficult to reconcile with a protective role.

As compared to other agricultural species, dairy cattle are unique in the value of each animal, the long generation interval, and the very limited fertility of females. Thus unlike plant and poultry breeding, most dairy cattle breeding programs are based on selection within the commercial population. Similarly, detection of quantitative trait loci (QTL) and marker assisted selection (MAS) programs are generally based on analysis of existing populations. The specific requirements of dairy cattle breeding has led to the generation of very large data banks in most developed countries, which are available for analysis.

SUMMARY

An isolated polynucleotide includes a coding region of the ABCG2 gene having a missense mutation. The ABCG2 gene includes three splice variants. A promoter region for expression of ABCG2 and its variants are disclosed. An expression construct that includes the ABCG2 gene or its variants or a functional fragment there of, is disclosed.

A positional cloning of a QTL in an outbred cattle population is described herein. A single nucleotide polymorphism (SNP) capable of encoding a substitution of tyrosine-581 to serine (Y581S) in ABCG2 is responsible for a major QTL affecting milk yield and composition.

Sequences designated by GenBank accession nos. AJ871966, AJ871964, AJ871963, AJ871176, AJ871967, AJ871968, AJ871965, AJ877268 are incorporated herein by reference.

A functional role for ABCG2 gene in natural milk secretion is disclosed.

A method of determining whether a mammal has a ABCG2 gene that includes a missense mutation as described herein, includes obtaining a suitable sample from the animal and determining the presence or absence of a missense mutation in ABCG2 locus. At least three such missense mutations are disclosed in ABCG2 locus.

Methods for cattle breeding and cattle selection for increased milk production based on ABCG2 missense mutation analysis are disclosed.

A cattle herd in which the individuals carry the ABCG2 gene having a missense mutation as described herein in a homozygous or heterozygous form, is disclosed.

A kit includes reagents for executing the methods disclosed herein. Small molecules or drugs are used to control expression of ABCG2.

A single nucleotide change (A/C) in exon 14 capable of encoding a substitution of tyrosine-581 to serine (Y581S) in the ABCG2 gene affects milk production traits. A polymorphism that is in linkage disequilibrium or in allelic association with the ABCG2 polymorphisms disclosed herein are within the scope of this disclosure. Closely linked or tightly associated polymorphisms with the ABCG2 locus are useful in marker assisted selection programs for increased milk production and other desirable traits such as time to weaning.

Table 10 presents terminology used herein.

BRIEF DESCRIPTION OF THE DRAWINGS

FIG. 4: Conservation of the $5^{th}$ extracellular domain of ABCG2 protein in mammals. The ClustalW (Thompson et al., 1994) alignment of predicted amino acid sequences of nine orthologous ABCG2 genes is shown (SEQ ID NOS: 190-198, respectively in order of appearance). Identity and similarity between the amino acid sequences are indicated by black and grey boxes, respectively. White boxes indicate non-conservative amino acid changes between the proteins. Dashes indicate gaps introduced by the alignment program. The position of 581Y in Bos taurus for which the sires heterozygous for the QTL were 581Y/581S is indicated by an arrow. A conserved phenylalanine residue is located in this position for most of the other mammals.

FIG. 6 is a schematic representation of the bovine ABCG2 gene, including the three alternative first exons (variants 1a, 1b and 1c). Black boxes and numbers from 2 to 16. First ATG is located in exon number 2.

FIG. 7 shows expression data for variants 1a (dark), 1b (dark grey) and 1c (light grey) in the first exon of bovine ABCG2 gene: (A) in the mammary gland (B) in the liver, during lactation, comparing to day 15 on dry period. Expression levels were analyzed using real-time PCR analysis.

DETAILED DESCRIPTION

Figure 1:
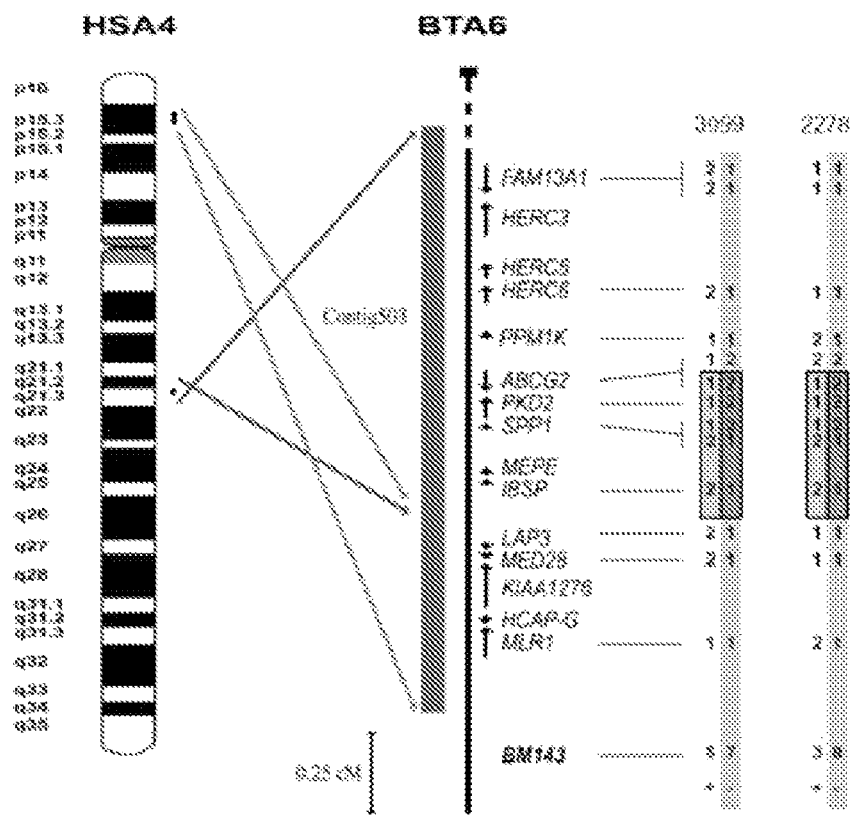
FIG. 1. Genes within the critical region of the QTL on BTA6 proximal to BM143 were ordered based on the cattle-human genome comparative map, 23 bovine BAC clones representing contig 503; with SPP1, IBSP, and LAP3 as anchors for the orthologous regions on HSA4. BM143 is indicated (in bold type) as the most informative marker for the QTL in cattle. Polymorphism is displayed at the respective gene positions for the two sires 2278 and 3099, heterozygous for the QTL (+/−). The alleles of the diallelic markers are denoted as either 1 or 2, with the more frequent allele denoted 1. BM143 alleles were numbered consecutively for shortest to longest based on all alleles detected in the population. Shared haplotypes in concordance with the segregation status of the two sires for the QTL are displayed.

A quantitative trait locus (QTL) affecting milk fat and protein concentration was localized to a 4cM confidence interval on chromosome 6 centered on the microsatellite BM143. The genes and sequence variation in this region were characterized, and common haplotypes spanning five polymorphic sites in the genes IBSP, SPP1, PKD2, and ABCG2 for two sires heterozygous for this QTL were localized. Expression of SPP1 and ABCG2 in the bovine mammary gland increased from parturition through lactation. SPP1 was sequenced, and all the coding exons of ABCG2 and PKD2 were sequenced for these two sires. The single nucleotide change capable of encoding a substitution of tyrosine-581 to serine (Y581S) in the ABCG2 transporter was the only polymorphism corresponding to the segregation status of all three heterozygous and 15 homozygous sires for the QTL in the Israeli and US Holstein populations. The allele substitution fixed effects on the genetic evaluations of 335 Israeli sires were −341 kg milk, +0.16% fat, and +0.13% protein (F-value=200). No other polymorphism gave significant effects for fat and protein concentration in models that also included Y581S. The allele substitution effects on the genetic evaluations of 670 cows, daughters of two heterozygous sires, were −226 kg milk, 0.09% fat, and 0.08% protein (F-value=394), with partial dominance towards the 581S homozygotes. Y581S in ABCG2 is likely the causative site for this QTL.

The variation in SPP1 (OPN3907) is an indel (insertion and deletion) in poly-T tract ~1240 bp upstream of SPP1 transcription initiation site. Accurate genotyping of such region would require a tedious subcloning of the PCR products to allow separation between the homologous chromosomes present in each heterozygous individual. In several instances OPN3907 region was sequenced using cloned DNA or homozygous individuals revealing three distinct alleles that are present in this locus. Interestingly all cloned sequences deposited in GenBank (AJ871176, AC185945, NW_931635) were of the allele with nine thymines (T9) described as rare (frequency 0.05). The latter also sequenced an allele (T10, AY878328) from a homozygous individual. Sequencing of sire 3208 revealed the third allele with nine thymines followed by three adenines. Hence this locus displayed length variation typical of a microsatellite with different numbers of repeats of either thymines or adenines. These alleles were designated SPP1M1-M3, respectively. Sequencing of heterozygous individuals resulted in superimpositions, which were traced as follows: SPP1M1 and SPP1M2; SPP1M2 and SPP1M3; SPP1M1 and SPP1M3. Using this scheme a sample of genotypes of sires that segregate (Y) and do not segregate for the QTL (N) and sire homozygous for the ABCG2 581 S allele were found. While the status of the ABCG2 mutation was in concordance with the QTL status, concordance was observed with neither the length of the T track nor the allele status of the SPP1 microsatellite. For example, the traces of the three sires segregating for the QTL were all of the type M1/M2 and were indistinguishable from that of the non-segregating sire 3241. This indicates that the variation in ABCG2 is probably responsible for the QTL Sequencing of sires homozygous for the Y581S haplotype (2182; 2227; 3573; 3396; 3094) associates it with SPP1M1 (T9). The results indicate that sire 2176 that has one of lowest protein % ever recorded in Israel is homozygous for Y581 S but heterozygous for SPP1M. Moreover within the BAC clone of Holstein breed (AJ871176) the SPP1M1(T9) is associated with the ABCG2 Y581 plus allele, and thus demonstrating that there are Holsteins available for such a linkage disequalibrium study. Sire 3028 has one of the highest protein % and therefore is unlikely to be homozygous for the minus QTL allele. This sire is indeed homozygous the ABCG2 581 S allele but also for SPP1M3(T9) and would have been considered to be homozygous for the minus QTL allele. Sire 5117, segregating for the QTL is Carlin-M Ivanhoe Bell that was used heavily in global breeding programs.

Tests for concordance of the ziygosity state between the QTL segregation status and the candidate polymorphism is a powerful tool for identifying the functional mutation underlying the QTL.

A polymorphism that is in linkage disequilibrium or in allelic association with the ABCG2 polymorphisms disclosed herein are within the scope of this disclosure. Closely linked or tightly associated polymorphisms with the ABCG2 locus are useful in marker assisted selection programs for increased milk production and other desirable traits such as time to weaning, meat quality and quantity. For example, a person of ordinary skill in the art can readily identify polymorphisms that are closely linked to the Y581S and other polymorphisms disclosed herein. Thus, the Y581S polymorphism serves as an anchor polymorphism to find other closely linked polymorphisms.

Comparative and Physical Mapping of the Critical Region for the BTA6 QTL

By combining comparative genomics and in-silico gene cloning, a map was produced of genes and sequence variation in the critical region of the QTL (FIG. 1). Gene order was confirmed by physical mapping of PCR probes in BAC clones that are part of genomic contigs 503 and 8342 disclosed herein. BM143 and SLIT2 were identified within contig 8342. Fifteen genes within 2 cM centromeric to BM143 were identified within contig 503 orthologous to two different regions on HSA4. FIG. 1 shows the predicted order, size, and orientation of transcription of the genes within contig 503, based on their corresponding features in the human genome.

Polymorphism Detection, LD Mapping, and Haplotype Analysis

Figure 5:
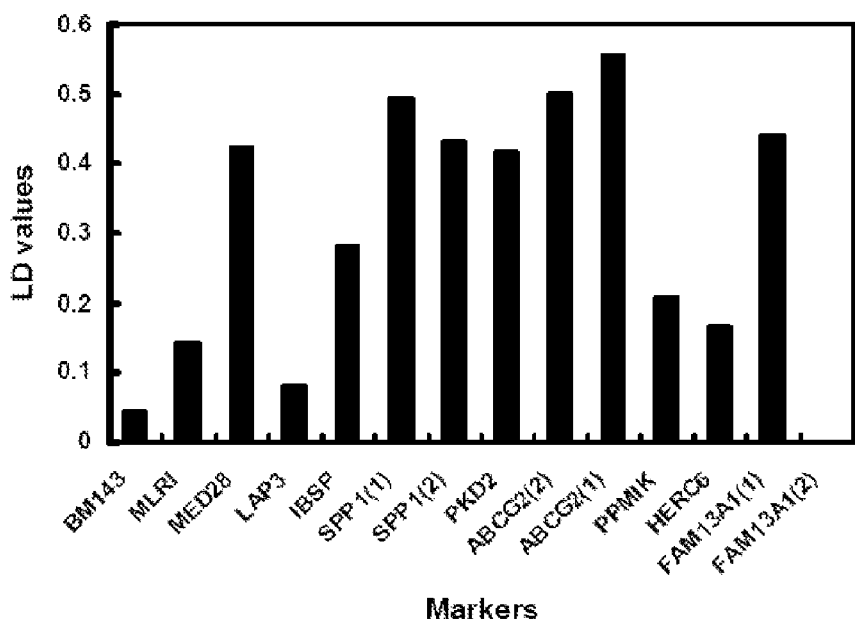
FIG. 5: Linkage disequilibrium values for adjacent markers computed from 411 Israeli Holstein bulls.

A total of 31,655 bp was sequenced in intergenic, exonic, and intronic regions of 10 genes within the critical region of the QTL using DNA of two sires (2278 and 3099) heterozygous for the QTL (Table 1). Thirteen sites heterozygous in at least one of the two sires were selected as markers and genotyped for 411 sires. A single polymorphic site was genotyped in seven genes, and two polymorphic sites were genotyped in each of the three genes SPP1, ABCG2, and FAM131A1. Henceforth, the polymorphisms will be denoted by gene symbols for seven single gene polymorphisms, and by the gene symbol followed by either (1) or (2) for the genes with two polymorphisms. All sites of polymorphism were in highly significant LD ($P<0.0001$) with at least one other site. LD values of adjacent markers are plotted in FIG. 5. Generally LD values between adjacent markers were >0.2. Exceptions were the BM143-MRL1-MED28 segment, LAP3-IBSP, and HERC6—FAM13A1. The two sires heterozygous for the QTL share common haplotypes for the polymorphic sites at IBSP, SPP1, PKD2, and ABCG2 (FIG. 1). For both sires the same haplotype was associated with increased protein concentration.

Cloning of Bovine ABCG2, PKD2, and SPP1 Genes

A bovine BAC clone containing the three genes, SPP1, PKD2, and ABCG2 (GenBank accession AJ871176) was shotgun sequenced. By aligning this sequence with bovine ESTs and human orthologous genes in this BAC the last 15 exons of the bovine ABCG2 gene were identified in this BAC, which included the whole putative polypeptide sequence of the ABCG2 transporter (protein CAI38796.1). In the opposite orientation on the BAC 15 exons of the gene orthologous to human PKD2 (CAI38797.1), and seven exons of bovine SPP1 (CAI38798.1) were annotated. The entire description of the cloning procedure is presented in the Materials and Methods.

Expression of Candidate Genes in the Bovine Mammary Gland

Figure 2:
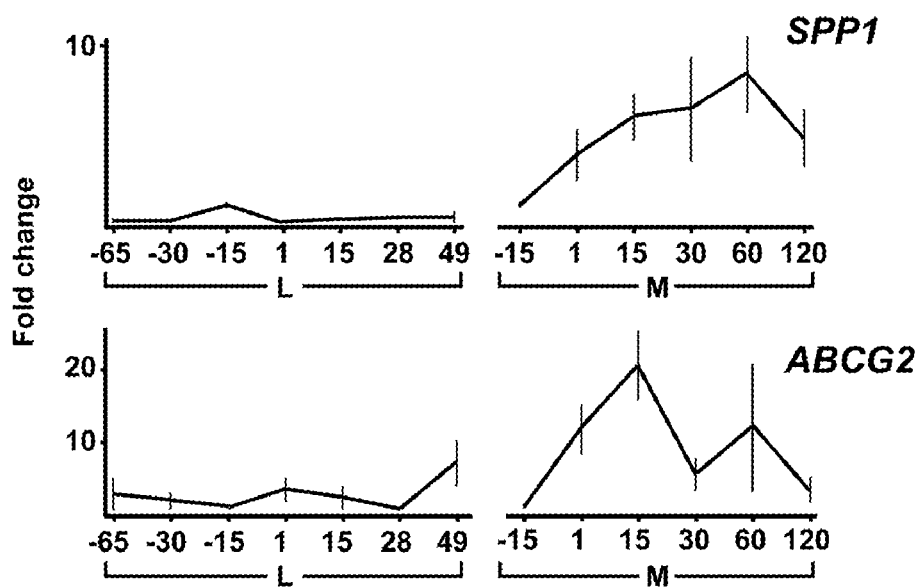
FIG. 2. Expression data for SPP1 and ABCG2 in bovine mammary (M) and liver (L) tissues. Fold-change values are normalized intensity during pregnancy (−65, −30 and −15 d to calving date) and lactation (1, 15, 30, 60 and 120 d postpartum) using day −15 d as a base for comparison.

Of the eight genes analyzed, three genes; SPP1, ABCG2, and MED28 showed significant differential expression in the mammary gland during lactation, as compared to the dry period ($p<0.02$). Significant differential expression was not found in liver tissue. Expression of SPP1 and ABCG2 in the mammary gland and liver during lactation and the dry period is shown in FIG. 2. The increase in the mammary gland was 8- and 20-fold for the two genes respectively.

The ABCG2 Missense Mutation Y581S

Using this BAC data, the exons, introns, and part of the regulatory region of SPP1, and all the coding exons of PKD2 and ABCG2 for the two Israeli sires heterozygous for the QTL were sequenced. The single nucleotide change, A to C, denoted ABCG2(2), capable of encoding a tyrosine to serine substitution at position 581 (Y581S) in the $5^{th}$ extra-cellular region of the ABCG2 protein, was detected. Henceforth, the A allele, capable of encoding tyrosine, which was the more frequent allele in the population, will be denoted the +QTL allele. The +QTL allele decreases milk yield, and thus increases fat and protein concentration. Of the 341 sires with valid genotypes, 12 were homozygotes −/−, 109 were heterozygotes, and 220 were homozygotes +/+. The +QTL allele frequency was 0.805 and the genotype frequencies corresponded nearly exactly to the expected Hardy-Weinberg frequencies. ABCG2(2) was the only polymorphism corresponding to the segregation status of all three heterozygous and 15 homozygous sires for the QTL in the Israeli and US Holstein populations. The probability of concordance by chance, computed as described in the Materials and Methods=$(0.68^{15})(0.16^2)=0.00008$.

Allele Substitution Effects and Dominance

The Model 1 effects of the markers on the quantitative traits are given in Table 2. This model estimated the effects associated with the polymorphisms on the sire evaluations for the milk production traits, with each polymorphism-trait combination analyzed separately (Cohen et al, 2004a). The number of bulls with valid genotypes and the frequency of the more common allele for each marker are also given. Most of the markers had highly significant effects on protein concentration, but the effect associated with ABCG2(2) was more than double the next largest effect. LAP3, MED28, ABCG2(2), and HERC6 had significant effects on fat and protein yield, while ABCG2(2), SPP1(1), SPP1(2), and PKD2 were associated with milk yield. The effect associated with ABCG2(2) on milk was double the next largest effect, and the effect associated with % fat was triple the next largest effect observed.

The effects on the quantitative traits associated with 670 daughters of the two sires heterozygous for the QTL are given in Table 3, both as class effects, and as regression effects. The class effects are given relative to the 581S homozygote (−/−). Dominance was estimated from the class effects, relative to the 581S homozygote. The regression effects estimated from the animal model analyses of the entire Israeli Holstein population are also given. Israel and Weller (1998) demonstrated that QTL effects will be underestimated by the analysis of genetic evaluations, especially genetic evaluations of cows, which have relatively low heritability, while estimates derived from animal model analyses of the entire population will be unbiased. The effects derived from the animal model for milk, percentage fat, and percentage protein were more than double the regression effects from the analyses of the genetic evaluations. This was not the case for fat and protein yield, but these effects were only marginally significant in the analyses of the genetic evaluations. For all five traits, the heterozygous effect was within the range of the two homozygous effects. Significant partial dominance was obtained for both percentage fat and percentage protein towards the 581S homozygote, which was also the less frequent allele among the daughters of the heterozygous sires.

Variance Components and Marker Substitution Effects from REML Analysis

The numbers of genotyped bulls and ancestors included in the variance component analyses are provided herein for the analyses of ABCG2(2) alone, and the analyses of ABCG2(2) with SPP1(2), HERC6, and LAP3. These analyses are presented because these markers gave the greatest Model 1 effects on the production after ABCG2(2). In each analysis the number of ancestors was slightly greater than the numbers of genotyped bulls. The total number of bulls included in each analysis ranged from 641 to 758.

The variance components are presented herein for all four analyses. The residual effects were generally low, because genetic evaluations were analyzed. In all four analyses, the variance components and the substitution effects associated with ABCG2(2) for fat and protein percentage were quite similar. The substitution effects were close to 0.21% for both traits in all analyses. These values are also close to the values of 0.22 and 0.19 for fat and protein percentage obtained from the animal model analysis. The variance components for all the markers other than ABCG2(2) were near zero for fat and protein percentage. The variance components associated with SPP1(2) were near zero for all five traits. These results correspond to the hypothesis that ABCG2(2) is the causative mutation for the QTL affecting fat and protein concentration.

The variance component associated with ABCG2(2) for milk was similar in all analyses, except for the analysis that included HERC6. In this analysis the variance component for ABCG2(2) increased to 160,000. This can be explained by postulating that two QTL are segregating on this chromosome that affects milk production, and that in general these two QTL are in repulsion throughout the population. Thus a greater effect was observed associated with ABCG2(2) with HERC6 included in the model, because the "masking" effect was removed. Sire 2278 was also segregating for the QTL proximate to the centromere, but the effects on milk were in repulsion for this sire. This QTL affects milk, fat, and protein production, but not fat or protein concentration. The effects associated with LAP3 affected milk and fat yield and protein concentration. Unlike the analyses including ABCG2(2) and HERC6, in the analyses including ABCG2(2) and LAP3, the variance components associated with both markers were positive for fat and protein yield. This corresponds to the hypothesis that neither of these markers are in complete linkage for the QTL responsible for fat and protein yield.

Genetic Trend

Figure 3:
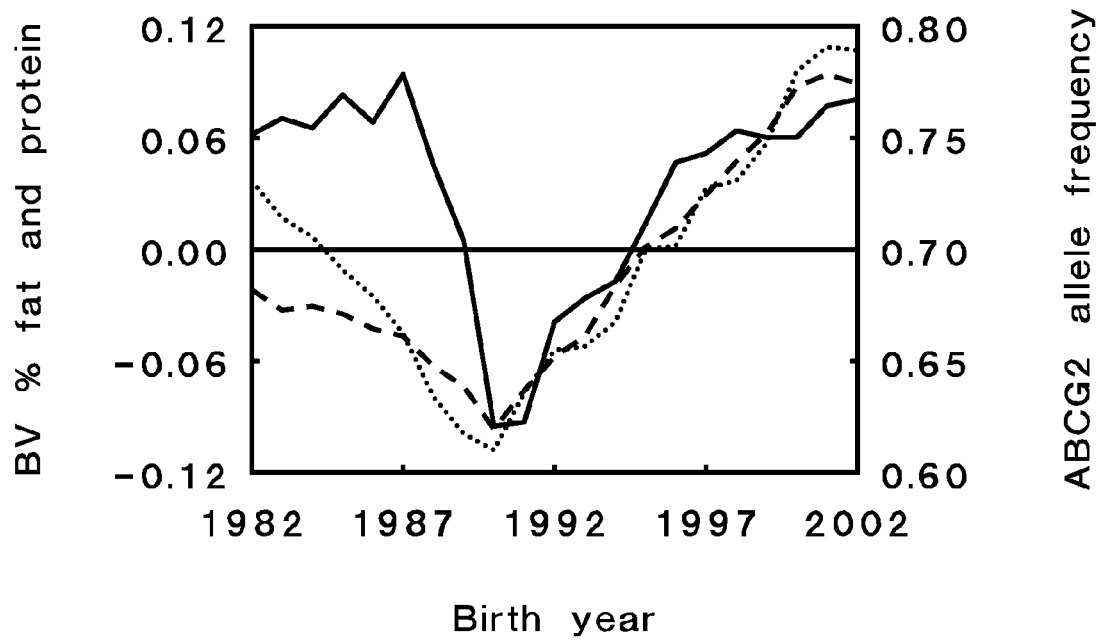
FIG. 3: Genetic trends for protein and fat concentration and frequency of the ABCG2 581 Y allele in the Israeli Holstein cow population by birth year. —, ABCG2 581Y allele frequency, •••, mean yearly breeding values for % fat; - -, mean yearly breeding values for % protein.

The genetic trend for the 581 Y of ABCG2 (2) in the entire cow population is shown in FIG. 3. The mean annual breeding values for fat and protein percent are also given. The frequency of 581Y allele by birth date of cows decreased from 0.75 in 1982 to 0.62 in 1990, and then increased to 0.77 in 2002. These trends correspond to the change in the Israeli breeding index, which was based chiefly on milk production until 1990. Since then the index has been based chiefly on protein with a negative weight for milk yield.

Conservation of ABCG2 581 in Mammals

Comparison of this protein domain across mammals is presented in FIG. 4 for the region spanning amino acid 557 to 630. The arrow indicates position 581 for which tyrosine and serine were found for the three sires heterozygous for the QTL. Phenylalanine is the conserved amino acid in the mammals analyzed, except for Canis familiaris and Bos taurus with tyrosine at this position. Both tyrosine and phenylalanine are aromatic acids, while serine is a nucleophilic acid.

Proof for identification of a gene underlying a QTL in commercial animal populations results from multiple pieces of evidence, no single one of which is convincing, but which together consistently point to a candidate gene.

Diverse pieces of evidence support the conclusion that ABCG2 is the segregating QTL on BTA6:

1. The shared haplotypes of the two sires segregating for the QTL spanned five sites of polymorphism in the genes IBSP, SPP1, PKD2, and ABCG2. This is equivalent to the 420 Kbp region found in the Norwegian cattle (Olsen et al., 2005), except that it is shorter on the 5' end of ABCG2 (exons 1 to 3) and the 3' end of LAP3 (exons 12 and 13). The same haplotype was associated with the +QTL allele in both sires.

2. The two genes within the shared haplotype, ABCG2 and SPP1, were preferentially expressed in the bovine mammary gland at the onset of lactation. Furthermore, large scale analysis of human and mouse transcriptomes revealed that ABCG2 had the highest expression in the mammary among 61 organs and tissues tested.

3. Of the polymorphisms genotyped only ABCG2(2) was in concordance with the segregation status of all three heterozygous and 15 homozygous sires for the QTL in the Israeli and US Holstein populations. The probability that this would occur by chance is 0.00008.

4. ABCG2(2) is capable of encoding a non-conservative amino acid change (Y581S) that may affect this gene transporter function.

5. The highest population-wide substitution effects on milk yield and fat and protein concentration were obtained for the Y581S polymorphism in ABCG2, and these effects were more than double the next largest effects associated with any of the other polymorphisms.

6. In the analysis of over 300 genotyped bulls, none of the other polymorphisms gave significant effects for fat and protein concentration in models that also included Y581S.

7. The high Y581S allele substitution effects on the genetic evaluations of 670 cows, daughters of two heterozygous sires, represent the joint effects of both paternal and maternal alleles. The F-value was 394 for % protein.

8. Protein and fat concentration for cows homozygous for the 581S allele was lower than the heterozygotes, even though the second 581S allele was of maternal origin, and therefore unrelated to the daughter design effects.

9. The frequency of 581Y allele by birth date of cows decreased from 0.75 in 1982 to 0.62 in 1990, and then increased to 0.77 in 2002, in correspondence with the changes in the Israeli Holstein selection index. The close correspondence between the two analyses supports the conclusion that ABCG2(2) is the QTN, although it could also be due to a "hitch-hiker" effect.

10. Weller et al. estimated the frequency of the +QTL allele in the Israeli Holstein population as 0.69 and 0.63, relative to fat and protein percent, by the modified granddaughter design for cows born between 1992 and 1996. This corresponds closely to the frequency of 0.69 for 581Y as estimated in the current study for cows born in 1994.

All 18 Israeli and US sires with known QTL genotypes were sequenced and shown that this chromosomal segment is hyper-variable. At least four single nucleotide changes were found within the 20 bp region centered on the poly-A sequence. All sires except one were heterozygous for at least one of these polymorphisms. The conclusion was that OPN3907 is not the QTN. However, as long as the entire chromosomal segment within the confidence interval of the QTL has not been sequenced in the sires with known QTL genotypes, it is not possible to completely eliminate the possibility that the QTN may be some other polymorphism in strong LD with Y581S.

This is the first example of a functional role for the ABCG2 gene in natural milk secretion.

Identification of Three Promoters for the Bovine ABCG2 Gene

The existence of three different promoters for three different 16-exon transcripts of ABCG2 gene is reported in GenBank accessions BE480042 and CK838023. The 5' region of this gene is assembled and the sequence is disclosed herein.

The current sequence of the bovine genome is based on sequence derived from a Hereford cow. The WGS trace files were BLAST searched with the cow genome database using the sequences of the three different variants. All the trace files were downloaded and their corresponding mates and assembled them using the GAP4 computer program, monitoring the consistency of the mate-pair data and adding or removing trace files accordingly. The contigs of each of the three variations were expanded using additional trace files that were found by searching against the contig end sequences. Eventually all the contigs were merged into one assembly, confirming the existence of three alternative first exons of ABCG2 including the GT motives for splice donors at their ends. The final assembly spanned 627 sequence reads in a length of 235,109 bp (FIG. 6). Following confirmation of the existence of the three promoters, their expression was verified in lactating cow mammary gland.

The promoters of ABCG2 gene and its splice variants are useful in increasing expression of a gene of interest in a suitable tissue such as, mammary gland, and during a specific period, e.g., during lactation.

Expression of the Three Splice Variants of ABCG2 Gene in Bovine Mammary Gland

All three variants showed significant expression in the cow mammary gland during lactation, as compared with the dry period (p<0.0002), using real-time PCR analysis. Significant differential expression was not found in liver tissue which was used as a control. Expression of the three variants in mammary gland and liver tissues is shown in FIG. 7A-B. Variant 1c showed the highest expression, of 5-fold in the mammary gland on day 120 in lactation. Variants 1a and 1b showed an expression of 3 and 4 fold respectively on day 60 in lactation.

Materials and Methods

PCR primers and their corresponding numbers are presented in Table 7. All GenBank and other publicly available database accession numbers disclosed herein are incorporated by reference.

Physical mapping and bioinformatics. The order and location of the genes in the QTL region were determined in the bovine bacterial artificial chromosomes (BACs) from the CHORI-240 BAC library (Warren et al., 2000). Repeat-masked end sequences from CHORI-240 clones obtained from the GenBank for BLASTN search against the human genome sequence (NCBI build 33) were used. The cattle fingerprint contigs (BCCRC, Vancouver, Canada) were identified that contain clones anchored to the human genome by sequence similarity. Cattle fingerprint contig 503, which covers the confidence interval region of the QTL upstream to BM143 in HSA4, is diagramed in FIG. 1. The contig is represented on the axis of HSA4 in the following positions: 89,077,921-90,827,214 and 17,255,215-17,699,645 available at website (genome.ucsc.edu/goldenPath/hgTracks.html). A minimum tiling path of 23 cattle BACs between these positions covering the region of the QTL from FAM13A1 to MLR1 were selected. The exact position of each gene in the human genome was identified using the UCSC Genome Browser database. Bovine BAC clones presumably containing the same gene in cattle were identified by their end sequence similarity to the human genome and presented in Table 5. When there was no BAC clone with both ends covering the whole interval of the candidate gene, several overlapping BACs with single ends matching the upper and lower boundaries of the gene interval and covering the whole region were selected for PCR analysis. The BAC templates were prepared by picking colonies grown overnight and boiling them in 200 µl of ddH$_2$O for 10 minutes. Bioinformatics procedures, management of DNA sequences and EST assembly were done as previously described (Cohen et al., 2004a).

Identification of polymorphism in genes within the critical region of the QTL. To search for relevant informative genomic variation in the critical region of the QTL the genomic DNA of the two sires heterozygous for the QTL served as a template. PCR amplified genomic fragments of the bovine orthologs of the human genes are listed in Table 1. In most cases the bovine sequence required for the design of PCR primers was obtained from bovine ESTs of the orthologous genes. The PCR products were sequenced for polymorphism detection. Nucleotide substitution was detected by double peaks for the specific nucleotides, and insertion was detected by sequence overlap that was analyzed using Shift-Detector (Seroussi et al., 2002).

Experimental design and haplotype analysis. The search for the QTN was based on genotyping of the following samples:

1. Two sires heterozygous for the QTL (2278 and 3070), and seven sires homozygous for the QTL in the Israeli population as determined using a daughter design (Ron et al., 2001).

2. A single sire heterozygous for the QTL (DBDR family 9), and eight sires homozygous for the QTL in the US population (DBDR family 1 to 8) as determined using a granddaughter design analysis (Ashwell et al., 2004).

3. Six-hundred-and-seventy daughters of two Israeli sires heterozygous for the QTL with genetic evaluations for production traits (Ron et al., 2001).

4. Four-hundred-and-eleven progeny-tested Israeli sires with genetic evaluations for production traits (Cohen et al., 2004a).

5. Eight cows with mammary biopsies and five cows with liver biopsies.

The 411 Israeli Holstein sires with genetic evaluations for all five milk production traits were genotyped for the 13 markers listed in Table 1 and BM143. Eleven markers were SNPs, one was a two-base polymorphism, and two were microsatellites (BM143, and the polymorphic site in MLR1). Twenty daughters of each of the two Israeli sires heterozygous for the QTL were also genotyped for all 14 markers to determine the haplotypes of the two sires. Genotyping of polymorphism was performed following Cohen et al., (2004a). The genotyping platform and specific assay for each site are presented in Table 6.

Statistical analysis. LD parameters values were computed between each pair of markers as described by Hedrick (1987). Probability of concordance by chance between the QTL and a polymorphism was computed only for ABCG2(2), which was the only marker in complete concordance with the 18 sires with known QTL genotype (Ron et al., 2001; Ashwell et al., 2004). Since only polymorphisms heterozygous in at least one of the sires heterozygous for the QTL were genotyped on the complete sample of bulls, the probability of concordance with the QTL only considered the remaining 17 sires. This is computed as the probability that all 15 sires homozygous for the QTL should also be homozygous for the polymorphism, and that the two remaining sires heterozygous for the QTL should also be heterozygous for the polymorphism, and that in all three heterozygous sires the same QTL allele should be associated with the same marker allele. Thus probability of concordance=$p_1^{15}(p_2/2)^2$, where $p_1$=probability of homozygotes, and $p_2$=probability of heterozygotes. $P_2$ was divided by two, because for concordance to be complete, the two additional heterozygous sires must have the same ABCG2(2) allele associated with the +QTL allele as the original genotyped sire.

Genetic evaluations for milk, fat, and protein were computed by a multitrait animal model analysis of the entire Israeli Holstein population (Weller and Ezra, 2004). Evaluations for fat and protein percent were derived from the evaluations for the production traits. The following fixed linear model, denoted Model 1, was used to estimate the effect associated with each one of the polymorphisms for each of five traits analyzed (Cohen et al., 2004a):

$$Y_{ijkl}=a_iJ+b_iK+c_i(K)^2+e_{ijkl}$$

where, $Y_{ijkl}$ is the genetic evaluation of sire 1 with marker genotype j and birth year k for trait i; J is the number of "+" alleles (j=0, 1 or 2); K is the sire's birth year; $a_i$, $b_i$ and $c_i$ are regression coefficients for trait i; and $e_{ijkl}$ is the random residual for each sire for trait i. The "+" allele for ABCG2(2) was the allele associated with increased protein concentration. For all the other markers, the allele in LD association with the "+" for ABCG2(2) was denoted the "+" allele. BM143 was analyzed as a diallelic marker, as described herein. The linear and quadratic effects of the sires' birth year were included to account for genetic trends in the population. The effects of the markers were also analyzed with three marker genotypes as class effects. Linear and quadratic birth year trends of the markers were also estimated.

Model 1 does not account for the relationships among sires or linkage among markers. Thus the genetic evaluations were also analyzed for a subset of the markers with the greatest effects by the following model, denoted Model 2:

$$Y_{ijk}=a_iJ+g_{ik}+e_{ijk}$$

Where, $g_{ik}$ is the additive polygenic effect for animal k on trait i, and the other terms are as defined previously. This model differed from the previous model in that all three effects were considered random, and the numerator relationship matrix was used to compute the variance matrix for the polygenic effect. In order to obtain a more complete relationship structure, all known parents and maternal grandsires of the genotyped bulls were included in the analysis. The numbers of animals in each analysis are given in Table 6. REML variance components were computed for the "a" and "g" effects by the MTC program University of Georgia, Department of Animal and Dairy Science, Athens, Ga.). Marker substitution effects were derived as: $[(\text{Var a})/(2\text{ pq})]^{1/2}$ where "Var a" is the marker variance component, and p and q are the frequencies of the two QTL alleles, as derived from the sample of 411 genotyped sires (Weller, 2001). This model was also used to analyze marker pairs with highly significant effects on the quantitative traits as determined by Model 1.

Dominance of the QTL effect can only be estimated by comparison of cows that are heterozygous for the QTL to cows that are homozygous for the two alternative alleles (Weller et al., 2003). The genetic evaluations for the five milk production traits of 670 daughters of two Israeli sires heterozygous for the QTL were analyzed by a model that also included the sire effect. The QTL was considered a class effect and significance of dominance was estimated by significance of the difference between the midpoint of the two homozygote effects and the mean of the heterozygote effect. The dominance effect was estimated as the ratio of the difference between the heterozygote effect and the mid point of the homozygote effects, divided by half the difference between the homozygote effects. Cow genetic evaluations are based on relatively few records, and are therefore highly regressed. Thus the QTL effects estimated from this model will also be underestimated (Israel and Weller 1998). However, this should not have a major effect on the estimate of dominance, which was derived as a ratio of the estimated effects.

Genotype probabilities for ABCG2(2) were determined for the entire Israeli Holstein milk-recorded population, including 600,478 cows and 1670 bulls, using the segregation analysis algorithm of Kerr and Kinghorn (1996), based on the 335 bulls with valid genotypes. Finally, the QTL effects for milk, fat, and protein yield were estimated from the entire Israeli Holstein milk-recorded population based on the genotyped cows, as proposed by Israel and Weller (1998). These QTL estimates should be unbiased, unlike the estimates derived from analysis of the genetic evaluations. The effects for fat and protein percent were derived from the estimated effects for the yield traits as described by Weller et al., (2003).

The detailed procedures for biopsy procedures, RNA extraction, BAC clone selection, subcloning and shotgun sequencing, real-time PCR, and computation of LD parameter values and ABCG2(2) genotype probabilities for the entire Israeli Holstein population are presented herein.

The cattle BACs covering the region from FAM13A1 to MLR1: E0152P21, E0375J15, E0259M14, E0101G10, E0181A19, E0303P06, E0274F22, E0098H02, E0445L10, E0060K13, E0367N10, E0174N17, E0049M05, E0331116, E0338G15, E0263K19, E0351N06, E0039I05, E0062M13, E0351N06, E0308O12, E0393F21, and E0417A15.

BAC clone selection, subcloning and shotgun sequencing. Filters from RPCI-42 bovine library Children's Hospital Oakland Research Institute, Oakland, Calif.) were hybridized with $^{32}$P-labeled PCR primers specific for SPP1 gene (Rediprime II Random Prime Labelling Kit, Amersham Biosciences). Three clones positive for SPP1 were identified. The clones were PCR-screened for the presence of SPP1, PKD2, and ABCG2 genes. A clone H005K14 positive for all three genes was identified and selected for the shotgun sequencing. The H005K14 clone was grown and its DNA was purified using the Large-Construct kit (Qiagen, CA) following the manufacturer's instructions. To separate the genomic DNA insert from the BAC vector, the purified DNA was digested with NotI and applied to a 0.8% low melting point SeaPlaque agarose gel (Cambrex, Me.) as previously described (Kaname and Huxley, 2001). The isolated insert fragment was sheared with a nebulizer. Blunt-ended fragments 1.6 to 5 Kbp were purified from a 0.8% low melting point agarose gel and cloned into the pCR ®4Blunt-TOPO vector using the TOPO® Shotgun Subcloning kit (Invitrogen, CA) according to the manufacturer's instructions. Individual transformed bacterial colonies were robotically picked and racked as glycerol stocks in 384 well plates. After overnight growth of the glycerol stocks, bacteria were inoculated into 96 well deep cultures and grown overnight. Plasmid DNA was purified with Qiagen 8000 and 9600 BioRobots (Qiagen, CA). Sequencing of the 5' and 3' ends was performed using standard primers M13 forward and reverse and ABI BigDye terminator chemistry on ABI 3700 capillary systems (Applied Biosystems, CA). All 384- and 96-well format plates were labeled with a barcode and a laboratory information management system (HTLims) was used to track sample flow. The shotgun sequences were trimmed of vector sequences and stored in a local Oracle database. To assemble the shotgun sequences into contings, Contig Express software (Vector NTI v 7.0 package, InforMax Inc.) was employed.

Cloning of bovine ABCG2 and PKD2 genes. BLASTN search of bovine dbEST using the sequence of these 15 exons of ABCG2 revealed 31 ESTs. Two ESTs indicated alternative splicing of 5' non-translated first exons suggesting existence of three different promoters for three different 16-exon transcripts of this gene (GenBank accessions BE480042 and CK838023). Twenty-three of the ESTs were assembled into a tentative consensus 2198 bp cDNA transcript (TIGR tentative consensus TC264405) capable of encoding a polypeptide of 658 aa (protein CAI38796.1) with a predicted molecular mass of 73 kDa. Alignment of the ABCG2 orthologs (partially displayed in FIG. 4) indicated that the homology between the bovine ABCG2 predicted protein and its putative porcine ortholog (GenBank accession NP_999175, 87% identity, 94% similarity) was higher than to the human and murine orthologs (GenBank accessions AAQ92942, 84% identity, 91% similarity; AAH53730, 79% identity, 91% similarity, respectively). All orthologs shared sequence motifs that included cytoplasmic ATP binding cassette and six putative transmembrane domains typical of a half transporter structure. The BAC sequenced contains 66.1 Kbp of the bovine ABCG2 gene. Following an intergenic region of 10.3 Kbp and encoded on the complementary strand, the last exon of a gene orthologous to the human polycystic kidney disease 2 (PKD2) was observed. Using BLASTN, 20 ESTs that matched the 3' end of the 4941 bp putative cDNA transcript deposited with this BAC were found. 5' end of this transcript was predicted using orthology to the human mRNA. This transcript is capable of encoding a polypeptide of 970 aa (protein CAI38797.1) with the predicted molecular mass of 110 kDa. Alignment of the PKD2 orthologs indicated that the homology between the bovine PKD2 putative protein and its human ortholog (GenBank accession NP_000288, 94% identity, 97% similarity) was higher than to the murine ortholog (GenBank accession NP_032887, 88% identity, 93% similarity). All orthologs shared sequence motifs that included: a. ion transport domain that typically contains six transmembrane helices in which the last two helices flank a loop that determines ion selectivity; b. EF-hand; a calcium binding motif associated with calcium sensors and calcium signal modulators.

PKD2 spanned 58.7 Kbp of the bovine BAC. Following an intergenic region (21 Kbp), and in the same orientation, we detected seven exons of the previously characterized bovine SPP1 mRNA (GenBank accession NM_174187, Kerr et al. 1991). The length of this gene was 7 Kbp. No other genes were found in the region upstream to SPP1 with a length of 9.7 Kbp.

Identification of polymorphism in genes within the critical region of the QTL HERC6. The region orthologous to the human intron 5 of hect domain and RLD 6 gene (HERC6) was PCR amplified with PCR primers (#705 and #706) that were designed according to the sequence of a bovine EST (GenBank accession BE664068) which was highly similar (86%) to human HECR6 (GenBank accession NM_017912). Three sites of variation in this intron sequence were identified and the polymorphism at position 151 (Table 1, Table 6) was genotype.

PPM1K. The human protein phosphatase 1K (PPM1K) is a member of the PP2C family of Ser/Thr protein phosphatases. The bovine PPM1K ortholog that maps to critical region of the QTL on BTA6 was cloned. Two splice variants PPM1K_v1 and PPM1K_v2 that were capable of encoding 372 and 324 amino acids, respectively were observed. The orthologous protein in humans mostly resembles the putative protein encoded by the first variant (GenBank accession AAR06213-92% identity, 98% similarity). As in other gene family members the second exon was large and encoded most of the catalytic domain (Seroussi et al. 2001). A di-nucleotide in this exon variation was identified that is capable of encoding an amino acid substitution (R26H) and we used it as a genetic marker (Table 1, 6). Two other SNPs in exon 2 and 5 were identified (GenBank accession AJ871967).

ABCG2. PCR primers for amplification of 15 coding exons of ABCG2 were designed (#615 to #638). Three SNPs in intron 3 were annotated (GenBank accession AJ871176), and the SNP on 29183 position, designated as ABCG2(1) was genotyped (Table 1, Table 6). In exon 6 (position 33437), a SNP (G or T) that was capable of encoding an amino acid substitution (D219Y) was identified. The two Israeli Holstein sires that were heterozygous for the QTL were homozygous for 219D. The 219Y allele was detected in Hereford genomic sequence and Holstein (GenBank accession BE480678). Within the translated region, a SNP (A or C) that was capable of encoding an amino acid substitution (Y581S) was revealed in exon 14 (position 62569 in AJ871176). This polymorphism, designated as ABCG2(2) was genotyped (Table 1, Table 6).

PKD2. PCR primers were designed for amplification of coding regions in the 15 exons of PKD2 (#252 to #261). The promoter and the first exon of PKD were cloned 2, but no polymorphism was detected, even though this segment included a highly repetitive GC rich region, and was therefore considered as hot spot mutation (Stekrova et al., 2004). For PCR amplification in exon 1 region, 0.5M G-Melt additive (Clontech Laboratories. Inc.) was added. Using primers (#261 and #262) we PCR amplified a region upstream this gene promoter, and observed a length variation within a stretch of adenine residues which was used as genetic marker (Table 1, Table 6).

SPP1. The products amplified by PCR primers (#121 to #142) of secreted phosphoprotein 1 (SPP1) were sequenced, including 0.8 Kbp upstream to the initiation site in the promoter region, and all seven exons, and seven introns. The two SNP detected in intron 5 and the 3' non-translated region of exon 7 and designated them as SPP1(1) and SPP1(2), respectively (Table 1, 6). The three segregating and 15 non-segregating Israeli sires for the QTL, for the OPN3907 poly-T polymorphism at 1240 bp upstream of the SPP1 transcription initiation site (Schnabel et al., 2005) using primers #155 and #156.

IBSP. Bovine integrin binding sialoprotein gene (IBSP) has been previously cloned (GenBank accession NM_174084, Chenu et al. 1994). This sequence was used to design PCR primers for amplification of exon 7 (#801 and #802). A SNP that was capable of encoding an amino acid substitution (T252A) was identified and genotype (Table 1, 6).

LAP3. Bovine leucine amino peptidase 3 gene (LAP3) has been partially cloned (GenBank accession S65367, Wallner et al. 1993). This sequence was used to design PCR primers (#400 and #401) for amplification of intron 12 and the adjacent exons. Three polymorphic sites in intron 12 and a sense mutation in exon 12 (Table 1) were detected. We genotyped the polymorphism at exon 12 (Table 6).

MED28. The bovine gene (TIGR tentative consensus TC274468) is 91% similar to the human mediator of RNA polymerase II transcription, subunit 28 homolog (yeast) (MED28, GenBank accession NM_025205). This sequence was used to design PCR primers for amplification of exon 4

(#500 and #501). Four polymorphic sites were detected in this exon and genotyped the site at position 1345 (Table 1).

MLR1. The human chromosomal region that encodes the last exon of transcription factor MLR1 gene (MLR1) also encodes on the opposite strand the last exon of chromosome condensation protein G (HCAP-G). We sequenced the orthologous genomic region in cattle. There was 93% identity between the coding regions of bovine and human HCAP-G genes. Using primers #500 and #501 we detected a polymorphic repetitive four base sequence (TGAT)n (Table 1, 6). We annotated it as part of the last exon of MLR1, on the basis of its orthologous position in the 3' non-translated end of the human gene. Bovine ESTs (GenBank accessions CK831694 and CO883952) confirm the expression of the bovine MLR1 ortholog.

Biopsy procedures and RNA extraction. Biopsies were collected from mammary and liver tissues of Holstein cows in the herd at the University of Illinois Dairy Research Facility (Dept. of Quantitative and Molecular Genetics, Institute of Animal Science, Volcani Center, Israel) as previously described (Drackley et al. 1991; Farr, 1996; Veenhuizen, 1991). Biopsies of mammary gland and liver were collected from eight cows at six time points relative to parturition (−15d, 1d, 15d, 30d, 60d, 120d), and five cows at seven time points relative to parturition (−65d, −30d, −15d, 1d, 15d, 30d, 50d), respectively during the dry period and lactation. Tissue samples were put in TRIZOL and RNA was extracted immediately using RNAse-free vessels. Mammary and liver tissues (0.5 to 2 grams) were homogenized and centrifuged at 12,000 g for 15 min at 4° C. Chloroform was added (200 μl/ml) to the supernatant and the samples were centrifuged at 12,000 g for 15 min at 4° C. Acid-phenol: chloroform (600 μl/ml) was added to the aqueous supernatant. Samples were votexed and centrifuged at 12,000 g for 15 min at 4° C. and the upper phase was discarded. Isopropanol (500 μl/ml) was added to samples and following an overnight incubation at −20° C. the supernatant was aspirated and washed with 75% ethanol (1 ml 75% ethanol/ml Trizol). Samples were centrifuged at 7,500 g for 5 min at 4° C. Supernatant was aspirated. Tubes were air-dried at room temperature for 10 minutes. RNA pellet was resuspended in a suitable volume (20-400 μl) of RNA storage solution. Concentration of RNA was 2-5 μg RNA/μl buffer.

Quantitative Real-time PCR analysis for gene expression. Quantitative Real-Time PCR was carried out for the following genes: SPP1, ABCG2, PKD2, LAP3, MED28, PPM1K, HERC6 and FAM13A1. Table 5 shows the list of primers designed for Q-PCR analysis. The 18S ribosomal RNA gene was used as control.

One μg mRNA was transcribed in a total volume of 20 μl using 200 U Superscript II (Invitrogen), 500 μg oligo dT(18) primer, 4 μl 5× first strand buffer, 2 μl 0.1M DTT, 40 U RNasin and 1 μl 10 mM dNTPs. Specific primers were synthesized for all genes in 3' UTR non-coding region of the last exon (Table 5). All reactions were performed on ABI PRISM 7700 sequence detection system using 2× Syber Green PCR Mastermix (Applied Biosystems, Foster City, Calif.), 1 μl RT product, 10 pmol forward and reverse primer in 25 μl reaction volume. PCR thermal cycling conditions were as followed: initial denaturation step 95° C., 10 min, followed by 40 cycles of denaturation for 15 seconds at seconds at 95° C., annealing and extension for 60 seconds at 60° C.

Computation of LD parameter values. LD parameters values were computed between each pair of markers as described by Hedrick (1987). The microsatellite BM143 had 13 alleles ranging in fragment length from 90 to 118 bp. Most of allele frequencies were quite low, and the distribution of the allelic frequencies was strongly bimodal. Thus, for estimating LD, BM143 was converted to a "diallelic" marker by assigning all alleles <108 the value of 1, and all allele >108 the value of 2. For individuals that were heterozygous for both markers, computation of the LD value requires that phase be known, which was not the case. For these individuals both phases were considered to be equally likely, and the LD value was computed accordingly. Thus, the LD values presented slightly underestimate the true values. X 2 values for independent association between each marker pair were also computed.

Computation of ABCG2(2) genotype probabilities. Genotype probabilities for ABCG2(2) were determined for the entire Israeli Holstein milk-recorded population, using the segregation analysis algorithm of Kerr and Kinghorn (1996), The number of animals analyzed by the segregation analysis algorithm was reduced to 44,135 by four "pruning" steps (Weller et al. 2003). At each step, animals that were not genotyped, and were not listed as parents of animals remaining in the data file were deleted. The pruning did not affect the segregating analysis, because these animals by definition include no information with respect to the allelic frequencies. The algorithm requires an estimate of the allelic frequencies in the base population. The initial estimate was derived from the frequencies of the 335 genotyped bulls. After application of the algorithm this estimate was revised, based on the allelic frequencies of all animals with unknown parents. The segregation analysis algorithm was rerun with the updated base population allelic frequencies until convergence for the base population allelic frequencies was obtained at a frequency of 0.75 for the A allele. The genotype probabilities for the "pruned" cows were then regenerated from the genotype probabilities of their parents, assuming random distribution of alleles. For cows with either one or two unknown parents, the allelic frequencies of the base population were used for the unknown parent. The estimated allelic frequencies as a function of birth year were computed for the entire population of cows.

T

Dairy cattle breeding programs. In most developed countries, dairy cattle breeding programs are based on the "progeny test" (PT) design. The PT is the design of choice for moderate to large dairy cattle populations, including the US Holsteins, which include over 10,000,000 animals. This population consists of approximately 120,000 cows of which 90% are milk recorded. Approximately 20 bulls are used for general service. Each year about 300 elite cows are selected as bull dams. These are mated to the two to four best local bulls and an equal number of foreign bulls, to produce approximately 50 bull calves for progeny testing. At the age of one year, the bull calves reach sexual maturity, and approximately 1000 semen samples are collected for each young bull. These bulls are mated to 30,000 first parity cows to produce about 5000 daughters, or 100 daughters per young bull. Gestation length for cattle is nine months. Thus the young bulls are approximately two years old when their daughters are born, and are close to four when their daughters calve and begin their first lactation. At the completion of their daughters' first lactations, most of the young bulls are culled. Only four to five are returned to general service, and a similar number of the old proven sires are culled. By this time the selected bulls are approximately five years old.

Dairy cattle breeding in developing countries. The genus *Bos* includes five to seven species, of which *Bos Taurus* and *Bos indicus* are the most widespread and economically important. *Bos Taurus* is the main dairy cattle species, and is found generally in temperate climates. Several tropical and subtropical cattle breeds are the result of crosses between

*taurus* and *indicus*, which interbreed freely. In the tropics, cows need at least some degree of tolerance to environmental stress due to poor nutrition, heat, and disease challenge to sustain relatively high production levels. Tropical breeds are adapted to these stressors but have low milk yield, whereas higher productive temperate breeds cannot withstand the harsh tropical conditions, to the point of not being able to sustain their numbers. Furthermore, most topical countries are developing countries, which lack systematic large-scale milk and pedigree recording.

Methods and theory for marker assisted selection (MAS) in dairy cattle. Considering the long generation interval, the high value of each individual, the very limited female fertility, and the fact that nearly all economic traits are expressed only in females, dairy cattle should be a nearly ideal species for application of MAS. As noted by Weller (2001), MAS can potentially increase annual genetic gain by increasing the accuracy of evaluation, increasing the selection intensity, decreasing the generation interval.

The following dairy cattle breeding schemes that incorporate MAS have been proposed:

1. A standard progeny test system, with information from genetic markers used to increase the accuracy of sire evaluations in addition to phenotypic information from daughter records (Meuwissen and van Arendonk 1992).

2. A multiple ovulation and embryo transfer (MOET) nucleus breeding scheme in which marker information is used to select sires for service in the MOET population, in addition to phenotypic information on half-sisters (Meuwissen and van Arendonk 1992).

3. Progeny test schemes, in which information on genetic markers is used to preselect young sires for entrance into the progeny test (Kashi et al. 1990; Mackinnon and Georges 1998).

4. Selection of bull sires without a progeny test, based on half-sib records and genetic markers (Spelman et al. 1999).

5. Selection of sires in a half-sib scheme, based on half-sib records and genetic markers (Spelman et al. 1999).

6. Use of genetic markers to reduce errors in parentage determination (Israel and Weller 2000).

Spelman et al. (1999) considered three different breeding schemes by deterministic simulation:

1. A standard progeny test with the inclusion of QTL data.

2. The same scheme with the change that young bulls without progeny test could also be used as bull sires based on QTL information.

3. A scheme in which young sires could be used as both bull sires and cow sires in the general population, based on QTL information.

They assumed that only bulls were genotyped, but once genotyped, the information on QTL genotype and effect was known without error. It was then possible to conduct a completely deterministic analysis. They varied the fraction of the genetic variance controlled by known QTL from zero to 100%. Even without MAS, a slight gain is obtained by allowing young sires to be used as bull sires, and a genetic gain of 9% is obtained if young sires with superior evaluations are also used directly as both sires of sires and in general service. As noted previously, genetic gain with MAS used only to increase the accuracy of young bull evaluations for a standard progeny test scheme is limited, because the accuracy of the bull evaluations are already high. Thus, even if all the genetic variance is accounted for by QTL, the genetic gain is less than 25%. However, if young sires are selected for general service based on known QTL, the rate of genetic progress can be doubled. The maximum rate of genetic gain that can be obtained in scheme 3, the "all bulls" scheme, is 2.2 times the rate of genetic gain in a standard progeny test. Theoretically, with half of the genetic variance due to known QTL, the rate of genetic gain obtained is greater than that possible with nucleus breeding schemes.

The final scheme, with use of genetic markers to reduce parentage errors, is the most certain to produce gains, since it does not rely on QTL genotype determination, which may be erroneous. Weller et al. (2004) genotyped 6,040 Israeli Holstein cows from 181 Kibbutz herds for 104 microsatellites. The frequency of rejected paternity was 11.7%, and most errors were due to inseminator mistakes. Most advanced breeding schemes already use genetic markers to confirm parentage of young sires.

The current status of MAS in dairy cattle. Two ongoing MAS programs in dairy cattle have been reported so far, in German and French Holsteins (Bennewitz et al. 2004; Boichard et al. 2002). Currently in the German program markers on three chromosomes are used. The MA-BLUP evaluations (Fernando and Grossman 1989) are computed at the VIT-computing center in Verden, and are distributed to the Holstein breeders, who can use these evaluations for selection of bull dams and preselection of sires for progeny testing. The MA-BLUP algorithm only includes equations for bulls and bull dams, and the dependent variable is the bull's DYD (Bennewitz et al. 2003). Linkage equilibrium throughout the population is assumed. To close the gap between the grandsire families analyzed in the German granddaughter design, and the current generation of bulls, 3600 bulls were genotyped in 2002. Only bulls and bull dams are genotyped, because tissue samples are already collected for paternity testing. Thus additional costs due to MAS are low. Thus even a very modest genetic gain can be economically justified. This scheme is similar to the "top-down" scheme of Mackinnon and Georges (1998) in that the sons' evaluations are used to determine which grandsires are heterozygous for the QTL and their linkage phase, and this information is then used to select grandsons, based on which haplotype was passed from their sires. It differs from the scheme of Mackinnon and Georges (1998) in that the grandsons are preselected for progeny test based on MA-BLUP evaluations, which include general pedigree information, in addition to genotypes.

The French MAS program includes elements of both the "top-down" and "bottom-up" MAS designs. Similar to the German program, genetic evaluations including marker information were computed by a variant of MA-BLUP, and only genotyped animals and non-genotyped connecting ancestors were included in the algorithm. Genotyped females were characterized by their average performance based on precorrected records (with the appropriate weight), whereas males were characterized by twice the yield deviation of their ungenotyped daughters. Twelve chromosomal segments, ranging in length from 5 to 30 cM are analyzed. Regions with putative QTL affecting milk production or composition are located on BTA 3, 6, 7, 14, 19, 20, and 26; segments affecting mastitis resistance are located on BTA 10, 15, and 21; and chromosomal segments affecting fertility are located on BTA 1 and 7. Each region was found to affect one to four traits, and on the average three regions with segregating QTL were found for each trait. Each region is monitored by 2 to 4 evenly spaced microsatellites, and each animal included in the MAS program is genotyped for at least 33 markers. Sires and dams of candidates for selection, all male AI ancestors, up to 60 AI uncles of candidates, and sampling daughters of bull sires and their dams are genotyped. The number of genotyped animals was 8000 in 2001, and is intended to reach 10,000 per year, with equal proportions of candidates for selection and historical animals.

TABLE 1

Polymorphism detection in the course of positional cloning to the QTL on BTA6

| Gene | Number of exons total | Number of exons sequenced | Sequencing size (bp) exons | Sequencing size (bp) introns | Sequencing size (bp) promoter | Polymorphism type[a] | Polymorphism location |
|---|---|---|---|---|---|---|---|
| MLR1 | 7 | 2 | 482 | 228 | | Insertion TGAT | Exon 7 (AJ871966) |
| MED28 | 5 | 2 | 133 | 1,268 | | C to T | Exon 4 (AJ871964) |
| LAP3 | 13 | 2 | 147 | 450 | | C to T | Exon 12 (AJ871963) |
| IBSP | 7 | 1 | 560 | | | A to G | Exon 7 (NM_174084[b]) |
| SPP1(1) | 7 | 7 | 1,362 | 5,633 | 1,205 | A to G | Intron 5 (AJ871176) |
| SPP1(2) | | | | | | T to G | Exon 7 (AJ871176) |
| PKD2 | 15 | 15 | 3,023 | 2,485 | 2,931 | Insertion A | Promoter (AJ871176) |
| ABCG2(1) | 16 | 15[c] | 2,029 | 3,416 | | A to T | Intron 3 (AJ871176) |
| ABCG2(2) | | | | | | A to C[d] | Exon 14 (AJ871176) |
| PPMIK | 7 | 1 | 490 | | | GC to AT | Exon 2 (AJ871967, AJ871968) |
| HERC6 | 23 | | | 330 | | Insertion C | Intron 5 (AJ877268) |
| FAM13A1(1) | 18 | 18 | 2,580 | 2,190 | | A to G | Intron 9 (Cohen et al., 2004a) |
| FAM13A1(2) | | | | | | C to A | Exon 12 (Cohen et al., 2004a) |
| Total | | | 10,806 | 16,713 | 4,136 | | |

[a] The more frequent allele is listed first.
[b] At position 802.
[c] Coding region of this gene starts in exon 2.
[d] Y581S

TABLE 2

Effects of the polymorphisms on the bulls' breeding values for the quantitative traits with each marker analyzed separately.

| Marker | Number of bulls | Frequency of the more common allele | Milk | Fat | Protein | % fat | % protein |
|---|---|---|---|---|---|---|---|
| BM143[b] | 346 | 55.1 | −34 | 0.7 | 3.5** | 0.019 | −0.022* |
| MLR1 | 298 | 50.5 | −67 | −2.8 | .7 | −0.005 | 0.025* |
| MED28 | 316 | 57.2 | 80 | 6.0*** | .4*** | 0.031 | 0.018* |
| LAP3 | 341 | 57.3 | 13 | 6.1** | .7*** | 0.053** | 0.039**** |
| IBSP | 336 | 61.3 | −35 | 1.1 | .6 | 0.021 | 0.015 |
| SPP1(1) | 366 | 57.0 | −123** | −0.1 | .8 | 0.039* | 0.043**** |
| SPP1(2) | 309 | 72.9 | −171** | −0.7 | .4 | 0.048* | 0.061**** |
| PKD2 | 326 | 67.1 | −141** | 0.6 | .9 | 0.046* | 0.048**** |
| ABCG2(2) | 335 | 80.5 | −341**** | 5.3* | .1** | 0.159**** | 0.135**** |
| ABCG2(1) | 282 | 55.4 | −67 | 0.8 | .4 | 0.029 | 0.042**** |
| PPMIK | 369 | 73.6 | −58 | −1.7 | .8 | 0.001 | 0.033** |
| HERC6 | 328 | 67.9 | −14 | 4.9** | .6**** | 0.049** | 0.056**** |
| FAM13A1(1) | 381 | 81.8 | −64 | 0.3 | .1 | 0.023 | 0.028* |
| FAM13A1(2) | 370 | 41.1 | −107* | 2.0 | .2 | 0.053** | 0.042**** |

[a] For ABCG2(2) effects were computed relative to the Y581 allele. This allele, denoted the +allele was associated with increased protein concentration. For all the other markers, the effects were computed relative to the allele in LD association with the +allele for ABCG2(2).
[b] This microsatellite was analyzed as a diallelic marker as described herein. Significance: *, p < 0.05; , p < 0.01; *, p < 0.001; ****, p < 0.0001

TABLE 3

Effect of ABCG2(2) on the breeding values of the daughters of the heterozygous sires, and QTL effects derived from the animal model analyses.

| Analysis | Genotype[a] | Number of cows | Kg Milk | Kg Fat | Kg Protein | % fat | % protein |
|---|---|---|---|---|---|---|---|
| Class effects[b] | −/− | 78 | 0 | 0 | 0 | 0 | 0 |
| | +/− | 328 | −185 | 0.4 | 1.2 | 0.059 | 0.065 |
| | +/+ | 264 | −432**** | 4.2** | 3.3** | 0.169**** | 0.145**** |
| % dominance[c] | | | 14.3 | 80.9 | 27.3 | 30.2* | 17.2* |

TABLE 3-continued

Effect of ABCG2(2) on the breeding values of the daughters of the heterozygous sires, and QTL effects derived from the animal model analyses.

| Analysis | Genotype[a] | Number of cows | Quantitative traits | | | | |
|---|---|---|---|---|---|---|---|
| | | | Kg Milk | Kg Fat | Kg Protein | % fat | % protein |
| Regression[d] | | 670 | −226**** | 2.6** | 1.8** | 0.093**** | 0.076**** |
| Animal model[d] | | | −597 | 2.2 | 1.3 | 0.225 | 0.193 |

[a]581S was denoted the "−" QTL allele, and Y581 the "+" QTL allele.
[b]Significance of the class effect is indicated in the +/+ row. Effects are computed relative to the −/− homozygote.
[c]Relative to the −/− homozygote.
[d]Allele substitution effects assuming additivity.
Significance: *, $p < 0.05$; , $p < 0.01$; *, $p < 0.001$; ****, $p < 0.0001$

TABLE 4

Variance components and marker substitution effects from REML analysis of the sire evaluations.

| | Trait | | | | |
|---|---|---|---|---|---|
| | Kg milk | Kg fat | Kg protein | % fat | % protein |
| Variance components | | | | | |
| ABCG2(2) | 86,640 | 13.0 | 12.9 | 0.0145 | 0.0128 |
| Polygenic | 272,720 | 553.0 | 286.4 | 0.0481 | 0.0101 |
| Residual | 84,504 | 1.2 | 0.1 | 0.0005 | 0.0001 |
| Substitution effects[a] | | | | | |
| ABCG2(2) | 520 | 6.4 | 6.3 | 0.213 | 0.200 |
| Variance components | | | | | |
| ABCG2(2) | 103,080 | 2.71 | 5.1 | 0.0135 | 0.0129 |
| SPP1(2) | 0 | 0.0 | 0.0 | 0.0000 | 0.0000 |
| Polygenic | 270,550 | 563.0 | 289.1 | 0.0480 | 0.0096 |
| Residual | 77,542 | 1.6 | 0.0 | 0.0000 | 0.0007 |
| Substitution effects | | | | | |
| ABCG2(2) | 568 | 2.9 | 4.0 | 0.213 | 0.201 |
| SPP1(2) | 0 | 0.0 | 0.0 | 0.000 | 0.000 |
| Variance components | | | | | |
| ABCG2(2) | 161,952 | 0 | 0 | 0.0158 | 0.0153 |
| HERC6 | 15,178 | 20.6 | 22.6 | 0 | 0 |
| Polygenic | 267,670 | 521.3 | 282.3 | 0.0456 | 0.0093 |
| Residual | 86,103 | 1.0 | 0.1 | 0 | 0.0002 |
| Substitution effects | | | | | |
| ABCG2(2) | 711 | 0 | 0 | 0.222 | 0.219 |
| Variance components | | | | | |
| HERC6 | 218 | 8.0 | 8.4 | 0 | 0 |
| Variance components | | | | | |
| ABCG2(2) | 85,277 | 4.7 | 8.4 | 0.0133 | 0.0134 |
| LAP3 | 2,697 | 9.2 | 7.1 | 0 | 0 |
| Polygenic | 291,069 | 556.9 | 286.0 | 0.0493 | 0.0094 |
| Residual | 77,829 | 1.0 | 0 | 0 | 0 |
| Substitution effects | | | | | |
| ABCG2(2) | 516 | 3.8 | 5.1 | 0.204 | 0.205 |
| LAP3 | 92 | 5.4 | 4.7 | 0 | 0 |

[a]Computed as described in the Materials and Methods section.

TABLE 5

Primers for physical mapping and real-time PCR analysis
(SEQ ID NOS: 1-24), respectively in order of appearance).

| Gene | Primer | Sequence | Number of BAC clone[1] |
|---|---|---|---|
| BM143 | BM143_F | TET-ACCTGGGAAGCCTCCATATC | E0199P19 |
|  | BM143_R | CTGCAGGCAGATTCTTTATCG |  |
| SLIT2 | SLIT2_3'UTR_f | GTCAGAATGGAGCTCAATGC | E0380G22 |
|  | SLIT2_3'UTR_r | GATGTTTGTTTGAGGCCGGA |  |
| MED28 | MED28_3'UTR_f | TAAGACATTGGCAGCAGGTG | E0060K13 |
|  | MED28_3'UTR_r | CTAGTGTTCGGGTGCCTTTC |  |
| LAP3 | LAP3_3'UTR_f | TGCCTTGATTTTTCATTTTATGC | E0060K13 |
|  | LAP3_3'UTR_r | CTGACAATCGCACAGCAACT |  |
| IBSP | IBSP_3'UTR_f | GCAGCAACAGCACAGAGGTA | E0393F21 |
|  | IBSP_3'UTR_R | TGGTGTGGGGTTGTAGGTTT |  |
| SPP1 | SPP1_3'UTR_f | CATTAAAGCAGGGTGGGAGA | H0005K14; E0049M05 |
|  | SPP1_3'UTR_r | ATGCTGTGATGGTTTGCATT |  |
| PKD2 | PKD2_3'UTR_f | TGGGACCAACCATTTCACTT | H0005K14; E0049M05 |
|  | PKD2_3'UTR_r | AGCCACACGAAAAGACT |  |
| ABCG2 | ABCG2_3'UTR_f | CCCCCAATTAAAAAGGGACT | H0005K14; E0049M05 |
|  | ABCG2_3'UTR_r | GAGGCAAGTGAAAAGAAGACAA |  |
| PPM1K | PPM1K_3'UTR_f | TGCCTGGGGAAAATACAAGA | E0331I16; E0412B12 |
|  | PPM1K_3'UTR_r | GGGTCACCACTTACAGTTCACTT |  |
| HERC6 | HERC6_3'UTR_f | GAAATTTCAGGGGGATT | E0417A15 |
|  | HERC6_3'UTR_r | TTCATCAAGACTCGGTGCTG |  |
| FAM13A1 | FAM13A1_3'UTR_f | CATCCATCACCTCAGTGTGC | E308O12 |
|  | FAM13A1_3'UTR_r | AAAGGCAGAGCTGCAGAAAC |  |
| 18SrRNA | 18S_f | GATCCATTGGAGGGCAAGTCT |  |
|  | 18S_r | AACTGCAGCAACTTTAATATACGCTATT |  |

[1]E0380G22 and E0199P19 in contig 8 42 and all other BAC in contig 503

TABLE 6

Primers for SNP genotyping
(SEQ ID NOS: 25-59), respectively in order of appearance)

| Genotyping platform | Gene | Location | Primer | Sequence |
|---|---|---|---|---|
| Mass Spec | FAM13A1 | Exon 12 | Fam13A1_ex12F | ACGTTGGATGCCACGCCAAATCTTTTCTC |
|  |  |  | Fam13A1_ex12R | ACGTTGGATGTTCAAGTTGGGAGCCGAAAC |
|  |  |  | Fam13A1_ex12E | GAAGATATCAGAGGAGGAC |
|  | SPP1 | Exon 7 | SPP1_ex 6F | ACGTTGGATGTCTCCCACCCTGCTTTAATG |
|  |  |  | SPP1_ex 6R | ACGTTGGATGGCCTCTTCTGAGGTCAATTG |
|  |  |  | SPP1_ex 6E | CTGCTTTAATGTATCCTTTTC |
|  | IBSP | Exon 7 | IBSP_ex 7F | ACGTTGGATGTAAACCTACAACCCCACACC |
|  |  |  | IBSP_ex 7R | ACGTTGGATGGCCTGTTTGTTCATACTCCC |
|  |  |  | IBSP_ex 7E | ACCGTTTGGGAAAATCACC |
|  | PPM1K | Exon 2 | PPM1K_ex 2F | ACGTTGGATGATTTCGGCTCTGAAGTGGAG |
|  |  |  | PPM1K_ex 2R | ACGTTGGATGTAAGAAGTGGTGGGAACCAG |
|  |  |  | PPM1K_ex 2E | CCTGTCATCCTGCAGACC |
|  | ABCG2 | Intron 3 | ABCG2F | ACGTTGGATGGATTGTGTCCTGAGGAAGTC |
|  |  |  | ABCG2R | ACGTTGGATGCAAGTCATAGCTGACAGCTG |
|  |  |  | ABCG2E | CTGAGGAAGTCTTATTAGGT |
|  | ABCG2 | Exon 14 | ABCG2ex14F | ACGTTGGATGGAATCTCAAAACCGTCGTGCC |
|  |  |  | ABCG2ex14R | ACGTTGGATGCGGTGACAGATAAGGAGAAC |
|  |  |  | ABCG2ex14E | GAGCATTCCTCGATACGGCT |
|  | MED28 | Exon 4 | MED28F | ACGTTGGATGGCTTCTCACTTTGTAGGATG |
|  |  |  | MED28R | ACGTTGGATGTTGTCAAGTGCTTCTGGACC |
|  |  |  | MED28E | TTCGCTGTAATTCATTCCTTA |
| ABI377 | LAP3 | Exon 12 | LAP3_ex12F | ACGTTGGATGCAAGACAGGTTATAGATTGCC |
|  |  |  | LAP3_ex12R | ACGTTGGATGCTGAAATGCTCATTTTGGC |
|  |  |  | LAP3_ex12E | GTTATAGATTGCCAACTTGC |

TABLE 6-continued

Primers for SNP genotyping
(SEQ ID NOS: 25-59), respectively in order of appearance)

| Genotyping platform | Gene | Location | Primer | Sequence |
|---|---|---|---|---|
| | HERC6 | Intron 5 | HERC6F | HEX-CTGAGTCCCAACCACTGGAC |
| | | | HERC6R | TGTATGCTGAATGGGTATCTTCA |
| | PKD2 | Intergenic | PKD2F | TGCTATGGATCAAATACTATCCAAGTT |
| | | | PKD2R | FAM-CCCCGTCCTCTAAAGAATGC |
| ABI7000 | MLR1 | Intron 5 | MLR1F | FAM-TGTGCGATTCCACATTGTTT |
| | | | MLR1R | AAAGCAAGCAGCCGCTAAT |
| | SPP1 | | SPP1int5_365F | CTCTGATCCCCTGAGAATTTTCA |
| | | | SPP1int5_486R | CACTGTTTTTCCTTGTTCATAATAAACAC |
| | | | SPP1int5_486P1 | FAM-ATCTGTATTTAcTGGATCAT |
| | | | SPP1int5_486P2 | VIC-CTGTATTTAtTGGATCATT |
| | FAM13A1 | Intron 9 | FAM13A1int9F | AACTTTAAAAGGGAGAGGAATGTTACC |

TABLE 7

Primers for sequencing in the critical region of the QTL
(SEQ ID NOS: 60-181, respectively in order of appearance)

| Primer code | Gene | Primer Name | Sequence |
|---|---|---|---|
| 1102 | MLR1 | MLR1ex21F | AAACAATGTGGAATCGCACA |
| 1103 | | MLR1ex21R | AAAGCAAGCAGCCGCTAAT |
| 500 | MED28 | MED28ex4F | CCTGGATATTGCAAGACA |
| 501 | | MED28ex5R | TAAGACATTGGCAGCAGGTG |
| 502 | | MED28ex4Fnes | TCTGTCCAGAAACCAGAGCA |
| 503 | | MED28ex5Rnes | GAAAGGATGCTCTGGTCCAG |
| 400 | LAP3 | LAP3ex12F | CATTGAAACAGGAGACCGTGT |
| 401 | | LAP3ex1 3R | TGTGACTCATCCTAAGTGGGC |
| 801 | IBSP | IBSPex7F | CTGGGGCTACAGGAAAGAAG |
| 802 | | IBSPex7R | ATTCTGGGATTTTGTGTGGC |
| 155 | SPP1 | SPP1prom 1602F | AGATCCCACATGCACCTAGC |
| 156 | | SPP1prom1147R | CCCGGCCCTCCAAGGCATGC |
| 121 | | SPP1prom771F | CAGTAACCCTGCTCGGTCAT |
| 122 | | SPP1prom28R | TCTGGGAGATCCTGGTTGTC |
| 123 | | SPP1ex1aF | CACAGGGGACTGGACTCTTC |
| 124 | | SPP1ex1aR | TTGCTGTCTCCATTTTCCAA |
| 125 | | SPP1ex1bF | CCCTTTTCTGAATATTTTCACCTC |
| 126 | | SPP1ex1bR | GAATTGCTTCTGCCTCTTGG |
| 111 | | SPP1ex1F | AGCATCTGGAGCAGCCTTTA |
| 112 | | SPP1int2R | ACTCCTGTCCTCTCTGTGCG |
| 113 | | SPP1int1F | TGGAGTGTTTCCACACAAAA |
| 114 | | SPP1int3R | TTGTGTGCCTGCTATGCTTC |
| 115 | | SPP1int3F | TCACTTAGAGACCCCTGTTT |
| 116 | | SPP1int4R | TTTGGGCTGGTTAAATGGAT |
| 127 | | SPP1int3aF | TGCAACTTCTGCAAGATGTACT |

TABLE 7-continued

Primers for sequencing in the critical region of the QTL
(SEQ ID NOS: 60-181, respectively in order of appearance)

| Primer code | Gene | Primer Name | Sequence |
|---|---|---|---|
| 128 | | SPP1int3aR | TGCTCAATGAAGATGTTAGGAGA |
| 129 | | SPP1int3bF | CAAACGGGTATTGTCCCAAG |
| 130 | | SPP1int3bR | GAAGAAAACCCTTCTTTCAGC |
| 131 | | SPP1int3cF | GAACCTTTGAACTCATCTACAGC |
| 132 | | SPP1int3cR | GCTAATTAAGGGCACCTCTGC |
| 133 | | SPP1int3dF | TCTTCCATAGAGGAAGGAAAA |
| 134 | | SPP1int3dR | AAATACCCAGATGCTGTAGCC |
| 117 | | SPP1int4F | AAATTCTCACAATTAAAGAACAACCA |
| 118 | | SPP1int5R | UCAAATTCCGGCAAAATTC |
| 135 | | SPP1int4aF | AAATTCTCACAATTAAAGAACAACCA |
| 136 | | SPP1int4aR | TCTGAGGAAACTGATGACAACAA |
| 109 | | SPP1ex5F | CCTCTGAGGAAACTGATGACAA |
| 110 | | SPP1ex5R | CGTTAGATCGGCGGAACTTCT |
| 137 | | SPP1int5aF | TCTGATGTCTGTTGTGCCTTAGA |
| 138 | | SPP1int5aR | GCACTGTAAAGCCTAAGGGACA |
| 139 | | SPP1int5bF | GCCATTAAGTGCTTTGTTGTGA |
| 140 | | SPP1int5bR | GTTTTTGCGCTCAAGTCCAT |
| 119 | | SPP1int6F | CCCTTCCTAGCTGTTCGTTG |
| 120 | | SPP1int7R | AAGCAGGGTGGGAGACAATA |
| 141 | | SPP1int6aF | CGTACGTGTTCATTCAGCA |
| 142 | | SPP1int6aR | CAGAGTCCAGATGCCACAGA |
| 261 | PKD2 | PKD2ex1365812F | GGCCCAAGGAAGAAACGAAC |
| 262 | | PKD2ex1370002R | GGAATGGTGGTGGAGATGGA |
| 212 | | PKD2ex1F | CGAGGAGGAAGAGGAGGAAG |
| 255 | | PKD2ex1R | CGACCTCCTCTTCCTCCTCT |
| 221 | | PKD2int1F | AACAGGAGAGCCTCCCTTAAA |
| 222 | | PKD2int2R | TTGCATATTTGCCCTGTCAA |
| 245 | | PKD2int2Fe | GTGCGGTCTGTAAGGGTCAG |
| 246 | | PKD2int3Re | TATGGGAAGGGAATTTGGAG |
| 247 | | PKD2int2F | TTGGCTTGTTCTGTCTTCCA |
| 248 | | PKD2int3R | GCTGTGCACTTAACACTGGG |
| 223 | | PKD2int3F | AAAATGTTGCCTTTGCTTTCA |
| 224 | | PKD2int4R | AAGTGTCTGTGGCTTGTGGA |
| 267 | | PKD2int4F | TCAGGAACCAGTTGTCTCTGTAA |
| 268 | | PKD2intSR | AAACTGCAGGCAATGGTTTT |
| 227 | | PKD2intSF | CCTGACTGCATCCATGTGTT |
| 228 | | PKD2int6R | AGGTTGGAGAACAACACCAAA |

TABLE 7-continued

Primers for sequencing in the critical region of the QTL
(SEQ ID NOS: 60-181, respectively in order of appearance)

| Primer code | Gene | Primer Name | Sequence |
| --- | --- | --- | --- |
| 229 | | PKD2int6F | TCTTCATTTAATCTTTTGTTTTCCA |
| 230 | | PKD2int7R | TGTTGAAGGACCTGAATTTGCT |
| 231 | | PKD2int7F | ATTTCCCCTCTCTTTTGCAG |
| 232 | | PKD2int8R | GAAACCTTCATGGTGGCTGT |
| 233 | | PKD2int8F | TGTCAAAAGAATGCTGGACA |
| 234 | | PKD2int9R | CATCATCTCTTCTTTTCTTCCACA |
| 235 | | PKD2int9F | TTTTCCCAAAGAATTTGGTAGC |
| 236 | | PKD2int10R | GTTGTTTCAGCCAGATTGCC |
| 237 | | PKD2int10F | GGCAGAACAAACGAAAAAGG |
| 238 | | PKD2int11R | AAGAATCTCAATTTGCCCGT |
| 239 | | PKD2int11F | GATCGTGTGCATGGATGAGT |
| 240 | | PKD2int12R | GATTGGTTCAACACCTGCAA |
| 241 | | PKD2int12F | CAGTGATCCCGTGTTCTTCA |
| 242 | | PKD2int13R | TTCGAGTTGACAAGGGGC |
| 263 | | PKD2int13F | CACAAGATGTTTTGTCCCTC |
| 264 | | PKD2int14R | TGTTTTCCCCATACATGCAA |
| 265 | | PKD2int14F | TTCCGAAGGCAATTCCTAAA |
| 266 | | PKD2int15R | ATATGGTGGTCAGGGCACAT |
| 214 | | PKD2ex1SF | TGGAAAAGAATCCCAAACCA |
| 215 | | PKD2ex1SR | GCTCACCAAATTTATGGGGA |
| 251 | | PKD2ex153152SF | ACCAACCGTACTTTGGCTTG |
| 252 | | PKD2ex1532487R | GATTCAGCTTGCCTACCTGC |
| 603 | ABCG2 | ABCG263223F | CCTCTTGATTGCCAGGAAAA |
| 604 | | ABCG263906R | GATTCCTGTGAGCTCAACCC |
| 605 | | ABCG2 65770F | CACACACCACAAAAACCCTC |
| 606 | | ABCG2 66373R | TTCATCTTGTCAGATGGTAACCA |
| 615 | | ABCG2int1F | TGTTTACAGTCTCATTTACCTGGA |
| 616 | | ABCG2int2R | ATGCAGATTTTGGCAGGTTT |
| 617 | | ABCG2int2F | AACTGGCTTTAAACTGGGTCA |
| 618 | | ABCG2int3R | TTTCTTTGTAGTTTTCATGTGTGG |
| 642 | | ABCG2ex3F | CATGAAACCTGGCCTCAATG |
| 643 | | ABCG2ex4R | TCCATGTGGATCCTTCCTTG |
| 619 | | ABCG2int3F | AAGAGGTAAAGCCTGATTTGG |
| 620 | | ABCG2int4R | TTCATATGGGCAAGTGCCTT |

TABLE 7-continued

Primers for sequencing in the critical region of the QTL
(SEQ ID NOS: 60-181, respectively in order of appearance)

| Primer code | Gene | Primer Name | Sequence |
|---|---|---|---|
| 621 | | ABCG2int4F | GAGTGATGGTATTAGAAAAGACCTG |
| 622 | | ABCG2int5R | TAGGACCTCACCTGTGTGGA |
| 613 | | ABCG2int5F | CAACAAATGATAGTGGCAGAGG |
| 614 | | ABCG2int6R | TCCTGAAGAGGTAAATGCCATG |
| 623 | | ABCG2int6F | CCAAGAAATGTAAGTTTCAGATGTTT |
| 624 | | ABCG2int7R | ACAAGGAGTCACTTGGAGCA |
| 625 | | ABCG2int7F | TTTACCAGGACTATCAATTTTGTG |
| 626 | | ABCG2int8R | TAAACCACGGCTGTTTGAATT |
| 627 | | ABCG2int8F | AAAGGGGTTGTAGAAAAATGGA |
| 628 | | ABCG2int9R | CATTTGGGGACATTATGCT |
| 629 | | ABCG2int9F | GGAGAGATTTGATTAAGTAGCCAGA |
| 630 | | ABCG2int10R | GAATTTGAAACAAGCACAGGG |
| 631 | | ABCG2int10F | TTGGGGAAAGAATTTTGCAG |
| 632 | | ABCG2int11R | GGTCAGACTGGTCACATCCA |
| 644 | | ABCG2int11F | GCAAATGGTTTAATCTCCTGGT |
| 645 | | ABCG2int12R | ACAGAAAGTCCCCTCCCATC |
| 633 | | ABCG2int12F | TTGGATTAACCCCCTCTTTG |
| 634 | | ABCG2int13R | ATTCCTACCCCCAAACTTGC |
| 635 | | ABCG2int13F | ATTTGCTAGACGGCACCAGA |
| 636 | | ABCG2int14R | TATCCTTGGCCATGAGCTGT |
| 637 | | ABCG2int14F | TTTCTTTATCCTGCTCCCACTT |
| 638 | | ABCG2int15R | ACTGGGCTGAGGAATCCTTT |
| 1000 | PPM1K | PPM1Kex2F | GGCATCCCATTATTGTTCCA |
| 1001 | | PPM1Kex2R | TACCCACATGGAGAAATGCA |
| 705 | HERC6 | HERC6ex5F | TGAAGACTCTCGGTGTGGTT |
| 706 | | HERC6ex6R | GAATTGAAGGCCTCGTCTCA |

TABLE 8

Number of animals included in the variance components analyses for ABCG2 polymorpshism.

| | Number of: | | |
|---|---|---|---|
| Markers analyzed | Genotyped bulls | Ancestors | Total |
| ABCG2(2) | 336 | 422 | 758 |
| ABCG2(2), SPP1(2) | 274 | 367 | 641 |
| ABCG2(2), HERC6 | 298 | 396 | 694 |
| ABCG2(2), LAP3 | 308 | 399 | 707 |

TABLE 9

Number of animals genotyped per breed and allele frequencies of the ABCG2 gene with standard errors (SE).

| | Animals | Allele frequencies | | |
|---|---|---|---|---|
| Breed[1] | genotyped | ABCG2$^A$ | ABCG2$^C$ | SE |
| Aberdeen Angus | 25 | 1.00 | 0.00 | |
| Anatolian Black | 31 | 1.00 | 0.00 | |
| Angler | 30 | 1.00 | 0.00 | |
| Asturian Mountain | 43 | 1.00 | 0.00 | |
| Ayrshire | 32 | 1.00 | 0.00 | |
| *Banyo Gudali* | 67 | 1.00 | 0.00 | |
| Belgian Blue (beef) | 28 | 0.95 | 0.05 | ±0.041 |
| Belgian Blue mix | 8 | 0.94 | 0.06 | ±0.084 |

TABLE 9-continued

Number of animals genotyped per breed and allele frequencies of the ABCG2 gene with standard errors (SE).

| | Animals | Allele frequencies | | |
|---|---|---|---|---|
| Breed[1] | genotyped | ABCG2[A] | ABCG2[C] | SE |
| Bohemian Red | 35 | 0.99 | 0.01 | ±0.017 |
| British Friesian | 37 | 0.93 | 0.07 | ±0.042 |
| Casta Navarra | 19 | 1.00 | 0.00 | |
| Charolais | 10 | 1.00 | 0.00 | |
| Chianina | 36 | 1.00 | 0.00 | |
| East Anatolian Red | 28 | 0.88 | 0.12 | ±0.061 |
| Gelbvieh | 6 | 1.00 | 0.00 | |
| German Angus | 18 | 0.92 | 0.08 | ±0.064 |
| German Black Pied | 22 | 0.93 | 0.07 | ±0.054 |
| German Brown | 22 | 0.95 | 0.05 | ±0.046 |
| German Brown Swiss | 21 | 1.00 | 0.00 | |
| German Holstein | 27 | 1.00 | 0.00 | |
| German Simmental | 22 | 0.86 | 0.14 | ±0.074 |
| Hereford | 39 | 1.00 | 0.00 | |
| Israeli Holstein[2] | 341 | 0.80 | 0.20 | ±0.022 |
| Menorquina | 15 | 0.97 | 0.03 | ±0.044 |
| N'Dama | 7 | 1.00 | 0.00 | |
| *Nellore* | 8 | 1.00 | 0.00 | |
| Pezzata Rossa | 18 | 1.00 | 0.00 | |
| Pinzgauer | 9 | 1.00 | 0.00 | |
| Polish Red | 11 | 1.00 | 0.00 | |
| Santa Gertrudis | 11 | 1.00 | 0.00 | |
| South Anatolian Red | 17 | 1.00 | 0.00 | |
| Toro de Lydia | 13 | 1.00 | 0.00 | |
| Turkish Grey Steppe | 9 | 1.00 | 0.00 | |
| US Holstein[2] | 9 | 0.95 | 0.05 | ±0.073 |
| White Fulani | 9 | 1.00 | 0.00 | |

[1]*Bos indicus* breeds are in italics; other breeds are *Bos taurus*.
[2]Cohen-Zinder et al. (2005)

TABLE 10

Notation of alleles, polymorphisms and QTL status

| Nucleotide allelic designation | ABCG2 allelic designation | Amino acid allelic designation | QTL status |
|---|---|---|---|
| A (adenine) allele | ABCG2(1) | Y581 allele (tyrosine) | +QTL, decreases milk yield |
| C (cytosine) allele | ABCG2(2) | 581S alleleallele (serine) | −QTL, increases milk yeild |
| A-->C | | Y581S, denotes that at position 581 of amino acid sequence of ABCG2 protein, a serine (S) is present instead of a tyrosine (Y). | |

Sequence btABCG2 exon 1a 1553.1760 btABCG2 exon 1b 11688.12023 btABCG2 exon 1c 58161.58260 btABCG2 exon 2 84261.84479

```
ABCG2 splice variants of first exon and exon 2 are highlighted in bold.
                                                     (SEQ ID NO: 182)
         AGGAGAGACT CCATCTTGAA GCCTGTCATC CGTCTTAAAG ACAGGATGTG AACTGGGCCG

GAACCCTGCT TAAGAGTGAG GAAACAGTTG CTAGTGAAAA CCAGGTCTCC TGGAGACTTC

ACTCCCTACA GATGGCAAAC GGAGATTGTA GTTGTGGTCA GGCTGCCCCT GTTAGATTAA

TCATGGAGAC ATCCTCCCTT GATGTATAAT CATTGTTCCC CCCTCCCGGC CCCACCTCCC

CCGTTAACCT TAATTGTTTG TTCTCCTAGC ACCTACTTGT AAAACTCAAT CATATACAAC

AAAAAGATTG TTAACATGTA ACCAGTCACG TGTGTGTGTG TGTGTGTGTG TGTGTGTGTG

TGTGTAAAAC TGGGCCTCTC AAAAACATCA GGGTCCTTGT TGGGAACTGA TTCCCCTTGG

ACCTGCTGGC ATAATAAACT GTACTCCAGT CTTGAGTGTC CCCTGAGGTG TGTTTTGCAA

CTCAGGATTC CACAACATTT CCAGAAGGAC ATCAGTGTTG ACCTAGACAG GTGAAGCAAA

AATGTTTGGA GCCAACAGAG ATCTAACCAG TGAAGTCACT GAACCTTGTT CACAAATCAA

GGGTAGATTC TTTCAAGGAC CAGGTGACTA GGAGGCAAGC GACCAAAGGC AGGACTGGTT

ACATATTTCG TGACAGTGTT GGTCGCTCAG TCGTGTCCGA CTCTGTGCAA TCCCATGGGC
```

```
            -continued
TGTAGCCTTT CAGGCTCCTC TGTCCAAGGG ATTCTTCAAG CAAGAATACT GGAGTGGGTT

GCCATACCCT CCGCCAGGGA ATCTTCCCCA CCCAGGGACT GAACCTAGGT CTCTCGCATT

GTAGGCAGAT TCTTTACCAT CTGAGTCACC AGCTGGGTCC TGTGCAGCTG TACAGGTCGT

ACCCCCGTAT CCGGAGGGGA AATACTTTCA AAGCAAACGC GGCAAGTTAA TGCAGAGCAC

GGGAAAAAGT AGGGCGCCCA TTCACTGCAT CTCAAGGCCT TCCAGCACTG AACAAGTAGC

ACTGTGGGTG GTGCCTGGCC CCAGGTGGTG ACTGAGGCTG CTGCCTCGGA TTCCCCAACC

AGGTACACCC GGAGCAGCTC GCATCCTGGC TTCATAGGCA GAGACGAGAA TAGCGGTGTG

GGGCGCTCTG CTCACTCTCA GGAAGGGGGC GAGAGGCTGC GCCCAGACCC TGTAACCCCC

GCCCCGCGCC CCTCCATCCC CCGCCCGGAG CCCCTGTATC CCCGGCCCGG CGCCCCTCCG

GCCCCTGCTC CACTGGTCTA GCGGCTGCGC CTCGGGAGGG CCTGGCGGAG CCCCGGACCT

GCGCCAGAAA ACGGTCCGAA CAGCTAGCTG CCCTTCCGGT CCTCCTTTTC CGCTTTGTTT

CTTCTCGGTT TCCATCCACC CTAAGTCCTT TTCTCCTCTC CTCTCCCCGC CCCGCGGTGT

CAATCTCCCC GGATTGACAG AGAACGTAGC CTAAATACTA AAGCTGAGAG AATCGCGCGC

GGAGGCGCTC GCTGGTCCCG CCTCCTGCCG GCTTTCTTTT CTCTGTGCGC CCCGGGTGGG

CTTGGCGGAA CTGGCCTCTA CACCCCGACA TCCTCCATCG ACTGCCGGGG GCCGACTGTT

TGGAAAGAGG ATGGGCTGG TGGCGGCGGG GAAGCGCTCA TCTGCCCGGG AAAATAGCTG

GAGAGGAGTG CGGGATTAGA GCTATGCCCC TGATAGTGTC CCCGCAACCA GCGAGACCCT

GTAGTTCCTC GGTCCTGGAG GTATGTTCTG GGCAGCACAA CACAGCAACT GCTATGTATT

AACTGTCTTT GCAGATAATA CTGAAGAGAT GAAAGGACTT GTCTGAGGTT TCAGACAAAT

CCTCATCCCC AGGAACTGCC CTGTTCCTAG CTCTTGCTTA AATGGTGGGC ATGAGTGGCT

ATGTGTGTCC AAACTGACAC ATTTTTGCTG TTTGGATGGC AGGATCCTGA AGAGAACCAT

TCCTTAGCTA GTCAGAGACC AAAGTCTATA CTAAAGGAAG GATCAGCTCT CTAACTGTAT

AATGGGAGGA GCTGGTTTTG AGAGATTGTG TCAGCTGGCA TGGCCATTTC TAGATAATAC

ACACACTTTT GACTTTGGAG AGAGGAGATA CTTCCCCAGA GTGTGACAGG CAAATGGAGG

GAACAGCTGC CTCTGCCGTG TTGTGTGTGT GTGTGTGTGT GTGTGTGTGT GTGTGTGTGT

GTCCTCAGTC GCCTCTGACT CTTTAACACC CCATGGATTG TAGCCTACCA GGGTTCTCTG

CCCATGGAAT TTTCCAGGCA AGGATACTGG CATGAGTTGC CATTTCCTTC TCCAGGGGAT

CTTCCAGCCT AGGGATAGAA CCCTCATCTC CTGCGTCTCT TGCATTGGCA GGTGGATTCT

TTACCACCGC ACCACCTGGG AAGCCGCCTC CACCCTATGA GAGTCTCAGT TCCAACCCAT

GGCTCGTTTG ATAGGACTTC TGCACAGGCC TAAACTCCTG CAGGTAACAA AATACAAAAA

GTTACTGCCT AAGGGTGCAG CTAGGGATTA AAACACAGCC CTATTACTGC AAATTTTTCC

ACAACAGAAG TCAGGTAAGG TTAATAAGCA CTTATATATT AAGAATTAGG TGGGAAAATA

TTTCAGAAGG AACTGAGAAT GCTGCAGTTG TTCATTGAAA GCCAGGAGGA ATAATCGGGA

AATGTGTCAG GCTCCCTCTG TCCATTCTCC ACATGCTGAT CACCACACAC TCATGTTTGC

ATTCTTTCAA TCTCACCTCC CAGATAATTT AAAACACTTT AGCATTGCAT AAAAAAAAA

AAAAAGCCCT TCCTTCCTGG TCTATTCCCT GCCTCTACTC CCTTGTCATT TTTTCTAACT

TTCCTTCTTG AACTTTATCC CAGCCTGTGT ACGTTCTTCT CTCTCCCTGT AACACAATCC

CACTTCTTTC CCAGGTAAAC TTCAAGTTCA GATGTCATGT CCCATCGGAT GTTTTATTCT

GCCATTCCTT CAGTCTAAAT GTCCCTTCCA TTTAGTCCTC TGCCATCCAA TATTTACTTC

TATTCTAACA CCTGTTACCC TGTGTCAGAA CTCTTTGTTT CCTTCCCTTT CTTCACCCTT
```

-continued
```
AGGGTGAATT GTTTGAGGGC AGGGGCTAGG TCTCTTTCCT AAATAATCCT AACAGCACAG
TAGGCATTTG GTAAAGTTTG GAATGCATGA ATGACATGCT TAAAATAGAG AAGTTATTAT
CTCATTCCTG AACCTTATCT TAGTGCTTGA GTGTACACCG TTCCAAAATG ATGAATCATG
GAAAGAATAA AAATGCACTG TGTTACTAAG AAATGAAGCC TTAAGGTTTC TAAAATTACA
ACCAAAGTGG GCAGGTGGGC CCAGCACCAT TGTATGAAGA TCTTATTCAG TCAGTTCTAG
CAAGCTAGGA TGGCATGGCT GAGGAAGTAC GGCAGTGGTA CTTGAAGTAA GAAACAATGA
TAATGTAAGA ATATCCAAGT CTAAGGGTTT TTGTAGGTCC TGCAACGTCT TTACACTGTG
ATATTTCCGT GATGCTAAAC ATAGGAACTA AAAAGCCTCT TGATGAGGGT GAAAGAGGAG
AGTGAAAAAG CTGGCTTAAA ACTCAACATT CAGAAAACTA AGATCAAAAA CAAACAAAGA
TCATTGAATC TGGTTCCATC ACTTCATGGC AGATTGATGG GGAAAAAGTG GAAACAGTGA
CAGATTTTAT TTTCTTGGGC TCCAAAATCA CTGCATATGA TGACAGCAGT CATGAAATTA
AAGGCACTTG CTCCTTGGAA GAAAAACGAT GGCAAATCTA GACAATATAT TCAAAAGCAG
AGATATCACT TTGATGAGGG TAAGAGGAGG AAGGTGTGGC AGAGGATGAG ATGGCTGGAT
GACATCACCA ACTTAATGGA CATGAGTTTG AACAAACTCC GGGAGATAAT GAAGGACAGG
GAAGCCTGGA GTGCTGCAGT TAATGGGTCA CAGAGTCAGA CATGATTTAG CGACTGAACG
ACAATAAAAC ATAATGAGAA GCTTGTCTAC TGCCAAAGCC TAAAACCAAG TTCATTGAAG
AGAATCCCTG CCTCAAGGTT TCAATTTGGA AAGTCAGAGA ACAGTAGAAT TTGGTTTTCT
AATAGTTAAC CTCTTACTTT CAAGGTCACA CAGTTTATTA GGTGTTAATC CAGAAATTGT
TCCAAGCTGT ACCCCATGGG GCTTCCCCAG TGGCTCAGCG GGTAAAGACT CCTGCAATGC
AGGAGACACA AGAGAGGGGG GTTCGATCCC TGAGTTGGGA AGATCCCCTG GAGGAGGGCA
TGGCAACCCA CTCCAGTATT CTTGCCTGGA GAATCCGATG GACAGAGGAT CCCGGCGGTC
TACGGTCCAT ATGGTCACAA AAGAGTCAGA CATGACTGAA GTGACTGAGT GTATACCCGT
AGGTCACTGT GCAGTTTTTG AGGACAGGGC CTAGGTGGTT TTACTCAGTC ATGCACACAC
ACAGTACCTG TTGCAGACCT GCCACAGTGG GTACTCAGCT TGCTGAATGA AGGAAGAAAT
GAATAAATGT GCTCTACCAT AGGGGTGTAG ATGAGAGGGA AAGGCACTGT CATTTCTCCA
AAGATGGAAG GCTTTAGAAT CTGGGGAAA ATAAATATTT ACTTTGAAAA TAAACTTATC
AAAGTAAAGG CAAAAAACTA TTTTAGATGT CACAAAGATC TATGTTAAGT TGCTGAATCA
GTTGTTACTA TTTTAGAGGA TGATGGAAAC TTATCTTCTG AAATGTTGGC TTGTCTGCCT
AAGAGGGGTC AAAGCAAAAT GGTCCAGTCT GGAGTTTCCT GAATCCTGAC CTCCTTACCT
GAAAAACTGA GCAGTTATTT GGCCCAGTTA TTTAACAGAT GACTCAGTTT TGTCATTTGT
AAAATGGGGA TGATTATACC ACATGGGTTG TTGAGAGACA TTAAATAGTT AATACACAAC
CTATGAAGTA ATTTGTATCC CATTTTCTGC CACTATTTCC TATTTCTCTA GGTGTCATTT
TGCCTTTCAC TGTGGCATAA AACATTTCTG TTTTTTCTCG GTCCACTTCT GTGCTTTTTT
CCCTCTCACT ACCTTTCTGC TTTTTTCTTT TTTACTATCT CTCTCCCTAA CCAAATTCTT
CTTTTTTTTT TTTTTTTCCT TTGGCCATAT GAGGAATGTT AGTTCCCTGA CCAGGGATGC
ATTCCTCTCC CTATGCAGTG GAAGCACAGG ATCTTAACCA CCAGATGGCC AGGAAAGTGC
CAATTTCTTC TTAACGTTCT CATAGTTTTT CCTCACTCAC CTAAAAAAAT GACTGAGGGC
TATGAACTTC AGTAAACTTA TAGAATAAGA AAGTTAATAA TGACTATTAA AACACTATTT
TCTTTTCCCC AAACTGATTT CTCATCTCTG CCGTGCTTAT GCATACTTTT TTTGTATTTG
AAAATCAGTG AATACGTTCA GGCTAATTTA GCTCTGATTT TCTTCACTTA ATATAACTTT
```

-continued

```
ATACTGAAAG GGTCAGGATA TGTCCTTCCC CAATATGCCA CTTTGGCATG AGGATTAATT

TGAGCTGAAT GCAATTAAGA ATCAACAGAT ACAGAAAGAA GCCTTCTCAG CATTTCCCTT

ATCTTATTAA AAAGCAGAAA CTTTTGAGAA ATGAGGCTGT CATAAATTCC CTCTTCAGGA

TGGGCTTATT CCTAGGAGAG AGATAAAAGT AAATATACCG TAAATCTCTC TGGGAGTTTC

ATGGCCATGA AGACAGAAAA GACCACTTGC ATTTTCACAA ACAAATATTA TATCAAACTT

TATCTCCAGT TTATTCTCCT AAAAATCCTT TTGTCTTTCC TACAGAAACT CACTTGTTCT

TTCCATAGAA GATTTTTCTG CATTTCCTTT CTTCCCCTAC TAAGTTAGGT ACATAAGCTT

CTATCTTTAA CCAGTGAGCT ACTAGCTATT TCCGTATGAA TAAGCCCTTT TTTCCTCCTT

TTGTCTTTTG TCAGCTTAAT TCAGAGGTCC CCAGGGAGGA AACCTAAGAG GGCAGAGCAA

ACATTTTTCC TCCCATATGC CATGATCAGT GTAGACCACA CGGTTGTTAT TAATTTTTAT

GACTGTGGTT CATATACCGC AGTTTGTCAC ATTCCTCTCT CATGGGGCAC ATTGATTGAT

TCTGATTTTT TTACTCTTTA AATATATCCT TCCTTTATGA CACTTTCCCT TGCCTTCTCT

ACTTCATAGA TATATACAAA CATACACATG TGTAATTATG TAAATATATA AAATTTGCTG

CATTTGTTGT CTAAATCTTC AGTTTTTGAG TCATCAGGCA GTGCTTCCCT CTTGAGAGTC

TCTCTTTATA GAGGTGATCA AGGCACCAGT CATAAACTAT TGTACCTAGA TTTCTTAAAC

TCTAAATATT TATTAACAAC CATACCAATG TGGGAGGCAA TAAAGAGAGG TGGGGTTGGT

TGGTTCAGTA AAAATTATTG CGTTGATTTG AGTCCCTCTT CTCTCCTAGA GTTTCTTGTG

CTGCCGGTTC AGGACATAAA AAACATGTAT GAAGAATTTA CAAGAAAAAT CTGTCAGAAT

TACTGCTTTT CTGCTGTGGT GTTTGGCTTT AAAATTTTTT AAAGCACCAT GGAAGCAGAT

TTGGTGTTTC AAAGTTCTGC CACAAGAGTG ATTTTAAGTA ATGTTCATAG CCTCTGTTTA

TATTATCGTA TGGTTTATAA TTATGACTGT AAGTCTCAGT TAAATGATTA CCATGTGAAC

AGCACCATAC TGTGGGACTA CAAAACCTAA GATGTGGTCT TTAACTCTGG AGGACCTTAT

AATTGCAAAG TGAGAAACAC AAACTATGAG TTCTGAGGTA CTTGTACATA GTAGTCATTG

ACAGTCTTAA TAATAAAAGT ATGCAGCATA GGATTTTTGA CTCTATAAAC AATACTGTCT

TGAGTTTGCT TCTAAACCTT AAAGAAAATT TGGAGCAACT TTTCCATACC CTGGAACAAA

GGAATAGATC ATCATAAATT TGCATGGATG GATTCTGGAG AATTCTGAAG ACTCCATCAT

AAACCAACAC AGGTTAGAAA ACGAAACAAG TTTTGCATAA TATCAAAGGT CCTTCCACCA

TTTTCAAATA ACTGACCTAA GCACTGCTGT CTGTTACAGC CTCTCAGAGC ACTGAGGAAT

GGTTAAAGTC CAGGGAAAAA CAAGACTGCA AAAATATTTG CCTGGGGACC ATCTTCTTGA

ACTCCCCACC TCGATAATTT GGATTAGCTT CCTCCCTATT CCATGCCATG GATTCTGATT

AGAAAAAAGT CTTCTCTAGT TGAAGGACTT CATTGTTCTT TGAGTTAGAG GATGAGGCTG

GCTGTTTGAA ACCTTTCTCA CTTTTCCTAT TCCAAAGTGT TCAGTATCTA CTCAAACAAA

ATTGGGAATT AAACTCTATG TACATTTAAG GGATATACGT ATTTGTGAAA GATAAAGGAG

GCCTCCAAGA ATTAGATAGG ATTTTTACTA CACCTCTTCA CCTGGACACA ATGCTTCCTT

TATAAGAAAT AAGGGATAGT CAGCGGTTCT TTGCCTTTGT AAAGAAATAG CTAGGGATTT

CACAGAAGTT CCTAGGAATG ATTAGCTTAT TCCCAGTTGC TTGGAAAATA GGTGATCCAG

GACAAGATAA TATGCATTGT TAGATAGTGT GCCCAATAGG TGATCCAGGA CAAGATAATA

TGCATTGTTA GATAGTGTGC CCAAGTCAAT AGAAGGGATT CCATTCAAGA AGCTGCCTTC

CCGTATATTT TATCTTATTT AATAACTTTA AACCAAAGAT GTTCAAATCT TATTTCACAG

AACCCAGTGA GTCCTTAAAC ATTTTGTTCT GACTTTTTGT TTGTGGATTG GTGGATATCT
```

-continued

```
TTTATTTTAA AAATGCACAA ATATATTTTT GTGACAATTT GTGAATTGAT TAATCTATTT
TATCAAGTTC CTACTGGTAT ACTAGGTACA ATCCTAGAAA CTAAGGCTCT GTCAATGAAC
AAAGCCATAA ACATTCATAC CCCCATAGAG CTTATATTCT AATGGAATCA GAAATACAGA
TATAATAAGT AAGGAAATTA CATAATATGT TAGAAGGTAA TAAGTGCTAG TAACAAAAAT
AAGATATGGC AGATCAAGAA TGCTAGTAGG AGGAATTGCA ATTTTTAGTT GGTCAGGGTA
GTCCTCATGA GAAGTTACCA TTTGAGGAAA AACTTGAAGG AAGTGAAAGA ATGAGCTAAA
TAGATGAATA GGGGAAGAAT TGCCCAGAGC AGCTAGGGCA CTGGCCAGGA AGTGGGTCAG
TGTGTGTATA TTTGAGCTAT AACGGAGATA TGTCTCGCTA TATTACAATT AGTAAAGGGG
AACGTCAGAG TAGGGGTGGA AGATACATAT TGTAAAGGTG TTTGGCTTTT ACTCTTAAGA
GAAATAGGAA AATAGACGAA TACATTGTGA GAAGTATTTG AACAATAGAG ATATGTATTT
TCAAAACAGT ATCTCCACTT CCTAAACCTA TACTTCCCAG ACATTGCTGC CATTTGGGGT
CATATCTTTC TAAAGGCTTT TCTCCATGAT TACATGCATA GATGGGTACA AATAGAAATA
CACAATTTTG TTTCGTGAGG ATATGTGTGT GTGTCTCTGT CTACATGTGT GCATTTTAAC
ATAAAAAAAT AAGGTCACTC AGTTGTGTCT GACTCTTTGC GACCCCATGG AATATACAGT
CCATGGAATT CTCCAGGCCA GAATACTGGA GTGGGTAGCC ATTCCCTTCT CCAGGGGATC
TTCCCAACCC AGGGACTGAA CCCAGATCTC ATGCATTGCA GGCGGATTCT TTACCAGCTG
AGCCACCAGG GAAGCCCAGT GAACTTATAT TCACTGGGGA GGTAGGAGAC AGGGGACCTC
TGGGTGGGAC AGTTTCCCAG GTGGTGCAGT GGTAAAGAAC CCACCTGCAA TGCAGGAGAC
GCAGGACACG TGGATTCAAT CCCTGGGTCA GGAAGATCCC CTGGAGAAGG AAATGGCAGC
CCATTCCAGT ATTCTTGCCT AGGAAAGCCC ATGGAAAGAG GAGCCTGGCA GGCTGTAGTC
CATGAGGTGA CAAAGAGTTG GCCACAACCG AGTGAGCACA CACACAGGGC CAGATATCAG
GTGTTTGTCA AGCAGAGTAA AATTCAAGCT TTGTTCTTAC CCAGACACTT CAAGGACAAA
GCTAGTGGCA AAAGCTGAGC TCTGCTAAAG TAAAGAGATA AGATGCCCGC TCCTGAGGTC
AAGGAAGACT TCCCTGTCTA TACATGTACA GGAAGGCTTC TTGGGGGTCT AAAAAGGGAG
GGGTCCCCAC CCCATAAGTG TGGACATGCA TCCATAGGCC TCTGCAGTGG GATCTATCTT
AGAAAAATAT TGTGCTCCGC AAGGACTCTC TTGGAGAGGG TCCTAGGACC AATCAGATGT
GAAGAGAGAA ACAAGATGAT TGGTTAAATA TATACAAAGA CCCGGAAGGA CCGCCCTATA
TAAGGGATTG GTTAAATATA TACAAAGACC CGGAAGGACC GCCTATATA AGGGATTTGC
AGCACCTTCT TACTGTGCTC CTCTTCGCTC AGGATGCCTG CCCTCCTCTC CGGGTGTGTA
TCTCTGCCTA GCTTCTGACT TCCTGCACTC CTCATGAGAG AGGATGCCCG GACCCTTTCT
CTCTGGATGT GTATCTCTGC CCTGCTTTTG ACATAAATTA ACAATTTTCA GTGTGCTTTC
TCATACATTG TGTTGTATCT CTAATAATAA ACTTTGCATG TGTTTTTACA GCTTTTGCCT
TCTTGAAATA GTCTTGCTTT CAAATCAGGG AAAACCACAG GGCCATTTTG CTTCTAGCCT
CTAGCCCCTG GCAATCTAAT GGCTAGGATT CCTAGTTTTC ATCCAGGTTA CCCAGGTTCA
ATTCTTGGGC AGGGAACTAA GATCTCTCTT CAGGACCACT CACTGCTCCT TCCTCCAAGA
TCAATATTCT TGTGTTAATT AGCAACTTGG TTTTTATAAT TGACGTGTCT TGGAGACCTT
TCTTTGTCAT GATAGTACAC ATATTTCTAT TCATTCCTTT TTAACTATT ACATAATAGT
CTATTGTACA CATATGCTAC ATTTTGTTTA ACCATACTTT TATTGGTAAA TGTGTGTGTG
TGTGTGTGTG TTTGTGTGTG TGTGTGCTCA GTTGCTTGGT CGTGTCTGAC TCTTTGTGAC
CCCATGGTCT GTAGCCCACC AGGCTCCTCT GTCCATGGCA TTTTCCCAGC AAAAATTCTG
```

-continued

```
GAATATTTAA GTTCTAATTT GCCTCGTAGC TTCTTTCCTT TCCATGTTGA ATTACTATTG
TCTTAATATT ACATTTAATA ACATAAAATT ACGTGTTGCA TGAAACACGG GAGGAAACTT
AAAAATTAAA TTTGTGTTAC CTTCTCTCAG AAAAGCAATG TTTCTTAAAT TAGAATCATT
TAGACTTACC TTAATGGAAA CAATGGCTTC ATTTACTTCT TCATCAAGGA CTTATGTAAT
GTTTGTTGTT CTGGAACAAA TGGCATTATG AGAGTTTGAG CCCAATTATT CTGAGCTTTG
CCTCCCTCGT GGCTCAGGTG TTAAAGAATC CAACTACAAT GCGGGAGACC CAGGTTCGAT
CCCTGAGTCG GGAAGATCCC CTGGAGAAGG GAATGGCAAC CCACTCCAGT ATCCTTGCCT
AGGAAATCCC ATGGACAGAG GAGCCTGGCA GGCTACAGTC CATGGGGTTG CAAAGAGTCA
GACACAACTG AGTGACTAAC ACTTTGACAT TTCGACTTGC TATGAGTTCA CTCAGTCACC
TTAACTGAGT TGACCATGGG TCTTTATCAG TAGGGAGTAA GGATCCATTA TCCACGATCC
GCAATCCATT GACTGCCTGA CCTGTGCTTA GGTATGCACC ACAGAGAGGA AAATTAGCAC
TTGATTCCAA AGAGGACTTC TGGCAAGGTT GATTTAGTAA TCAGCATTTC AGGGATCTCT
TAATATTGTT ATGTCAACTC TAAGGAATGC ATTATTGTTA CCGCAGGTTT ATATTGAGAA
GGCTTGGATT AAAAATAAAA ATAAAAACT TGTCATGGCT GGTAAAGAAT GGAGCCAGAA
GCTCTTAGTA TATGTCATAT TTTGTCACTT GACATGCTTC ATGTTTTCAG AATATGAAAT
GCCTGCTTAA TACAGCCTTA ACTTCCTATT ATACTTCTGG ATTAGGAAAG AGAACATTAG
AAGGATGGTG TGTTCCAAAT AAAACTTCTC TCTTCAAATC CCTAGTGGGC TTTTGCAATG
CAACCTAACA CTGTCTGTGC TTGGTTTCTT TCACTTCCTT TCTGAATTAG TGTTATCTTC
CTGCTTGCAC ACTTTTGCTA GAAAGCAGAG CTTGTAAAAG GAGACCACAT TATGTCAGAG
GTAGCAGAAG ACAGGAAGTT TACACAGAAT AAAACTGTTT GCTCAAATTG CTTTAATTAG
TCCTTATTAA AGTTGCCGTT AGTGTCAGAG ATGCTGTCGT CGGGATTCTA TTGCACAAAA
AGGATATCTC TGACACGTGA ATTTTTCCTT TTCCCATCTC CTTGCCAGGA ACACCAGAAA
AAGATCTCAG ACTGGTTAGA AGCATTAGGT TGTCAGTTTG AATCCGAGTG ATGGAGAAGG
AACTGTGGTT AATAACCAGC TAACAGTGGA GAAAAAAGGA AGTCAATTAG ATATGAGAAC
TGGACATTTT CCCAAGACTA GCTTGTTTGG AAAGCCTCAG TCTTTCTGGT AGTTGCAGGG
GGCTGATAAG GTTCCTCTCT GGTACTTTCT CTTGCGCCTT GAAAGCTGGC AGGAAGGGAA
GCTCCTGGAC TGTTAATAGA TGCGGCTCTT GCTTGAAGTT TCTATGAGAA AGCCGACAAG
AGTCGAAATC TTCTCTGTAT CCCCACTGCC TCTCTACAGA GGTTTGGGCT GTTTTCCTTC
CAACATCACA GATCATAACT GAGGTGAGTT GTCTGTTTTT GTTTTTCAAA TGTTCGTACT
GAGTGGAGAG TCTTGATTCT TTTTCGGTAT GTTCTTTAAC GAGTGTGTCA TTTTAAAATG
GTACTTCTCA AACTTGAATG TGCATATGAA CCTGAAGATC TTGTTTAAAA GCAGCAGAAT
TCAGTGGATC TAGGGTGGCT TGAGATTCTG CATTTCTGAG AAGTGCCCAG ATGACCTCAG
TGCTGCTGGC CCATGAAACA GAGTAATAAT GGCTTAAGAC CTTCTAGGTT TATTGCTCTG
TAGGGCAAGC AGTTGGGAGA TGTTGGCAGA ATCAAGGTGT CTGGCTGAGC ACATGATTTG
TGTAGAGCGC CTGGAAGGAA AATGAGACAC TGTTAGTGTC CAGATTGACT TGCTTTGATG
GACTAGCTCA GAGTTTGGGG GGTTGTGTTA AATAGTTCCT AGATATGGTA AGCCATGTCA
CCCCAAGTGA GACAGAATGT TGGTCTGCTC CTTAGATTGC ATGGACCACT TTGAGCAGAG
CCAGAAATAT TTTTGCAGTT TGGGGAATAG TAGTCATATC ATGCCTTAAC TGGGATAACT
AGTGGTCACT TGAATATTTC AGCTTCGATT GAAAATTATG CATCTAGAAA AATAACTGAT
GTCGTCCTCC TCCCATTTGG AGGTTAAGGT TGTGAGGCAT ATACATCTAT GATATGATTT
```

-continued

```
AAAGTCAATT TGAGCAAGGA ATATAATTGA TATGTTTTAT CATCTTGTGA GAGTGTTCCT

CTTTAAATTG AATAGCTCCC TGCCCTAAAT GGTACGTGTT TATCTGAAAG TTGCTTTTAA

TCCAAAAGTG CCAAGCCAAG AAGGAAAAAA ATAAATAATA GGAAGTGTGC CTTGCTGAGG

GTAGAAAACA GTAGTGGGAG AAAAACAGGG AAAGAAAGGA AAGTGATGGC CGTGGAAGTC

AAGTTTGCAA AATGAATAAA AGAAACCCCA GCCTGAAAAT AGGATTCTTT TTCCGACATG

CATGGGAGTT TTTCTAGAGT GGTAGCTTGC GTCTTCCTCA GCTAGAGAAA TGTGCTTAAG

ATAGAATAGG CAAATTAAAA TTTGTGTTGT TTTAAAGTAC ATGCTGAAAC TATTTGTCAT

CGAGTCAAGG GTAGTCAGTG GAATCAAAGG TCAGTGGCAT GAACAGACCT GGTGAGGCCC

AGTATGAATC CATTTAAACT ATCTCAGACA GAGGGGAATT GCTTCTGTTT GAAATAAGCT

TCAGATAACT TTCCTTTCTA TTATGGAGTA TAACAGAGGA GTTACATACA AGTTTAACAA

CCTATATGGC TACTGTTCTG ACCAATCAGA ACAGTAGCTA CTGTAAACAG CCCATATAAT

GGGAAACCAC TTGTAGGCAG TAAGAAGTAC ATGGGGTTGA ACATCAGCCT AAGCTAGGTT

TTCATGAACT TTTATTGGGG GGAGAAATTG TAAAGCTACA AATGAGTTCA GAGACATACA

ACCTATAACA TATATTCAGA GTTCAGAAAC ATATATTCCT ACTAGCATCT GTCAGCACGT

TAGCCCCATT CTCTCCAGTG AGGCCACTTC CCTGTCTTTC CAAGCTTTCA TTCTGGCTGT

GTATCTCCTG CAACCTTCAC TAAAGAAAGT AGGGTTCTCT TAAGTCATTG TAGGTGACTC

AAAAGTCCTA TCCATTCCCT CAGTAGAGGG AAAATGCCTA TACTCTTTTG TAAAGAGATA

CTGCAGAAAA TGAAATGATC ACTACGCTAT CCTTCCATAC AAAGCATGGT CACATACTTT

ACCTTGCTTG ATTTTTCACA ACTATCATGG GGATATGTCA TGTCAAGGGG ATTTTTGTTT

TTACCTGTCA TGGAGGAAAA TGAAGTTCTT GTTAAGCGAT TTGTGAGGAG GCACACAGCC

GGTTAGTGGG TGTATTGAAA TTAAACTCGC TTGTTTGCTC TAAGTTCAGG TTTATCCTGT

ACTTTTCTTC ATCTTCCCAA GCATCCCCTT AAGACCTATG ACAGCCCTTA TTGTTCTCTA

CTAGAGTTCA TTGGCTTTCC CTGTCAAAAT TTGAAACCTT TGTGCCTTAA AAAGAGTCCT

TTTTCTACTT GTTTTGTCAA AATTTTTAGT GTGTTTGTCA CAACCTTTAT ATCCATTAAA

ACCTTTAGTT CCCAGGGGTA AACATTTTAG AGGAGGGCCT CTAAACTTTA TTTTGACTGA

AAATTACCTG GGGAGTTTGC TAAAACTCAG ATTTCTGGGT CCTAACTTGA GAGATCTGAT

TCAGTAGATC TAGGACTAGG CCTAAGAATT CACATACCTA AAAGCTGCCA GGTGATTTTA

ACGCTACCAA CCAGAGAGCA TGCTTTGAGA CTACAGGCAT AGCTTCAGTC AGTATCTTGA

AATAACACAT TTCTGGTTTA GATTCCACGT ATGTGATATC ATATGGTGTT TGTCTTTCTC

TTTCTGACTT ATTTCACTTA GTATAATAAT CTCTAGGTTC ATCTATGTAG CTGCAGATGA

CATTATTTCA TTCTTTTTTA TGGTTGAGTA GTAGTCCATG GTATATGTGT ACCACATCTT

CTTTATGTCT TCATCTGGAC ACTTAGGTTG TTTCCATGTC TTGGCTATTG TGAATAGTGC

TGCTAGGGGT GCATGTTTCT TTTTAGATTA TAGTTTTGTC TGAATATATG CCTAAGAGTG

TCCGACTCTT TTTGACCCCA TGAACTGTAG CTCACCAGAT CCTCTGTCTG TGGGATTTCC

CAGACAAGAA TACTGGAGTG GGTTACCATT TCCTTCTCCA GCAGATCTTC CTGACCCAGG

GATCAAACCC TCACCTCTTA CATCTCTTGC ATTGGCAGGA AGGTTCTTTC CCACTAGCGC

CACCTGGGAA GCTCCAATGG TGGGGGGTGT AAAAAAAAAT CAGATGATCA AGAGGATATA

TTAGGAAATG TCAGGAAGCC TCCTTCTCCA GGTATCCCAT CAATGGGTCA ATATACAAAG

TAGCCACAGC AGCATAGAAG AAAGTGTGAG CTAATAATAA AGTTTTCACT TCCCTAAGTG

GCTGCTGTTC TTGTTGTTCA GTTGCTAAGT TGTGTCTGAC TCTTGGTGAC CCCATGGACT
```

-continued

```
GTAGCCCACC AGGGCTCCTC TGTCCATGGG ATTTTCCAGG CAAGAATACT GGAGTGGGTA

GCCATTCCCT TCTCCAGGGA TCTTCCCAAC CTAGGGATCA AACCCAGTTC TTCCACATTG

CAGGCAGATT CTTTCCTGGC TGAGCCACCA GGGAAACCCA CAGCATTGGG TACATGCCTT

AAACCAGCAG CCAGTAATAC AGAGCCAGAA CGTGTGGCTG TGGGGACCAC TGAGAGAAAT

AATTCCTCCA TCCACACTGG CTGCCTAAGG TGCTTCTCTC ACATGCTAGA CATACTCCTG

CCTCCATTCC CTTTGCCTAA ATGTTTTCCT CTGGTCTATT TAAAATTGCA AAACCTTCCT

TTACCTTCTA GACTACTGCT TCCTTCCCCA TGTGCCTCTC TCCAGGACTT CTCACCTCTA

ACATACTAGA CTATCTAGAT TGAGTTACTG TTTATTATCT GTCTTCTTCC AAGACCAGGG

TTCTGTTTCA TTCACTGTCC TATCCTCAAT ATCTAACGTT GTGCCTAAAA CATGCCTTGT

TGGTGTTTAG TCGCTAAGTC GTATCCGACT CTTTTGTGAC TCCGTGGACT ATAGCCTGCC

AGGCTCCTCT GTCCATGGGA TTTTGCAGGC AAGAATACTG GAGTTGACTA CCAATTCCTT

CTCTAGGGGA TCTTTCTGAC CAGGGATTGA ACCCATGTCT CCTGCATTGG CAGGCGAGTT

CTTACCACTG AGCCAACTGG GAAGCCTGTG CCTGAAACAT AGTAGGTAGA CCAACTACAT

AAATACCATT AATGTTCTTG GAGAAGAGTA AACAAATGTC TCTAGTGTCT CTAGAGAAGT

TCAAGGTAGG CGGAGATCAG CATGCTGGGA AAATCACCTA TGTGTATACT GAATTCACTG

AGAGGTAAAA TAGAAGTAGT GTTTGTTAGA GACAGCAATA GTGTCTCAGT TACTGATAAA

TGGGAAAAGA GGTCACAGAG TCCAAAGATA GCAGCAGCCA TGGAAAGTAG CCAGTGATGA

AGTCTGGTGA CCTGAAACTC AAAGCTGAGA TTTGGAAGAA GTGAGTAGAT GATCCACTCT

GGGATGTTCA CATTTTGCAG TGGTTTCTTC TCTCAAAATA AACAAGATCA GAATGTGAAA

TTTTCCATCG TAACCTCAAG GAAAGCACTT TTGCTTCTGT AGTGACTTTT TATGCTTTAA

TCACAAGAGG GCACCAGAGT CTAGCAAAAG ATCACTTTTT TCCTTCATCT AAAGCTGCGT

GCGTGCTCTG TTGTTCAGTC GTGTCAGACA CTTTGCAACC CCATGGACTG TAGCCTGCCA

GGCTCCTGTC CATGGGGATT CTTCAGGCAA GAATACTGGA GTGGGCTGCC ATTTCCTACT

CAGGGGATCT TCCTGATCCA GGGATAGAAC CTGCATCTCC TGTGTCTCCT GCATTGGCAA

GCGGATTCTT TACCACTGAG CCACCTGGGA ATACCCTATC TAAAGCTTTT TGTTTTTCTG

TTGCTAAATC CGACTCTGCA ACCCCATGGA CTGCAGTAGG GCAGGCTCCT CTAACCTTCA

CTATGTTCCA GAGTTTGCTT GAATTCATGT CCATTGAGTT GGTGATGCTA ACTATCTCAA

CCTCTCGTCG CCTTCTGCTT TTGCCTTCAG TCTTTCCCAG CATCAGGGTC TTTTTTTTTT

TTAATGAAGT TGGCTCTTCA CATTAGGTGG CCTTTAATGG AGCTTTAGTT TCAGCATCAG

TCCTTCCAAT GAATATTCAT TGAAGAAGGG GTGCAATTAA TAATTACTTG GAGCCATATG

TGTAAACAGG GACTTTTCCT ATGCAAACTG GGACAAAAGC CCTGCACAAT ATGAGCATGA

CCAATTTAAT TATGGGGTAG CTCTACACTA AGGGCTCTTA TTCTCAAAAT CACTACAAAT

GCTTATGACA CACTAATAGA TTAGAAAGAA AAGTGACCAA ACTTGCTTTT ATCTCGAAGC

AAAGATCAAG AAAGGCTTTC CCCTGTACCC TACTTCCCTA ATTATCTTTA TTGCCTATCC

TATTTTTCTC CTTAGTGTGA TCTTAGTTTG ATTATACCCT CAAGTAAGAG AATTGTTTTA

TCCAAAATTA TCTCAATTAT TTGAAAGTGG TCCAAAGTGT TCTCTAAATT CTCACAGTTC

TTTTCTGCAT ATCTCTTATC TTCTATACTA TATATTAATT ATTTATATAC TTGTTTTATT

CTTTTGAACA TGACTTACAT GCTGGGGATG TGAAAAAATA GGTTTTGAAA ATGGCTTTTT

TTTTTTCCTT CTAGTTTTAT TGAGATACAA TTGATATAAC TTAGCACTGT GTAAGTTTGA

AGTATACAGC ATAATGATTT GGTTGTACAT CATGAAGTGA TTATCACAAT AAGTTTAGTC
```

-continued

```
AGTATCCATC ATCTCACTTA TGCAGAAAAT TAAAAGAGTC CTGTTATTAG CATAAATTCA
AAGTATGGTT GGAAGGAGAT TGTGGTGAAT AACAAAAGAA GCTCCTATGA GTCTTATCAC
TGAATAAATT ACGAGAGTTC TAGGGGACTT CCCTGGTGGT CCAGTGGTTA AGACTCGATA
CTTCGAATGC AGAGGACACT TGTCAGGGAA TTAAGATCCC ATGCACCACG CAGTATAGCC
AAAAACTTAA AAAAGTAAAG AGTTTTAGAA GCTGTGTCGG GAACCAAGGG CAAAGACCAA
ATATGTATTT CTTACTGTAT TTTTTTATGT CGCTCTTGAA AACATACTAT CAGCTTATAC
TAGCTAGCCA CCAGAGAATT TGAGGATGAG GGTAGTTGCC TGAGAAACCA ACCATGGGAT
TACAGAGTTG AACTTTCAGT CTCAACCTCC AGGAGGATAG AAGGCTGAAA GTTGGGTTAA
TCAGTAACTG TTGACAATTG ATTTAATCGA TCATGCCTAC GTAACGGAAC TTCCCTAAAA
CCCCCTAATT TAAGGGAGAG TTCGGAGAGT TTCTGGATTG TGTACACAT CAAGGGGCTG
AGACGTGGGG GTGCAGCCAG AGACTGCATG AAACTCTACG CTGCTTCTTC TGTCTTGGCC
CTATGGATCT CTTCTATTTG GCTGTTCCTG AGTTGTATCC TTTATAATAC ACCAGTAAGT
AAACCGTTTT CCCAATTTCT GTGAGTTGTT CTAACAAATT ATCACACTTG AGGAGGGAAT
GGTGGGAACA CCTGATTTGT AGCTGGAAAC CTGGGACTTG CAGCTGGTGA ACTGGGGCAG
TTTTGTAGGA CTGATTCTTT TTTTTTTTTT TTTTTAAACT TTACAAATTG TGTTAGTTTT
GCCAAATATC AAAATGAATC CACCACAGGT ATACATGTGT TCCCCATCCT GAACCCTCCT
CCCTCCTCCC TCTCCATACC ATCCCTCTGG GTCGTCCCAG TGCACTAGCC CCAAGCATCC
AGTATCGTGC ATCGAACCTG GACTGGCAAC TCGTTTCATA CATGATATTA TGCATGTTTC
AATGCCATTC TCCCAAATCT TCCCACCCTC TCCCTCTGCA ACAGAGTCCA AAAAATATGG
AACGCTTCAC AAATTTGCGT GTCATCCTTG TGCAGGGGCC ATGCTAATCT TCTCTGTATC
GTTCCATTTT TAGTATATGT GCTGCTGAAG CGAGCACTGT AGGACTGATT CTTACTCTGT
GTTCTGTTCA GTTCAGTTCA GTTCAGTTGC TCAGTCGTGT CCGACTCTTT GCGACCCCAT
GGACTGCAGC ACGCCAGGCC TCCCTGTCCA TCACCAACTC CTGGAGTTTG CTCAAACTCA
TGTCCATTGA GTCAGTGATG CCATCCAACC ATCTTATCCT CTGTTGTCCC CTTCTCCTCC
CACCTTCAGT CTTTTCCAGC ATTAGGGTCT TTTCCAATGA GTCAGTTCTT TGCATCAGGT
GGCCAAAGTA TTGCAGTTTC AGCTTTAACA TCAGTCCTTC CAATGAATAT TCAGGACTGA
TCTCCTTTAG GATGGACTGG TTTGATCTCC TTGCAGTCCA AGGGACTCTC AGGAGTCTCC
TCCAACACCA CAGTTCAAAA GCATCAATTC TTCAGCGCTC AGCTTTCTTT ATAGTCCAAC
TCTCACATCT ATACATGACT ACTGGAAAAA CCAAAGCTTT GACTAGACAG ACCTTTGTTG
GCAAAGTAAT GTCTCTGCTT TTTAATATGC TGTCTAGGTT GGTCATAACT TTCCTTCCAA
GGAGTAAGTT TCTTTTAATT TCATGGCTGC TGTCACCAGC TGCAGTGATT TTCAAGCCCC
TCAAAATAAA GTATATTGTT TCATCTATCT ACCATGAAGT GATGGGACTG GATCATGATC
TTAGTTTTCT GAATGTTGAG CTATAAGCCA ACCATTTCCA CTCTCCTCTT TTACTTTCAT
CAAGAGGCTT TTTATTTCTT CTTTGCTTTC TGCTATAAAG GTGGTGTCAT CTGCATATCT
GAGGTTATTG ATATTTCTCC CAGCAATATT GATTCCAGCT TGTGCTTCAT CCAGCCTAGT
ATTTTACTTG AAGTACTCTA CATATAAGTT AAGTAAGCCA GGGTGACAAT ATACAGCCTT
GACATACACC TTTCCCAATT TGGAACCAGT CTGTTGTTCC ATGTCCAGTT CTGTTGCTTC
CTGACCTGCA TACAGATTTC TCAGGAGGCA GGTGAGGTGG TCTAGTATTC CCATCTCTTT
AAGAATGTTC CACAATTTGT TGTAATCCAT ACAGTCAAAG GCTTTAGAAT AGCCAATAAA
GAAGAAATAG ATGTTTTTCT GGAACTGTCT TGCTTTTTCT ATGATCCAAC TAGACAGATG
```

-continued

```
TTGGCAATTT GATCTCTGGT TCCTCTGCCT TTTCTAAATC CAGCTCGAAC ATCTGGAAGT

TCTCGGTTTA TGTACTGTTG AAGCCTGGCT TGGAGAATTT TGAGCATTGC TTTGCTAGCG

TGTAAGATGA GTGCGATTGT GTGGTAGTTT GAGCATTATT TGGCATTGCC TTTTTTGGGG

ATTGGAATGA AAACTGACCT TTTCCAGTCC GTGCCCACTG CTGAGTTTTC CAAATTTGCT

GGCATATTGA GTGCAGCACT TTCACAGCAT CATCTTTCAG GATTTGAAAT AGCTCAACTG

GAATTTCATC ACCTCCACTA GCTTTGTTCA TAGTGATGCT TTCTAAGGCC CACTTGACTT

CACATTCCAA GATGTCTGGC TCTAGGTGAG TGATCACACC ATCGTGATTA TCTGGGTCGT

GAAGATCTTT TATGTATAGT TCTTCTGTGT ATTCTTACCA CCTCTTCTTA ATATCTTCTG

CTTCTGTTAG GTCCATACCA TTTCTGTCCT TTATTGAGCC CATCTTTGCA TGAAATGTTC

CCTTGGTATC TTTGATTTTC CTGAAGAGAT CTCTAGTCTT TCCCATTCTA TTGTTTTCCT

CGATTTCTTT GCATTGATTG CTTAGGAAGG CTTTCTTATC TCTCCTTGCT ACTCTTTGGA

ACTCTGCGAT CAGATGAATA TATCTTTCAT TTTCTCCTTT TCCTTTCACT TCTCTTCTTT

TCACAGCTAT TTGTAAGGCC TTGTCAGACT ACCATTTTGC CTTTTTGCAT TTGTTTTTCT

TGGGGATGGT CTTGATCACT GCCTCCTGTA CAATGTCCAT AGTTCTGTCC ATAGTTCTTC

AGTTCTCCGT GTCCCTCTGT CTACCAGATC TAATCCCTTG AATCTATTCA TCATCTCCAG

TGTATGTACA TAAGGGATTT GATTTAGGTC ATACCTGAAT GGCTCAGTGG TTTTCCCTAC

TTTCTTCAAT TTAAGTCTGA ATTTTGCAAT AAGTAACTCA TGATCTGAGC CACAGTCAGC

TCCTGGTTTT GTTTTTGCTC ATTGTATAGA GGTTCTCCAT CTTCAGCTGC AAAGAATATA

ATCAGTCTGA TTTTGGTATT GACCGTCTGG TGATTTCCAT GTGTAGAGTC ATCTCTTGTG

TTTTGGAAGA GGGTGTTTAC CATGACAAGT GCATTCTCTT GGGATTATTC ATTCAAAATT

GCACACAATA TGGCCTCCAT TTCAGGTATG CAGGGCTGGT TCAACATTTG AACTAAATTT

TTGTAATCTG TCACATTGAC AGGCCACAGG AAAAAAAATA CGTGATCATA TCAAAAGATG

ATAAAAAAAT TGCTAAAATG CAGTATGGAT TCATGATTAA GGACTCTTGT CAAACCAGGA

ATAGAGGAGG ACTCCCTCAA CTTGGTAAAG AAATCTACAA AAAGCCTACA GTCAACTTCA

TACTTCTGGT AAGAAAAGAG CTTTCTCACT AAGATCAGGA GCAAGGCAAG GATGATCTCT

CTCACACTTT CAAGATCACA CTGGAAGTCC TAGCGATGCA ATAAGACAAG AAGTCATGGC

ATTTAGGGAG GGATAAAACA GTTTTGGGTT GCAAATCACA TAATTGTCTA TGTAGAAAAT

CCAAACAAAT AAACAATAGC AACAACAACA ACAACACAAT AAAAACTAGA ACTAGTAAAT

GATATAGCAA GGCTGCAGAA CAATGTTAAT ATACAAAAGT CAACCACTTT CCTATATACT

AGCGGTGAAC ATTAAAGACG TAGTACCATT TACGTTAGAT CCCCAAAAGT GAAATTGTTG

TTGTTTTACT CTCAAAGTCG TGTCCAACTC TTGGAACCCT TGGACTTTAG CCCTCCAGGC

TCCTCTGTCC ATCAGATTTT TCAGGGAAGA ATATTGAGGT AGGTTGCTAT TTCCTTCTCC

AGGGTATCTT CCTGACCCAG GGTTCGAACC CACATCTCTT GCACCTCCTG TACTGGCAGG

CAGATTCTTT ATCATGGTAC CACTTGGGAA TCTTTATAGA TTACCAAGAA ATACTTTGTT

TTGGGCCAG AAAGCCCTAA AGCAGCAGCT AGACCAAAAG AATTTCTGTT CCTGAAAAGA

GAATATAACT GAAATAAGAT AATTACATAT TTCCTTAATC ACTTTGCAGA GCTTCTATTT

TTCTATCATT TTCTTCTCTT CAAGTAGGAA AGGATTGTTT GTTTCTGAAA GGCCCAACAT

ACTCTACCTA GAAAGAATTC AAGCAAGCCA GTCCTCTGCT GCAAGAATAA CAGGTATTGA

TTATATTTCT CAGTGTACCA TTTGGGTACA AAGGATGATT TGCTATAGA TGGTCAGGAA

TCAGCAGTGT GAGCATGAAG TTGTTCAGCC ACAGTTGCCA CATGTATCAT GAGTCTGCAG
```

-continued

```
TAGTTTTGTT ACATCTTCAG TACCTTTTAG GTTCTGGATC TGTTGGCCTC TTTGGCAGAA
CAAGAAAGTG ACATTTTATT GTATTTGTTC TGCTGCCTAC AAATTAAGGG GGTGATTGAC
AGTGTTTTGA AGGAATAGAG GACTTTGTTT GCTTTTGGTG AAAAACTTTT TATTCTCTCC
ATAATAGAAT GAATAATTGC ATGGTTTTAG AGGATTAGGA TGCTGATAGG AATATTTGAT
TTCATAATTT TAAGAGTAGT TGGTGCTATA TGGAAATAAG CTTGAAATCC AGATCTTAAG
CTGCTATAAA ATTTGTCAGT TAAATACAGA ATATGTTTGT GATTTCATGG AACAGGAAGG
CCAGGCTGGC CTAAACAGTG CTACTCAGCT TCTTAAGAGT GCTGCCAGTT CTTTGTTGTG
GCTTTGTTTT CTTAAAGGTG CTTCCTCTTT GGCCAGGGGC TCTTCACCCT TTCCTGAAGC
ACGTCTACCA GTTGGGACAC ATTAGGAAAT GGCCCCCAAA TCTGTTTCCT TCAACTTGCA
CTGGCAGAGA ACCAGACAGC CTGTCCCCTT TCCTGAAACA CAATCACCAA AGTTGTTTGT
GTCTTGGGCT CTTTTCTACA AAGTCTTGAA AAATCTTCCC GAGACCTCAG CAGATTGCAA
TATACCAGTT TATCGCTGTG TGCATTATCC CTCTAGATAT GAGTTGCTTG ACTCTCTCTG
AGCTTTGTTT GGCAAAACCA AGATTCTAAT ATTAAAATAC ATAAACATTA AACCTTTTGG
GCGTGCATTC CAATTACATT TTGAGTTGCA AATGTTCTTT TCTCTCTTGG AAAAGTAGGG
GTCTAAACTT TTCTTTTCAC ACTACCTTCT GATATACATG CTAATTCCAA CTCATTTGGT
ATAAAAGAA AATATGAAA TATAAACAAT GCACAGATAC ATACTTGATT CTGAAAATTT
ACTCCCCTCC TTCACTTTCA CAAACATACT CTTATCTTTC CTTTGGATGT GATAATCTAT
CCCATCACTT CTTCCTTTAC AATGCTTAAG AAATATGACT TAGTTTAGCC CTTTATTACT
TTATTTTGGG CTGTTTTCTA GCTACTGTAT TCTCTGCCAA CAATGCTCAC TCCTTTAATC
CAACCTAAAC CCTCCTACAC CTTATCCCTA GTATAATCTT TATTCCAGAG CCACCAAACT
ATTTCACCTA TCATTACTGT TGAAAAACTA TTCATTGTTC TCCCTGTGGA AAGAATCAAG
TCCAAATTTT TGAGCCTGAG AAACATGGCA TCACAACCTG GGGCTTAGAG GCTGTTCCCC
ACTCTTCTTT TTAAAAAATA TTTATTTATT TGGCTGCGAG AGGTCTTAAT TGTGGCATGT
GGCTTTCAGT TCCTTGACCA AGGATGGAAC TCGAGCCACC TGCCTTGGGA GCATGGAGTC
TTAGCCACTG GACCACCAGA GAAGTCCTTC CCTCTCTTCT TTTTTAAAGA TCTGGGCTGC
AATGCGAGAG AGTTAACATG CATCTCACTA TCATCTCTGT TATTTTCTTA TCATCTCACT
TTCATCATCT TTTGGCACAC TCTTACTTCT CAGACCTTTC CCCATTCTTA CATCTTCAAA
TCTAATGTAT TTTTCAAGGC CAAGATTTTT AAGACGAGCT GCCTCCGTGA AGCTTTTCT
GACCCCTGTA GCTTGCAGCC ATCTCTTACT TTGAGATCTT AATGCTTAAT CTCACTTCCA
TTAATTTGGC CACTTTTCAC TTACTTTCTC TTGTATGTCT TCAGAAGCAC TGTCTCATAT
TATCACTTCA CTTTGGGATG CTTTTATCTT GTCCCCTCAA CTAAATCATT AGCTCCTTCA
TTCATTTATT AGTATTTACT GTGTTTACTG CCGTGCTGTG CTTAGTCACT CAGTCATGTC
TGACTCTTTG CAACCCCATG GACTCTAGCA GTGTCAGGCA TGATGCTCTA GTGGAGACTC
CTGCCACACT CTTCATCACC CAATGGGGAA ATCTGTCAAA GGTTTTAAAG TATATTAAAA
GGATAATTTT TATTAACTTA TCCTGGGTCT TTAACACCAT GGAGTTACCA GCTATTACAT
GAGGCCAGTT GGACTCCCTA CCTACTGGTG CTTTTATAAA AGTTGTATTT TAATATCACC
ATTAGAAGCA GATTCTGTAA GTGAGGTGGT GTAATGTGGT TAACTAGTAA GTGGTATAAA
CAAGGCTGGA TCCTAGGCTC CTTTTTAACC GGAATCTAAG TGACATGAAA CTGTGGTTGA
TTTGAACAAA TGCTCTTCTT CCACTGAGAC CAGGACAAGC AGCCTGCTAT GGGCTGATGA
GATATACTAA ATATGAACTA TTTTGATCCC CTCAAGGGAC TTTTGGGGAG GGGGCTGAA
```

-continued

```
AGACCTCTTC AAAAGTTTAC TCGAGTTTTA GAAATTAATA TTTGGCGATC AAAGTTGTAA

ATTCAAACCT CTAGTTTTCC TTAAGTCTAT AAATTCAATT TACCAATGCT CTTGCTCTAT

TTATAAGTCT AGCAGATTTT ATTATTTACT TCTAATAGAT CTTTCAATGG TGTTTGATCT

AATTTATAAA CTTAGTTAAT TTAACACTTC CAAATACTTT GTATGTAGAG GAAAAATATT

CAATTTCTCT AGTGTGTTGG GAGACCCCTA GACTACCGTC ACCTTCAGAT TCACTGGAAG

GATTTATAGA ACTCAATGTA TAGGTCTACT CGTAGCTAAG ATTTATTACA GGAACATAGT

AAAGATACAC AGATAGTAAG GGAAAGACAA AGGCCGAGTC TGGAGGACGC CATCTATAAG

CTCTCTTATG CGTTTCTGCT CAGAATACAT GCTATTCCCC CAGCAACAGA AACTCTGCAA

CATGTGTGCA GTATTTTTA AATGTTAATT TTATTTTGGA GTATAGTTTA TTTACAATGT

TTCATTTGTT TTATGTATGT GGCAAAATGA TTCAGTTACT CATGTACATA TAATCCATTC

ATTTTAAGAT TTTTTTCCCA GGTAGGTTAT TTCAGAGTAT TGAGTAGAGT TCCCCATGCT

GTGCAGTAGG TCCTTGTTCT GGTGTGCAGT ATTTTGGCCT GGGGAAACCA CTAGGGAAAA

ACTAGAGCCC AAGGTTTTTC TTGGGAGCTG AGTATGTAGG CATTCATGCT CTGCCTAGCA

TGAACCAGAA TTCCATACTC CCAGAAGGTG AGCAGGCATT CTGCATAAAC CATATTGCTT

GCACAACCAG TTTAGGCAAA GTGAACCATC CTTATCAGTT AACTGTTGCA TGAGAATACT

CGGTGACTTA ACTTCCAAAT CCCAACCAAG GGCCAATCTT GAGAGCAGGC CTTTCTAAGG

ATAGCAGACT CAGACCTGCT GTGTTACTTC TATTTTCTAA TTTAACAAAC TAAGTTTTCC

CAATTGCTCA ATAATGAAT ATGAAGCAAA TAATTGAAAT TATAAATACG ATAAACTGTA

GTTCTTTTAA ATATCCTATT ATTTTCTACA AACTTAGTAG GATTTCAACT TTAAATCAAA

AGCCTAAATC ACTTATTTAA TTACATACTT GAAATTGGAC AGACAAGATT GATCTTATAC

TCTAATGGGT CAAATTCTAT TAAATAATGT AAATATATAA AATTTCTTTT TTTATGTATA

AACAAGACAC AAAAATTCTT TAATATCAAA GTATTAACAT AGATCTGATT ATCTTAAACA

TTTCTATGAT TACTCCCAAT CCTTCCTAGA ATGAAAAATG CTTTAACACT AAGGAAACTA

TATCACTCTT AACACTAAGC TAGTAAGGTA GCCTGACCTG GAACTGGAGA TTTCTGCAGA

GGTTGACTCC TTGCCCTGAC CATGAATCGT AGTTGATTAG GTAACTTTAA AATGAGTTAT

TATCATGTCC CTGAATTTAG GTTATATATT AGCTAATTCT TCTGATTGCT GACTGAAGTC

TACAATTTAC CCTAGGTTAA GCATTGACTG GAAAAGGCTT TTTAAAAAAA AAAATTGTGG

GAGAGAGAGA CCTTAATGTA ATTGTTATTT TGGTCTAAAT TTAAAGCTTT TTGAACTTAA

AGGAATTCTT CATTCTTTCA TATTGTTGCT ATCTTTTAAG ACAACAGTTT TTTAGAATAT

TTATTAGAAT ACTGAGAGTC AGTTCCTAGG CAGGTTGATA AGAAGTCCGG GAGGAGGAGA

AAAGGGTCTG GGACTCTCAA GGAGAAAAGG GCAAATGTTT TTTTCTATAT GTCTTAGTCA

ATATAACAAT GTATCATGCT CAAAAGACAT ATTTCTCCTT AATAAGAACC TTCTGACTAA

TCTTTATCTT AAAATGTGTA TTATGGAAGT GGGTCTGGTA AGATCTTTCT ATTGTTAGTT

CTAATCCTGT CATCTTAAAA TGTAAATTGT GGGAGTGGGT CTAGTAAGAT CTTTACAACC

TTGAAACATT CTTTTGATTT ATTGAAAAAG TATATAACTC CCTTTTCTTA GACTAGCAAG

TGGGGCACTC TCCATCACCC TTTTGATGTC TGTGTCAGAA GCTTTCTCTG TCCCTTTTTC

ACTTTAATAA AACTCTGCTA CACAATGCTC TTGAGTGATC AAGCCCGGTC CCTGGTCCCA

AAGCTAAATC ATCTTTGGAG ATCGTGAATC CGTCATCGTT CACCATGAGC TATCAATACT

GGATATGTGT TATGGTTTTA CCTATGTAGT CACAACTTTC AAAGTAATTT TTCCCCTAAT

TTTTTAATAT ATTAAAAAAA AGAAACAGT TGTAGGTTCA CAGCAAAATT GAATGGAAGA
```

-continued

```
TAGACAGATT TTCCATATAT CCTCTGCTCA CTACCCCAAA CGTACTCTCG TCCATTATCA

ATAGCCCCCA CCAGAGTGGT TCATTTGTTC CAATCAGTGA ACCTACACGG ATTCATCGTC

TCCCCAAGTC CATCGTTTAC ATTAGGGTTT ACTCTTGGTG GTGTACATTT TATGTGTCCA

TAGACTCTGA CAAACGCAGC CATCACTGTA GGGTCACACA GAAAGGTTGC CCTGCCCTAA

AAATCCTCTG TGCTCCACAT TCTTCCCTGT CTCACTGCAC CTGGCAACCA CTGACTTTTT

ACTGTCTGCA CACTTTTACC TTTCCCTGAG TGTCATGTAG TTGGAATCAT ACAGTATGTA

GCCTTTACAT AGTGGCTTCT TTGACTTAGT AATATGCATT GAAGTTTCCT CCTTGTCTTT

TCATGGTTTG ATAGCTCCTT TCTTTTTGAC ACTGAATAAT ATTTCATTGT CCAGTTGTAC

CACAGTTTAT TTATCCGTTA ACCAATTGAA GGATATCTTG GTTGCTTCCA GGTTTTGACA

GTTAATAACT ACATCTGCTC TAATCATCTG TGTTCGAGTT TTGGTGAGGA CTTAGCTTTT

CAGCTCATTT GGGTAAATAC TGAGGAATGT GATTGCTAGA TCTGGTGGTA AGGGTATGTT

TAATTTTATA AGAAACTGTG ACAGTCTTCC AAAGTGGCTG TATTGATGTG AATTTCCACC

AGCAATGAAT GAAAGTTCCT GTACAGCATT TGATATTGTT TTAGAGTTTG ACTTTTTTTT

TTTTTTTTGG CCACCTGATG TGAGCAGGAT CTTAGTTCCC TGACCAGGGA TTGAAACCAG

TCCCTGGCAG TGAAAGAGCT GAGTCCCAAC CACTGGACTG CTAGAGAATG TGCTGGAGTT

TGGCCTTTTT AATAGGTGTG TAACGGTATC TCATTCTTGT TTTAATTTGC ACTTCCATAA

TGACATGATG TAGAACATCT CTTCATATGC TTATTTGCTG CCTGTGTAAA TATCCTCTTT

GGTGAGATGT TTGTTCAGGT GTTTGGTCCA TTTTTTAATG TGGTTTGTTC TCTTTTTTGT

TGTTGTTGTT GTTTTGTTGT TGTTTTGTTG TTGTTGTTGC TAAGTTATCT CTGACTCTTT

TGCAACTCCA TGGACTATAG CCCGCCAGGC TCCTCTGTCC ATGGGGTTTC CCAGGCAAGA

ATACTGGAGT GGGTTGCTAT GACCTTCTTC AGGGAATCTT CCTGACTTAG GGATCAAACC

TGCATCTCCT GCATTACAAG TTTGTTGTCT TAGTATTGAG TTTTAAGAGT TCTTTAGTAA

GATGCTCTTT TCCTATGGCC TCTTTCAAGA TTGTTTTCTT TGTCTTTGAT TTTCTGCAGT

TTGAATATGA CATGTCCAGG TGTAGTTTAC TTGACATTTA TTCTCCCTGG TGTTCTCTGA

GCTTCTTGTG GTTTGTGATG AATGGTTTTA AATGCCAATT TCTGTCCTCA ACAGTGATGG

CAAACACATT TTTTTTTTGA TGTGTTTCTA TGTCTGAATT GGTTACCAAA TGATTAATTG

ATGCTCAAGC AGCAATAATT AGTACTTGGT AGTATTGGGG AAGGGGAAAT TTCTTGAGTT

CTTTTTACTG GTCTAATAAC TGAATTGACA CAAGACAGAT TAACAAGAGA ATAAAACAAT

TTAATTTGTA TGCATGAAGG GTCTCTAGAA ATGGGACCGC CTGAAGCAAC TGAAGCAGGC

TGTTGATATA TAAAGACCAA GAAATAACTA TTTGCAAAGA TTTAACAAAA CAATTGGGTT

TATGCATGGC GTATCAGATT AATGAAGAAA TAACAAAGTT TACACAGCTT CTTAGCCTC

AAATTCCCCA ACTCTCTTGA CAAGACTGCT TTCTATTCTC CTGGTATAGG GAGGGAACGT

TCATGGGGA GATTCATTTC CCACTGAAGG GAGAAAGAGG AGGGTCTGAG GTTTTTTAAA

ATATTTTTTC CCACCAGCTG TTTTTCATGG AACTTTAATT CAGTGTAATC ATCATGCCAT

TGAGGCATAT TCTGTGGTAG CCTGCCCTAG ATCCCAGTAC TAAACTGTAC TGAGGTAAGA

ACAACTTAGT TAAGATGCTG GCTTCACTTT GCAGGCTCAG AAATTGGATC TTTTCACTGT

GTACTTATGC TAGGTTGGAA CTCATAGTTG CTGATTCATG ACAGTTAAAC TCAAGAAGCT

GAGGTGATCA GCTTGAATCA GAATGATAAT TAATTGATTC TCTTAAGGGA CACTCCTTCC

TATGACAGAA GTACTCAGGT CACCTATACA GTCACTTCTG GGTATGAGAG TAAAGATAAG

TGTATACGCT TGAGAGATGT TTTATCCAAG TAATGGAAAA TGCTTGTGTC AGCTATCTCA
```

-continued

```
ACCTATGACA GAGGAAAACA TCTTTAGGAA CTGGGTGTTT CATGTTGCCC TGCTCTAACG
TTGAAAATGT AGTTAAATAT TCTCAAACTC TAATAATTGT GACTAGTAAC GATAAAGACA
TGGCTTATCA TTTATCATCA GTTCAGTTCA GTCGCTCAGT CATGTCTGAC TCTTTGCAAC
CCCATGAATC ACAGCATACC AGGCCTCCCT GTCCATCACC AACTCCCGGA GTTCATCCAA
ACTCATGTGC ATCGAGTCGG TGATGCCATC CAGCCATCTC ATCCTCTGTC GTCCCCTTCT
CCTCCTGCCC CCAATCCCTC CCAGGGTCTT TTCCAATGAG TCAACTCTTT GCATGAGGTG
GCCAAAGTAC TGGAGTTTCA GCCTTAGCAT CAGTCCTTCC AATGAACACC CAGGACTGGT
CTCCTTTAGA ATGGACTGGT TGGATCTCCT TGCAGTCCAA GGGACTCTCA AGAGCCTTCT
TCAGCACCAC ATTTCAAAAG CATCAATTCT TCGACGCTCA GCTTTCTTCA CAGTCCAACT
CTCACATCCA TACATGACCA CTGGAAAAAC CATAGCCTTG ACTAGATGGA CCTTTGTTGG
CAAAGTAATG TCTCTGCTTT TTAATATGCA GTCTAGGTTG GTCATAACTT TCCTTCCAAG
GAGTAAGCGT CTTTTAATTT CATGGCTGCA GTCACCATTT GCAGGGATTT TGGAGCCCAG
AAAAATAAAG TCAGCCACTG TTTCCCCTGT TTCCCCATCT ATTTGCCATG AAGTGATGGG
ACTGGATGCC ATGATCTTCG TTTTCTGAAT GTTGAGCTTT AAGCCAACTT TTTCACTCTC
CTCTTTCCCT TTCATCAAGA GGCTTTTTAG TTCCTCTTCA CTTTCTGCCA TAAGGGTGGT
GTCATCTGCA TATCTGAGGT TATTGGTATT TCTCCTGGCA ATCATAGAAG GTGATAAATC
ATAGAAGATG TGATTTATCA TTTATCATAG AACATGATTC TTCTATGCCA GAAAATTGGC
TAAAAACTTC ATCCTCACAA AATCTTCAGA GATAAAGATG ATTACACTTT GGTAGATTAG
GAAGGTTAAA TGATTTATTC AAACTCATCC AAACAATTAA TAAAATCCAG AGACAGAATT
TGAACGTAGT ATTCTCTGAG CCCTCCATAC ACTATCTTAG ACCAGTTTTA GTTTCTATTT
ATTAATAGAA CAAACCCTTG TGTTAACACA TTAGTTTTTC TGACAGGTTA CTCTAATACT
AGTTATCAGT GGTTCCTGTT TAGCTTTGGC AAGTTAATAA AGGTGACTGT GCGAAGCTTT
CCATGAAATT GTATAACCTG GTATGAAAAT TAATAAGTAA AACCTCACTA AAATGAGGTT
TTTCCAGTAG TCATGTATGG TTGTGAGAGT TGGAATATAA AGAAAGCTGA GTGCCTGAGA
ATTGATGGTT TTGAACTGTG GTGTTGGAGG AGACTCGTGA GAGTCTTTTG GACTGCAAGG
AGATCCAACC TGTCCATCCT AAAGGAAATC AGCTGAATAT TCATTGGAAG GACTGACACT
GAAGCTGAAA CTCCAATACT TTGGCCACCT GATGCGAAGA GCTGACTCAT CAGTAAAGAC
CCTGATGCTG GGAAAGATTG AAGGTCGGAG GAGAAGGGGA TGACAGAGGA TGAGATGGTT
GGATGGCATC ACTGACTCAA TGGACATGAA TTTGAGTAAA TTCCAGGAGT TGGTGGTAGA
CAGGGAGGCC TGGCGTGTTG CAGTCCATGG GGTCACAAAG AGTCGGACAT AACTGAGTGG
CTGAACTGAC TGACGCTAAA ATGAAGCTG GGAGGCCAGA AGGGGAGCT TCATGCAGG
ACAACTCCAC ATCCATTACA GGAAGAAATG CCAATGATAG ACCCAAAAGA AGCATTAACA
AAGACTCATC ATTTATAGTC TCCAAAAGGA AAAGTATAC ATAGCATCTC CAGGAAAAGA
TGTGTATCAT GCCTCCTAGA GGAAATCCAC TTCCTAGCAA CTCAGTCAGT GAGAAACCAT
CATCACTCTG AACTCTCACT TTTCTCCAAG GGACTTTGAT TCAAAACAAC CTCTTGCAAC
ATCCCCTCTT TTCTCCATGT TTCTTTTTTA AAATAATGTT TCTTTCCTTT GTTCATTGGG
CTTGCCTATG GTTTCTGCCA TGAGTTGTTT GTCCCAAATT GTAATTCTCT GCTACACCCA
GATAAACCCC TCCTTTTTTG CCAGGAAAGT AGTTGACTTT TATTTTAAA ATCAGTAGTA
GAATATTTTA AACAAATAAA AATATAGAGC ATATTGTAAT AAATGGGCTT CCCTGGTGGT
TCAGTGGTAA AGAATCCGCC TGCAATGAAG GAGATAAGGA TGCGCCGGTT CTATCCCTGG
```

-continued

```
GTCGGGAAGA TCCCCTGGAG GAAGGCATGG CAACCCACTC CGGTATTCTC TCCTGGAGAA

TCCCATGGAC ATAGGAGCCT GGTGGGCTGC AGTCCACAGG TTCACAAAGA GTCGGACACA

ACTGAAGTGA CTGAGCACAG CACACATAAA AATATGAGCA TACTGTAATA AATAGTTATG

TACCTACCAT GAGGATTTAA TGCATTGACA TCTGTCTATT TTCTACAAAG AAATTCTTTA

AAAATATAAA TCAAACAAGT CACTTTTCTT CTTGAAACAC TCCACTGGTT TTCTACATTT

AAATAAAAGC TCAAAGACCC AGTGAGCCAC TAGGCCCTAC ACCATCTGCC TCCCCATCAG

CCGTCACCCT GTCTCCTAAC ATTCTCTTTC CCATTACAGA TGCCCTAGCC TGTTTACCTT

GCTGGTCCAT GGAGATGCCA AGCACTTCCA ATCTGAGGGC TTTGGGCCTA TTGCTCCCTC

TGTAGCACCA TTCTGATCTC AGTGTGCTCT TTTGAGTTTA GTTGTATGAC TGTGGTATAA

AACAGTCGTT ATATTGTCTC ATTCATCTTA CAATTTTATG ATTTTCTCTG ATTATGTAGA

TGTTTGTCTC TCATGTTCAA AAAATCCAGA GGTAAGCATT CCAGAGACAG TATACCAATT

TCCTGGTTTC AGGAACTCAC ATTCCTTCTA TCTTTTTACT TTGCTATCTG TGGTTTCTAT

TCTGAGTCAT CTCACTGTCC ATGATAGTGA TAGCTATTAG GAATGCCAGT CCTGTTTGAA

TTTCAGCCCA GAGGAAAGAG GAAGCAGGAA AGAGCATTCC AGGTTTCTAA GAAATGCTGG

GTAAAGGAAG AAATGGAAAC CTGAGTTTTT TATTTTTTAA TGTTTTTTGA AGTTAAAACT

TTGATGTCAG AAAAAAAAAA AAATCCCAAA ACTTTGTTGT CTAAGTAAAA TCTCATCTAC

CTTCATGGGA GCCTCAGAGG ACAATAATAA AGTATTCTTT TAAACTTATT TCTAATCACC

ATACTAGTAA AACTGTAGTT AAGCTTGATC TTTTTGTGCC ACCTGTGGCC CAGGAGAGTT

TAGCTCCTTT TTGTTTGTTT TAGCAATAGA AACATTTTTA AAAATTAAAA ATGGATGCAC

AACTTCAATA TTTTAAAAAT GTATTTTTAA ATGTTAAAAT TTATATATTT ACTTATTAGG

AAGTTAGTAT AAGCAGTATT TTTGATGAGC ACAGAGATGT TGTGTAATTT TTTATAGTTG

TAGAAAGTCT CTGAAATAAA TTTATTTCTA AATTTGGTTG TGTAGTATTG AGAAAAATCT

GATTCAGAGA CTAGTAGTCA GAAATGGCTT CAGGTTTTGA AGTTTTGTTC ATCTTACAAT

TTTATGATTT TCTCTGATTA AACAGAGATG AAAAGGGAAA ATTTATTCTG AGATACATAT

AAAAATGACA CAAGTTAACA CATAGGCTTC CAGTGTGGTA GATAGTACAT GAGAAGGCAC

AGGAAGTGTG TTTTTATACA ATTTCTTAAG TGTCTTAAAT GAATAGATAA ATACACATAT

ATGTTTTCAA ACTGTGGTGC TAGAGAAGAC ACTTGAGAGT CCCTTGAACT GCAAGGAGAT

CAAAACTAGT CAATCCTAAA GGAAATAAAC CCTGAATATT CATTGGAAGG ACTGATGCTG

AAGCTGAAAC TCCAATACTT TGGCCATCTG ATGTGAAGAG CTGACTCATT GGAAAAGATC

CTGATGCTAA AAAGATTGAA GGCAGGAGGA GAAGGGGCAA CAGAGGATGA GATGGTTATA

TAGCATCACT GACCCAACGG ACATGAGTTT GAGCAAACTG TGGGAGATAG TGGAGGACAG

AGGCACCTGG GGTGCTGCAG TCCATGGGGT CATAGAGTCG GTAACTTAGT GACTGAACAA

CAACATATAT ATATATATAC ACAAAAATAT ATAAATATA TATGTAATGT ATATAATATA

CTATATATAA TAATAAATAT ATAAATGAG CATATTGTTG TTGTTGATTG GCTTGAAACT

GCTCTAAAAC TGCTTTATTG AAATTTGGAT ACCACACATG TTAATTGTAC AATTCAATGA

ATTTTCATAA ATTTATAGAG TTGTGTAACC ATTACTGATC TAATTTTAGA ACTTTTCTAT

TACCTCAAAA AGCTCGCAAC AAACTTATGC TTACTGGTGC CAGTTGTACC CTCTCTGCTT

CCTTCCCCTC TTTACCTGAG AGGAGTAGAT GGTCTGAGAG CTGGTGTCTT AATGCCTGTG

TAAAAGTATC CATGATCTGT GTTCCTGTAA ACAGTGTCTG AACATAACTG TAGAACTTGT

AGTCAAAGAT AAAAATTAAA AGTGATTTTG TTGTTGAGAG GCCTGTGAGC TGATTCATTG
```

-continued

```
TAAGTACTGT GTAATAATGC ATAACTGGGA CTGAATTGTG TTATATGTCG AACTGGAATG
TTCATATGTA TCAGAGGACA ATTCTTCTGA TGTCCAGAGT TTTCACTACA TAATGCTGTT
TTGTTTTTTT GGCTGTGCTG GGTCTTTGTT GCTGCAAGGG CTTTTCTCAA GTTGTGGCAA
GTAGGAGCCA CTTTCTAATT GCAGTGTGTG GGCTTCTCAT TATGGTGGCT TTTCTTGTTG
CAGAGCATAG GCTCTAGGCC CGCGGGCTTC AGTGGTTGTG GCACATGAGC TGTAGAGCAC
AGGCTCAGTA GCTGTGGTGC ACGGGCTCAG TTGCTCCGTG GCATGTGGGA TCTTCCCGGA
CCAGGGATAG AATCCGTGTC TCCTGCATTG GCAGGCAGAT TCTTTACCAC TGAGCCACCC
GGGAAGCCCA ACGCTTTCTT GTTGACTGGC AAGTTGCAGA TGACATTCTC TGTGGCTTTG
GATGCCTGCC AGAGGGAAGA CTTACAATTC CCAACAAATT TGAAGGCATG CTTGCTAGAT
ACGATACTTG ACATTAAGTA AGCAGGTTCA CTATACACAG TGTGTAATCA AGAACTATC
TTTCACAAAC TCTTATCTTT GTTTCTGACA GAACACTTGC AGTTCTACA AAACTGCTGT
AAAAGTTGGC CTCAGTAAAA GTTGTTTATC TCTCAGTAAA AGTAGTAACA CTATACAGGA
CTTCCCCCCA CCTGCTTTTG ACAGATTGAC TCCATGGGAT TTAAAACTTC CTTTTTTTCT
TGAGTTGATA AGGTGACAAT GCTCTTTTGA AACAGATACA GGTGAGATAT ACCAGGTGGA
CTAAGCAGGT GTGAAACAGG CCCTGGGGTA GGGTAGCTGA CCTTATTGAT AAAGTAGTGA
CAAGGGACAG TCAGTTACAT CATAATGTAC TAAGGTATGT TACAGAAGGA AAGAAGTGAT
ACAAAGGATG GGTTTGGGCA AAAGCCTGTG AGACTATAGA GACTTCTTCC TTGACTAGCA
AATGAGGTCA CCCTGCAAGC TGTGCGGGCA AGACAGGAGT GGAGCTCACG TAGTTCTCTG
GCTGACCCTG CTGCTGAAAC AGCAACCGCA GAGCAACTAA GCCCACTCAC CGCAACTACT
GAGCCTGTGC TCTAGAGCCC AGGCGCCACA ACTACTGCAC CTAGAGAGTA GCCCCTGCTC
CTTCTGTAGC ACCAGTCTGT GATGATCCTC TGTTGGTTGT TGTCAGCTTC CAGTGGCTGG
TCACCATGCT CATCATCTTC AAGCCCTCGT CTCCTTTGCA GATCTTCTTA AACTACCTCT
GCCCTGTGCG TTCCTTAGGA GTTCCTGGGC CAAATGCCTT GTTGGTGTTG CAAGTTGTCT
TTACTGCTTT ACGACCCATT TTGAACTTGA GTAAGAAAAT TGCTTGAATT TACTTTTTGT
CTAACGTCTT TTCCCTAGTC CAAAATAAAT ATAAAATAAA CAGCAACTAA TAAATCATTA
GCAAAAAACA TAAAGTGAGA AATGTGCATT AAAATGACAT ATAACCACAT TTATTTAAGA
ATGTATTCCA ATTTCAAACA GCAAATTTCA ACAGTGCAAA ACCACAGTTA CTTTTGCAAC
AACCTAAGCA TATTAAAAAG CAGAGACATT ACTTGACCAA CAAAGGTCCA GCTAGTCAAG
GCTATGGTTT TTCCAGTGGT CATGTATGGA TGCAAGAGTT GGACTGTGAA GAAAGCTGAG
CGCCGAAGAA TTGATGCTTT TGAACTGTGG TGTTGGAGAA GACTCTTGAG AGTCCCTTGG
ACTGCAAGAA GATCCAACCA ATCCATTCTG AAGGAGCTCA GCCCTGGGTG TTCTTTGGAA
GGAATGATGC TAAAGCTGAA ACTCCAGTAC TTTGGCCACC TCATGCAAAG AGTTGACTCA
TTGAAAAGA CTCTGATGCT TGGAGGGATT GGGGGCAGGA GGAGAAGGGG ACGGCAGAGG
ATGAGATAGC TGGATGGTAT CACCGACTCG ATGGACATGA GTTTGAGTAA ACTACGGGAG
TTGGTGATGG ACAGGGAGGC CTGGTGTGCT GCCAGGGCAA ATCATGGGGT TATTGCGATT
CATGGGGTCG CAAAGAGTCG GACATGACTG AGCGACTGAA CTGAACTGAA CTGAATGGTA
TTGAGTTGTA AGGATTCTTT ATATATTTTG AATACAAATT GTTCCTCTAC TCCATACATT
TTTTAAAAGG CATAGGTAAT ATTTGTGTTT AATTTCATTT ACAGAATGAA ACCAAAATGT
ATAAATATTA TTTATGATGC GGGGGTATCA TTGAGGATTA ACAACCTCAA TCGTAGAGGT
TGTTATGAGA TATACAGTTT GCAAATATTT TCTCTTAGTC TGTGACTCAT ATGTTCTTTT
```

-continued
TTTTTTTTTT TTTGGTGGCC AAAGTACTGG AGTTTCAGCT TCAACATCAG TCCTACCAAT

GAACACCCAG GACTGATCTC CTTGCAGTCC AAGGGATTCT CAAGAGTTTC TCCAACACCA

CAGTTCAAAA GCATCAATTC TTTGGTGCTC AGCTTTCTTT ATAGTCTCTC ACATCCATAC

ATGACCACTG GAAAACCAT AGCCTTGACT AGACGAACCT TTGTTGGCAA AGTAATGTCT

CTGCTTTTTA ATATGCAGTC TAGGTTGGTC ATAACTTTCC TTCCAAGGAG TAAGCGTCTT

TTAACTTCCT GGCTGCAACA CCATCTGCAG TGATTTTGGA GCCCAGAAAA ATAAAGTCAG

CCACTGTTTC CCTTGTTTCC CCATCTATTT GCCATGAAGT GATGGGACCA GATGCCATGA

TCTTCGTTTT CTGAATGTTG AGTTTTAAGC CAACTTTTTC AGTCTCCTCT TTCACTTTTA

TCAAGAAGCT CTTTAGTTCT TCTTCACTTT CTGCCATAAG GGTGGTGTCA TCTGAAACTC

CAATACTTTG GCTGACTCAT TTGAAAAGAC TCTGATGCTG GAAAGACTG AGGGCAGGAG

GGAAAGACTG AGGGCAGGAG GAAAAGGGGA CAGCAGAGGA TGAGATGGTT GGATGGCATC

ACCGACTCAA TGGACATGGG TTTGAGTGAA CTCCAGGAGT TGGTGATGGA CAGGGAGGCC

TGGCGTGCTG CGGTTCATGG GGTCGCAGAG TCAAGACACG ACTGAGCAAC TGAACTGAAC

TGAACTGACT GAACTGAATG GCAAAAACGG TTTAAAAACA ATATTTAAAT AAAAGGTTTG

TGAAGTCCTA AAGCCTGTTC TTGGCGTTCT AGGATTATTA TACCATAATT TGCAACCTAT

TGCTAGGAAG TGTTTGAGTG GCATTTAAAC TCAGCAAGCT GAGTATCTCA TTTTTAGCAG

AATCCCGGAC TGATGGAGTT GGAAAGGACC TAAAACTTAA GCAGAATTAA CACTTCTAAT

TCTGTAAATA AACTCCTACA TGTTTGAATG ACTTAATTGC AATGCTGTAT GAAACATTTT

ATGGAGCACT GGAGGCACAG CTGGATTTGA GGACAAACAA AAACACCAGG AGTCAGAAGT

TCAGTTAAGG CAGGAGTACA AAAAAATCAA TGTTTCCTGA TAAGACTAGG GATTTATTTG

CTGGCTCATG ATAAACAACA GGTTAAGCAT CAAAGAAGAG TAAGGAAGAA CTCTAAACTC

TGTAGAAACC AGGCTTTAAA AATAGAAATT CACCTCAATG ACTGTTGTAA ATACTAACAA

AGAAAAAGAA TTCATGCTGA TAAGGGAATT GTATTGTGTT CAGTATTTGA GGGTTAACTT

TGTACATTTA CCTCAAACTA TGCCATGCCT CATTTGCATT TGTGATTTAT GTATATTTCT

TTTTGTTTAC CTCTTTAAAC TTATTCATTC ATTTAACACT GAATTTATTG AGTACCTATT

TAAAGCTAGA AACTAACCTT AAAAATTAAT TCTCACTCTT ATAAAGAAAA TACATAAGTA

GCAGTTATAA AATTATGGGA GTAAGTACTC TAACATATTT TATAAGTAGG TATATTTTTG

AGTATAAAAA TACCATGAAA AAAAGTTGT TTTTTTTGGA AAGATCAATA AAGCTTTAAC

TATATTGACT AAGGAAAAAC AGAAACCACT TAAAAGCAGA AATGAAAGTG GGGTCATTAC

TATAAATTTT ATAGAAATAA AAATAATATA AAAGGATACT ATGAAGAATT GTTTGTCAAC

AAATTGGGTA ACCTAGGTAA GGTGGACACA TTGCTAGAAA ATACAATCT GCCAAAACCA

ACTCATGAAG AAATAGAAAA TCTGAACAGA CCTATAACTA GGAAGGAGAT TGAATCAGTA

ATTAAAAACC TCCCGAACAA AGAAAAGCAA TGGACAAAAT GGCTTGACAG GTAGATTCTG

CCAAATATTT AAATAACTAA CTCTTCCAAA AAAACCTGAA TCTTCCTAAT TCATCTGTGA

GATCAACAGC CCCCTGATAC TAAAGCCACA CAGAGACACT CTAGAGAAAA CTAAATCACT

ATCCCTTGTG AATATAGATG CAAAAGTTCT CAATATAATA CTCACAAGTT TAATTGAGCA

CCATATTAAA TGGATTATAT GCCATGACCA GGTAGGATTT AACCCTGGAA TATGAGGATG

GTTCAACATA GGAAAATCAA TGTAATACAC CATATTAACA TAATGAAGGG AAGAAATTAC

ATGATCATCT TAATTGATGC AGAAAAAGCA TTTGACAAAA TTCAGTACCT TTTATGATTA

AAAAAAAAA AGAAACCTCA AACTAGAAGT AGAAGGATAC TTCCTTAACC TAAGGGCCAT

-continued

```
ATATGAAAAA CCCATAGCTA ACATCTTACT CAATGGTGAA AGACAAAGCC TTTTCCCTAA
AATTAGGAAT GAGACAAAGA TGCCTGCTTT TGTCACTTCT GTTCAGCAAA GGCTTCCCAG
GTGACTCAAT GACAAAGAAT CCACCTGCCA AGCGGGAGAA GTGGGTTCAA TCCCTGGGTC
CAATCCCTGG GTTGGGAAGA TCCCCTGGAG AAGGAAATGG CAACCCACTC CAGTGTTCTT
GCCTGGAGAA TCTCAGGGAC AGCAGAGCCT GGTGGGCTGC CGTCTATGGG GGTCGCACAG
AGTCGGACAC GATTGAAGCG ACTTAGCAGC AGCAGCAGCA GCAGCCAGTC TTTTTGCCTG
GGAAATCCCA TGAACAGATG TGAAATTTTT TTTTCACTGA TTTTTTAAAA CTTCTGAATC
GTTTGAATCA CTTGAAACGA GACGCATAAT TCTTATATTA AAAAGAATT TTTAAATAAA
TGAAGTTCCC AAAGGGTCAG TTAGCCAGTT TAACTTTCTA TGTTAAGGAT AGTTGTCAAA
AAAGATACCC CACTAGATGA AGATTTCTCT TCCAACTCTG AAAATATGCT ATTAACATCA
CACAAATCTT TTTTCAGTCT TGCAGTGGTT TCAAGTGAGA GCAGTGCATC CCCCGCCCCT
CTCAGAGACG ATGTTTAGAG ATGTCTGCTA CCCTTTTTGG TGGTCATATG TCTGAGGGTT
GCTATTGGCA TGTAGTGGTC ATAGGCCAAG GAGGGAAAGC ATACTGTAAA GTAAGCAAGT
GTCATATTGA AGAAATCATT GCCAAATCTA TTCTTAGGAT GATTTTAGCT CTCAGGTTTA
GTTCTTTTAT CCGTCTCGTT AGTTTTCTGT CTGTGGTGTA AAGAAAGTTT CCATATTCAT
TCTTTTGCAC ATAGACTTAG TTTTCTCAAC ACCGTTTTTT AAAATTGAAA TATAATTGGT
ATACAATATT ATTTAGTTTT AGGTGTACTA TATAGTGACT TGACATTTGC ATATATTATG
AAATGATTGC CATGATAAGT CTAATAACCA TCTCTCATTC AAAATTATTA CAATATTGTT
AACCATATAT ACTGTATATT ACATCCCCAT GGCTTATTTA TTTTATAACC TGATATCTGT
ACCTGTCAGT CTCCTCCGTC TATTTCTTCC CCCACCCTCC ATTCTGGCAA CCACCCTTTG
TTCTCTGAGT CTATGAGTCT TTTTTCATTT TTGTGTTTGT TTTTTAGATT ACACATATAC
ATGAGAATAT ACAGTATTTG TCTTTCTCCA TCTAATTTAT TTCACTTAGC ATAACACCCT
ATAGATCCAC TCATGTTGTT GCAAATGGCA AGTTTATTTT TATGACTGTG TAGTTTTCTA
CTGAATACAT ATACCACATC TTCTTTATCC ATTCATCTTT TGATGGACAC TTAGGTTGCT
TCCATATCTT GGCAATTGTA AATATTGCTG CTGTGAACAT GGAGTTCAT GAATTTTTTT
GAATTAATGT TTTTGGTTTT CTTTGGCGGG GAGGGGTGAG TATACCCAGG AGTGGAATTA
TTGGGTCATA AAGTAGTTCT ATTTTCAGTT TTTTGATAAA CCTTTGTACT GTTTTCCACA
GAAGCTGCAC CAATTTACAT TCTCACCAAC AGTGTGCAAA GCAAAGCTTC CCTTTTCTCC
ACATTGGGTG ATAATTTTTA TCTGTCAATA TTTTAAATAT ATCACTCCAC CTTCTCTTGC
TCTATAGTTT CTGCTGGGAT AGCTTAATGG GGGTATCTTT GTAGGTTACT ATCTTTTGTC
CCCTGTGTGT GTGTTAGTCA CTTGGTCGTA TCTGACTCTG CAACCCCATG ACAGTAGCC
ACCAGGTTCC TCTGTCCATG GAATTCTCTA GGCAAGAATA CTGGAGTGGG TTGCTGTTCA
CATTTCCAGG GGATCTTCCT GACCCCAGGG ATTGAATCCA GGTCTCCTGC ACTGCAGGCA
GATTCTTCAC CAACTGAGCC ACCAGGGAAT AGCTATCTTT AAAATTCTTT CTTTATTATT
AAATTCTGTC TTGGAGAAGA TTCTTTTGCA TCAAGATAAT TAGGTATTCT GTTAACTTGG
TAGATTTGTA TGTCCAGTTC CTTCCCCATC TTTGGGACAT TCTCAGCTAC TATTTCTTTA
AATAAGCTTT CTGCTCCATT TTCTCTCTCT TCTCCTGGGA TACCCATTTT CTTTATGTTG
CCTTCTCTAA TGGAGTTGGA TAGAGTTTCT TCAATTTCTT AAGATCTTGG TTCTTTCTCC
CCTTCTGCTT AAATCACTTC TAGATTTCTA TCTCTGAGCT CACTAATTTT CTCTTCTTTG
TGAGAAAATG GAATTTCCCA ATACTTCTAA TGCATTCTCC ATCTCATTTA TTGAGCTCTT
```

-continued

```
TAGCTCAGCA GTTTGTTTGG TCCTTTTTTA AAGTTTCAAT CTCTTTGGTA AAGTATTGGT

TCGTTCCTTA CTTTTATTCC TAGGCTCACT AAACTGCCTT CTGAGCTTTC TCATGCCCGT

TGAGTTTTTC ATGATGGCTA TTTTTAATTC TTTGTCATTT GGATCACAAT CTTCCTTGAC

TTCAAGTTTG GTCATTTTCT TTTTGTGATA CTGTGTGACT GGGTTTTTTC ACAGTGTTTG

ATGAGTTGTT TCTCTGCTGG TGCATTTAAA GTAACAAGAA AGAAAAGAAA GAAAGAAAGA

AAGTCGCTCA GTCGTGTCTG ACTCTTTGTG ACCCCATGGA CTGTAGCCTA CCAGGCTCTT

CTGTCCATGG GATTTTCCAG GCAAGAATAC TGAAGTGGGT TGCCATTTCC TTCTCCAGGA

GATCTTCCCA ACCCAAGGAT TGAAACCCCG TCTCCCGCAT TGTAGGCAGA TGCTTTAACC

TCTGGAAAGC CCCTGGTTTG AAGTAGCAAA CCCCTTTCTA ATTTAGATGA AGTTTTGTTT

ACTTAGATTC TAACAATTCA ACAGATTGAT AATTAGAGGT CTTTCTTCTG TTTTTTAGTA

GATGGTGCTA TAGCACAAGT TTTCAACTTT TCTTGCTGAG CTGCCTCTGA CAATATTTGA

GAATTGGCAC TTTCCACCCT TCACTGCCTT TGCCAGAGGT GTCACAGGTG CCCTCCGTGG

TCCCTGCTTG TGCCTCTGGG CTCATTGGTG CCCTGCTGAT GTTGGTGCCA TTGCTGTCAC

TGTCATTGCT GCCAGGGGAA CTGGGATGAT GGGTGCCCCG CTGTGTCCGG GGTCACTTGG

TTAGTCTCAG CAGGAGGGGT GGGTGGGAGA AGCTGGGGTC AGACAGGTGC CTCCACCACA

GCTGGGGTTG TCAGGTTTGT AGGCACCACC ATGGGCAGGG GGATGAGGGT CACGGGCACC

ACCATGGCTT GAAGGACCGG AGTCATGGGC CCTGCCACTA CTGCTGCCTG GTTCTGCCAT

GACCAGGAAG CCATATGCAC TGCCTCCACA GCTGCTGCCT GGCTCTCTGG GACTGCAGGC

TTAGCCATTT CAGAAGAGAA GCGGGGGTTG TAGGCACTGC CGCCACTGTT ACCCTAGTTC

CACCTCCTCT GTGTGTTCCA ACCACCCAC CTTCAGGTAT ACAGATGTGT GGGTCTCTGC

AGCATCCTGG TAGTTTGAAC AGAGGCAAGT TATGAATGTC TTACTAGTTG GAAATTGAGG

GGGAGAAATA AAGCATCTTA CACTGCCATG ATGCTGATAT TCAGTTCAGT CGCTCAGTCG

TGTCCGACTC TTTGCGACCC CATGAATCGC AGCACGCCAG GCCTCCCTGT CCATCACTAA

CTCCCAGAGT TCAACCAGAC TCACGTCCAT TGAGTCAGTG ATGCCATCCA GCCATCTCAT

CCTCTGTTGT CCCCTTCTCC TCCTGCCTCC AATCCCTCCC AGCATCAGAG TCTTTTCCAA

TGAGTCAACT CTTCGCATGA GGTGGTCAAA GTACTGGAGT TTCAGCTTTA GCATCATTCC

TTCCAAAGAA ATCCCAGGGC TGATCTCCTT CAGAATGGAC TGGTTGGATC TCCTTGCAGT

CCAAGGGACT CTCAAGAGTC TTCTCCAACA CCACAGTTCA AAAGCATCAA TTCTTTGGCG

CTCAGCCTTC TTCACAGTCC AACTCTCACA TCCATACATG ACCACAGGAA AAACCATAGC

CTTGACTAGA CGAACCTTTG TTGGCAAAGT AATGTCTCTG CTTTTGAATA TGCTATCTAG

GTTGGTCATA ACTTTCCTTC CAAGGAGTAA GTGTCTTTTA ATTTCATGGC TGCAGTCACC

ATCTGCAGTG ATTTTGGAGC CCCCAAAAAT AAAGTCTGAC ACTGTTTCCA CTGTTTCCCC

ATCTATTTCC CATGAAGTTA CTCTCCAGCA ATTTTTGAAA TCAGAAAGTG TGAGAACTCC

ACTTTGTTCT TCATTTTCAA GATTACTTTG GGTATTTGGG ATTCTTTGAG ATTCATGTGA

ATTTTAGGAT GAATTTTTCT ATTTCTGCAA AAACACACTG GAATTTAGAG AGTAATTGCA

TTCAATCTGT GGATCATTTT GGGTAGTATT GTCATTTTAA CAATCTTAAA TCTCCAATCC

ATGAATACAT GATGTCTTTC CATTCATTTA TGTTTCTTT AATTTATTGT ATTGTCTTGT

ATTTAAATTA TTGTATTGCC TTGTAGTTTA CAGTGTACAA GTCTTTCACT TTGTTGGTTA

AATTTATTTT ATTCTTTTTG AAGCTATTAT AAATGAAATT GTTTTCTTAA TTTCCTTTTC

AGATTGTTCA TTGCTAGAGT ATAGAAAATC CACTGATTTT TATGTATTGA CTTTGTATGC
```

-continued
```
TGAAGCTTTG ATGAATTTAT TAGCTCTAAG TTTTTTTGTG TGAAATCTTT AGCATTTTCT
TCATAAAAAA TAATGTCACC TATTAACAGA AATTATTTTA TTTCCTTCAA GTCTGGTCGC
CTCTCCTTTT CTTGCCTAAT TTGCTTTAGC TACAACTTCC AGTACCATGT TGAATATTGT
TGTTGAAGTC GCTAAGTTTT GTCCAACTCT TTTGCAACTC TATGGACTAT AGCCCATCAG
GATCAATTGG CAGCCCACCT GCCAAAGCAG GAGACATGGG TTTGATCCCT GATCTGGGAA
GATCCCACAT GCCACAGAGT AACTAAGCCT ATGCACCACA ACAATTGAGC CTGTGCTCCA
GAGCCTGGGA GCCACAACTA CTGAGCTCAG GTGCTTCAGT TATAGAAGCC CGTGTGCCAC
AGAGCCTGTG CTCTGCGACA AGAGAAGCTG TGGCAATGAG AAGTCCACGT ACTGCAGCTA
GAGAGTAGCC CCCACTTGCT ACAACTAGAG AAAAAGACCA GGCATCAAGG AAGGCCCAGC
ACAGCCAAAA ATAAATAAAT AAATTAATTA AATTATTTTT TTTAAGTTGG TGAAAGATGA
ATATTTGAGA TAAAATGAAA ATTACTAAGA TCCACATCTT CAGACATGAA AGAAAATATT
TATGAAATAA AATTATTTGT TGTCTGAAAT TTGTTTCAAA GTAATCTGTG GGAAAGGGGG
AAAAAAGAGG AGTATCAGTG AAATGAAAAT TGACTACCAG TTGAGATTAG CATATAGTCA
TTCATCATAC TATTCTTTCT ACTTGTGAAA TGCTTGGAAA TTTCTGTGTA TGTGTGTGTT
AATCATTCAG TCATGTCCTA CTCTTTGAGA CTGTAGACTT CCAGGCTCCT CTGTCCATGG
AATTCTCCAG GCAAGAATAC TGGAGTTGGT AGCCATTCCC TTCTGCAGGG GATCTTTCCG
GCCCAGGGAT TGAACCTGGG TCTCCTACAT TGCAGGCAGA TTCTTTACTG TCTGAGCCAC
TACAGTGGTA AGAAAAAGTG AAAAAGATGA CAGATACATT TGAGAATTTC TAGTTTCAGC
AATATTGCAG AGTTAAGAGG CCCTGAAACT ATTCAGCTAC ATAATATCTA AAAATGCTTG
ATAAAATATT AAAACCACTC TTATTTTTTA ACTTAAACTT TTTATTTTCC ATTGAGGTAT
AGCCAATTAA CAATATAGTG ATAGCTTCAG GTAAACAGTG AAAGGACTCA GCCATATATA
TACATGTATC CATTCTCCCC CAAACTCCCT TCCCATCCAG GCTGCCACAT AACACTGAGC
AGAGTTCCAT GTGTATATAG TAGGTCGTTG TTGAAAATAT TGAAACCACT CTTAATTGAT
TGGATGATTC CCACTAAGAT CAGAATGGAG TACAGACTAG GCAGGTAAAC TAAATTTTAG
AGCCTTGGAT ACTCTGAGGC CTACAGTATT CTTTATTGAC ACTCTGAACT GCATTGCACA
GAAGGGACAG AAACAAAGCC TGAAGTCACG TAGAAGGGAA GCATAGTACC TACATCTAAG
AGAGGCATAC CCTCACAACG GGCAAACTCA AGGTGAACCA TAAGAACACG TTTCCTTACT
GGACTGGGCT ATGAATGGAA GTTAAAAAAA AAACCAACAA CATTTTCTTT GAGAACTTTT
TCTTCTGGCT AGATGTCACA TAGTTTGGGA CTCAGTCCAC ATATTTTGCC TGATCCCAAA
ACACAAGCCT ATAATTTAAA GAGTAGCAGG TTAGGTACTA TCCCCAGGTG CCTGAGAGAA
GTAAAATAG ACTTTTCCAG ATGAGCATAC CCTCAAGCAG GCCTCAAAGA ATTCCTGGAG
ACAGTCAACA AAAAGCTCAT AGTAAAAAGT ATAAAACAAA AATCAAGCAA GCCATAGATA
GCAAACCCAG AACCATAGAG AGTTCAACTT TTATAATTAA TTATCATAAG TAAACTAAAA
AAATAAGTCT GCTTGAAATG CTTTTAGATT AAAAAAGGAC TTTGAAAACA TGAGCAAAAA
TAGGAGACTA ATGATTAGGC CAATTTGAAG AAGAACAAAA TATTACTCTT AGAAATTAAA
AAAAATACTT ACTGAAATCC CATCCAGGCT GCCACATAAC ACTGAGCAGA GTTCCTGGAT
TCAAATGGAT AGACAGTTAA AAGAAAGATT AATGGAAATA AAGAGCAACC CACCCCAGTA
TTCTTGCCTG GGAAAGCCCA TGAACAGAGG AGCCTGGTGG GCTATAGTCC ATGGGGTCTC
AAAGAGTCGG ACATGTACTT AGCTGTACTT TTTTTTTTAA TTTTGGGATT AACATGATTT
ATTTCATTAT CAGTCTTACA AATTACTGAG GTTGGGTAAG GCCGGGATTG TAGCTTGAAT
```

```
TTCACACTTT GGTTGAGGAA CAGTCTGTTA GTGAACAGAA GGCCGTGGAG GTGCCACAGT

TCATCCAGCA GTGTTAGAGA CCTTCTCAGA AGCAACAGGT GAGACCAGGC ACATCACAGT

CAGAGGTCCA CTCCAGTGGC TCTCAGGGTC CACTGCCTGC CCCCGCCCAC CCTGCTTTAT

GGAGGCACGG AGGCCCCTAG AGGCCCCAGG GAGACATGAT GGGCTGAGGG GCTTCACCAT

CAGGTGGTGT GTCTCTGCCT CAGCATTTCC ATCCATACCA CACATCACTT TCTCCCACTA

TCTACACTCT TATTTATTTT TAATACTAGT GTATTTTAA AAATATACTT TTATTTGGCT

GCGACGGTCC TAGTTGCAGC ACATGGGATC TTCAGTCTTC ATTGAGGCAT GCAGGATCTT

TAGTGGTGGC ATGTGGGATC TAGTTCCCCA ATCAGGGATC AAACCTGGAC CCCCTGCATT

GGCACTGAGT TTTTGCACCA CCAGGGAAGT CCCACTCCAC CCTTTTATAA GTGGGCAGCC

TCATCCCTGC CTGGGCTTCA AGCAGAGAGC CTGGTTCTGG TCCCAACTT TTTGTCAGTG

GAGTCCCCTT TATTGCGCCA AACTCCTTAC CACCATTACC TGTTCCTGGA CTCAAGACCT

TCAACCCACA AGCTTGGTAA TTCTCACCAC TTTGGATTTC TTTCATGGAG ATATTCATCT

TGGTTTTGCA ACTGCCTGGA TTTTCTTGTT TTTCTTCTTT TATTTGGATC CATTGTGACT

GAGAAGGGTG AACAAATTTA TTTTACTTTC TCTCTCCAAA GAAATCTTAT AGCAGTTTTT

GCATAATCCC ACTATGCTTC AGTTTCATCT TCAAGATAAA AATTTTAACA GAACCCACCT

AAAGGCATTG TTGTAAAGAT CAAATGAGAT TTAGAAAAAA CTGCACAAAA CCTAAAGGCA

CTTAGAACAC TGCCTGGCAA GTACCAAGTA CTCAATAAAC ATTAGCCACT ACTATTGGTA

CTGGGGAAAG ATTGAGGCTA CCTTATATTT TCCAAATATA CATAATTTTA TTGTCTTTAT

TCAACCCCGT GGCATAGGTA TTATCACCCT TAATTTGAAG TAAAGAAATT GAGGCACCCA

AGGGTCAAAT AGCAAAAGCT GTAGAGATGA GATGAACCTT GGGTACATCT AGACTGGCTG

TTGACTTTGT TATAAAATAG AATAATTAAT GTATATTTCT TGCTCTAATA TGGGTGATGA

CATGGAGAAG ACTAAAATCT CATTCTGGAT GAAGTTATAA GCTTTGGCTC TGTTGACATC

ATCTGTTATA ATAGATGGCA TGACAGCCAG AAATGAAAAA AGTCTAAGGC ATTATATAAT

GAATGATGTG TCACTTAATG CTCATTACAC TTTAACTTCA GTTGCTCCCA CGAATGAATT

CTTGTCTCTA CAGGCAATAA AATGTTATAG TAGTCAGTAA GGTATCATAG AAAAAGGGCA

GTCTCAATAA ACCCTTCTCC ACTTTTACAA CATTCAGGTC AGGGTGGATA AGCCCCTGAA

TTACATGAGA TAAACTCACT TTTATTATTC AGTCAATAAA TATTTATCAA GTATCTGTTG

TGTTCAAGGC TCTGAGCAAG GCAACATTTA GGAAATACAC TGAGGTGGGA GACATACTTT

CTACTTTCGT AATTCCCTTT AATGGCCCAC AAGACGTTCC AGCTTCTTTG TCTCTCCCAT

TCAATGTTTT ATCTGTTACC AGGACTGTAA ATTCTTCCTT TATGGTGTTT CTTTCCTCAC

AAATTTTTTT CCACCATAAA ACTCTAGTTC AGTCTATTTT TTTCATTCCC AGACTGTTCA

CTGCTTTCCC ACATCCGCCA TCCATCCTAT ACGTAAACAG ATTACTCTTC CTAAACACCA

CTTTGACAGT GTCATCCCTC TACACTAAAC TTTCAATGGT TTCTCACTCT CAAGATAAAT

CTGCACTCTT GGTTTGGCCT TAGGGCCTCC ACATTTGGCC CCAGAAGATT CTCTTACATT

TTTGTTAGTA TGTTTCTGAG AATACAGTGA TTGAGCTACT TTTTGGTGAA GAGCTTCCAT

GAACAAATGC TGTATACGTG TTCTGCAATG ATGAAACCTA CTTAATCAGC TTGTTTTAAT

CTAGCATCTC CTCGTCTTTC TTTTCCCCAT ATCACGTGTT CATAAAGTCT TTTGTTTAAG

TAAACTTTTA AATTGCAGTA TAACATACAT ACAGAAAAAG CAAAGAAAAT CTTAAGTAAA

CGATTTGGTG TATATTTAAA AAGTGAACAT ACCTGTATAT CTGCCACCCT AACCTCTTTC

TCTATCTCTC TGTCTATATA TATGTGTATA TATACTTTTA TATTTGTTTA TTCTCAATAT
```

-continued

```
CCCAGAAGTT TCCATTATGT TCTACCCTAG TTATTGTCCC TTCCAAAGAT AACTACTCAT

CTCACTTTTA TCACTATATA TGAGTTTTGT TTATTTGGTT TTTTTTTTTT TGGCTTGTTT

ATTTTTATTG AAATATAATT GACATATAAC AAATACACAT ACAAATATAT ATGCATACAT

TTGATCTGAG TAACAGATAT ACAAGTGTGT TTACTTTGTA AATATACATC AAGCTGTTTA

CTTAGATTTT CTGTACATTT TCTATATGTG TATTATACTT CAATTAAAAA GTTTAAAGAC

TTTATAGATA TGTGAAATTT AGTTTGGTGA ACTGTCAACG TTTAAACTTT CAGTCTATTT

TTCAAGGACA AATGTTACAT CTTCTGCCCC ACTTTCTAAC TCTGCAGATT AATTATCTGT

ACCTAATTAT ATACATTTTC CCCTCTACTA TGCTTATTTT TTAGGGCTTG ACTACCTCTG

TGAACTTTAC AACCAAATGA ATTATTTGGT CTCTTGTCTC CTACATAAAG AAAATTATTA

GAATCAAGGT GATCGGGCTT CACATCTGGC CTCAACACCT CCACCACACC CTGCTCTCTC

ACCACTCCCC TTTCCCCCCC ATTATGCTGT CTCTCTGTAT TAATGCCAGC CTCTTTTCTC

CATACCCATA AAAGACATTG ATAATTGGTT TTTGATATTT CTCTTCTTTC CAAGATGGTC

ACTACCTTGG CAGAGTCTGT GTTTATTTAG ATGACCAAGC CATCACCCTA GCTTTTGTGT

TCTTTGATCT CAACATAACC TTCAGTGTAG GCAGAATTCT AAAAATCCCC ATCTGGGAAC

TGCTCTGAGG AATTCTGAAG TTGTGACTGA AGTTCCAAAT GAATTCACCC CAAAATAGTG

AAATTATCTA GATGGCCTGA TGTAATCACA CAAGCCCTTT AAAAAGAGGG ATATAAAATC

CGAGAGAAGT TTGAGGATGT GCTTTGAGAT GAGGAGTCAC ATGAGAAGGA ATGTGGGCAG

CCTGAAGAAG ATGGTTGACT GTCAGCAAGG AAACACAGAC CTCAGTCCTA AAACTACAAA

GAAATGGATT CTGCCAACAA TTGGTCCTTA GCAGATTCTT CAGATGGAAG TCTTCGGATA

AGAATCCAGC TGACCGACTG GATTGAATGC ATGATAGCCT AAGCAGAGCC CAGCCTAGCC

CACCTAGATT CCTGACCTCC AGTGAAATAA TAAATGAGTA TTGCTTTAAG ATGCTAAACC

GATGCCAAGT TCTTACTCAG CACTAGAAGA CAGATATACC TTTCTTCCAT TTCCGTAATT

CAACTGTCAT GTTCAAATCA TGAGACCTTG TCAAGCCTGG ATTGCTAATA CTATATTATA

TGCTAATATT ATATTATATG CTAATATTAT TGCTAATAAT ATAATATTAT TATATTCAGT

GACTTCACCC TCTGGTTTCA GCTCTTTAGC CTCCAAGTGA CCCTAATTTA GGTCCCCTCA

CCACCTCTGT CTTCCTGCCT TCACTTTTCT GTGATGAATC ACTTAACCTG CTCAAACTCT

TGCTCCATTT TTCTGTTGCC TTACCCACCT AGCAAAACCA CATCCTCAAA TTTATTCAGC

CTTCTAACCT GCTCTAGCTT TACTTCTCTG TGATTGGGAA AGCCATGTCC ATTTGTAACT

CTGATGTCAC CACATTTATA GAATCCAGTC TTAGGGGTCT TGGTGCTCGG CAATCTCTCT

TTAGGTCCCT TGGAAGAAAA ACTTTTTGTC TACAATTTAG GTCTAGTGGT GGGGGGGGAT

GAGCTGAAAG TTAATTGACA ACAGATTAAA GGAAAAAAGA TAAGGTCCTG GGGTTTATAG

ACCAGTTTAA TAGGGAAAG TGGGATGGGG AGAAAGGGAT TCTATGGGAA AACAAAGGAC

TTTTAAGAAA GACAAGTAGG CGTTTAGGGA AAGAAGCAAA GATATTTCTT TCAATTTTCT

CTCTTTTCCC TAATTAAAAC ATTTATCTAC ACATCTTGAC TCCCTTCCCT TTGGTCACAA

CTTAAAAAAT ATATAATATT TGCTTTTCTT TTCTAATTCC TCTGAATTCT AGATCCATTC

TGTTTTCTAA GTTACCTGAT TAACCACCTT TTCCTCTTTA TGGCTTGTCT TCCTGGCATG

CACACCTATT CTGGCCTAAT TTAAACCAAA CAAGAAATAT TTTCTCAGAG CCCCAAGATA

GGCTTTAGAT ATACTGCTTT CTCTCACCTT TCTTTTATAG TGAGACTTTT GGAAAGTGTT

GTTTATACCC TGTTTCTATT TAGAGACTAA CTGTTCTCTC ACTGAATTGA TCGAAGGCCC

CTGGTAGCTG ATAAGCAGAG CCATGGTGGG GGTCATGGTG CATACAGCCT CTTGCACTGG
```

-continued

```
TTTTTATTTG CTTCAACTTA AGTAGTAGTG AAAATAAATA TACTGGAAGC CAATACAGAT

ATTATATTCC CAAATGCCCC CAGGGCTATA ATAAGCCCTG CCTGACACCT GACATCTCAC

ACGCTAGTAA AGTAATGCTC AAAATTCTCC AAGCCAGGCT TCAACAATAC GTCAACTGTG

AACTTCCAGA TGTTCAAGCT AGTTTTAGAA AAGGCAGAGA AACCAGAGAT CAAATTGCCC

AACATCCATT GGATCATCGA AAAAGCAAGA GAGTTCCAGA AAAACTGCTG CTGCTGCTGC

TGCTGCTGCT AAGTCGCTTC AGTCGTGTCC GACTCTGTGC GACCCCATAG ACGGCAGCCC

ACCAGGCTCC GCCATCCCTG GGATTCTCCA GGTGAGAACA CTGGAGTAGG TTGCCATTTC

CTTCTCCAAT GCATGAAAGT GAAAAGTGAA AGTGAAGTCG CTCAGTTGTG TCCGACTCTT

CGCGATCCCA TGGACTGCAG CCTGCCAGGC TCCTCTGTCC CTGGGATTTT CCAGGCAAGA

ATACTGGAGT GGGTTGCCAT TGCCTTCTCT GAGAAGAACA TCTACTTCTG CTTTATTGAC

TATGCCAAAG CCTTTGACTG TGTGGATCAC AATAAACTGT GGAAAATTCT GAAAGAGATG

GGAATACCAG ACCACCTGAC CTGCCTCTTG AGAAATCTGT ATGCAGGTCA GGAAGCAACA

GTTAGAACTG GACATGGAAC AACAGACTGG TTCCAAATAG GAAAAGGAGT ATGTCAAGAC

TGTATATTGT CACCCTGCTT ATTTAACTTA TATGCAGAGT ACATCATGAG AAATGCTGGG

CTGGATGAAG CACAAGCTGA AATCAGGATT GCTGGGAGAA ATATCAATAA CCTCAGATAT

GCAGATGACA CCACCCTTAT GGCAGAAAGT GAAGAACTAA AGAGCCTCTT AATGAAAGTG

AAGGAGGAGA GTGAAAAAGA TGGCTTAAAG CTCAGCATTC AGAAAATTAA GATCATGGCA

TCCAGTCCCA TCACTTCATG GCGAATAGAT GGGGAAACAG TGGAAACAGC GGCAGACTTT

ATTTTTTGTG GGCTCCAAAA TCACTGCAGA TGGTGACTGC AGCCATGAAA TTAAAAGATG

CTTACTCCTT GGAAGAAATG TTATGACCAA CCTAGACTGT GTATTAAAAA GCAGAGACAT

AAGCAGGAGG AGCGGCGGGC AGGAGGCTGC AGGATGGTGA AGCTGACGGC GGAGCTGATC

GAGCAGGCGG CGCAGTACAC TAACGCGGTG CGGGACCGAG AGCTGGACCT GCGGGGGTAT

AAAATTCCTG TCATTGAAAA TCTCGGTGCC ACCTTAGACC AATTTGATGC CATTGATTTT

TCCAACAATG AAATCAGGAA ACTGGATGGT TTTCCTTTGT TGAGAAGACT AAAAACATTA

TTAGTGAACA ACAATAGAAT ATGCCGTATA GGTGAGGGGC TTGATCAGGC TCTGCCTTGT

CTGACAGAAC TCATTCTCAC CAATAACAGT CTTGTGGAAC TGGGTGATCT GGACCCTCTG

GCATCTCTCA AGTCACTGAC TTATCTGAGT ATTCTAAGGA ACCCTGTAAC AATAAGAAG

CATTACAGAC TCTGTGATTT ATAAAGTTCC ACAAGTCAGA GTACTGGATT TCCAGAAAGT

GAAACTAAAA GAGCGTCAGG AAGCAGAGAA AATGTTCAAG GGCAAACAGG GTGCATAACT

TGCAAAGGAT ATTGCCAGGA GCAAAACTTT CAATCCAGGT GCTGGTTTGC CGACTGACAA

AAAGAAAGGT GGGCCATCCC CAGGGGACGT GGAAGCCATC AAGAATGCTA TAGCAAATGC

GTCAACTTTG GCTGAAGTGG AGCGGCTGAA GGGCTTGCTG CAGTCCGGTC AGACACCTGG

CAGAGAACGC AGAGCAGGCC CCACTGATGA TGGTGAAGAG GAGATGGAAG AAGACACCGT

TGCAAATGGG TCCTGAGCAG GGCGGCCTCA GCACCTCAGG ATGTGTAACA GTCCACCTCG

GACAGGTCCT GCCTTGTGTC AGCAAAGTAG AGTTCATCAA CATTGTTGAA ATGCTCAAAA

CTGCTGCTTG TAATTTTGTA ATACAGATTT TGAAATCTAA AACCCAGTTT TCTACCAGTA

GTACAAATAA AGGACACTCG CTATGCTGCG GGTTGTGCGT CACTGGGGCG TGTGCAGTGA

GGTATGGATA TGGAGAGTTG GAAATGCAGC AGGGCGGCTC TGTGGGCAGG CTTCACAGTC

CTCTTGAAAT GTTTAGATTT TTAAATTCAT AATAAAACTT AGATTATCTG TGTGCTGCTA

CTGGTTGTTA GAATTTGCGA TATGGGCTGC ATTTTTTTCT TCATGAAGGC TCACAAACAT
```

-continued

```
CATTAAAGAC AGCCAGGCCC CAGGGCTTTG CAAGAAAAAA AAAAAAAGCA GAGACATCAC
TTTGCCAACA AAGATCCGTC TATTTTCCAG TAGTCATGTA TAGATGTGAG AGTTATTTTC
TTTATAGAAA GCTGAGTGCT TAAGAATTGA TGCTTTTGAA CTGTGGTGTT GGAGAAGACT
CTTGAGAGTC CCTTGGACTT CAAGGAGATC CAACCAGTCC ATCCTAAAGG AGATCAGTCC
TGAATGTTCA TTGGAAGGAC TGATGTTGAA GCTGAAACTC CAATACCTTG GCTACCTGAT
GTGAAGAACT GACTTATTTG AGAAGACCCT GATGCTGGGA AGATTGAAG GTGGGAGGAG
AAGGGGATGA CAGAGGATGA TATGGTTGGA TGGCATCACT GACTCAATGG ATATGAATTT
GAGTAAATTC CAGGAGTTGG TGGTAGACAG GGAGGCCTGG TGTGTTGCAG TCCATGGGGT
AATTAAGAGT CGGACAGGAC TGAGCGACTG AACTGAGCTG ACACCTGAAT TTGCTAAGGG
GGAATTGTGT TCACCACTTA GAGAACACAT AAGGAATGGG CCAAGTCCTT ACCACTTCCT
TGCAATTGGT AGCCAGGCAA GCAGACAGAG AGAGCTCAAG GGGGCTGGGA GAGGTTTGGA
GGATATTAAG AATTCTATGA GAAGGATGAA GAGAGCTTCT AATAGGTCCA TATAAGAGCT
TTGATAATAG GGTTGCCTGA TTGATGGCAT TATAGGCCCA GGAAGCTTGT TCCTTTAATG
AGAAGACTTT GTTTTTGATT TTTACTTTCT TGCCATTCTG TATAATAAAT CATACCCTTT
ATACTTTGTC AACATTAAGT TAATTTATTA ACTTTATTAA TAAAGTTTAT CAACATTACA
TTTATCAACA TTAAGTTGAT ATCAACTCAT CTGTTGCTGA CATTCCATCA AGCACTGATA
CCCCTGTGAA AGCCATACAA GCAAACACCC TTCACTGGTG TGATGATTGG AAAGGAGTAT
TAGGCTCCCT CCCTGCCCCC ACTGCAAAAT CTTCCAGTTA TTTTTAGAGT TTTCAAAAGG
GTGGCTCAAG TGATTTTATG AATAAGACCA TTGGCTTCCT TCCTGAAGGC ATTTTTTCTG
AAACATCTAG CTATGCCTAT GTGCACTGCC TACAGAAACG CATGGTGACA CCTAGGCCCT
TCTAGTGCTC ATTTAAGATC GCCAATGATA CCACTCTAAT GGCCAAAAGC AAGAGGAAT
TAAAGAGCCT CTTGATGAAG GTGAAAGAGG AGAGGGAAAA AGCCGGCTTA AAATTTAAAA
TTCAAAAAAC TAAGATCATG GTATCCAGTA CCATCACTTC GTGGCAAATA GATTGGGAAA
AAATGTAAAC CGTGACAGAT TTTATTTTCT TGGGCTCCAA AATCATTGTG AATGGTGACT
GCAGCCATGA AATTAAAAGA AATGTGCTCC TTGGAAGAAA AGCTATGACA AACCTAGACA
GCATATTAAA AAGCAGAGAT ATCACTTTGT GAACAAAGGT CCATATAGTC AAAGCTATGG
TTTTTCCAAT AGTCTGATGC TGGGAAAGAT TGAGGGCAGG AGGAGAAGGG GGAGACAGAG
GATGAGATGG CTGGATGGCA GCACCGACTG AGACATGAGT TTGGGCAAAC TCCAGGAGAT
AGTGAAAGAC TGGGAAGCCT GATGTGCTGT AGTTGCATAG GGATGCAAGG AGTCAGATAC
GGCTTAGCTA CTGAACAACA ATGATATGTG TATCAAAGGT GTGAACTCCA GTTGACCTCA
TAGCTTTCAG TTGGGAAATC TTGACTTTGA TAAGTCTATG ATTTGACTGT AAGGCATGTA
AAACATGACT ATGACTTCAA GGGCAGAGGC AAATGGGACT GAGCACAAAG CACTCTTAAA
TTGTTGGGAG ACTGAATCTG GGACCAACTT TTTGTGGGAA ATTTAGCTAT ATGTATTAAA
AACTTTTAAA TGAGCATACC TTTTGCCTCA GCAATTCCCT GTCTGGAATT TACCTGAGTG
TGTGTGTAAT GACAGAGCTT ATAAAGATAT TTTGTGAATA ATAGGAAGAT TGGTTAAAGT
ACATAACAAA CACTGAATAC CATGTGCCCA TTAAATATAA AGTTGTAGAA AGATTTTGAA
TGACAGGGAA CCATGTTGCA AAATAGCAGT TTTACAAAAT ATTAATAGTA ATAGCTACCA
TCTAGTGTGT GTGCGCGCTC AGTTGTGTCT GACTCTCCAC AAAGCCCACC AGGCTTCTCT
GTTCATAGAA TTTTCTAGGC AAGAGTACTG GCATGGGTTG CTGTTTCCTA CTCCAGGGGA
GCTTGCTGAA CCAGGGATTG AACCTTGGTC TCTTGCCTCT CCTGCATTCA GTTCAGTCGC
```

-continued

```
TCAGTCGTGT CCGACTCTTT GCAACCCCAT GGACTGCAGC ACTCCAGGCC TCCCTGTCCA
TCACCAACTC CCGGAGTTTA CTCAAACTCA TGTCCATTGA GTTGGTGATG CCATCCAACC
ATCCCATCCT CTGTCGTCCC CTTCTCCTCC CACCTTCAAT CTTTCCCAGC AACAGGGTCT
TTTCAAACGA GTCAGCTCTT CGTATTAGGT GGCCAAAGTA TTGGAGTTTC AGCTTCAACA
TCAGTCCTTC CAATGAACAC TCAGGACTGA TTTCCTTTAG GATGGACTCC TGCATTGGCC
AGCAGATTCT TTATCACTGA GCTACCTAGG AAGCCCCAGC ATCTATTAAG TGCTATCTAA
TGACATTACA TACATTATCA GTGCTTTATA CACATTGTCT CATTTAATGT AACTATCCTG
AGAGACCCTT TCCCCTGATT ACCGATAACT ACTTAAAGGC TAAGGAACTA GTTCAGGTCT
CCAGGGTTTG AGAGAGCCAG AATTCAGACA CAGACTATCT GACTCCAGAG ATAATGATGT
CCATCCCCGT ACTCTGTATA CAAGCCCATT TTTGTTTTTT AAGAAAATAT GTATGCAGAG
AAAGAGACTA AAAGCAGATG GTATGTGGCT GGTGGGTATA GATGATTTTC ATCTATTTCT
TGATATGTCA TAAGAGAGGA ACAAAAAGCT TAGTTACATG GAAATGAAAA AGTGTTAGAT
TAAGAACACA TCTAGGGACT TCCCTAATTG TTTAGTGGTT AAGACTCCAT GCTCCCACTG
CAGGAAGCAT TGGTTTGATC CCTGCCCGGA GCTAAGATCT TCATTGGCTG AAACAGTGGG
TACTGTGGGG TCAAAGAAAA AAGAGAACAC ATTCAGTAGT TGTCCCAATA ACCAGGCACT
ATAAATACTG GGCAGTTATT CTGTTCAAAG AGGGTGAGCA GAGGGCAGTG GTCTGAGAAA
CTGAGTCACC CATTTATCCT CCTAACTTTT GACCTTGTGC AAGATGGCCT CATTTGGACC
AGGTGGGTCA TCTTAAAATT AGGAAGGTAG TCTTTAGGTT CCTCCCTCCC TAATATTCTA
TTACCTAAAA TACCCAAACA CTAAATGAGA AAACAGGGCA TTTGAAAATA GTTGGTTTTG
TTCAGTCACT AAGTCGTGTC TGACTCTTTC TGACTCCATG GACTATAGCC AGCCAGGCTC
CTCTGTCCAT GGGATTCTCC AGCAAGAAGA CTGAGTGGGT TGCTATTTCC TTCACCAGGG
GCTCTTTCTG ACCCAGGGAT CAAACCTGTG CCTCCTGCTT GCAGGTGGAT TCTTTACTAC
TAAGAGCAGC AGCAGCAGCA GGCAAATTCT TTACCACTGA GCCACCTGTG AAGCTTAGCC
CAAAGTAAAA TGTTAACTTA GAACTTAAAA CGACTCATTT CTATAATGCA ATGCAATTAT
GAAATGCTGG CTTCAATCTT AAATTTTCGA ACAGAATTTG ATGGCAATGA TCCGCTTGAG
AAAGCATTAG GAAGAGGTTA TGTACTCTTT TCCTGAATCT GCACACTCTT ACAGCTTTTC
TACACGATCG GAGTATTGAA TAGATGCATG TATCACAGGA TTGTGAGGAA CATATTTAAA
CTATTCACTG AATATTTTCA TTCAAAAAGT TTTGTTTCCC CCTCCGAACA CCCTTAGATT
CAGTTCCTGA TTTTATTGGC CCTGGGAAGC AGGGACCTTA TTTCTCAGAA GCTCATTCAT
TAGAGACCGC CTACTTGCCC CGGGGGTGGA CAATGTGTGT GACAGGAAAA AACCTCGGTG
CCAGGGTCCC CGGGTATTTA GGGGCGTGGG ACACTGGCAG TGGCCAAATC CGCCCAGGTC
AGACCAGGTA TTGATCCCCC CGGGTAGCAT TTTGTGGTTG GTCTCCAGGG GTACTCCCCA
CTGTCTATTT CATACCAGCC CGGGAAGCAG GATTTGTAGC GTTGTCGCCG CAAGCCCAGG
GATATAGTCA TTTCCCTGAC CTCTTCCCGG CGGCCGGGTG ACGGTCAGGT CCAGTACCTG
GCTGGGTCCT CTAATGACAC TTGCGTGCTC TCAGCCCAGA CGCCGGGCGC TTATCGCAGC
CAGGCAGGCA GCGCCACGCC TTTCACGGGC CCTCGGGCAT CGACCCTGAG GGAACAGGGG
CGTGAGGGTG GGGCCGCTGC CGGGCGCTGT CCCGGTCAGC AGTCTAAAGC TTGCGAAGTG
AGGCTGAAGT CGGTGCTGCC **TGCGCTCGCT CGTCGGCCCT CGACCGCCGG CTCGCCGCCC
GCTCTCTCCG ACGTGACGGT AACCCGGGGC CAGTGCCTTC CCAGGTCAGC CGCTGCGCCG**
GTGAGTGCGG GGTGCTAGGG GGGCGCGTGG GCGCGGTGGG TGGGCTGCCG CCGGGGGTCG
```

-continued

```
TGGGCGTCGG TCGGGGAAAG TCGCCCCCGG CCGGGCTTTG CCTCCAGCGC GGGCTGTGTC

CTGAATCCCA CGCCGTTACC GGGCGAATCC CGAGCGAGCG GGAGTTTCCG GCGGTCTGAT

AGGGACTGGG GAGACGCTGG AAGGAGGAAA GGAGCCAGAG AGTTTTCGTA AAAGCTTTTC

ATCATTTAGG AAGCACTGTA CGGATGCCTG ATGTCATTGT TAAGTAGGAG ATGCTTCCGT

AGGGTATATT TGGAAGGTCC AGCTGACTCA GCGTTTTATA TAAATGATTG TTAGTGCTCT

GCCTCTGAGC ACAACAGCTC CTGAGATTGA AGCCCTCGGT TAAAACTGAA CCGCTAACTG

TGAGTAAATT GTGAAAACCG TTTGGAATAT ATGGCATAAA AGGTCCGTGG CTATTGTGTG

TGCATTTGGT AGGCAATAGA AAACTGTACA ATTGAAATGA CTAGGTTTTA ATTATTCCCT

CTCAGTTTTA TTTGAAAGTG AGTATGAAAC AGACTGAAAA TTTAGACTCC CCTAAATTTG

GACCTCCACC CCGCCTCCAG AAAACAGCTC CTTGGTGCAA CCGATTTCGT GTCTGGTAGC

ATGGGTCAC ACAGAGTCGG ACACGACTGA AGCGACTTAG CAGCAGCAGC AGCAGTGTGT

TTTAGCCGGT TGGTAAAACT CTTCCCTTTC CCCAAATGTA TGATATTGGA TAGATAAAAG

TTATTGAGTA TGGAGGTAGC AGAGAAACTT GTTAATATTG GTACCTTTAA AGGGATTAAC

CGATATATTC TATGCCCATT TCTTCTCCCT GGGACATAAA GTTTGTCCAC AACTTTGGTT

GGTGTGCTAA AGCATTATTG AGCTGCCTTT TGTAATTTTT CTGTGGATAG TTGACTCAAT

GATTAACTTC AAAAAATTAA CCAGCTTATT AAAAATACTT GTTAAAAATG CTACTAAAGT

TAGAATACAG AAAAATACAT AACCAAAAAA GTTAGATTGT AAATCTAGCA AACAGTTAAA

AAAAATACCC ATAATGTTGC TTTGTTTCAT TTTCTCACTC AGTGGTAGAA ATATAAAAGC

TCATTCCACT TTCACGAAAA AAAAAAAGA TTTATAGTAA CAAATGTTCA TTGGTCATCT

TTGTTCTGGA CCCTGAACAT TTAGCTAGAG CCCCCTGAGG TGCTGTTGCA TCAAAATGAT

ATTAAAATAC ACTTACCAAA ATCAATTTCT ACATTTAGTT GTGTTAAGTG TTCATGAGCT

TTTGAGGCAA GCCTAAGTAT TACAAATGGA AAGAGAAATG CACCAAGAAA AGAGTCACTG

TGGGGAGTA CATTTGAATG TATGTGGACA GCAAATTAAA GTTATATCTT GGAAGCTAGA

ATAAAAATGG ACCAATCAGT CACACAATTC AGTGAGGACA AAGGCAGGAA ATATACATGA

GCTCCTTAGA GAAGCTTTTC CTGGCACCTA CTTCTGAGAG AAATGTCTAA TATCACAGAA

GGCTGCAGAT GAGACTGAAG TATAGCGGTG GAAGAGTCTC CTGGGTGCCC ACCCATAGTA

CATGCGGTCG TGCATTTTCT AGGACTGCTT GCTGTAGTTG TCATTCTCCT TACCATAAGT

ATTATGAGAA ACACTCGTAG GATGCTAAGC CTCTATGGTT CCACATGCTG TGGTTTGATA

GTTTGGGAAT AAATCTGGAT TTTATAGAGG GGTAGGTAGA CCTCATGTTT TCAGATACTG

TTTCTCTCAG GCATTTCTGA CAGAAGTTTG GTGTCAGTTG AAGGTTATAT CAAGTGAGAA

GTTTTATTCT ATGTTGCTTA CTGGGGTTAG AGGTTAAGGT TGAGGCTCTT TTAGTGAAAC

TTAAAGAACC TGAATGATCA TCCTTGATAC AGGGTATATA GGTCTGTGCT ATGCTGTGCT

TAGTCGCTCA GTCGTGTCTG ACTCTTTGCG ACCTCATGGA CTGTAGGCTG CCAGGCTCTT

CTGTCCTTGG AGATTCTTCA GGCAAGAATA CCTGAGTGGG TTTCCATGCC CTCCTCCAGG

GGGTCTTCCC AACCCAGGAT CAAACCAATG TCTCCCTCTT TGCAGTTGGA TTCTTTACCG

TCTGAACCAC CAGAGAAGCC CAAGAATACC GGAGTGGGTA ACCTATCCCT TCTCTGGGAA

CCCTATTCCG ACCCAGGAAT CAACCAGGGT CTCCTGCATT GCAGGTGGAT TCTTTACCAG

CTGAGCTACC AGGGAAGCCC GTATAGGTCT ACAGTAAGCT AAAGTTTATC CTTTTAAAAA

ATCAGTTCTG AGTTCAGAAT GTGAACCAAT AATGATGGAG TATCTAGATG AATTTGGCTT

TATAGTTTTT TTTTCCCCCC AACATTAGTT TATGAGATCT AATTCACATA TCATACAGTT
```

-continued
```
CATGCCTATT TAAAGTGTAC AGTCTCTGCA GTCTTCACAT TTTCATCATT CTCGCCCCTA

AAAACCAGTT AACACTCACT CCTCCTTCTC ACCATAATCC CTTAATCTCT GTAGTTTTTT

GGAAACCAGT GTTCTGCTTC ACAAGGAGAC CATTAGAAAG TGGACATCTA ATTTTTGAGC

CACATACTTA GCTTGTTTAT AGAAATAAGT AAAATATTCA GAGAATCGTA ACAATGAAAG

TTAGTGGTGT TCTGTTGTTT AAAATGAGGT GGGTGGGTGT GGGTGAAGCA GAAGTGCTGC

CCACATCCCA ATTCCAGTGA AGAAGTTTTG TTTTTGGCAA GAAGGGTAGA ATGAAATCTT

AAAACTCCAT TGAAAATGCT GATTACTAGC TCAGTCCCTT TGCAGCTGAA AAGACCTGTT

ACTCTTTAGA GCAATGGTTG GCTGGGAATT ACTGCTTAGA TGGAGGTAGC AGTAGGTAGT

TCTCTGTCAT TTAACGGGAT TTAAGTTCTT ACCTGGAAGC ATAAAAAGGA AAGTCTCTAG

AAAGCAGCAA GCCCTGTTAG CTCCCTCTGA AAACACTTGA GCTGAGTGTC TTACAAGGAA

AAAGGAAAGA TTGCCTGAGG GGTACCCAAA CTTCAGATGT TTTGCACAGG AGACCTGTCT

CTTCTCTTCT GGTCCTGCTG CATGGGCAGT TCTACGCTGA CCACACCCTG ACTTCACCCT

GAAGTGAAGT GAAGTGAAGT GAAGTCACTC AGTTGTGTCT GACTCTTTGT GACCCCACGG

ACTGTAGCCT ATCAGGTTCC TCCCTCCATG GGATTCTCCA GGCAAGAGTA CTGGAGTGGG

TTGCCATTTC CTTCTCCAGG GGATCTTCCC AACCCAGGGA TTGAACCCGG GTCTCCCGCA

TTCCAGGCAG ACGCTTTAAC CTCTGAGCCA CCAGGGAAGC CCTGGACTTC ACCCTAGAGG

AGTGAAAAGA AGGGATGCAA AAGGTACAGG GAACACAGGA TCCTTAGAAA GGGAAAATAA

AGTATTTCAT TTTACAACTT TTCCTCCACC ATCCCATATT ATTTTGAAAT GCCATATGAG

AGTTGGACCA TAAAGAAGGA TGAGCGCTGA AGAATTGATG CTTTCAAACT GTGGTGTTGG

ACAAGACTCT TGAGAGTCCC TTGGACTGCA AGGAGATCAA ACCAGTCAAT CCTAAAGGAA

ATCAACCCTG CATGTTCATT GGAAGGACTG ATGCCGAAGC TGAAGTTCCA ATTCTTTGGC

CACCTGATGT GAAGAACCGA CTCACTGGAA AAACCCTGA TGCTGGGAAA GATTGAAGGC

AGCAGGAGAA GGGGACGACA GAGGATTAGA TGGTTGGATG GCATCACCAT CTCAATGGAC

AAGAGTTTGA GCAAGCTCTG GGAGTTGGTG ATGGACAAGG AAGACTGATG TGCTACAGTC

CATTGGATCA CAAAGAGTCA GACATGACTG AGCAACTGAA CAGAATTGAA ATTAAAAAAA

TTTTGAGAAG CTGAAGCAGT AGCTATATTT TCCATCCACA TTTTTCTCCA GTACTTTGGC

CACCTGATGT GAAGAACGAA CTCACTGGAA AAGACCCTGA TGCTGGGAAA GATTGAGGGC

AGGAGGAGAA GGGGGTGACA GATGAGATGG CTGGATGGCA TCATCGATTC AGTGAATGTG

AGTTTGAGCA AGTTCTTGGA GACAGTGAAG GACCAGGAAG CCTGGTGGGT TGCAGCCCAT

GGGGTCACAA AGACTTGGAC ATGACTGTGA CTGAACAGCA ACAACAAAGA TAAGATGAGC

AGGTCTTCAG AATTAATAAA CGGAAATGGC CATTAACTGG TGAATGCTTG CTGTCTGCAG

GTGGTTTTTA TATTTATTCT CATTTTTTGG TCACACCAAG CCTTTCAGGG AAGTATTGGA

GTTTCGTACT TACAGAGGAG GAGGCAGAGA ATTGTACAGG GTTATTTATT GCTGGGACAA

AGTACTTTAT TAAAGATCAC CAACCCTTTC TTTTTTTTTT TTTAAACAGC CTGGTCATTT

GTTTCACATT TTCTTTCCAT GTTCACAGAG CAGCTCAGTT CATTGTAAAG GCATGCAGGG

ACAGTGAAAA GAGCCTGTGA GAGCAGGGAG GCCCAGACCT ACCTAACTTG GGTCTAGTCA

CTGTGCCATG AAATCTCTTC ATCTTTGTGG ACCAGTTTCT TCGTGGGACT AAAGAATATA

GGAATTTGAG CAAGAGAGGT CTGATTTTAT TTAAGGAGTC CAGAAGTAGA ATATGAGTTA

GTAGAAATTG CCTGAATAGT AGTGTTAGGT ATGCTGAGAA TTCTTAGTAT TCTTACCTGA

TCCTACAATA AAGGATTCTG CAAACCATCT ACTTTGATTT AGAATCTTTC TGATCCATTT
```

-continued

```
CTCCTTTTCA TAACATAGGG AGACTGTTAC ATGTCTTTCT AGAATATATC ATATGATACT

AATAGTTACC CCAAGTAAAC ATATGTACTT GAGAAACCTA AAGTAGTAGG CTAACTGTAG

TAAAAACCCA ATAGTATCAT TTCAGTTATC TCTTCAATCT AATAGTACTG TTATTATCAT

GCCAGACCAT TCACTGCTTC CTCTGGAATC TAAGCTATGA GTATAATCCA TTTGACATGT

GCAATGTTGT TTTATACCCA GCTATTACTA GCAACCTAGG GCCAGGTGAC TCATTACATT

GCTACAGTGT ATGTGCTGAT TAGCTCTTTC CTCGAGCTAC AAGCTATTCC TTGTGTTCTG

ATTTCATACT TAGATATATA CCTGCCCTCT CCCCCAGTGA GATATGTTCT ATCTAGCCTC

CTAGAAGTAC TCCTTACCCA GAAGTAAATT CAAGTGGTTT AAATTTTTCA ACAAAAATAA

AATTGCTATT CTCTCCCTCT ATAATATGAG AAACTAGAAA AAGAGCTCTT TGGTGCATTA

GTCTTCATAA AACAATGCTT TTCCAAATAT ATACAGCTGT GGCTGGGTTG CATCGGTCTT

GATAAGGAAG TTTTAAAGAA CAAAGATGGC AGTTTAAGTT TAATATTACA CTAGCATTAT

AAACATTAAA AAATATTGGG GTTATTTTTT TTTAATTTTT AATTTTGAAA TCATTTTTAG

ACTTACTTAA ATGTTGTAGA AAATGGTACA GAGAGTTCCT ATAACATCTT ATGTAACTAT

AGTACCACTG TTAAAACTAA ACTATAAACT TATTTGGATT TCATCAGCTT TCCACTATCT

TTTTTTCTAT TCAGGATCCA GCCTCAGAGC TCACATTGCA TCTGATTTTT GTATATCCTT

AATTTCCTTC AAACTATGAC AGCTCTTCAA CCTTCTATTG TTTTCCCTGA TCTTGACACT

TATAATGAAT ACTGTTCAGT TATTTTGTAG AATGTCTTGC AATTAATACT GGATATTTTC

TCATGATTAG ATTGAAGTTA TGCATTTTAG GAAGAAATTG GAGAAGGAAA TGGCAACCCA

CTCCAGTATT CTTGCCTGGA AAATCCCATG GATGGAGAAG CCTGGCAGGC TACTGTCCAT

GGGGTGGCAA AGAGTCAGAC AGGACTGAGC AACTTCACTT TCACTAGAAG TAATCCCAGT

GCATCATATC AGGGGTACAT GATGTCTTAT TACTGATGTA AACTGATGTA AACTTTGGTT

AAGAGCCGTT TGTCAGGTCC CTGATGGTTA TCATTTTTTC CCTTTGTATT TAATATATAT

CATGGGAGAG AAACTTGGGC CTTGCAAATA CCCTGTTTCT CCTTAAGTCC TTATTCACTG

GTTTTAGTCC ATTGGTGGAA CTGGATGCAC ATGGTACTGT GTTGTTCTAA CAGTGATTTA

AAGATTGTTT CTCATTACTT CTCTTTATTA ATGAGAATTT TATAAGGAAG AGCTGTTCCT

TCATTTTTTT ATTCAACTGT ATGAATATAG ACTCATGGAT ATTTATTTTA TTGTATAGGT

TATAATTGAA TACAGTCATT ATTTAATTGC TGATCAAATG GTTCCACCAT TGGCCACTGG

GAGCTCTTCT TTCAGGTTGG CCACTGTGCC CTTTTGATGT ACCACCTCCC CATCCTCCCT

TTTGAAAAAG CATTTCCTTG CTTTCTGGTA TCATGAAATG CTCCAGGCTG ATTTTTCTAT

TTTCCATGCC CCGACCCTTG CATCAACCAT TTTTCCAAGG CACTCTGGTT CCTTGTTTTA

GAGGCTGTTA TTATCAGAAA CCAAGATCTG GGTACTAGGT GTGTTACTGA AGTTGCTTTG

AACTTTTTAA GTTTCATAGA TTTGTGACCT AGCAAATGCA TCTCTATAGG AGGAGTAATG

CCTTAAATTT CAAAGACTCT AGAGACCATA GTTGCCAATT TGCATTCAGT CTCTTATGGG

AAAGAAATAC AATTGGAAGG GCTAGAATTT TAAAAGTTCC CAGTTTTTCT CAAATGAAGA

CCTGTAAGTG TTTATAAAAC AAATAGAATA AACACATTAA TTTTTATTTA CTCAGGCTCT

GATAAGAAAT TAGCTTGTTA CTTACTGAAT GTATGTGAAG GGGAGATATG CATAGATCAT

ATCTTTCAGA AATGCAAAAT GTCTTTAAAT GAATTGTGAG ATCCTGGCCT CTACTTCCCC

ACACAAAAAA GACTTCTGGG TAAGTCTTTG AGCCTACTTT CTCATTCTGA AAAGAAAGGT

TTTAGGCAAG ATTTTCATTT CTCTTGACTC TTAGTGGGCT CAGAGGACCC TTTAATATCC

AGAAAATTTG GACCCTTTTT CTATATTTTA GGTATAATTT AGTGTGTGTT TATTGGTTCA
```

```
-continued
CTGGTTAAAA AGATTCAGTT TAATTTCATA TCTAATTTAT GTTAATCATG CCAGCTTACT

TTTAACACTG AAATTTACTC AGTTAAACTT TATTTTAATC TAAGACAGTC CGGACCACGT

ACAGAAGTCT TTTCTAAGAG TTCCATTTCC ACAAACCTTC TTTAACTTTC TTTTTACTGA

TAGGTTTTGT CCTATGCTTT TCCTTTCTCT CTCTCTAGGA TAAAATTACT TTCTTTTCCC

TCAACAAATT GTATTTTCAT TTCTTATACC TTTTTTCCTT TCATGCAAGA TGTTTTCCTT

ACCAATTTTA GTTGTCTCAA TTACATACAT TAACCAGAAT TCTAACTTTT TAAAAACCTC

AATTTCTAGT GAAAACTAAG AAGTATGCAG TTATAAACTG TTTTTCAATT ATTATTCTGT

AGATTGTCAA AATCACAAAT ACTGTTTATG ATTTCTAAAA AATGTGTGGT TTTTTAATGA

AAATTTTTCA ATGTGATATT TTTATTAGTA GACCTAAATA TCTTCTCTGT AAAAAGGCAG

CCTATGTTGA GTAATTAATG TTTCAGTATC TTATTTTATT TGGGAATGAT CTAGATATTT

AAACGGAAAA GAACATGGCA ACCCACTCCA GTATTCTTGC TTAGAGAATC CCATGGACAG

AGGAGCCTGG TGGGCTGCTG TCCATGAGGT TGCACAGAGT CGGACACAAC TGAAGCAACT

TAGCATGCAT GCATGCACTG GAGAAGGAAA TGGCAACCCA CTCCAGTGTT CTTGCCTGGA

GAATCCCAGG GATGGAGGAG CCTGGTGGGC TGCTGTCTGT GGGGTCACAC AGTCGGACAC

GATTGAAGCA ACTTAGCAGC AGCAGCAGCA GATATTTCAT AATTTCCATC ATTTCATTTA

ATTTAGCAAA ACTATAAATA TTAAGTCATC TAAAATCTAG AGAAATTATT TTTAAGTAGA

CAAACCGTAA GACATAATTA TTCTTAAAGA ATTTACCTCA AAATTGTTAC TCTGTTTATA

TCTGTTGAAT TATAGTTATG TTTAGATTAC CATGAAAACT AATGAGACAT TACACAAAAT

AAGCCATCAT TTCAAGATTT TTTTTTTTGA AAATTTTATA ACAGAGACAG TATGACCTAT

TTAACTTTTG GTAAACCTAG GTGCAATAAA AGTAAGAATG GTCTGTATTC ATTAAACCAA

CAAATTTAAA CTTTAAAACT GATTCAGTTC AGTTCAATTC GGTCGCTCAG TCGTGTCTGA

CTCTTTGTGA CCCCATGAAT CGCAGCACGC CAGGCCTCCC TGTCCATCAC CAACTCCCGG

AGTTCACTCA GACTCATGTC CATCGAGTCA GTCATGCCAT CCAGCCATCT CATCCTCTGT

CGTCCCCTTC TCCTCCTGCC CCCAATCCCT CCCAGCATCA GAGTCTTTTC CAGTGAGTCA

ACTCTTCACA TGAGGTGGCC AAAGTACTGG AGTTTCAGCT TTAGCATCAT TCCTTCCAAA

GAAATCCCAG GGCTGATTGC CTTCAGAATG GACTGGTTGG ATCTCCTTGC AGTCCAAGGG

ACTCTCAAGA GTCTTCTCCA ACACCATAGT TCAAAACCAT CAATTCTTCG GCACTCAGCT

TTCTTCACAG TCCAACTCTC ACATCCATAC ATGACCACTG GAAAAACTAT AGCCTTGACT

AGACGGACCT TTGTTAGCAA AGTAATGTCT TTGCTTTTCA ATATGCTATC TAGGTTGATC

ATAACTTTGC TTCCAAGGAG TAAGCATCTT TTAATTTCAT GGCTGCAGTC ACCATCTGCA

GTGATTTTGG AGCCCCAAAA AAGAAAGCCT GACACTGTTT CCACTGTTTC CCCATCTATT

TCCCATGAAG TGATGGGACC AGATGCCATG ATCTTTGTTT TCTGAATGTT AAGTTTTAAG

TCAACTATTT CACTCTCCTC TTTCACCTTC ATCAAGAGGC TTTTGAGTTC CTCTTCGCTT

TCTGCCATAA GGGTGGTGTC ATCTGCATAT CTGAGATTAT TGATATTTCT CCCGGCAATC

TTGATCCCAG CTTGTGCTTC TTCCAGCCCA ACATTTCTCA TGATGTACTC TGCATATAAG

TTAAATAAGC AGGGTGACAA TGTACAGCTT TGACGTACTC CTTTTTCTAT TTGAAACCAG

TCTGTTGTTC CATGTCCAGT TCTAACTGTT GCTTCCTGAC CTGCATACAC ATTTCTCAAG

AGGCAAAACT GATTATTAGT ATAATATTGA CTATTTCCCA GATCACAAGA ACTTGAAATT

TATTTGGGTT GGCTTTCTTT TAAGTAACTT AATTAAAAAA CTTTTTTTTT TTTCCAAGAT

TTTTTATTTT TAATTTTTTG GCCAAGCCCT GCAGCATGTG GGATCTTAAT TTGCTGACCA
```

-continued

```
GGGATCATCC TAGGCCCCTT GTCAGTGAGC ACGTAGAGTC CTAACCACTG GACTGCCAGG

CAATTTGCAG GCTAGTTTTT TATTATATTT TTAAAATATC AATTTGTAAG TGATTACTTT

GTCAACAAAG GTCCGTCTAG TCAAGGCTAT GGTTTTTCCA GTAGTCGTGT ATGGATATGA

AAGTTGGACT ATAAAGAAAG CTGATCACAG AGGAATTGAT GCTTTTGAAC TATGGTGTTG

GAGAAGACTC TTGAGAGTCC CTTGGACTGC AAGAGTTCCA ACCAGTCCAT CCTAAAGGAG

ATCAGTCCTG GGTGTTCATT GGAAGGACTG ATGCTAAAGC TGAAACCCCA ATACTTTGGC

CACCTGATGC GAAGAGCTGA CTTGTTGGAA AAGACCCCCT GATGCTGGGA AGATTGAAG

GTGGGAGGAG AAGTGGACGA CAGAGGATGA GATGGTTGGA TGGCATCATG GACTCAATGG

ACATGAGTTT GGCTAAACTA CGGAAGTTGG TGATGGACAG GGAGGCCTGG CATGCTGCGG

TCCATGGGGT TGCAAAGAGT CAGACACGAC TAAGCACATG AACTGAACTT TTACATCAGT

TAAATACAGC TTTTTTATAT GTGTAATTTT GATAATATTA TCTGGAGTTA GGAACATATC

ATATGTATAA TGTACACATA GAAATATAAA AAGACATAAC TAGAGACCTC ATAGCTTCAT

TTGAAAACTT AGTTATGTAT CAGTTATTGC ATTATAAATT TACTAGTTTA TAAATAACAA

TTTGAATAAG TTAAATATAT TTGCTCAGAT GACTAAAGCT TTTCACTGTT TGTGAAGAAT

ATTTTAAAGT TTGTATTTGT CCTTGATAAA TCCTGAAGGA GGCTGTGAAT TAGATATGAT

GAGGGATGCT TTCTAGCAGT TTGAGTTCAG AAAAGCCTGT TTCTCTCTCT TTCTCTCTTT

CTTTTTTTTT TGGTGCAGGT TCTACCTGAT TGAGCTAATT CATAAGCTCA GTCTTAGGTC

CTTGTGGGAT GTACTTATGT TTCTGATATG TAGAGATTTG TAAGACAAGA CAGTTGCTTT

TAATTCCTCA GAGAACTGGT CTGTCACCTA TATGGTATTG AAAGATTGAT TTGCCCAACT

ACATTTTCTT TATTTGCTTC TTTATATCAG TAAAAAGATT TCCAACTACA GTGAAAATCA

AGAGTTATAT GTTCTAGAAC TTTAGGGTTC AGTTTATCCT GCTTTCCAAA CTTTGCACAA

GCTATTCAAT AAAGGCCCTC TTTTTTGAGT ATACAAATTA AACCCAGAGC AGTTCACTCT

AGGGGCTAAA AGTCTTCATT ATTTTTATTA ACTCCTGAAT ATTAGCCCCC AGTTTTATTT

CATATTGTGT GGGCTCAGGT AACCCTATTG ATTTTCCTTA GTGTGTTTAA TCAATGTTGC

CTGAGGGGCA GATTTATAAG CCCTATCTTA CACCAGGCAA GGGTGACCTA AGTTTATTCC

ATAATATAAT TGGCAGAAGA GATTTAACCA TCTTATATAA AGCCCATTTA AACATACCAA

CTTTTATAAA CATTCATCTC AATTCTCTCA GCTCTTATAT CTGTAATTTT AACCTCCATT

AAGTCCCCAT CAACCTGTCT TGGTCTTACA CAGAGTCCCA GAAACGTTTC TTTTTATCTC

CCTGACCACG TTATCTATCT TTATATAAAA GGCTTTGGGT TTCCCAGCCG AGGGGTTGAG

CCAAGGGACT CAGGCCTTTC ATTGATATTT TAACTTGATT AATTGGCCTA ACTGTTGCCC

CAAGCAATTG AATTTTCTAG CAGCCTTTTA AATATGTATA TGTTTTGCTG TGCTTAATTT

TGCTCAGTGT GTCTGACTCT TTGCGACCCC ATGGAGTGTA GCCCACCAGG CTCCTCTGGC

CATGGGGGAT TCTCCAGGCC AGAATACTGG AGTGGGTTGC CAGGCCCTCC TCCAGGGTAT

CTTCCTAACC CAGGGATCGA ACCCAGGTCT CCTGCATCAT AGGCAGATTC TTTACTGTCT

GAGCCACCAG GGAAGCCCAA ACTGGGGTAA ATAGAGTGGA CTTGTTTGGG GTTCTTTAAT

GATGGAGACC GATAGGGAGT CCCTTTGGCC ATCCAACCTT AGCATTGTAT CAAAATGTTT

GTTTTGATAC ATGTATTTAT TGGTTTATTT ATCCCATTTC TTAACCATCT AAAGATTTTT

ACTGTTTTGG AACAAGTCTC TTTAAAATTT CTTCCTTGTT GGGAAGATGT CTCTAGACTT

TCTCTGCAGT TTTTTCTTAT TCCTGTTAAT CAACCTAACT TAACAATCTA ATGCTTTTAT

TAGCATCTGT AAGACCCGTT GAGGGGAAAT TGACCACAAA TTTAGTTTCC CAAACTTTTT
```

-continued

```
TGTTGTTGCT TTTTGTTCGT TTAAACTAAG GGAGTTATTA AGGTTAGCCA TTATATTTTT

TTGTATCCAC TTTCTACTTT GGTCTTTTCA TAGGTGCCAG TAATCCAGCT GTTAATAGTG

AGAGTTCTCT AAAAATTTCC CAGTTTAGAA GTTTCTTCAA TTTTAATCTC CATTGTCTGG

CCATTGCCAG AGCTCTCATA ACACAGGGAG GAAAAAAAG TCTTAAGATC AGGTAAAACA

TTTATATCTC AAAGACACAG TGGGAGAAAT GCTAGTTCCT CCTTTGAAAA GTTTTTTGTT

CCTTTAAGGT CAGAATTCCG AGAAGATGTT TTATCAAGCT GGCTTTTTCT AGCTGCACAC

ATGCACACAA AAATTAACTT GGAGTGTTA AAAGAACCCA CATTTGGTCC TTTTTAAGGT

GAGGTTTCCT TTAATTCCCA ACAAAGCAGG TACTTGTAGG AATAAATTCT GTTCATACAT

AATAAAGTCT TCCCAGCGTC TCTCAACTGT GGTAATCCAG TTTTCAACTG AGCAAAATCT

TTCCCTTGTC AGTTCATCTG GGATAACCCA GGTACCTCTT CTTGAAATTA AGTTCAAGGA

AAATCTCCTC CAGCGAGGAT TTTATTCACC ATCAAATAAA ACTAAGGATA ATCAGCCAAT

AGTGGAGATC CAGGACCCAG AAGAGATTTA CCTAAATTCA TATGGACTCT GAGGAGGTGG

CTAGGCACAA GAGGTCTTTG CTGGTACCAA GGCTCCAGAT TCTTGTAGCG TTCGGGTGAG

GGAGAGAAGT CTGCTCTGGG TCCCTTTGTT GCTAACTAAA GCGGTCGACT GAAGAAAAAC

GCATAACCTA AAAGTTGCAA GTTAAGTTTT ATTTGAGGAT CTTACTGAGG ACTGTGGTTC

AGGAGACAGC CTCTCAGATC ACTCTGAGGA ACTGCTCCAA ACACAAAAGA ATAAGGGAGT

AGCCAGGGTA TTTAGGAAAT TTTGCTGAAA CGAAAAACAA CAACAGGAAA AACCAAACCA

TGTAGTCAAA CATCAAAGAT AGTCACAAAA AATAGACATT ACTAGTTAAT GATTTAGTA

CTTTTCTGTA TGAGAAGATA CAAGACTCTG GGCTCATTGT AATTATTCCT TAGATATGCA

TCTTAACTTA TCTAGGGCCA GTGCCCAGAA CACACAATGC TTCCTTTTTT TCTCTATCCT

AATTTCTCCT CAGCTGTACC TGGGGGGTTT GGGGAATGCG ACTGCAGTGG CTAATGGCTT

GATCCTTGTT TACTGGAATA AGAGGCAACA TTCTTTGTTT ACTAGAATGG CAGGCAACAT

TCCCTGTCCA CGTCCACGTC TGTCAGTTTC CTCTTAAATG TAAATGAGTG TGAATGTAAA

TGTAAAATGA ATATAAAATG TAAATGAGTT TCCATGGACC TGAAGCTGGA CCATTACTAT

ACTTGCCCTT GTTTTCCCTT AATTGGGCAA ATTTGGGGA GGTTGAGAGT GAGATTGCTT

TGAAATGGGG CAAACAGTAG AGAGTCATTA TAAAACTCCC ATTGGCTGTG ACCTTGCTGT

GGGAATAGGT GCCTTTTGCT TGTTGGAATG CTGGATCTTC CTTGCTCTAC CAGCCCCACT

CTTTTGTGTA TAAAGGCTGC ACACCAAGGG TAACCGGCAT CCTAAGATAT ATATCTGAAT

ACACTCTTCC TTAGAAACCA GATAATGTTT TTACATACAG TTTCAGAGTG CTTGTTTTGT

GTCTGGTGTT GTATTTAAGA GGCTTCCCTG GTGGCTCAGA TGGTAAAGAA TATGCCTGTA

GTGCAGGACC TAGAGGACAG TGTCCACATC TTGGCTCTTG AATGACTACA GTAGCCTCTA

TGTAGTCTCC CTGCTCTGCT CCTGTCTCCA GCACCCCAC CCCCACCCCC AAGTCAGAGT

GATCTTTTTA AACATAATTA GATTATGTTA TTCCTCCACC GAGAAGCCAA GCAAAGTTCT

TATAGTGGCC TGAGGTATGG ACACTGCCAG AATTGACCTG AACCTCTGAC TTCATATCCT

ATGCTCTCCC TCCCTCTGCT TCAGTCCCCT TGGCCGTGCT CTTCCTCAGG CTAGCACTTG

ATCTTGGCAT CACAACTCCA GAGAGCCACC CTCAGGTTTC TGCTCAAAGA CCTCATTGGG

AAGGCCTTCC CTGACTTCAT TTCCTCCTTC ACTTTTATTT TTTTCTCTTT AGCACTGCTG

ACTCTGACGT TTTTCATCAA AAGGAAAAAG GAATAGGAGT TAGGGACATA CCCCCATGCA

GTCAAAAATC CATTATAACT TTTGACTCCT CCAAAACTTA ACACATATTT TATATGTTAT

ATGCATATCT ACATATATTT TATCATTGAT GACATATCTA ACTTTCTTGG TTTTTTTCAA
```

-continued
```
TATTTCAAAT TTTTTCAAAT TGTTGCAAAT CTTGAAAAAA AAAATCTCCC AATATATTTA

TTGAAAAGAA ATCCACAATA TAAGTGGACC TGCACAGTTC AAATCTGTTT GTTCAAGGTA

TGGCCAAACG CAAGTTCATA TGCTCGACAC ACAGTAAGGC CAAACTGAAA CACTGGAGTT

TGGAACAGAG AAAGGTTTAT TGCAAGGACC AAGGAAAGAG AATGGGTGGC TGTACTCAAA

AGATGTGAAC TCCCTGATGG TTTTCAGGAA AGTGTTTTTA TAGGCAAAAT TTGGGGTGAG

GGCTGCAGGG TGTGTGACTT CTGATTGGTT GGTGATGAGT TAGCATGGTG GTGTTTCAGA

AATCTTGTGC TCAGCCTGAA GTTACTGTTG TCCATCCTGG TGGGGCCTT ACTTCCTATA

GAAAAACTCA AAGATATTGT AATGTATATC CCTTGAGGGG GAACCAGGAC CCTGCTCCTT

GGCTGTCCTA TAGTTTCTTG ACTGCCTTTC CTTGGTTTCT GCATTCCTTC ACTCTTCTAA

TTAGCAACCA TTTGAATCTG CCCTTTGAAA CTCAGGGAAG GTCTGAGAAA CTGAAATTTT

TTCCCTGCAA ACAAGAAATG GGATACAGAG AGACTTTGT ATGCAAGAGG GCCACACAGG

GTCCTGCCAG GTTTCAAGGG TCAGTTATAG TTGCATTAGG TACACTTGTA TCTATTTAAA

GAGAGGATTA GGATTAAATG GAGGGACCTC CCTGGTGGTC AAGTGATTAA AACTCTGCCT

TCTAATGTAG GGGGTGTGAG TTCAGTCCCT GGTCAGGGAA CTAAGAACCC AGATGTCTCA

GGGTGCGGCC AAAAAGTAAA AAAATAGTAA TAATAAAAAA ATTTTTTTTA AAGATTAAAT

TAAAAAAGGG ACAGGAAACA GATCTATGGT TGTCATGGGC TGGGGTGGGA GAGGGAATTT

CTTTGGGATG ATAGAAATGG TCTTTGTCCT ACTTTTCATG ATTACATGTC TGTATACACC

TTCAAAGTCC AAAAACTGTA CTTAAAGAGG ATGTTTGATG GTCTACAACA CTGTTTACTA

TTGACACGTT TTGAATAAAC ATGACAAAAA ACAGAGATTA GGCTGAACCA TGAGTAGAGT

TGGTGTTATG TTGGAAGGAA TGTTATATGT ACCAAAACGT TCCCCCTCTT GTTTGTTATC

TATTCCTTTT TCCTCTGTGT TTTGTGTGTG TTAGTCACTC AGTTGTGCCC GACTCTTTGT

GACCCCGTGT ACTGTAGCCC ACCAGGCTCC TCTGTCCGTG GGATTCTCCA GACAAGACTA

TCAGAGTGGG TTGTCATTTC TTCACTAGGG GATTTTCCTA ACACAGGGAT CAAACCCGGG

TCTTTACCAT CTGAGCCATA AGTCACCAAT TCTCCGTGGA TCCCTCACTG GTCTTACTGC

GTATCTCCTC AGTGCAGGAA GGACGGGGAT CTGTAGAATG AGGGAGGAGA TGGCTGAGGG

GACCTGTGGA GCTTCCAAAG TCAAGTCTTA GCTCCCTACA GGGCATACGT CACTCTCTGA

TGAACTTTGC TGCCTCTCCA GCCTAATTTT CTTACTGCCC TTTCCCCAAA GCTGAACTTT

AATATAATGA ACTTACCAAC TAAAAAAAGT CACAACCTAA AAGTTGAGGG TTATGCTGCA

TTTGGTGGGA ATTTTTAGGA CTTCAGGACC GGGAGGCAAC ATTTCAAGTA GCCTTGAGAG

AACTGCTCTG AGGAGGCAGG GTGGAGGAGT CAGGTTATAT AGACCTTGGC AACGAAGGAC

AGGTAGTCTG AACATCAAAA GTATTTTTGT GAATTAAAGA AAACCAGCTA TCTCAAGTTA

AGGAATTTAG CACTTTTCTG TATATGGCAA GATGCAAGCC TCTGAGCTCA CTGAAGTCTT

TCCTTTCCTA TGTATCTCAG CTATCTGGGG CCAGTATCTT GTGGTTTTTC ACATCCTGAG

TTCTCCTGGG CTCCCCATAG GGAGTGGCTG CAGCCTGAAG GCTGTCAGAT CTTGCTGGTG

TTCTTCTCCT TCCTGGGTGC CCTGGAGGGC TGGGATCACT GGTGACTGTG ACCTCATTGT

TTACTGATAT GGCAGGAAGT ACTCCATTTC TCAAACAGCA TGCATTTCCC AAAGCAATCT

CTTTCAGTTT AATGATTTTG CTTTCCTTTA CTAGGTCAAC TTTCTTTTCT CTTCTCTCCT

TCCTATATAA CTGGTTAGTC TCCTTTAATA GGCCACTTCT AACCACTGTG ACCCCCACCC

CCACCCGCCC TGCCCCAAGC CATGTATTCC CTGAGAGATG AATCTGGTCT TAATCCCTCA

AGTAATTTTG AAGCTCTAGG CAAAGGGGTA GGGAAGGACA TTCCTGGCTG GAAATTCTGC
```

-continued

```
TTTGAAACAG GATAATTATA TTTTCTCTCA ACTCCACCTG GGTTAATACA GTGAGTTTTT
AGGGGGTATT CATTAAGCTT TGTCCTTACC TTCCACAAAG TCCAGGTGAA ATCTTTGGTG
GTATTTGTGT CCTTTCTAAT TTGTACATAT AGTTTACTAA TCCTGGCAGA ATTTAACTTC
TGTAGATGAC CTCTCTAAAT AGGGTGGTTA GTGACTTCCT CTTGTTTGTG CTCACAATAT
CTTTATGAAG CTACTTTGCT TAATACAGGG GTGTGGCATA TTGTAATTTA GTCTTTCATT
CAGCGGGAAT AATTGAGAAT ATGATATGAG TGACCCCAAA GGATACAAGG GCTTCCCTGG
TGGCTCAGAG GTTAAAGCGT CTGCCTGGAA TGCAGTAGAC CCGAGTTCGA TACCTGGGTC
GGGAAGATCC CCTGGAGAAG GAAATGGCAA CCCACTCTAG TACTCTTGCT TGGAGAATCC
CATGGAGGGA GGAGCCTGGT AGGCTACAGT CCATGAGGTC ACAAAGAGTC GGACACAACT
GACCAACTTC ACTTTACTTA AAGGATACAA AATTGATGGA CATTAGGTCC CTGCTCTTAC
AACAGACATG TGGGCAAATT TTTAGTTTGC AAATGCATAT ATGGCTTTCT GAAATGGCAG
GTTTGCAATA AAGTCCAAAG GAGATAACTT TAAAATATCA TGATTTTACT TATAATTTGG
GAGATAGCTG AAGGCCAAAA GGGCATGAGA AGAATGTTCC TGCACTGTGA GCTAGGGCTA
GAAAAAACAT TTAATGATAA ATTTGCTTGA TGAGCTGTGA TCCAAATACT GGTCATACAT
TGTTAGATAA AGCTTTGTGA CTATTATTAG AAAGCTTTGG AGGGTGGCTG GAAGGTCTAT
AGTTCATTTA AATTTATTAT TTTTCTTTCA TCAGCCCACC TTCAGTATTT GAAATTCGGA
ATAAAGTAGT CTGAAATTTA CCATGAAAAT GCTATGAGAT TTGTTATTGT TAGGGAACCA
TTAATTGCCC ACTTTGGCCG GGCATGATAA TAATTGCTTG CCTGAGTTGT CTCACAATAG
GAGGTCCTGG TAAAGAAGGA GGTACTACCT CCAAAAAGTA ACAGGAAAGA GTTCAGATCA
GATCAGTCGC TCAGTCGTGT CCGACTCTTT GTGACCCCAT GAATTGCAGC ACGCCAGGCC
TCCCTGTCCA TCACCAACTC CCGGAGTTCA CTCAGACTCA TGTCCATCGA ATCAGTGATG
CCATCCAGCC ATCTCATCCT CTGTTGTCCC CTTCTCCTCT TGCCCCCAAT CCCTCCCAGC
ATCAGAGTCT TTTCCAATGA GTCAACTCTT CACATGAGGT GGCCAAAGTA CTGGAGTTTC
AGCTTTAGCA TCATTCCTTC CAAAGAAATC CTAGGGCTGA TCTCCTTTAG AACAGACTGG
TTGGATCTTC TTGCAGTCCA AGGGACTCTC AAGAGTCTTC TCCGACACCA CAGTTCAAAA
GCATCAGTTC TTCGGCGCTC AGCCTTCTTC ACAGTCCAAT TCTCACATCC ATACATGACC
ACAGGAAAAA CCATAGCCTT GACTAGACGA ACCTTTGTTA GCAAAGTAAT GTCTCTGCTT
TTGAATATGC TATCTAGGTT GGTCATAACT TTCCTTCCAA GGAATAAGCA TCTTTTAATT
TCATGGCTGC AGTCACCATC TGCAGTGATT TTGGAGCGAG CCCAGAAAAA TAAAATCTGA
CACTGTTTCC ACTGTTTCCC CGTCTATTTC CCATGAAGTG ATGGGACCGG ATGCCGTGAT
CTTCGTTTTC TGAATGTTGA GCTTTAAGCC AACTTTTTCA CTCTCCACTT CACCTTCAGG
AAAGAGTTCA GGAGGGGCCA AAAGGAGAAG GGAGGAGTCA ATATATCCTA TCAACCTCCC
AGAATCCTTC TCGCTGAAAT CCATCTTGGC TGAGAGATGT ATGCACCACC AGGGAGGACC
CTGAGTCAGA ATGATTGGCC AGAGACAACC TGGAAACCAA CCCCATTACC ATAAACGCGG
AGACTCTGAG CCATGTGGTG GAGCAGTTCT CCTGGGTTCC CTTCCCCTGC TGCTCTCCGC
TGAGGCACCC CTCTCTAATA AAGTCTTTTG CTTTGTCAGT TCGTGTGTCT CCTTGGACCA
TTCATTTCTT AGAGCTCACT CTTGGGCCCT ATAAGGGGGT CCCCTTCCTG TACTCAGTAG
TAAAAAATGT TTTGATAAAA TGTGAATTCT GTTTGGGGAC CAGATACTTT AGGGATTCAT
CTTGTTTGTT TTACTTGAGG AAAGTGATTT AATTCAATTT AGCTATTGTT CAAAAGACAG
TTCTAAAATA ATGGAAGCAT TGCCTTTTTT CAGCCATTGT ATATATGATC ATTTTATAGA
```

-continued

```
TTTGTTATTC TTAACCTGAA ACATATAGCA CTGTCCTATT TTTGAAATAA ATATATCTCT
TTCTCTCTCT TTAGTCGCTA AGTCGTGTCC AACTCTTGAG ACCCCATGGA CTGTAGCCTG
CCAGGCTCCT CTGTCCATGG GATTCTCCGG GCAATAACAC TGGAGTGGGT TGCCATTTCC
TTCTCTAGGG GATCTTCCCA ACCCAGGAAT CGAACCCAGG TCTCCTGCAT TGCAGGCAGA
GTCTTTACTG ACTGAGCTAT AAATATAGTA TAGTTTTATG GTATTTGAA ATCTAAGAAT
GAATTTGATA ATAGCATATA GCAAGTATTA TTTTTTTTTT TTTTGATGCA GGATGAATAT
GGGAGTGCTT GGGGTGTCCT CATAGTGTTC AAGTATATGT GTCTTTTATG GGGTTATAAA
ATTGACTGTT TATAAAGTAA CCCAAGAATG AGAAAATACA TTTTTAAAAA GTAAGCACTT
TAGACCTGTG TTGTCCTATA TGGTAACTAT TAACCACGTG TGGCTATTTA AGTATAAGTG
AGTAAGTTAA ATAACATAAA ATATTCACCA GCTATATTTC AAGTGCTGAG TAGCAGCCAT
ATGTGTCTGG TGGACAGCAC TATTTTATTA TCCCTATGCG TATTAATAAA GAACATGGAA
AGGAGCACAG GCACTTTTCC ATCTGACCTC TGATTATCTT GAACTCAAGA GAATCACTTC
TTGGGCCTCA TTTACAGCCT TTTTACACAT AAGAAACCAG ATTACCATCT ATGAGATCAG
TGGTTGTGTA ACTTGTGAGA ATGAAGGGAA TTGGTAATTT TATTTTGTGT GTGTGTGTGG
GGGGGGGGGT GGGGGCGGGG GCCTGTGCTG CTAAGCATGA AGGATCTTAA TTCCCTAACC
AGGGATTGAA TCCATGCCTC CTGCAGTGGA AGCACAAAGT CCTAACCACT GTACCATCAG
GGAATTCCAG GGAGTTGGTA ATTTTTATCT TGTCAAGTTA TATATCTCTT AGCTGGTGCT
CCCTAATCTC CACTATTTTA AACATATCCT CAGCACTCAG TCCTTGATAA ATCCTTCTCT
TAGCTATAGA GGAGGGGAGA AAAAGTTTT CATTACCAGG CCCATTCCTG TGTCTCACTG
TTAGCGTGTC TCACTGTTTT TCTGCAGTAG CCTCCTAACG CCCTTGCTTC CACACTTGTC
TCACAGTAGC AGCTACAGTG ATTTTTAAAA AACAGTTAAG ATCATGAGCC TTTCCTGCTT
GAACGGCCTC AGCGGCTTCT CTTGGACTAT ACAGACCTTC CGCAATGGTA TTTCTTCCTG
TCTGTCTGTC TGACCTCGTT CTTTGTGCCG CCCTCCCCAG ATCACTCTGC TGCAGCGCTG
TGGGGGCCTT GAGTGCCAGA TCGTTTCCTT GACCTGAAGA CATCAGCCCT CTGACTCCAA
CGCTGCAGTG CCGATGTCAA CACTGGATGT TTGCTCCAGG GTGGAACTGT TAGATGAGAG
ATGATGTGAA AACCCATTGA TGGATAGAGG ACTCTTTAAA CTTCAGGGAT TTATTGTGGA
AGTTACAGCT CAGATTTTGA GTTCCTTTTC TAACAATGTT CAAAACTATC CAGCTTCTAT
TTCTGTTTGT TCATAAGTTT TGTAGCAGTC ACCTGACAGT GACCCAAGAA GCCTAATTCC
TTGTCAGGGT AGCGAGGTCT GGGCGTCACA GTAAATAGCT GAAGAAGGTG TGTTTACCCA
GCATGTCCTC TTGGCTATGA GGCAGAGTGT CACTTTTGCT ATTATTATCC CTAGGGGAAA
AAAAAGTAAG AAGAAGGCCT GAACTCTTGA CCTGAGGCTG CTCTGGCTTC TACCAGCAGG
TGCAATATTT CCAGCTATGG ACAGCTGTCT GGCTGAGGAC TTTAGAACTG AACTCTACTT
TTATTACCTG TGTGCAATTT CTATTGACTT ATGTACTCTG TTTATAGTAG ACTGTCTGAT
TAAGAGTATG ATAAAGAGTA AGATAGAGAA AAATGGTATT TTTTTTTTTT TAAGCGAGTC
CTATATTATT GAATTCTGCA ATAGGGAGCA GAATTATATA TGGTTGAGTG TGTGGGCTTC
AAAGGCAGCA GGCCTATTTT GGCTTTTTTT TTTTCAATTA ACTAATTTAT TTTAATTGGA
GGATAATTAC TTTATAGTAT TATGATGGCT TTTTTCATAT ATCAACCTGA ATCGGCTACA
GGTATATGTG TCGCCCCCAT CCTGATCCCT CCTCCCACCT CCCTCCCCAC CCTATCCCTC
TGGGTTGTCC CAGAGCACTG GCTTTGGGTG CCTGGCTTCA TGCGTTGAAC TTGCACTGGT
CATCTGTTTT ACATATGGTA ATGTACTTGC TTCAATGCTA TTCTCTTAAA TCATCCCACT
```

-continued

```
CTTGCCTTCT CCCACTGAGT CTAAAAGTCC ATTCAAAAGT GGTAGTTTTA ATGCAAGTTA
TCATTCTTAT AATAGATATA CCAGTGTCTA TGGAAGAAGA CTTTCCAAAA AGTAAAAAT
GTACCTCATT AGTTAGAAAA CAAGAAGAAG AGAGGAAAGG TGACAAAGGT AGACACAGGT
AGAAAAGAGA TAGCTGGGAA GGGGGAAAGA ATCTCGTTAT TCAAAGCCGC TCAGTCATGT
ATGGAAGACT GTTCCAGCTG GTGAAAAGAT AATCAGGCCG GTTAACAGGG CAGGCTGGTT
CAGGCGAGTT GTATGAAGCC ATTTGGATGC TGCTTTTATT TTTCAAGTCT TTGAAGTGGG
TCTCAGATTC AGAAAACGAT TTAGCACATG CTCTGGAAGC TGAACTAAAC TGGAAGCAAG
GAAGCAGCAA CAAGGGGGGA AGTTGATTTT TGTCATAGGG AAATCTAGAT GTGGTGTATA
TATATATATC TGTAGGGAAA GATTAATGTT TACTTAGAGA CAGTTACTTT CAGTGATTCC
TCTATAAACC CAGGATACTG GGATAAACCC AGTATCTGGA TAAACCCAGT ATACTGTATA
CAGTATACCC AGGATACTGT ATAAACTGGA GACTTGAGTA CTTGAGGTTA ATATGGTGCT
GAGATGTGTG TTTTTAAAAT TTTGTTATCA TTCCTATAAG TTTTTTGTTT CATCTTAGAG
TAATATATTG TTTCATATTG GTGTTAGAAA TAAGTTTGGT TTTTGGTATA ATGTGCTTCA
GCTGGATGGT GTACTTCAGT TATGCCTGCT CATCTCTTGA TTTGTGACAC ATGAATTACT
AAGACCCTGT ACTAAGCATC TCCTATTCCT AAGCACCTCC TAGCAATGTG AATTACTAAC
TTAATCCTAT CACAGTGAAG ACGAACTCAG TATGCACATA CTTCTAGAAT TGTGATTGTA
TTTATCTGTT CTCTATCTTG GATGGATGGA TGGGTATGGA TGATCTTTCT TGGGTACTAT
AGTTCCAGTT GGTGCCTTTT ATTAACAGAA AATCTCACAA AGATTTTGTA TTAATGTTTG
TCTTGAGCCA ATGGCCTATT TAAATTTAGG TGGGATGTTA TTTGATTCTC TTAATGAGCC
TTGTGGAATA GGAAATGACA ACCCACTTTG GTATTCTTGA CTGGAAAATT CTATGGGCAG
AGGAGCCTGG CAGGCTACAT TCCACGGGTC GCAAAGAGTT GGACAGACTG ACCACACACA
CACACACACA CACACACACA CACAGAGCCT TGGGAGATTG TTAGAAAGTG TCCTTACGCA
CACACGCACA CACACACACA GCCTTGGGAG AGTGTTAGAA AGTGTCCTTG GAGCCTGAAC
ATCAAATGGG GAATGGCAAG AGAAGCAATT GCTCGTGTCA GGCTAGTATA GTTTGGCTTT
TGAAGACATG GGGGATGGCT TAAGAAGTTT ACAAAGTCGA TATGCAAGGT CTCTATAGTT
ATTTGCACCT TGAGCCTTCT CTTTCACTGC TTTCAGAGAG TAGGGCTTGA GCTAGTTATT
ACCATTCATT GTGCTCACAG ATTAAAACTA GGCTCTTTTA ATTTTCTGGG TGCCAGTCTA
TAAGTGGTTT CCTACTTTTG CAGTTTCCAA AGTGGAATAT GTTTAAATG TGATAACAAT
AGAGCAGTTT CCGGCTATAG GAAGAATTAC AGATTATTTT GATTTGGGGG AAGTTCTACT
ATGATATGCT CAGGTGTGTG TGGTTTTCTT ATGCATATCC TGTCTTGGTG TTCCTGGAGC
TCCTTCAGTC TGTGGCTTGA TACCTTCAGT TTTGGAAAAT GTTTGGCCAA TATTTCTTCA
AACACTGATT CTGCTTCATT TTTATTTTCT CTTTTTCAGG TCTCCAGTTA CTTGTATGCC
AGATCTTTTT CATCACATTT CATATGTTTC TTAGCTCTTT TATGTAGTTA AAAAAAAAA
AGCTACTTCT TCATTCTCTT CAGTCTGAAG TTTTTTGTTT CTTTTCCATG CTGATAATTT
TCATACACTC TTCAATCTGG ATGTTTTCCA CATGGAAGTC TGTCAGTTCA CTAATTCTTT
CCCAGTCTGT ATCTAAACTG CTATTAAACT CATCTACTGA TTTTTAAAA ACTATTGATT
AGTTCTTTGG TGATAGCCTA TCTTTTCATT TATTTTCTTA GACATATTAC TCAGTTATTT
TAACGCAGAT GTCTGATGAC TCCAACGTGC AATACTTATG GGTCTACTTC TATTTTCTTG
TTTTGGAACA TTAGGTCTTA TTTTCTGGCG TGCTTGGTAA TTTTTTATTG AAAATTTGGA
TGATGATGAC TTTGGAATAG ATTTAAATTT CTTTTAGCAA AATATGAGTG GATCACATTG
```

-continued

```
CTTGAGTAAA GGCTGGTCTG CTTCTAGGTT GCTCATATTT CCAGGTCATA GCCCTACTGG

TACGATCTCA AAAACTTGGG GTTTTCAACT GGTAAACTCA CAGCTCCAAA CTTTGTCTCC

CTGTTAATGA GCTGCTACTG CTGCTAAGTC ACGTCAGTTG TGTCTGACTC TGCGACCCCA

TAGACGGCAG CCCACCAGGC TCCTCCATCC CTGGGATTCT CCAGGCAAGA ACACTGGAGT

GGGCTGCCAT TTCCTTCTCC AATGCATGAA AGTGGAAAGT GAAAGTGAAG TCGCTCAGTC

GTGTCTGACT CTTAGTGATC CCATGGACTG CAGCCTACCA GGCTCCTCCA TCCATGGGAG

TTTCCAGGCA AGAGTACTGG AGTGGGTGGC CAGTGCCTTC TCCGCCTATT AATGAGATGC

TACTTAAATA TATTCATTCA GCTTTTGAGC AGCTCTTTCT GCCTGGTTTT TCTGGGTTTT

GCCCCATGTA TGTGTAATTT GCCTCAAGAA TGCTGGGCAT GGAATGCTTC ATCTTTTCTC

TTTTCCAGAA TTTTAGATAC TTAAGTCCTG GCTGCTTTGG TTACACCCAT CAGAAAACAT

TCTTCAAAGA GCTGCATCTT GTATTTGTC TGCTTCTACA GTTGTCCTTA GGAGGATGAT

TGGTTTGGAC AAGCTACTCT ACAGTAGCCA GAGAGAAAGT TCTTCATTGA TTACTTTGAT

TTTTAAGAAT TAAAACCAAG TTTATGGAAG TTTCATTTTT CAAAGCTATT GCACAAGCTG

TTAAGTTCAC CTTAAGATCC TACTCTAAAT CCTTATAAAG GGGCCTTTTC TAACTTGTTA

AATGAAATAT TTTAAACTTC ATTTATAAAT TTAATACTCA CTTGTTGTTT TAAATTCTTT

AACTACTTAA CTCTTGGTTT GATCTTCTCA ATCATTTTTA TACATAATTC TAAACCTTCC

TAGAATTTAT ATGTTGTCCA TTAAGAAAAT GAGTTTATCA TTCCAAACAA TTTTGGAGTT

TGTCTTCTTA GTTGATTAAA GGAACATAGC AACCAGAGAT GTAAAGTCAG GAGCTTTAAA

TTCAAAGAAA TGTCTCTTGT CACTGACTGC TTGGCCACCC CCCTTTTTGT AATATCTATG

TCATACACTC AAATAAGAAT GGAGTGATGG TGATCATGTA GCCTGTCCCT GATCTTGAGT

CATATTAATA ATATATTTTT TAAGTCAGCT CTAACTCCCA TTTATCTTTT GCTGTTTCAT

GAGTTTTGAG TAATTTTCAT ACTCTCCCTA TTTACTTGTT AGATGTTTAA TTGACATCTA

ATTGGAGTTT ATATATTCGG AGTTGTGTCT GCCTCCCTAA TGTAGGTTCC AAGCTTGTTA

TTGTTGTTGT GATATGGCCT ATTCATTGGA AATGGAGCTG CTTATTGCAT TGAAGTTTAA

AATGGACTTG TTTTAAAATT TTAAAAATAC ATTTAATTGT ATTAAATATA GCCAAACTAT

TTTTACTTAA ACATGTTATC AATATAAAAT GACCAATAAG GCATTTTACA TTAAACTTTT

TTTGATCTCT AAAATTTTTA ACAAATTGAA ATAATTGACA TAATAACATT AGTTTCAGGT

GTACAACATA ATGACATAAT ATTTGTATAT TTTGTGAAGT GATCACCAAA ATAAACCTAC

TTAATATCCA TCACACACAA AAGTCACACA TTTTTTTCTT CTTATGGTGA GGACTTTTAA

GATCTCTCTT GGCTACTTTC AAATATACAA TACAGTATTA TTACCTATAG TTACTGTGCC

ACACATTATA TCCCCAGGTC TTATTTATTT TATAACTGGA AGTTTGTACC AAAGCAGTTT

TGTTTTAAGT GTATTGTTAA CTACTGTTTA CAGTCTCATT TACCTGGACT ATCAACTTAT

TGTTGCTTTT CCCTCCACAG GAAGGCGGAA ATGCTCAAAA TGTCTTCCAA TAGTTACGAG

GTTTCTATCC CAATGTCAAA AAAACTCAAC GGCATTCCAG AGACAACCTC TAAGGACCTG

CAGACATTAA CTGAAGGAGC TGTGTTAAGT TTTCATAACA TCTGCTATCG AGTAAAAGTG

AAGACTGGCT TTCTACTTTG TCGGAAAACA ATTGAGAAAG AAATACTAGC AAATATCAAG
```

PUBLICATIONS CITED

These are incorporated by reference to the extent they relate to materials or methods disclosed herein.

Ashwell, M. S. et al. (2004), *Dairy Sci.* 87: 468-475.

Bennewitz et al. (2003). Session G1.9, 54st Ann. Meet. Europ. Ass. Anim. Prod. Rome, Italy.

Bennewitz et al., (2004). *J. Anim. Breed. Genet.* 121:307-318.

Boichard et al., (2002). *Proc. 7th World Cong. Genet. Appl. Livest. Prod.* Montpellier, France. 33:19-22.

Chenu, C., et al. (1994), *J. Bone Miner. Res.* 9: 417-421.

Cohen, M., et al. (2004). *Genomics* 84: 374-383.
Cohen, M., et al. (2004) *29th Int. Conf. Ani. Gen., ISAG*, Tokyo, Japan. F015.
Drackley, J. K., et al. (1991) *J. Dairy Sci.* 74: 4254-4264.
Ejendeal, K. F. and Hrycyna, C. A. (2002). Review. *Curr. Protein Pept. Sci.* 3: 503-511.
Everts-van der Wind, et al. (2004). *Genome Res.* 14: 1424-1437.
Farr, V. C., et al. (1996) *J Dairy Sci* 79: 543-549.
Fernando R. L. and Grossman M. (1989). *Genet. Sel. Evol.* 21:467-477.
Georges, M., et al. (1995) *Genetics* 139: 907-920.
Glazier, A. M., et al. (2002) *Science* 298: 2345-2349.
Gottesman, M. M., et al. (2002) *Nat. Rev. Cancer* 2: 48-58.
Grisart, B., et al. (2002) *Genome Res.* 12: 222-231.
Grisart, B., et al. (2004) *Proc. Natl. Acad. Sci.* 101:2398-403.
Hedrick, P. W. et al. (1987) *Genetics* 117: 331-341.
Israel, C. et al. (1998) *J. Dairy Sci.* 81: 1653-1662.
Israel and Weller (2000). J. Dairy Sci. 83:181-187.
Jonker, J. W. et al. (2005) *Nat. Med.* 11(2):127-129.
Kashi et al., (1990). Anim. Prod. 51:63-74.
Kaupe, B., et al. (2004) *Anim. Genet.* 71: 182-187.
Kerr, J. M., et al. (1991) *Gene* 108: 237-243.
Kerr, R. J. et al. (1996) *J. Anim. Breed. Genet.* 113: 457-469.
Kaname, T. et al. (2001) *BioTechniques* 31: 273-278.
Kuhn, C. et al. (1999) *Anim. Genet.* 30: 333-340.
Litman, T. et al. (2000). *J. Cell Sci.* 113: 2011-2021.
Mackay, T. F. et al. (2001) *Ann. Rev. Genet.* 35: 303-339.
Mackinnon and Georges (1998). Livest. Prod. Sci. 54:229-250.
Meuwissen and Arendonk (1992). J. Dairy Sci. 75: 1651-1659.
Nadesalingam, J. et al. (2001) *Mamm. Genome* 12: 27-31.
Nauli, S. M., et al. (2003) *Nat. Genet.* 33: 129-137.
Nemir, M., et al. (2000) *J. Biol. Chem.* 275: 969-976.
Olsen, H. G., et al. (2002) *J. Dairy Sci.* 85: 3124-3130.
Olsen, H. G., et al. (2005). *Genetics* 169: 275-283.
Ron, M., et al. (2001) *Genetics* 159: 727-735.
Schmitz, G., et al. (2001) *J. of lipid Res.* 49: 1513-1520.
Schnabel, R. D., et al. (2005) *Plant & Animal Genomes XIII conf.*, San Diego, Calif., USA. P532.
Seroussi, E., et al. (2001) *J. Mol. Biol.* 312: 439-451.
Seroussi, E., et al. (2002) *J. of BioInformatics* 18:1137-1138.
Spelman, R. J., et al. (1996) *Genetics* 144: 1799-1808.
Spelman et al. (1999). J. Dairy Sci. 82:2514-2516.
Stekrova, J., et al. (2004) *Nephrol Dial Transplant.* 19: 1116-1122.
Su, A. I., et al. (2002) *Proc. Natl. Acad. Sci.* 99: 4465-4470.
Thompson, J. D., et al. (1994) *Comput. Appl Biosci.* 10: 1929.
Veenhuizen, J. J., et al. (1991) *J Dairy Sci* 74: 4238-4253.
Velmala, R. J., et al. (1999) *Anim. Genet.* 30: 136-143.
Wallner, B. P., et al. (1993) *Biochemistry* 32: 9296-9301
Warren, W., Smith, et al. (2000) *Mamm. Genome.* 11: 662-663.
Wayne, M. L, et al. (2002) *Proc. Natl. Acad. Sci.* 99: 14903-14906.
Weichenhan, D., et al. (2001) *Mammalian Genome* 12: 590-594.
Weikard, R., et al. (2004) *29th Int. Conf. Ani. Gen., ISAG*, Tokyo, Japan. D060.
Weller, J. I., et al. (2001). *Quantitative Trait Loci Analysis in Animals*. CABI Publishing. London. 287 pp.
Weller, J. I., et al. (2002) *Genetics* 162: 841-849.
Weller, J. I., et al. (2003) *J. Dairy Sci.* 86: 2219-2227.
Weller, J. I., et al. (2004) *J. Dairy Sci.* 87: 1519-1527.
Wiener, P., et al. (2000) *Anim. Genet.* 31: 385-395.
Winter, A., et al. (2002) *Proc. Natl. Acad. Sci.* 99: 9300-9305.
Zhang, Q., et al. (1998) *Genetics* 149: 1959-1973.
http://genome.ucsc.edu/goldenPath/hgTracks.html; Human Genome Browser Gateway
http://nce.ads.uga.edu/~ignacy/oldprograms.html; Threshold model programs
http://cowry.agri.huji.ac.il/web/; biopsy procedures.

---

The invention claimed is:

1. An isolated polynucleotide comprising the bovine ABCG2 nucleotide sequence shown in SEQ ID NO: 183, wherein the nucleotide sequence comprises a missense mutation that encodes a substitution of tyrosine-581 to serine (Y581S).

2. An isolated polynucleotide comprising the nucleotide sequence shown in SEQ ID NO: 183, wherein at position 1742 the adenine (A) is replaced by a cytosine (C), resulting in the missense mutation Y581S.

* * * * *

SEQUENCE LISTING

```
<160> NUMBER OF SEQ ID NOS: 198

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acctgggaag cctccatatc                                                     20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctgcaggcag attctttatc g                                                   21

<210> SEQ ID NO 3
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtcagaatgg agctcaatgc                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatgtttgtt tgaggccgga                                                  20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
taagacattg gcagcaggtg                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctagtgttcg ggtgcctttc                                                  20

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgccttgatt tttcatttta tgc                                              23

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctgacaatcg cacagcaact                                                  20

<210> SEQ ID NO 9
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcagcaacag cacagaggta                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tggtgtgggg ttgtaggttt                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cattaaagca gggtgggaga                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atgctgtgat ggtttgcatt                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgggaccaac catttcactt                                              20

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agccacacga aaagact                                                 17

<210> SEQ ID NO 15
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 15
cccccaatta aaagggact                                                    20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaggcaagtg aaagaagac aa                                                 22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgcctgggga aaatacaaga                                                   20

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gggtcaccac ttacagttca ctt                                               23

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gaaatttcag ggggatt                                                      17

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttcatcaaga ctcggtgctg                                                   20

<210> SEQ ID NO 21
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 21
catccatcac ctcagtgtgc                                                     20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aaaggcagag ctgcagaaac                                                     20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gatccattgg agggcaagtc t                                                   21

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aactgcagca actttaatat acgctatt                                            28

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acgttggatg ccacgcccaa atcttttctc                                          30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acgttggatg ttcaagttgg gagccgaaac                                          30

<210> SEQ ID NO 27
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 27
gaagatatca gaggaggac                                                  19

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acgttggatg tctcccaccc tgctttaatg                                      30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acgttggatg gcctcttctg aggtcaattg                                      30

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctgctttaat gtatccttttt c                                              21

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acgttggatg taaacctaca accccacacc                                      30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
acgttggatg gcctgtttgt tcatactccc                                      30

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
```

```
                            primer

<400> SEQUENCE: 33
accgtttggg aaaatcacc                                                    19

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
acgttggatg atttcggctc tgaagtggag                                        30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
acgttggatg taagaagtgg tgggaaccag                                        30

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cctgtcatcc tgcagacc                                                     18

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acgttggatg gattgtgtcc tgaggaagtc                                        30

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
acgttggatg caagtcatag ctgacagctg                                        30

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 39
ctgaggaagt cttattaggt                                              20

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
acgttggatg aatctcaaaa ccgtcgtgcc                                   30

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
acgttggatg cggtgacaga taaggagaac                                   30

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gagcattcct cgatacggct                                              20

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
acgttggatg gcttctcact ttgtaggatg                                   30

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
acgttggatg ttgtcaagtg cttctggacc                                   30

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 45
ttcgctgtaa ttcattcctt a                                               21

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
acgttggatg caagacaggt tatagattgc c                                    31

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
acgttggatg ctgaaaatgc tcattttggc                                      30

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gttatagatt gccaacttgc                                                 20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ctgagtccca accactggac                                                 20

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgtatgctga atgggtatct tca                                             23

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
```

-continued tgctatggat caaatactat ccaagtt         27

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ccccgtcctc taaagaatgc         20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tgtgcgattc cacattgttt         20

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
aaagcaagca gccgctaat         19

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ctctgatccc ctgagaattt tca         23

<210> SEQ ID NO 56
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cactgttttt ccttgttcat aataaacac         29

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57

```
atctgtattt actggatcat                                                 20

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ctgtatttat tggatcatt                                                  19

<210> SEQ ID NO 59
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
aactttaaaa gggagaggaa tgttacc                                         27

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aaacaatgtg gaatcgcaca                                                 20

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aaagcaagca gccgctaat                                                  19

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cctggatatt gcaagaca                                                   18

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
taagacattg gcagcaggtg                                                 20
```

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
tctgtccaga aaccagagca					20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
gaaaggatgc tctggtccag					20

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
cattgaaaca ggagaccgtg t					21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
tgtgactcat cctaagtggg c					21

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
ctggggctac aggaaagaag					20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
attctgggat tttgtgtggc					20

```
<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
agatcccaca tgcacctagc                                               20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cccggccctc caaggcatgc                                               20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cagtaaccct gctcggtcat                                               20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tctgggagat cctggttgtc                                               20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cacaggggac tggactcttc                                               20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ttgctgtctc cattttccaa                                               20
```

```
<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ccctttctga atattttcac ctc                                              23

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gatttgcttc tgcctcttgg                                                  20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
agcatctgga gcagccttta                                                  20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
actcctgtcc tctctgtgcg                                                  20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tggagtgttt ccacacaaaa                                                  20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ttgtgtgcct gctatgcttc                                                  20

<210> SEQ ID NO 82
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tcacttagag acccctgttt                                                20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tttgggctgg ttaaatggat                                                20

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tgcaacttct gcaagatgta ct                                             22

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tgctcaatga agatgttagg aga                                            23

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
caaacgggta ttgtcccaag                                                20

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gaagaaaacc cttctttcag c                                              21

<210> SEQ ID NO 88
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gaacctttga actcatctac agc                                          23

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gctaattaag ggcacctctg c                                            21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tcttccatag aggaaggaaa a                                            21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
aaatacccag atgctgtagc c                                            21

<210> SEQ ID NO 92
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
aaattctcac aattaaagaa caacca                                       26

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ttcaaattcc ggcaaaattc                                              20

<210> SEQ ID NO 94
<211> LENGTH: 26
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 94
aaattctcac aattaaagaa caacca                                          26

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
tctgaggaaa ctgatgacaa caa                                             23

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
cctctgagga aactgatgac aa                                              22

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cgttagatcg gcggaacttc t                                               21

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tctgatgtct gttgtgcctt aga                                             23

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gcactgtaaa gcctaaggga ca                                              22

<210> SEQ ID NO 100
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 100
gccattaagt gctttgttgt ga                                              22

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gtttttgcgc tcaagtccat                                                 20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
cccttcctag ctgttcgttg                                                 20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
aagcagggtg ggagacaata                                                 20

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
cgtacgtgtt cattcagca                                                  19

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
cagagtccag atgccacaga                                                 20

<210> SEQ ID NO 106
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 106
ggcccaagga agaaacgaac                                                   20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ggaatggtgg tggagatgga                                                   20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
cgaggaggaa gaggaggaag                                                   20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cgacctcctc ttcctcctct                                                   20

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
aacaggagag cctcccttaa a                                                 21

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ttgcatattt gccctgtcaa                                                   20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 112
gtgcggtctg taagggtcag                                              20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
tatgggaagg gaatttggag                                              20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
ttggcttgtt ctgtcttcca                                              20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gctgtgcact taacactggg                                              20

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
aaaatgttgc ctttgctttc a                                            21

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
aagtgtctgt ggcttgtgga                                              20

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 118
tcaggaacca gttgtctctg taa                                          23

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
aaactgcagg caatggtttt                                              20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
cctgactgca tccatgtgtt                                              20

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
aggttggaga acaacaccaa a                                            21

<210> SEQ ID NO 122
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tcttcattta atcttttgtt ttcca                                        25

<210> SEQ ID NO 123
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
tgttgaagga cctgaatttg ct                                           22

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 124
atttcccctc tcttttgcag                                              20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gaaaccttca tggtggctgt                                              20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
tgtcaaaaga atgctggaca                                              20

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
catcatctct tcttttcttc caca                                         24

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ttttcccaaa gaatttggta gc                                           22

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
gttgtttcag ccagattgcc                                              20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
```
ggcagaacaa acgaaaaagg                                               20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
aagaatctca atttgcccgt                                               20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
gatcgtgtgc atggatgagt                                               20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gattggttca acacctgcaa                                               20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
cagtgatccc gtgttcttca                                               20

<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
ttcgagttga caaggggc                                                 18

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
cacaagatgt ttttgtccct c					21

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
tgttttcccc atacatgcaa					20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ttccgaaggc aattcctaaa					20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
atatggtggt cagggcacat					20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
tggaaaagaa tcccaaacca					20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
gctcaccaaa tttatgggga					20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
accaaccgta ctttggcttg					20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gattcagctt gcctacctgc                                              20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
cctcttgatt gccaggaaaa                                              20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gattcctgtg agctcaaccc                                              20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
cacacaccac aaaaaccctc                                              20

<210> SEQ ID NO 147
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
ttcatcttgt cagatggtaa cca                                          23

<210> SEQ ID NO 148
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
tgtttacagt ctcatttacc tgga                                         24

```
<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
atgcagattt tggcaggttt                                                    20

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
aactggcttt aaactgggtc a                                                  21

<210> SEQ ID NO 151
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
tttctttgta gttttcatgt gtgg                                               24

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
catgaaacct ggcctcaatg                                                    20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
tccatgtgga tccttccttg                                                    20

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
aagaggtaaa gcctgatttg g                                                  21
```

```
<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
ttcatatggg caagtgcctt                                                     20

<210> SEQ ID NO 156
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
gagtgatggt attagaaaag acctg                                               25

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
taggacctca cctgtgtgga                                                     20

<210> SEQ ID NO 158
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
caacaaatga tagtggcaga gg                                                  22

<210> SEQ ID NO 159
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
tcctgaagag gtaaatgcca tg                                                  22

<210> SEQ ID NO 160
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
ccaagaaatg taagtttcag atgttt                                              26

<210> SEQ ID NO 161
```

<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 161
acaaaggagt cacttggagc a                                        21

<210> SEQ ID NO 162
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 162
tttaccagga ctatcaattt ttgtg                                    25

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 163
taaaccacgg ctgtttgaat t                                        21

<210> SEQ ID NO 164
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 164 aaagggttg tagaaaatg ga                                         22

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 165
catttggggg acattatgct                                          20

<210> SEQ ID NO 166
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 166
ggagagattt gattaagtag ccaga                                    25

<210> SEQ ID NO 167
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
gaatttgaaa caagcacagg g                                                    21

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
ttggggaaag aattttgcag                                                      20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
ggtcagactg gtcacatcca                                                      20

<210> SEQ ID NO 170
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gcaaatggtt taatctcctg gt                                                   22

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
acagaaagtc ccctcccatc                                                      20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
ttggattaac cccctctttg                                                      20

<210> SEQ ID NO 173
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 173
attcctaccc ccaaacttgc                                                    20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
atttgctaga cggcaccaga                                                    20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
tatccttggc catgagctgt                                                    20

<210> SEQ ID NO 176
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
tttctttatc ctgctcccac tt                                                 22

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
actgggctga ggaatccttt                                                    20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
ggcatcccat tattgttcca                                                    20

<210> SEQ ID NO 179
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 179
tacccacatg gagaaatgca                                                   20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
tgaagactct cggtgtggtt                                                   20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gaattgaagg cctcgtctca                                                   20

<210> SEQ ID NO 182
<211> LENGTH: 84480
<212> TYPE: DNA
<213> ORGANISM: Bos taurus

<400> SEQUENCE: 182
aggagagact ccatcttgaa gcctgtcatc cgtcttaaag acaggatgtg aactgggccg        60
gaaccctgct taagagtgag gaaacagttg ctagtgaaaa ccaggtctcc tggagacttc      120
actccctaca gatggcaaac ggagattgta gttgtggtca ggctgcccct gttagattaa      180
tcatggagac atcctccctt gatgtataat cattgttccc ccctcccggc cccacctccc      240
ccgttaacct taattgtttg ttctcctagc acctacttgt aaaactcaat catatacaac      300
aaaaagattg ttaacatgta accagtcacg tgtgtgtgtg tgtgtgtgtg tgtgtgtgtg      360
tgtgtaaaac tgggcctctc aaaaacatca gggtccttgt tgggaactga ttccccttgg      420
acctgctggc ataataaact gtactccagt cttgagtgtc ccctgaggtg tgttttgcaa      480
ctcaggattc cacaacattt ccagaaggac atcagtgttg acctagacag gtgaagcaaa      540
aatgtttgga gccaacagag atctaaccag tgaagtcact gaaccttgtt cacaaatcaa      600
gggtagattc tttcaaggac caggtgacta ggaggcaagc gaccaaaggc aggactggtt      660
acatatttcg tgacagtgtt ggtcgctcag tcgtgtccga ctctgtgcaa tcccatgggc      720
tgtagccttt caggctcctc tgtccaaggg attcttcaag caagaatact ggagtgggtt      780 gccatacccct ccgccaggga atcttcccca cccaggggact gaacctaggt ctctcgcatt      840
gtaggcagat tctttaccat ctgagtcacc agctgggtcc tgtgcagctg tacaggtcgt      900
acccccgtat ccgaggggga aatactttca aagcaaacgc ggcaagttaa tgcagagcac      960
gggaaaaagt agggcgccca ttcactgcat ctcaaggcct tccagcactg aacaagtagc     1020
actgtgggtg gtgcctggcc ccaggtggtg actgaggctg ctgcctcgga ttccccaacc     1080
aggtacaccc ggagcagctc gcatcctggc ttcataggca gagacgagaa tagcggtgtg     1140
```

```
gggcgctctg ctcactctca ggaagggggc gagaggctgc gcccagaccc tgtaacccc    1200
gccccgcgcc cctccatccc ccgcccggag ccctgtatc cccggccggg cgcccctccg    1260
gcccctgctc cactggtcta gcggctgcgc ctcgggaggg cctggcggag ccccggacct   1320
gcgccagaaa acggtccgaa cagctagctg cccttccggt cctccttttc cgctttgttt   1380
cttctcggtt tccatccacc ctaagtcctt ttctcctctc ctctcccccgc cccgcggtgt  1440
caatctcccc ggattgacag agaacgtagc ctaaatacta aagctgagag aatcgcgcgc   1500
ggaggcgctc gctggtcccg cctcctgccg gctttctttt ctctgtgcgc cccgggtggg   1560
cttggcggaa ctggcctcta caccccgaca tcctccatcg actgccgggg gccgactgtt   1620
tggaaagagg atgggctgg tggcggcggg gaagcgctca tctgcccggg aaaatagctg    1680
gagaggagtg cgggattaga gctatgcccc tgatagtgtc cccgcaacca gcgagaccct   1740
gtagttcctc ggtcctggag gtatgttctg ggcagcacaa cacagcaact gctatgtatt   1800
aactgtcttt gcagataata ctgaagagat gaaaggactt gtctgaggtt tcagacaaat   1860
cctcatcccc aggaactgcc ctgttcctag ctcttgctta aatggtgggc atgagtggct   1920
atgtgtgtcc aaactgacac attttgctg tttggatggc aggatcctga agagaaccat    1980
tccttagcta gtcagagacc aaagtctata ctaaaggaag gatcagctct ctaactgtat   2040
aatgggagga gctggttttg agagattgtg tcagctggca tggccatttc tagataatac   2100
acacactttt gactttggag agaggagata cttccccaga gtgtgacagg caaatggagg   2160
gaacagctgc ctctgccgtg ttgtgtgtgt gtgtgtgtgt gtgtgtgtgt gtgtgtgtgt   2220
gtcctcagtc gcctctgact ctttaacacc ccatggattg tagcctacca gggttctctg   2280
cccatggaat tttccaggca aggatactgg catgagttgc catttccttc tccaggggat   2340
cttccagcct agggatagaa ccctcatctc ctgcgtctct tgcattggca ggtggattct   2400
ttaccaccgc accacctggg aagccgcctc caccctatga gagtctcagt tccaacccat   2460
ggctcgtttg ataggacttc tgcacaggcc taaactcctg caggtaacaa atacaaaaa    2520
gttactgcct aagggtgcag ctagggatta aaacacagcc ctattactgc aaattttcc    2580
acaacagaag tcaggtaagg ttaataagca cttatatatt aagaattagg tgggaaaata  2640
tttcagaagg aactgagaat gctgcagttg ttcattgaaa gccaggagga ataatcggga  2700
aatgtgtcag gctccctctg tccattctcc acatgctgat caccacacac tcatgtttgc  2760
attcttcaa tctcacctcc cagataattt aaaacacttt agcattgcat aaaaaaaaa   2820
aaaaagccct tccttcctgg tctattccct gcctctactc ccttgtcatt ttttctaact  2880
ttccttcttg aactttatcc cagcctgtgt acgttcttct ctctccctgt aacacaatcc  2940
cacttctttc ccaggtaaac ttcaagttca gatgtcatgt cccatcggat gttttattct  3000
gccattcctt cagtctaaat gtcccttcca tttagtcctc tgccatccaa tatttacttc  3060
tattctaaca cctgttaccc tgtgtcagaa ctctttgttt ccttcccttt cttcacccttt 3120
agggtgaatt gtttgagggc aggggctagg tctctttcct aaataatcct aacagcacag  3180
taggcatttg gtaaagtttg gaatgcatga atgacatgct taaaatagag aagttattat   3240
ctcattcctg aaccttatct tagtgcttga gtgtacaccg ttccaaaatg atgaatcatg   3300
gaaagaataa aaatgcactg tgttactaag aaatgaagcc ttaaggtttc taaaattaca   3360
accaaagtgg gcaggtgggc ccagcaccat tgtatgaaga tcttattcag tcagttctag   3420
caagctagga tggcatggct gaggaagtac ggcagtggta cttgaagtaa gaaacaatga   3480
```

```
taatgtaaga atatccaagt ctaagggttt ttgtaggtcc tgcaacgtct ttacactgtg   3540
atatttccgt gatgctaaac ataggaacta aaaagcctct tgatgagggt gaaagaggag   3600
agtgaaaaag ctggcttaaa actcaacatt cagaaaacta agatcaaaaa caaacaaaga   3660
tcattgaatc tggttccatc acttcatggc agattgatgg ggaaaaagtg gaaacagtga   3720
cagattttat tttcttgggc tccaaaatca ctgcatatga tgcagcagt catgaaatta    3780
aaggcacttg ctccttggaa gaaaaacgat ggcaaatcta gacaatatat tcaaaagcag   3840
agatatcact ttgatgaggg taagaggagg aaggtgtggc agaggatgag atggctggat   3900
gacatcacca acttaatgga catgagtttg aacaaactcc gggagataat gaaggacagg   3960
gaagcctgga gtgctgcagt taatgggtca cagagtcaga catgatttag cgactgaacg   4020
acaataaaac ataatgagaa gcttgtctac tgccaaagcc taaaaccaag ttcattgaag   4080
agaatccctg cctcaaggtt tcaatttgga aagtcagaga acagtagaat ttggttttct   4140
aatagttaac ctcttacttt caaggtcaca cagtttatta ggtgttaatc cagaaattgt   4200
tccaagctgt accccatggg gcttccccag tggctcagcg ggtaaagact cctgcaatgc   4260
aggagacaca agagagggg gttcgatccc tgagttggga agatccctg gaggagggca    4320
tggcaaccca ctccagtatt cttgcctgga gaatccgatg gacagaggat cccggcggtc   4380
tacggtccat atggtcacaa aagagtcaga catgactgaa gtgactgagt gtataccgt    4440
aggtcactgt gcagttttg aggacagggc ctaggtggtt ttactcagtc atgcacacac    4500
acagtacctg ttgcagacct gccacagtgg gtactcagct tgctgaatga aggaagaaat   4560
gaataaatgt gctctaccat aggggtgtag atgagaggga aaggcactgt catttctcca   4620
aagatggaag gctttagaat ctgggggaaa ataaatattt actttgaaaa taaacttatc   4680
aaagtaaagg caaaaaacta ttttagatgt cacaaagatc tatgttaagt tgctgaatca   4740
gttgttacta ttttagagga tgatggaaac ttatcttctg aaatgttggc ttgtctgcct   4800
aagagggggtc aaagcaaaat ggtccagtct ggagtttcct gaatcctgac ctccttacct   4860
gaaaaactga gcagttattt ggcccagtta tttaacagat gactcagttt tgtcatttgt   4920
aaaatgggga tgattatacc acatgggttg ttgagagaca ttaaatagtt aatacacaac   4980
ctatgaagta atttgtatcc catttctgc cactatttcc tatttctcta ggtgtcattt    5040
tgcctttcac tgtggcataa acatttctg ttttttctcg gtccacttct gtgctttttt    5100
ccctctcact acctttctgc ttttttcttt tttactatct ctctccctaa ccaaattctt   5160
ctttttttt tttttttcct ttggccatat gaggaatgtt agttccctga ccagggatgc    5220
attcctctcc ctatgcagtg gaagcacagg atcttaacca ccagatggcc aggaaagtgc   5280
caatttcttc ttaacgttct catagttttt cctcactcac ctaaaaaaat gactgagggc   5340
tatgaacttc agtaaactta tagaataaga aagttaataa tgactattaa aacactattt   5400
tcttttcccc aaactgattt ctcatctctg ccgtgcttat gcatacttt tttgtatttg    5460
aaaatcagtg aatacgttca ggctaattta gctctgattt cttcacttta atataacttt   5520
atactgaaag ggtcaggata tgtccttccc caatatgcca ctttggcatg aggattaatt   5580
tgagctgaat gcaattaaga atcaacagat acagaaagaa gccttctcag catttccctt   5640
atcttattaa aaagcagaaa cttttgagaa atgaggctgt cataaattcc ctcttccagga   5700
tgggcttatt cctaggagag agataaaagt aaatataccg taaatctctc tgggagtttc   5760
atggccatga agacagaaaa gaccacttgc attttcacaa acaaatatta tatcaaactt   5820
tatctccagt ttattctcct aaaaatcctt ttgtctttcc tacagaaact cacttgttct   5880
```

```
ttccatagaa gattttcctg catttccttt cttcccctac taagttaggt acataagctt    5940
ctatctttaa ccagtgagct actagctatt ccgtatgaa taagccctttt tttcctcctt    6000
ttgtcttttg tcagcttaat tcagaggtcc ccagggagga aacctaagag ggcagagcaa    6060
acatttttcc tcccatatgc catgatcagt gtagaccaca cggttgttat taattttat    6120
gactgtggtt catataccgc agtttgtcac attcctctct catggggcac attgattgat    6180
tctgattttt ttactcttta aatatatcct tcctttatga cactttccct tgccttctct    6240
acttcataga tatatacaaa catacacatg tgtaattatg taaatatata aaatttgctg    6300
catttgttgt ctaaatcttc agttttgag tcatcaggca gtgcttccct cttgagagtc    6360
tctctttata gaggtgatca aggcaccagt cataaactat tgtacctaga tttcttaaac    6420
tctaaatatt tattaacaac cataccaatg tgggaggcaa taagagagg tggggttggt    6480
tggttcagta aaaattattg cgttgatttg agtccctctt ctctcctaga gtttcttgtg    6540
ctgccggttc aggacataaa aaacatgtat gaagaattta caagaaaaat ctgtcagaat    6600
tactgctttt ctgctgtggt gtttggcttt aaaattttt aaagcaccat ggaagcagat    6660
ttggtgtttc aaagttctgc cacaagagtg atttttaagta atgttcatag cctctgttta    6720
tattatcgta tggtttataa ttatgactgt aagtctcagt taaatgatta ccatgtgaac    6780
agcaccatac tgtgggacta caaaacctaa gatgtggtct ttaactctgg aggaccttat    6840
aattgcaaag tgagaaacac aaactatgag ttctgaggta cttgtacata gtagtcattg    6900
acagtcttaa taataaaagt atgcagcata ggattttga ctctataaac aatactgtct    6960
tgagtttgct tctaaacctt aaagaaaatt tggagcaact tttccatacc ctggaacaaa    7020
ggaatagatc atcataaatt tgcatggatg gattctggag aattctgaag actccatcat    7080
aaaccaacac aggttagaaa acgaaacaag ttttgcataa tatcaaaggt ccttccacca    7140
tttttcaaata actgacctaa gcactgctgt ctgttacagc ctctcagagc actgaggaat    7200
ggttaaagtc caggaaaaaa caagactgca aaaatatttg cctggggacc atcttcttga    7260
actccccacc tcgataattt ggattagctt cctccctatt ccatgccatg gattctgatt    7320
agaaaaagt cttctctagt tgaaggactt cattgttctt tgagttagag gatgaggctg    7380
gctgtttgaa acctttctca cttttcctat tccaaagtgt tcagtatcta ctcaaacaaa    7440
attgggaatt aaactctatg tacatttaag ggatatacgt atttgtgaaa gataaaggag    7500
gcctccaaga attagatagg attttttacta cacctcttca cctggacaca atgcttcctt    7560
tataagaaat aagggatagt cagcggttct ttgccttgt aaagaaatag ctagggattt    7620
cacagaagtt cctaggaatg attagcttat tcccagttgc ttggaaaata ggtgatccag    7680
gacaagataa tatgcattgt tagatagtgt gcccaatagg tgatccagga caagataata    7740
tgcattgtta gatagtgtgc ccaagtcaat agaagggatt ccattcaaga agctgccttc    7800
ccgtatattt tatcttattt aataaactta aaccaaagat gttcaaatct tatttcacag    7860
aacccagtga gtccttaaac attttgttct gacttttgt ttgtggattg gtggatatct    7920
tttatttaa aaatgcacaa atatattttt gtgacaattt gtgaattgat taatctattt    7980
tatcaagttc ctactggtat actaggtaca atcctagaaa ctaaggctct gtcaatgaac    8040
aaagccataa acattcatac ccccatagag cttatattct aatggaatca gaaatacaga    8100
tataataagt aaggaaatta cataaatgt tagaaggtaa taagtgctag taacaaaaat    8160
aagatatggc agatcaagaa tgctagtagg aggaattgca atttttagtt ggtcagggta    8220
```

```
gtcctcatga gaagttacca tttgaggaaa aacttgaagg aagtgaaaga atgagctaaa    8280
tagatgaata ggggaagaat tgcccagagc agctagggca ctggccagga agtgggtcag    8340
tgtgtgtata tttgagctat aacggagata tgtctcgcta tattacaatt agtaaagggg    8400
aacgtcagag taggggtgga agatacatat tgtaaaggtg tttggctttt actcttaaga    8460
gaaataggaa aatagacgaa tacattgtga gaagtatttg aacaatagag atatgtattt    8520
tcaaaacagt atctccactt cctaaaccta tacttcccag acattgctgc catttggggt    8580
catatctttc taaaggcttt tctccatgat tacatgcata gatgggtaca aatagaaata    8640
cacaattttg tttcgtgagg atatgtgtgt gtgtctctgt ctacatgtgt gcattttaac    8700
ataaaaaaat aaggtcactc agttgtgtct gactctttgc gaccccatgg aatatacagt    8760
ccatggaatt ctccaggcca gaatactgga gtgggtagcc attcccttct ccaggggatc    8820
ttcccaaccc agggactgaa cccagatctc atgcattgca ggcggattct ttaccagctg    8880
agccaccagg gaagcccagt gaacttatat tcactgggga ggtaggagac aggggacctc    8940
tgggtgggac agtttcccag gtggtgcagt ggtaaagaac ccacctgcaa tgcaggagac    9000
gcaggacacg tggattcaat ccctgggtca ggaagatccc ctggagaagg aaatggcagc    9060
ccattccagt attcttgcct aggaaagccc atggaaagag gagcctggca ggctgtagtc    9120
catgaggtga caaagagttg gccacaaccg agtgagcaca cacacagggc cagatatcag    9180
gtgtttgtca agcagagtaa aattcaagct tgttcttac ccagacactt caaggacaaa     9240
gctagtggca aaagctgagc tctgctaaag taaagagata agatgcccgc tcctgaggtc    9300
aaggaagact tccctgtcta tacatgtaca ggaaggcttc ttgggggtct aaaaagggag    9360
gggtccccac cccataagtg tggacatgca tccataggcc tctgcagtgg gatctatctt    9420
agaaaaatat tgtgctccgc aaggactctc ttggagaggg tcctaggacc aatcagatgt    9480
gaagagagaa acaagatgat tggttaaata tatacaaaga cccggaagga ccgccctata    9540
taagggattg gttaaatata tacaaagacc cggaaggacc gccctatata agggatttgc    9600
agcaccttct tactgtgctc ctcttcgctc aggatgcctg ccctcctctc cgggtgtgta    9660
tctctgccta gcttctgact tcctgcactc ctcatgagag aggatgcccg gacccttctc    9720
ctctggatgt gtatctctgc cctgcttttg acataaatta acaattttca gtgtgctttc    9780
tcatacattg tgttgtatct ctaataataa actttgcatg tgttttttaca gcttttgcct    9840
tcttgaaata gtcttgcttt caaatcaggg aaaaccacag ggccattttg cttctagcct    9900
ctagccoctg gcaatctaat ggctaggatt cctagttttc atccaggtta cccaggttca    9960
attcttgggc agggaactaa gatctctctt caggaccact cactgctcct tcctccaaga   10020
tcaatattct tgtgttaatt agcaacttgg ttttataat tgacgtgtct tggagacctt    10080
tctttgtcat gatagtacac atatttctat ttcattcctt tttaactatt acataatagt   10140
ctattgtaca catatgctac attttgttta accatacttt tattggtaaa tgtgtgtgtg   10200
tgtgtgtgtg tttgtgtgtg tgtgtgctca gttgcttggt cgtgtctgac tctttgtgac   10260
cccatggtct gtagcccacc aggctcctct gtccatggca ttttcccagc aaaaattctg   10320
gaatatttaa gttctaattt gcctcgtagc ttctttcctt tccatgttga attactattg   10380
tcttaatatt acatttaata acataaaatt acgtgttgca tgaaacacgg gaggaaactt   10440
aaaaattaaa tttgtgttac cttctctcag aaaagcaatg tttcttaaat tagaatcatt   10500
tagacttacc ttaatggaaa caatggcttc atttacttct tcatcaagga cttatgtaat   10560
gtttgttgtt ctggaacaaa tggcattatg agagtttgag cccaattatt ctgagctttg   10620
```

```
cctccctcgt ggctcaggtg ttaaagaatc caactacaat gcgggagacc caggttcgat    10680
ccctgagtcg ggaagatccc ctggagaagg gaatggcaac ccactccagt atccttgcct    10740
aggaaatccc atggacagag gagcctggca ggctacagtc catggggttg caaagagtca    10800
gacacaactg agtgactaac actttgacat ttcgacttgc tatgagttca ctcagtcacc    10860
ttaactgagt tgaccatggg tctttatcag tagggagtaa ggatccatta tccacgatcc    10920
gcaatccatt gactgcctga cctgtgctta ggtatgcacc acagagagga aaattagcac    10980
ttgattccaa agaggacttc tggcaaggtt gatttagtaa tcagcatttc agggatctct    11040
taatattgtt atgtcaactc taaggaatgc attattgtta ccgcaggttt atattgagaa    11100
ggcttggatt aaaaataaaa aataaaaact tgtcatggct ggtaaagaat ggagccagaa    11160
gctcttagta tatgtcatat tttgtcactt gacatgcttc atgttttcag aatatgaaat    11220
gcctgcttaa tacagcctta acttcctatt atacttctgg attaggaaag agaacattag    11280
aaggatggtg tgttccaaat aaaacttctc tcttcaaatc cctagtgggc ttttgcaatg    11340
caacctaaca ctgtctgtgc ttggtttctt tcacttcctt tctgaattag tgttatcttc    11400
ctgcttgcac acttttgcta gaaagcagag cttgtaaaag gagaccacat tatgtcagag    11460
gtagcagaag acaggaagtt tacacagaat aaaactgttt gctcaaattg ctttaattag    11520
tccttattaa agttgccgtt agtgtcagag atgctgtcgt cgggattcta ttgcacaaaa    11580
aggatatctc tgacacgtga atttttcctt ttcccatctc cttgccagga acaccagaaa    11640
aagatctcag actggttaga agcattaggt tgtcagtttg aatccgagtg atggagaagg    11700
aactgtggtt aataaccagc taacagtgga gaaaaaagga agtcaattag atatgagaac    11760
tggacatttt cccaagacta gcttgtttgg aaagcctcag tctttctggt agttgcaggg    11820
ggctgataag gttcctctct ggtactttct cttgcgcctt gaaagctggc aggaagggaa    11880
gctcctggac tgttaataga tgcggctctt gcttgaagtt tctatgagaa agccgacaag    11940
agtcgaaatc ttctctgtat ccccactgcc tctctacaga ggtttgggct gttttccttc    12000
caacatcaca gatcataact gaggtgagtt gtctgttttt gttttcaaa tgttcgtact    12060 gagtggagag tcttgattct ttttcggtat gttctttaac gagtgtgtca ttttaaaatg    12120
gtacttctca aacttgaatg tgcatatgaa cctgaagatc ttgtttaaaa gcagcagaat    12180
tcagtggatc tagggtggct tgagattctg catttctgag aagtgcccag atgacctcag    12240
tgctgctggc ccatgaaaca gagtaataat ggcttaagac cttctaggtt tattgctctg    12300
tagggcaagc agttgggaga tgttggcaga atcaaggtgt ctggctgagc acatgatttg    12360
tgtagagcgc ctggaaggaa aatgagacac tgttagtgtc cagattgact tgctttgatg    12420
gactagctca gagtttgggg ggttgtgtta aatagttcct agatatggta agccatgtca    12480
ccccaagtga gacagaatgt tggtctgctc cttagattgc atggaccact ttgagcagag    12540
ccagaaatat ttttgcagtt tggggaatag tagtcatatc atgccttaac tgggataact    12600
agtggtcact tgaatatttc agcttcgatt gaaaattatg catctagaaa ataactgat    12660 gtcgtcctcc tcccatttgg aggttaaggt tgtgaggcat atacatctat gatatgattt    12720
aaagtcaatt tgagcaagga atataattga tatgttttat catcttgtga gagtgttcct    12780
ctttaaattg aatagctccc tgccctaaat ggtacgtgtt tatctgaaag ttgcttttaa    12840
tccaaaagtg ccaagccaag aaggaaaaaa ataaataata ggaagtgtgc cttgctgagg    12900
gtagaaaaca gtagtgggag aaaaacaggg aaagaaagga aagtgatggc cgtggaagtc    12960
```

```
aagtttgcaa aatgaataaa agaaacccca gcctgaaaat aggattctttt ttccgacatg   13020 catgggagtt tttctagagt ggtagcttgc gtcttcctca gctagagaaa tgtgcttaag   13080
atagaatagg caaattaaaa tttgtgttgt tttaaagtac atgctgaaac tatttgtcat   13140
cgagtcaagg gtagtcagtg gaatcaaagg tcagtggcat gaacagacct ggtgaggccc   13200
agtatgaatc catttaaact atctcagaca gaggggaatt gcttctgttt gaaataagct   13260
tcagataact ttccttctca ttatggagta taacagagga gttacataca agtttaacaa   13320
cctatatggc tactgttctg accaatcaga acagtagcta ctgtaaacag cccatataat   13380
gggaaaccac ttgtaggcag taagaagtac atggggttga acatcagcct aagctaggtt   13440
ttcatgaact tttattgggg ggagaaattg taaagctaca aatgagttca gagacataca   13500
acctataaca tatattcaga gttcagaaac atatattcct actagcatct gtcagcacgt   13560
tagccccatt ctctccagtg aggccacttc cctgtctttc aagctttca ttctggctgt    13620 gtatctcctg caaccttcac taaagaaagt agggttctct taagtcattg taggtgactc   13680
aaaagtccta tccattccct cagtagaggg aaaatgccta tactcttttg taaagagata   13740
ctgcagaaaa tgaaatgatc actacgctat ccttccatac aaagcatggt cacatacttt   13800
accttgcttg attttcaca actatcatgg ggatatgtca tgtcaagggg attttgttt    13860 ttacctgtca tggaggaaaa tgaagttctt gttaagcgat ttgtgaggag cacacagcc    13920 ggttagtggg tgtattgaaa ttaaactcgc ttgtttgctc taagttcagg tttatcctgt   13980
acttttcttc atcttcccaa gcatcccctt aagacctatg acagcccta ttgttctcta    14040 ctagagttca ttggctttcc ctgtcaaaat ttgaaacctt tgtgccttaa aaagagtcct   14100
ttttctactt gttttgtcaa aatttttagt gtgtttgtca caacctttat atccattaaa   14160
acctttagtt cccaggggta aacattttag aggagggcct ctaaactttta ttttgactga  14220 aaattacctg gggagtttgc taaaactcag atttctgggt cctaacttga gagatctgat   14280
tcagtagatc taggactagg cctaagaatt cacataccta aaagctgcca ggtgatttta   14340
acgctaccaa ccagagagca tgctttgaga ctacaggcat agcttcagtc agtatcttga   14400
aataacacat ttctggttta gattccacgt atgtgatatc atatggtgtt tgtctttctc   14460
tttctgactt atttcactta gtataataat ctctaggttc atctatgtag ctgcagatga   14520
cattatttca ttctttttta tggttgagta gtagtccatg gtatatgtgt accacatctt   14580
ctttatgtct tcatctggac acttaggttg tttccatgtc ttggctattg tgaatagtgc   14640 tgctagggt gcatgtttct ttttagatta tagttttgtc tgaatatatg cctaagagtg    14700
tccgactctt tttgaccca tgaactgtag ctcaccagat cctctgtctg tgggattcc    14760 cagacaagaa tactggagtg ggttaccatt tccttctcca gcagatcttc ctgacccagg   14820
gatcaaaccc tcacctctta catctcttgc attggcagga aggttctttc ccactagcgc   14880
cacctgggaa gctccaatgg tggggggtgt aaaaaaaat cagatgatca agaggatata    14940
ttaggaaatg tcaggaagcc tccttctcca ggtatcccat caatgggtca atatacaaag   15000
tagccacagc agcatagaag aaagtgtgag ctaataataa agttttcact tccctaagtg   15060
gctgctgttc ttgttgttca gttgctaagt tgtgtctgac tcttggtgac cccatggact   15120
gtagcccacc agggctcctc tgtccatggg attttccagg caagaatact ggagtgggta   15180
gccattccct tctccaggga tcttcccaac ctagggatca aacccagttc ttccacattg   15240
caggcagatt ctttcctggc tgagccacca gggaaaccca cagcattggg tacatgcctt   15300
aaaccagcag ccagtaatac agagccagaa cgtgtggctg tggggaccac tgagagaaat   15360
```

```
aattcctcca tccacactgg ctgcctaagg tgcttctctc acatgctaga catactcctg    15420
cctccattcc ctttgcctaa atgttttcct ctggtctatt taaaattgca aaaccttcct    15480
ttaccttcta gactactgct tccttcccca tgtgcctctc tccaggactt ctcacctcta    15540
acatactaga ctatctagat tgagttactg tttattatct gtcttcttcc aagaccaggg    15600
ttctgtttca ttcactgtcc tatcctcaat atctaacgtt gtgcctaaaa catgccttgt    15660
tggtgtttag tcgctaagtc gtatccgact cttttgtgac tccgtggact atagcctgcc    15720
aggctcctct gtccatggga ttttgcaggc aagaatactg gagttgacta ccaattcctt    15780
ctctagggga tctttctgac cagggattga acccatgtct cctgcattgg caggcgagtt    15840
cttaccactg agccaactgg gaagcctgtg cctgaaacat agtaggtaga ccaactacat    15900
aaataccatt aatgttcttg gagaagagta aacaaatgtc tctagtgtct ctagagaagt    15960
tcaaggtagg cggagatcag catgctggga aaatcaccta tgtgtatact gaattcactg    16020
agaggtaaaa tagaagtagt gtttgttaga gacagcaata gtgtctcagt tactgataaa    16080
tgggaaaaga ggtcacagag tccaaagata gcagcagcca tggaaagtag ccagtgatga    16140
agtctggtga cctgaaactc aaagctgaga tttggaagaa gtgagtagat gatccactct    16200
gggatgttca cattttgcag tggttttcttc tctcaaaata aacaagatca gaatgtgaaa    16260
ttttccatcg taacctcaag gaaagcactt ttgcttctgt agtgactttt tatgctttaa    16320
tcacaagagg gcaccagagt ctagcaaaag atcactttt tccttcatct aaagctgcgt     16380
gcgtgctctg ttgttcagtc gtgtcagaca cttcaacc ccatgactg tagcctgcca       16440 ggctcctgtc catggggatt cttcaggcaa gaatactgga gtgggctgcc atttcctact    16500
caggggatct tcctgatcca gggatagaac ctgcatctcc tgtgtctcct gcattggcaa    16560
gcggattctt taccactgag ccacctggga ataccctatc taaagctttt tgttttctg     16620 ttgctaaatc cgactctgca accccatgga ctgcagtagg gcaggctcct ctaaccttca    16680
ctatgttcca gagtttgctt gaattcatgt ccattgagtt ggtgatgcta actatctcaa    16740
cctctcgtcg cctcctgctt ttgccttcag tcttcccag catcagggtc ttttttttt     16800 ttaatgaagt tggctcttca cattaggtgg cctttaatgg agctttagtt tcagcatcag    16860
tccttccaat gaatattcat tgaagaaggg gtgcaattaa taattacttg gagccatatg    16920
tgtaaacagg gacttttcct atgcaaactg gacaaaagc cctgcacaat atgagcatga     16980 ccaattaat tatgggtag ctctacacta agggctctta ttctcaaaat cactacaaat      17040
gcttatgaca cactaataga ttagaaagaa aagtgaccaa acttgctttt atctcgaagc    17100
aaagatcaag aaaggctttc ccctgtaccc tacttcccta attatctta ttgcctatcc     17160 tattttctc cttagtgtga tcttagtttg attatacct caagtaagag aattgttta      17220 tccaaaatta tctcaattat ttgaaagtgg tccaaagtgt tctctaaatt ctcacagttc    17280
ttttctgcat atctcttatc ttctatacta tatattaatt atttatatac ttgttttatt    17340
cttttgaaca tgacttacat gctggggatg tgaaaaaata ggttttgaaa atggcttttt    17400
ttttttcctt ctagttttat tgagatacaa ttgatataac ttagcactgt gtaagtttga    17460
agtatacagc ataatgattt ggttgtacat catgaagtga ttatcacaat aagtttagtc    17520
agtatccatc atctcactta tgcagaaaat taaagagtc ctgttattag cataaattca     17580
aagtatggtt ggaaggagat tgtggtgaat aacaaagaa gctcctatga gtcttatcac     17640
tgaataaatt acgagagttc taggggactt ccctggtggt ccagtggtta agactcgata    17700
```

```
cttcgaatgc agaggacact tgtcagggaa ttaagatccc atgcaccacg cagtatagcc   17760
aaaaacttaa aaaagtaaag agttttagaa gctgtgtcgg gaaccaaggg caaagaccaa   17820
atatgtattt cttactgtat tttttttatgt cgctcttgaa aacatactat cagcttatac  17880
tagctagcca ccagagaatt tgaggatgag ggtagttgcc tgagaaacca accatgggat   17940
tacagagttg aactttcagt ctcaacctcc aggaggatag aaggctgaaa gttgggttaa   18000
tcagtaactg ttgacaattg atttaatcga tcatgcctac gtaacggaac ttccctaaaa   18060
ccccctaatt taaggagag ttcggagagt ttctggattg tgtacacat caagggctg      18120 agacgtgggg gtgcagccag agactgcatg aaactctacg ctgcttcttc tgtcttggcc   18180
ctatggatct cttctatttg gctgttcctg agttgtatcc tttataatac accagtaagt   18240
aaaccgtttt cccaatttct gtgagttgtt ctaacaaatt atcacacttg aggagggaat   18300
ggtgggaaca cctgatttgt agctggaaac ctgggacttg cagctggtga actggggcag   18360
ttttgtagga ctgattcttt ttttttttt tttttaaact ttacaaattg tgttagtttt    18420
gccaaatatc aaaatgaatc caccacaggt atacatgtgt tccccatcct gaaccctcct   18480
ccctcctccc tctccatacc atccctctgg gtcgtcccag tgcactagcc ccaagcatcc   18540
agtatcgtgc atcgaacctg gactggcaac tcgtttcata catgatatta tgcatgtttc   18600
aatgccattc tcccaaatct tcccaccctc tccctctgca acagagtcca aaaaatatgg   18660
aacgcttcac aaatttgcgt gtcatccttg tgcaggggcc atgctaatct tctctgtatc   18720
gttccatttt tagtatatgt gctgctgaag cgagcactgt aggactgatt cttactctgt   18780
gttctgttca gttcagttca gttcagttgc tcagtcgtgt ccgactcttt gcgacccat    18840 ggactgcagc acgccaggcc tccctgtcca tcaccaactc ctggagtttg ctcaaactca   18900
tgtccattga gtcagtgatg ccatccaacc atcttatcct ctgttgtccc cttctcctcc   18960
caccttcagt ctttttccagc attagggtct tttccaatga gtcagttctt tgcatcaggt  19020
ggccaaagta ttgcagtttc agctttaaca tcagtccttc caatgaatat tcaggactga   19080
tctcctttag gatggactgg tttgatctcc ttgcagtcca agggactctc aggagtctcc   19140
tccaacacca cagttcaaaa gcatcaattc ttcagcgctc agctttcttt atagtccaac   19200
tctcacatct atacatgact actgaaaaa ccaaagcttt gactagacag acctttgttg    19260
gcaaagtaat gtctctgctt tttaatatgc tgtctaggtt ggtcataact ttccttccaa   19320
ggagtaagtt tcttttaatt tcatggctgc tgtcaccagc tgcagtgatt ttcaagcccc   19380
tcaaaataaa gtatattgtt tcatctatct accatgaagt gatgggactg gatcatgatc   19440
ttagttttct gaatgttgag ctataagcca accatttcca ctctcctctt ttactttcat   19500
caagaggctt tttatttctt ctttgctttc tgctataaag gtggtgtcat ctgcatatct   19560
gaggttattg atatttctcc cagcaatatt gattccagct tgtgcttcat ccagcctagt   19620
attttacttg aagtactcta catataagtt aagtaagcca gggtgacaat atacagcctt   19680
gacatacacc tttcccaatt tggaaccagt ctgttgttcc atgtccagtt ctgttgcttc   19740
ctgacctgca tacagatttc tcaggaggca ggtgaggtgg tctagtattc ccatctcttt   19800
aagaatgttc cacaatttgt tgtaatccat acagtcaaag gctttagaat agccaataaa   19860
gaagaaatag atgttttttct ggaactgtct tgctttttct atgatccaac tagacagatg  19920
ttggcaattt gatctctggt tcctctgcct tttctaaatc cagctcgaac atctggaagt   19980
tctcggttta tgtactgttg aagcctggct tggagaattt tgagcattgc tttgctagcg   20040
tgtaagatga gtgcgattgt gtggtagttt gagcattatt tggcattgcc ttttttgggg   20100
```

```
attggaatga aaactgacct tttccagtcc gtgcccactg ctgagttttc caaatttgct   20160
ggcatattga gtgcagcact ttcacagcat catctttcag gatttgaaat agctcaactg   20220
gaatttcatc acctccacta gctttgttca tagtgatgct ttctaaggcc cacttgactt   20280
cacattccaa gatgtctggc tctaggtgag tgatcacacc atcgtgatta tctgggtcgt   20340
gaagatcttt tatgtatagt tcttctgtgt attcttacca cctcttctta atatcttctg   20400
cttctgttag gtccatacca tttctgtcct ttattgagcc catctttgca tgaaatgttc   20460
ccttggtatc tttgattttc ctgaagagat ctcagtcttt tcccattcta ttgttttcct   20520
cgatttcttt gcattgattg cttaggaagg cttctttatc tctccttgct actctttgga   20580
actctgcgat cagatgaata tatctttcat ttttctcctttt cctttcact tctcttcttt   20640 tcacagctat ttgtaaggcc ttgtcagact accattttgc cttttttgcat ttgtttttct   20700 tggggatggt cttgatcact gcctcctgta caatgtccat agttctgtcc atagttcttc   20760
agttctccgt gtccctctgt ctaccagatc taatcccttg aatctattca tcatctccag   20820
tgtatgtaca taagggattt gatttaggtc atacctgaat ggctcagtgg ttttccctac   20880
tttcttcaat ttaagtctga attttgcaat aagtaactca tgatctgagc cacagtcagc   20940
tcctggtttt gttttttgctc attgtataga ggttctccat cttcagctgc aaagaatata   21000
atcagtctga ttttggtatt gaccgtctgg tgatttccat gtgtagagtc atctcttgtg   21060
ttttggaaga gggtgtttac catgacaagt gcattctctt gggattattc attcaaaatt   21120
gcacacaata tggcctccat ttcaggtatg cagggctggt tcaacatttg aactaaattt   21180
ttgtaatctg tcacattgac aggccacagg aaaaaaaata cgtgatcata tcaaaagatg   21240
ataaaaaaat tgctaaaatg cagtatggat tcatgattaa ggactcttgt caaaccagga   21300
atagaggagg actccctcaa cttggtaaag aaatctacaa aaagcctaca gtcaacttca   21360
tacttctggt aagaaaagag ctttctcact aagatcagga gcaaggcaag gatgatctct   21420
ctcacacttt caagatcaca ctggaagtcc tagcgatgca ataagacaag aagtcatggc   21480
atttagggag ggataaaaca gttttgggtt gcaaatcaca taattgtcta tgtagaaaat   21540
ccaaacaaat aaacaatagc aacaacaaca acaacacaat aaaaactaga actagtaaat   21600
gatatagcaa ggctgcagaa caatgttaat atacaaaagt caaccacttt cctatatact   21660
agcggtgaac attaaagacg tagtaccatt tacgttagat ccccaaaagt gaaattgttg   21720
ttgttttact ctcaaagtcg tgtccaactc ttggaaccct tggactttag ccctccaggc   21780
tcctctgtcc atcagatttt tcagggaaga atattgaggt aggttgctat ttccttctcc   21840
agggtatctt cctgacccag ggttcgaacc cacatctctt gcacctcctg tactggcagg   21900
cagattcttt atcatggtac cacttgggaa tctttataga ttaccaagaa atactttgtt   21960
ttggggccag aaagccctaa agcagcagct agaccaaaag aatttctgtt cctgaaaaga   22020
gaatataact gaaataagat aattacatat ttccttaatc actttgcaga gcttctattt   22080
ttctatcatt ttcttctctt caagtaggaa aggattgttt gtttctgaaa ggcccaacat   22140
actctaccta gaaagaattc aagcaagcca gtcctctgct gcaagaataa caggtattga   22200
ttatatttct cagtgtacca tttgggtaca aaggatgatt ttgctataga tggtcaggaa   22260
tcagcagtgt gagcatgaag ttgttcagcc acagttgcca catgtatcat gagtctgcag   22320
tagttttgtt acatcttcag tacctttag gttctggatc tgttggcctc tttggcagaa   22380
caagaaagtg acatttttatt gtatttgttc tgctgcctac aaattaaggg ggtgattgac   22440
```

```
agtgttttga aggaatagag gactttgttt gcttttggtg aaaaacttt  tattctctcc  22500
ataatagaat gaataattgc atggttttag aggattagga tgctgatagg aatatttgat  22560
ttcataattt taagagtagt tggtgctata tggaaataag cttgaaatcc agatcttaag  22620
ctgctataaa atttgtcagt taaatacaga atatgtttgt gatttcatgg aacaggaagg  22680
ccaggctggc ctaaacagtg ctactcagct tcttaagagt gctgccagtt ctttgttgtg  22740
gctttgtttt cttaaaggtg cttcctcttt ggccagggc  tcttcaccct ttcctgaagc  22800
acgtctacca gttgggacac attaggaaat ggccccaaa  tctgtttcct tcaacttgca  22860
ctggcagaga accagacagc ctgtcccctt tcctgaaaca caatcaccaa agttgtttgt  22920
gtcttgggct ctttctaca  aagtcttgaa aaatcttccc gagacctcag cagattgcaa  22980
tataccagtt tatcgctgtg tgcattatcc ctctagatat gagttgcttg actctctctg  23040
agctttgttt ggcaaaacca agattctaat attaaaatac ataaacatta aacctttggg  23100
gcgtgcattc caattacatt ttgagttgca aatgttcttt tctctcttgg aaaagtaggg  23160
gtctaaactt ttcttttcac actaccttct gatatacatg ctaattccaa ctcatttggt  23220
ataaaagaa  aatatgaaaa tataaacaat gcacagatac atacttgatt ctgaaaattt  23280
actccctcc  ttcactttca caaacatact cttatctttc ctttggatgt gataatctat  23340
cccatcactt cttcctttac aatgcttaag aaatatgact tagtttagcc ctttattact  23400
ttattttggg ctgttttcta gctactgtat tctctgccaa caatgctcac tcctttaatc  23460
caacctaaac cctcctacac cttatcccta gtataatctt tattccagag ccaccaaact  23520
atttcaccta tcattactgt tgaaaaacta ttcattgttc tccctgtgga aagaatcaag  23580
tccaaatttt tgagcctgag aaacatggca tcacaacctg gggcttagag gctgttcccc  23640
actcttcttt ttaaaaaata tttatttatt tggctgcgag aggtcttaat tgtggcatgt  23700
ggctttcagt tccttgacca aggatggaac tcgagccacc tgcctggga  gcatggagtc  23760
ttagccactg gaccaccaga gaagtccttc cctctcttct ttttaaaga  tctgggctgc  23820
aatgcgagag agttaacatg catctcacta tcatctctgt tattttctta tcatctcact  23880
ttcatcatct tttggcacac tcttacttct cagacctttc cccattctta catcttcaaa  23940
tctaatgtat ttttcaaggc caagattttt aagacgagct gcctccgtga aagcttttct  24000
gaccctgta  gcttgcagcc atctcttact ttgagatctt aatgcttaat ctcacttcca  24060
ttaatttggc cacttttcac ttactttctc ttgtatgtct tcagaagcac tgtctcatat  24120
tatcacttca ctttgggatg ctttatctt  gtcccctcaa ctaaatcatt agctccttca  24180
ttcatttatt agtatttact gtgtttactg ccgtgctgtg cttagtcact cagtcatgtc  24240
tgactctttg caaccccatg gactctagca gtgtcaggca tgatgctcta gtggagactc  24300
ctgccacact cttcatcacc caatggggaa atctgtcaaa ggttttaaag tatattaaaa  24360
ggataatttt tattaactta tcctgggtct ttaacaccat ggagttacca gctattacat  24420
gaggccagtt ggactcccta cctactggtg cttttataaa agttgtattt taatatcacc  24480
attagaagca gattctgtaa gtgaggtggt gtaatgtggt taactagtaa gtggtataaa  24540
caaggctgga tcctaggctc cttttaacc  ggaatctaag tgacatgaaa ctgtggttga  24600
tttgaacaaa tgctcttctt ccactgagac caggacaagc agcctgctat gggctgatga  24660
gatatactaa atatgaacta ttttgatccc ctcaagggac ttttggggag gggggctgaa  24720
agacctcttc aaaagtttac tcgagtttta gaaattaata tttggcgatc aaagttgtaa  24780
attcaaacct ctagttttcc ttaagtctat aaattcaatt taccaatgct cttgctctat  24840
```

```
ttataagtct agcagatttt attatttact tctaatagat ctttcaatgg tgtttgatct   24900
aatttataaa cttagttaat ttaacacttc caaatacttt gtatgtagag gaaaaatatt   24960
caatttctct agtgtgttgg gagacccta gactaccgtc accttcagat tcactggaag   25020
gatttataga actcaatgta taggtctact cgtagctaag atttattaca ggaacatagt   25080
aaagatacac agatagtaag ggaaagacaa aggccgagtc tggaggacgc catctataag   25140
ctctcttatg cgtttctgct cagaatacat gctattcccc cagcaacaga aactctgcaa   25200
catgtgtgca gtattttta aatgttaatt ttattttgga gtatagttta tttacaatgt    25260
ttcatttgtt ttatgtatgt ggcaaaatga ttcagttact catgtacata taatccattc   25320
attttaagat ttttttccca ggtaggttat ttcagagtat tgagtagagt tccccatgct   25380
gtgcagtagg tccttgttct ggtgtgcagt attttggcct ggggaaacca ctagggaaaa   25440
actagagccc aaggttttc ttgggagctg agtatgtagg cattcatgct ctgcctagca    25500
tgaaccagaa ttccatactc ccagaaggtg agcaggcatt ctgcataaac catattgctt   25560
gcacaaccag tttaggcaaa gtgaaccatc cttatcagtt aactgttgca tgagaatact   25620
cggtgactta acttccaaat cccaaccaag ggccaatctt gagagcaggc ctttctaagg   25680
atagcagact cagacctgct gtgttacttc tattttctaa tttaacaaac taagttttcc   25740
caattgctca aataatgaat atgaagcaaa taattgaaat tataaatacg ataaactgta   25800 gttctttta atatcctatt attttctaca aacttagtag gatttcaact ttaaatcaaa   25860
agcctaaatc acttatttaa ttacatactt gaaattggac agacaagatt gatcttatac   25920
tctaatgggt caaattctat taaataatgt aaatatataa aatttctttt tttatgtata   25980
aacaagacac aaaaattctt taatatcaaa gtattaacat agatctgatt atcttaaaca   26040
tttctatgat tactcccaat ccttcctaga atgaaaaatg ctttaacact aaggaaacta   26100
tatcactctt aacactaagc tagtaaggta gcctgacctg gaactggaga tttctgcaga   26160
ggttgactcc ttgccctgac catgaatcgt agttgattag gtaactttaa aatgagttat   26220
tatcatgtcc ctgaatttag gttatatatt agctaattct tctgattgct gactgaagtc   26280
tacaatttac cctaggttaa gcattgactg gaaaaggctt tttaaaaaaa aaaattgtgg   26340
gagagagaga ccttaatgta attgttattt tggtctaaat ttaaagcttt ttgaacttaa   26400
aggaattctt cattctttca tattgttgct atctttaag acaacagttt tttagaatat    26460
ttattagaat actgagagtc agttcctagg caggttgata agaagtccgg gaggaggaga   26520
aaagggtctg ggactctcaa ggagaaaagg gcaaatgttt ttttctatat gtcttagtca   26580
atataacaat gtatcatgct caaaagacat atttctcctt aataagaacc ttctgactaa   26640
tctttatctt aaaatgtgta ttatggaagt gggtctggta agatctttct attgttagtt   26700
ctaatcctgt catcttaaaa tgtaaattgt gggagtgggt ctagtaagat ctttacaacc   26760
ttgaaacatt cttttgattt attgaaaaag tatataactc cctttcttaa gactagcaag   26820
tggggcactc tccatcaccc ttttgatgtc tgtgtcagaa gctttctctg tccctttttc   26880
actttaataa aactctgcta cacaatgctc ttgagtgatc aagcccggtc cctggtccca   26940
aagctaaatc atcttggag atcgtgaatc cgtcatcgtt caccatgagc tatcaatact    27000
ggatatgtgt tatggttta cctatgtagt cacaactttc aaagtaattt ttcccctaat    27060 ttttaatat attaaaaaaa agaaaacagt tgtaggttca cagcaaaatt gaatggaaga    27120
tagacagatt ttccatatat cctctgctca ctaccccaaa cgtactctcg tccattatca   27180
```

```
atagccccca ccagagtggt tcatttgttc caatcagtga acctacacgg attcatcgtc   27240 tcccaagtc  catcgtttac attagggttt actcttggtg gtgtacattt tatgtgtcca   27300
tagactctga caaacgcagc catcactgta gggtcacaca gaaaggttgc cctgccctaa   27360
aaatcctctg tgctccacat tcttccctgt ctcactgcac ctggcaacca ctgacttttt   27420
actgtctgca cacttttacc tttccctgag tgtcatgtag ttggaatcat acagtatgta   27480
gcctttacat agtggcttct ttgacttagt aatatgcatt gaagtttcct ccttgtcttt   27540
tcatggtttg atagctcctt tcttttttgac actgaataat atttcattgt ccagttgtac   27600
cacagtttat ttatccgtta accaattgaa ggatatcttg gttgcttcca ggttttgaca   27660
gttaataact acatctgctc taatcatctg tgttcgagtt ttggtgagga cttagctttt   27720
cagctcattt gggtaaatac tgaggaatgt gattgctaga tctggtggta agggtatgtt   27780
taattttata agaaactgtg acagtcttcc aaagtggctg tattgatgtg aatttccacc   27840
agcaatgaat gaaagttcct gtacagcatt tgatattgtt ttagagtttg acttttttt   27900 ttttttttgg ccacctgatg tgagcaggat cttagttccc tgaccaggga ttgaaaccag   27960
tccctggcag tgaaagagct gagtcccaac cactggactg ctagagaatg tgctggagtt   28020 tggcctttt  aataggtgtg taacggtatc tcattcttgt tttaatttgc acttccataa   28080
tgacatgatg tagaacatct cttcatatgc ttatttgctg cctgtgtaaa tatcctcttt   28140
ggtgagatgt ttgttcaggt gtttggtcca tttttaatg tggtttgttc tcttttttgt   28200
tgttgttgtt gttttgttgt tgttttgttg ttgttgttgc taagttatct ctgactcttt   28260
tgcaactcca tggactatag cccgccaggc tcctctgtcc atggggttc ccaggcaaga    28320 atactggagt gggttgctat gaccttcttc agggaatctt cctgacttag ggatcaaacc   28380
tgcatctcct gcattacaag tttgttgtct tagtattgag ttttaagagt tctttagtaa   28440
gatgctcttt tcctatggcc tctttcaaga ttgtttttctt tgtctttgat tttctgcagt   28500
ttgaatatga catgtccagg tgtagtttac ttgacattta ttctccctgg tgttctctga   28560
gcttcttgtg gtttgtgatg aatggttta aatgccaatt tctgtcctca acagtgatgg    28620
caaacacatt tttttttga tgtgtttcta tgtctgaatt ggttaccaaa tgattaattg    28680
atgctcaagc agcaataatt agtacttggt agtattgggg aagggaaat ttcttgagtt     28740 cttttactg gtctaataac tgaattgaca caagacagat taacaagaga ataaaacaat    28800
ttaatttgta tgcatgaagg gtctctagaa atgggaccgc ctgaagcaac tgaagcaggc   28860
tgttgatata taaagaccaa gaaataacta tttgcaaaga tttaacaaaa caattgggtt   28920
tatgcatggc gtatcagatt aatgaagaaa taacaaagtt tacacagctt tcttagcctc   28980
aaattcccca actctcttga caagactgct ttctattctc ctggtatagg gagggaacgt   29040
tcatggggga gattcatttc ccactgaagg gagaaagagg agggtctgag gttttttaaa   29100
atattttttc ccaccagctg tttttcatgg aactttaatt cagtgtaatc atcatgccat   29160
tgaggcatat tctgtggtag cctgccctag atcccagtac taaactgtac tgaggtaaga   29220
acaacttagt taagatgctg gcttcacttt gcaggctcag aaattggatc ttttcactgt   29280
gtacttatgc taggttggaa ctcatagttg ctgattcatg acagttaaac tcaagaagct   29340
gaggtgatca gcttgaatca gaatgataat taattgattc tcttaaggga cactccttcc   29400
tatgacagaa gtactcaggt cacctataca gtcacttctg ggtatgagag taaagataag   29460
tgtatacgct tgagagatgt tttatccaag taatggaaaa tgcttgtgtc agctatctca   29520
acctatgaca gaggaaaaca tctttaggaa ctgggtgttt catgttgccc tgctctaacg   29580
```

```
ttgaaaatgt agttaaatat tctcaaactc taataattgt gactagtaac gataaagaca    29640
tggcttatca tttatcatca gttcagttca gtcgctcagt catgtctgac tctttgcaac    29700
cccatgaatc acagcatacc aggcctccct gtccatcacc aactcccgga gttcatccaa    29760
actcatgtgc atcgagtcgg tgatgccatc cagccatctc atcctctgtc gtcccttct    29820 cctcctgccc ccaatccctc ccagggtctt ttccaatgag tcaactcttt gcatgaggtg    29880
gccaaagtac tggagtttca gccttagcat cagtccttcc aatgaacacc caggactggt    29940
ctcctttaga atggactggt tggatctcct tgcagtccaa gggactctca agagccttct    30000
tcagcaccac atttcaaaag catcaattct tcgacgctca gctttcttca cagtccaact    30060
ctcacatcca tacatgacca ctggaaaaac catagccttg actagatgga cctttgttgg    30120
caaagtaatg tctctgcttt ttaatatgca gtctaggttg gtcataactt tccttccaag    30180
gagtaagcgt cttttaattt catggctgca gtcaccattt gcagggattt tggagcccag    30240
aaaaataaag tcagccactg tttcccctgt ttccccatct atttgccatg aagtgatggg    30300
actggatgcc atgatcttcg ttttctgaat gttgagcttt aagccaactt tttcactctc    30360
ctctttccct ttcatcaaga ggcttttttag ttcctcttca ctttctgcca taagggtggt    30420
gtcatctgca tatctgaggt tattggtatt tctcctggca atcatagaag gtgataaatc    30480
atagaagatg tgatttatca tttatcatag aacatgattc ttctatgcca gaaaattggc    30540
taaaaacttc atcctcacaa aatcttcaga gataaagatg attacacttt ggtagattag    30600
gaaggttaaa tgatttattc aaactcatcc aaacaattaa taaaatccag agacagaatt    30660
tgaacgtagt attctctgag ccctccatac actatcttag accagtttta gtttctattt    30720
attaatagaa caaacccttg tgttaacaca ttagtttttc tgacaggtta ctctaatact    30780
agttatcagt ggttcctgtt tagctttggc aagttaataa aggtgactgt gcgaagcttt    30840
ccatgaaatt gtataacctg gtatgaaaat taataagtaa aacctcacta aaatgaggtt    30900
tttccagtag tcatgtatgg ttgtgagagt tggaatataa agaaagctga gtgcctgaga    30960
attgatggtt ttgaactgtg gtgttggagg agactcgtga gagtcttttg gactgcaagg    31020
agatccaacc tgtccatcct aaaggaaatc agctgaatat tcattggaag gactgacact    31080
gaagctgaaa ctccaatact ttggccacct gatgcgaaga gctgactcat cagtaaagac    31140
cctgatgctg ggaaagattg aaggtcggag gagaagggga tgacagagga tgagatggtt    31200
ggatggcatc actgactcaa tggacatgaa tttgagtaaa ttccaggagt tggtggtaga    31260
cagggaggcc tggcgtgttg cagtccatgg ggtcacaaag agtcggacat aactgagtgg    31320
ctgaactgac tgacgctaaa aatgaagctg ggaggccaga aggggagct ttcatgcagg    31380 acaactccac atccattaca ggaagaaatg ccaatgatag acccaaaaga agcattaaca    31440
aagactcatc atttatagtc tccaaaagga aaaagtatac atagcatctc caggaaaaga    31500
tgtgtatcat gcctcctaga ggaaatccac ttcctagcaa ctccagtcagt gagaaaccat    31560 catcactctg aactctcact tttctccaag ggactttgat tcaaaacaac ctcttgcaac    31620
atcccctctt ttctccatgt ttctttttta aaataatgtt tctttccttt gttcattggg    31680
cttgcctatg gtttctgcca tgagttgttt gtcccaaatt gtaattctct gctacaccca    31740
gataaacccc tcctttttg ccaggaaagt agttgacttt tatttttaaa atcagtagta    31800
gaatatttta aacaaataaa aatatagagc atattgtaat aaatgggctt ccctggtggt    31860
tcagtggtaa agaatccgcc tgcaatgaag gagataagga tgcgccggtt ctatccctgg    31920
```

```
gtcgggaaga tcccctggag gaaggcatgg caacccactc cggtattctc tcctggagaa    31980
tcccatggac ataggagcct ggtgggctgc agtccacagg ttcacaaaga gtcggacaca    32040
actgaagtga ctgagcacag cacacataaa aatatgagca tactgtaata aatagttatg    32100
tacctaccat gaggatttaa tgcattgaca tctgtctatt ttctacaaag aaattcttta    32160
aaaatataaa tcaaacaagt cacttttctt cttgaaacac tccactggtt ttctacattt    32220
aaataaaagc tcaaagaccc agtgagccac taggccctac accatctgcc tccccatcag    32280
ccgtcaccct gtctcctaac attctctttc ccattacaga tgccctagcc tgtttacctt    32340
gctggtccat ggagatgcca agcacttcca atctgagggc tttgggccta ttgctccctc    32400
tgtagcacca ttctgatctc agtgtgctct tttgagttta gttgtatgac tgtggtataa    32460
aacagtcgtt atattgtctc attcatctta caatttatg  attttctctg attatgtaga    32520
tgtttgtctc tcatgttcaa aaaatccaga ggtaagcatt ccagagacag tataccaatt    32580
tcctggtttc aggaactcac attccttcta tcttttact  ttgctatctg tggtttctat    32640
tctgagtcat ctcactgtcc atgatagtga tagctattag gaatgccagt cctgtttgaa    32700
tttcagccca gaggaaagag gaagcaggaa agagcattcc aggtttctaa gaatgctgg     32760
gtaaaggaag aaatggaaac ctgagttttt tattttttaa tgttttttga agttaaaact    32820
ttgatgtcag aaaaaaaaaa aaatcccaaa actttgttgt ctaagtaaaa tctcatctac    32880
cttcatggga gcctcagagg acaataataa agtattcttt taaacttatt tctaatcacc    32940
atactagtaa aactgtagtt aagcttgatc ttttgtgcc  acctgtggcc caggagagtt    33000
tagctccttt ttgtttgttt tagcaataga acatttta   aaaattaaaa atggatgcac    33060
aacttcaata ttttaaaaat gtatttttaa atgttaaaat ttatatattt acttattagg    33120
aagttagtat aagcagtatt tttgatgagc acagagatgt tgtgtaattt tttatagttg    33180
tagaaagtct ctgaaataaa tttatttcta aatttggttg tgtagtattg agaaaaatct    33240
gattcagaga ctagtagtca gaaatggctt caggttttga agttttgttc atcttacaat    33300
tttatgattt tctctgatta aacagagatg aaaagggaaa atttattctg agatacatat    33360
aaaaatgaca caagttaaca cataggcttc cagtgtggta gatagtacat gagaaggcac    33420
aggaagtgtg tttttataca atttcttaag tgtcttaaat gaatagataa atacacatat    33480
atgttttcaa actgtggtgc tagagaagac acttgagagt cccttgaact gcaaggagat    33540
caaaactagt caatcctaaa ggaaataaac cctgaatatt cattggaagg actgatgctg    33600
aagctgaaac tccaatactt tggccatctg atgtgaagag ctgactcatt ggaaaagatc    33660
ctgatgctaa aaagattgaa ggcaggagga gaagggcaa  cagaggatga gatggttata    33720
tagcatcact gacccaacgg acatgagttt gagcaaactg tgggagatag tggaggacag    33780
aggcacctgg ggtgctgcag tccatggggt catagagtcg gtaacttagt gactgaacaa    33840
caacatatat atatatatac acaaaaatat atataatata tatgtaatgt atataatata    33900
ctatatataa taataaatat ataaaatgag catattgttg ttgttgattg gcttgaaact    33960
gctctaaaac tgctttattg aaatttggat accacacatg ttaattgtac aattcaatga    34020
attttcataa atttatagag ttgtgtaacc attactgatc taattttaga acttttctat    34080
tacctcaaaa agctcgcaac aaacttatgc ttactggtgc cagttgtacc ctctctgctt    34140
ccttcccctc tttacctgag aggagtagat ggtctgagag ctggtgtctt aatgcctgtg    34200
taaaagtatc catgatctgt gttcctgtaa acagtgtctg aacataactg tagaacttgt    34260
agtcaaagat aaaaattaaa agtgatttg  ttgttgagag gcctgtgagc tgattcattg    34320
```

```
taagtactgt gtaataatgc ataactggga ctgaattgtg ttatatgtcg aactggaatg    34380
ttcatatgta tcagaggaca attcttctga tgtccagagt tttcactaca taatgctgtt    34440
ttgttttttt ggctgtgctg ggtctttgtt gctgcaaggg cttttctcaa gttgtggcaa    34500
gtaggagcca ctttctaatt gcagtgtgtg ggcttctcat tatggtggct tttcttgttg    34560
cagagcatag gctctaggcc cgcgggcttc agtggttgtg gcacatgagc tgtagagcac    34620
aggctcagta gctgtggtgc acgggctcag ttgctccgtg gcatgtggga tcttcccgga    34680
ccagggatag aatccgtgtc tcctgcattg gcaggcagat tctttaccac tgagccaccc    34740
gggaagccca acgctttctt gttgactggc aagttgcaga tgacattctc tgtggctttg    34800
gatgcctgcc agagggaaga cttacaattc ccaacaaatt tgaaggcatg cttgctagat    34860
acgatacttg acattaagta agcaggttca ctatacacag tgtgtaatca agaactatc    34920
tttcacaaac tcttatcttt gtttctgaca gaacacttgc agtttctaca aaactgctgt    34980
aaaagttggc ctcagtaaaa gttgtttatc tctcagtaaa agtagtaaca ctatacagga    35040
cttccccca cctgcttttg acagattgac tccatgggat ttaaaacttc ctttttttct    35100
tgagttgata aggtgacaat gctctttga aacagataca ggtgagatat accaggtgga    35160
ctaagcaggt gtgaaacagg ccctggggta gggtagctga ccttattgat aaagtagtga    35220
caagggacag tcagttacat cataatgtac taaggtatgt tacagaagga aagaagtgat    35280
acaaaggatg ggtttgggca aaagcctgtg agactataga gacttcttcc ttgactagca    35340
aatgaggtca ccctgcaagc tgtgcgggca agacaggagt ggagctcacg tagttctctg    35400
gctgaccctg ctgctgaaac agcaaccgca gagcaactaa gcccactcac cgcaactact    35460
gagcctgtgc tctagagccc aggcgccaca actactgcac ctagagagta gccctgctc    35520
cttctgtagc accagtctgt gatgatcctc tgttggttgt tgtcagcttc cagtggctgg    35580
tcaccatgct catcatcttc aagccctcgt ctcctttgca gatcttctta aactacctct    35640
gccctgtgcg ttccttagga gttcctgggc caaatgcctt gttggtgttg caagttgtct    35700
ttactgcttt acgacccatt ttgaacttga gtaagaaaat tgcttgaatt tacttttttgt    35760
ctaacgtctt ttccctagtc caaaataaat ataaataaa cagcaactaa taaatcatta    35820
gcaaaaaca taagtgaga atgtgcatt aaaatgacat ataaccacat ttatttaaga    35880
atgtattcca atttcaaaca gcaaatttca acagtgcaaa accacagtta cttttgcaac    35940
aacctaagca tattaaaaag cagagacatt acttgaccaa caaaggtcca gctagtcaag    36000
gctatggttt ttccagtggt catgtatgga tgcaagagtt ggactgtgaa gaaagctgag    36060
cgccgaagaa ttgatgcttt tgaactgtgg tgttggagaa gactcttgag agtcccttgg    36120
actgcaagaa gatccaacca atccattctg aaggagctca gccctgggtg ttctttggaa    36180
ggaatgatgc taaagctgaa actccagtac tttggccacc tcatgcaaag agttgactca    36240
ttggaaaaga ctctgatgct tggagggatt ggggcagga ggagaagggg acggcagagg    36300
atgagatagc tggatggtat caccgactcg atggacatga gtttgagtaa actacggag    36360
ttggtgatgg acagggaggc ctggtgtgct gccagggcaa atcatgggt tattgcgatt    36420
catgggtcg caaagagtcg gacatgactg agcgactgaa ctgaactgaa ctgaatggta    36480
ttgagttgta aggattcttt atatattttg aatacaaatt gttcctctac tccatacatt    36540
ttttaaaagg cataggtaat atttgtgttt aatttcattt acagaatgaa accaaaatgt    36600
ataaatatta tttatgatgc gggggtatca ttgaggatta acaacctcaa tcgtagaggt    36660
```

```
tgttatgaga tatacagttt gcaaatattt tctcttagtc tgtgactcat atgttctttt   36720
tttttttttt tttggtggcc aaagtactgg agtttcagct tcaacatcag tcctaccaat   36780
gaacacccag gactgatctc cttgcagtcc aagggattct caagagtttc tccaacacca   36840
cagttcaaaa gcatcaattc tttggtgctc agctttcttt atagtctctc acatccatac   36900
atgaccactg gaaaaaccat agccttgact agacgaacct tgttggcaa agtaatgtct    36960
ctgcttttta atatgcagtc taggttggtc ataactttcc ttccaaggag taagcgtctt   37020
ttaacttcct ggctgcaaca ccatctgcag tgattttgga gcccagaaaa ataaagtcag   37080
ccactgtttc ccttgtttcc ccatctattt gccatgaagt gatgggacca gatgccatga   37140
tcttcgtttt ctgaatgttg agttttaagc caacttttc agtctcctct ttcactttta    37200
tcaagaagct ctttagttct tcttcacttt ctgccataag ggtggtgtca tctgaaactc   37260
caatactttg gctgactcat ttgaaaagac tctgatgctg ggaaagactg agggcaggag   37320
ggaaagactg agggcaggag gaaaagggga cagcagagga tgagatggtt ggatggcatc   37380
accgactcaa tggacatggg tttgagtgaa ctccaggagt tggtgatgga cagggaggcc   37440
tggcgtgctg cggttcatgg ggtcgcagag tcaagacacg actgagcaac tgaactgaac   37500
tgaactgact gaactgaatg gcaaaaacgg tttaaaaaca atatttaaat aaaaggtttg   37560
tgaagtccta aagcctgttc ttggcgttct aggattatta taccataatt gcaacctat    37620
tgctaggaag tgtttgagtg gcatttaaac tcagcaagct gagtatctca ttttttagcag  37680
aatcccggac tgatggagtt ggaaaggacc taaaacttaa gcagaattaa cacttctaat   37740
tctgtaaata aactcctaca tgtttgaatg acttaattgc aatgctgtat gaaacatttt   37800
atggagcact ggaggcacag ctggatttga ggacaaacaa aaacaccagg agtcagaagt   37860
tcagttaagg caggagtaca aaaaaatcaa tgtttcctga taagactagg gatttatttg   37920
ctggctcatg ataaacaaca ggttaagcat caaagaagag taaggaagaa ctctaaactc   37980
tgtagaaacc aggctttaaa aatagaaatt cacctcaatg actgttgtaa atactaacaa   38040
agaaaaagaa ttcatgctga taagggaatt gtattgtgtt cagtatttga gggttaactt   38100
tgtacattta cctcaaacta tgccatgcct catttgcatt tgtgatttat gtatatttct   38160
ttttgtttac ctcttttaaac ttattcattc atttaacact gaatttattg agtacctatt   38220
taaagctaga aactaacctt aaaaattaat tctcactctt ataaagaaaa tacataagta   38280
gcagttataa aattatggga gtaagtactc taacatattt tataagtagg tatatttttg   38340
agtataaaaa taccatgaaa aaaagttgt ttttttgga aagatcaata aagctttaac    38400
tatattgact aaggaaaaac agaaaccact taaaagcaga aatgaaagtg gggtcattac   38460
tataaattt atagaaataa aaataatata aaggatact atgaagaatt gtttgtcaac    38520
aaattgggta acctaggtaa ggtggacaca ttgctagaaa aatacaatct gccaaaacca   38580
actcatgaag aaatagaaaa tctgaacaga cctataacta ggaaggagat tgaatcagta   38640
attaaaaacc tcccgaacaa agaaaagcaa tggacaaaat ggcttgacag gtagattctg   38700
ccaaatattt aaataactaa ctcttccaaa aaaacctgaa tcttcctaat tcatctgtga   38760
gatcaacagc cccctgatac taaagccaca cagagacact ctagagaaaa ctaaatcact   38820
atcccttgtg aatatagatg caaagttcct caatataata ctcacaagtt taattgagca   38880
ccatattaaa tggattatat gccatgacca ggtaggattt aaccctggaa tatgaggatg   38940
gttcaacata ggaaaatcaa tgtaatacac catattaaca taatgaaggg aagaaattac   39000
atgatcatct taattgatgc agaaaaagca tttgacaaaa ttcagtacct tttatgatta   39060
```

```
aaaaaaaaaa agaaacctca aactagaagt agaaggatac ttccttaacc taagggccat  39120
atatgaaaaa cccatagcta acatcttact caatggtgaa agacaaagcc ttttccctaa  39180
aattaggaat gagacaaaga tgcctgcttt tgtcacttct gttcagcaaa ggcttcccag  39240
gtgactcaat gacaaagaat ccacctgcca agcgggagaa gtgggttcaa tccctgggtc  39300
caatccctgg gttgggaaga tccctggag aaggaaatgg caacccactc cagtgttctt  39360
gcctggagaa tctcagggac agcagagcct ggtgggctgc cgtctatggg ggtcgcacag  39420
agtcggacac gattgaagcg acttagcagc agcagcagca gcagccagtc ttttgcctg  39480 ggaaatccca tgaacagatg tgaaattttt ttttcactga ttttttaaaa cttctgaatc  39540
gtttgaatca cttgaaacga gacgcataat tctatatta aaaagaatt tttaaataaa  39600 tgaagttccc aaagggtcag ttagccagtt taactttcta tgttaaggat agttgtcaaa  39660
aaagataccc cactagatga agatttctct tccaactctg aaaatatgct attaacatca  39720
cacaaatctt ttttcagtct tgcagtggtt tcaagtgaga gcagtgcatc ccccgcccct  39780
ctcagagacg atgtttagag atgtctgcta cccttttgg tggtcatatg tctgagggtt  39840
gctattggca tgtagtggtc ataggccaag gagggaaagc atactgtaaa gtaagcaagt  39900
gtcatattga agaaatcatt gccaaatcta ttcttaggat gattttagct ctcaggttta  39960
gttcttttat ccgtctcgtt agttttctgt ctgtggtgta aagaaagttt ccatattcat  40020
tcttttgcac atagacttag ttttctcaac accgtttttt aaaattgaaa tataattggt  40080
atacaatatt atttagtttt aggtgtacta tatagtgact tgacatttgc atatattatg  40140
aaatgattgc catgataagt ctaataacca tctctcattc aaaattatta caatattgtt  40200
aaccatatat actgtatatt acatccccat ggcttattta ttttataacc tgatatctgt  40260
acctgtcagt ctcctccgtc tatttcttcc cccaccctcc attctggcaa ccacccttg  40320 ttctctgagt ctatgagtct tttttcattt ttgtgtttgt tttttagatt acacatatac  40380
atgagaatat acagtatttg tctttctcca tctaatttat ttcacttagc ataacaccct  40440
atagatccac tcatgttgtt gcaaatggca agtttatttt tatgactgtg tagttttcta  40500
ctgaatacat ataccacatc ttctttatcc attcatcttt tgatggacac ttaggttgct  40560
tccatatctt ggcaattgta aatattgctg ctgtgaacat tggagttcat gaattttttt  40620
gaattaatgt ttttggtttt ctttggcggg gagggggtgag tatacccagg agtggaatta  40680
ttgggtcata aagtagttct attttcagtt ttttgataaa cctttgtact gttttccaca  40740
gaagctgcac caatttacat tctcaccaac agtgtgcaaa gcaaagcttc ccttttctcc  40800
acattgggtg ataattttta tctgtcaata ttttaaatat atcactccac cttctcttgc  40860
tctatagttt ctgctgggat agcttaatgg gggtatcttt gtaggttact atcttttgtc  40920
ccctgtgtgt gtgttagtca cttggtcgta tctgactctg caaccccatg gacagtagcc  40980
accaggttcc tctgtccatg gaattctcta ggcaagaata ctggagtggg ttgctgttca  41040
catttccagg ggatcttcct gaccccaggg attgaatcca ggtctcctgc actgcaggca  41100
gattcttcac caactgagcc accagggaat agctatcttt aaaattcttt ctttattatt  41160
aaattctgtc ttggagaaga ttcttttgca tcaagataat taggtattct gttaacttgg  41220
tagatttgta tgtccagttc cttccccatc tttgggacat tctcagctac tatttctta  41280 aataagcttt ctgctccatt ttctctctct tctcctggga tacccatttt ctttatgttg  41340
ccttctctaa tggagttgga tagagtttct tcaatttctt aagatcttgg ttctttctcc  41400
```

```
ccttctgctt aaatcacttc tagatttcta tctctgagct cactaatttt ctcttctttg    41460
tgagaaaatg gaatttccca atacttctaa tgcattctcc atctcattta ttgagctctt    41520
tagctcagca gtttgtttgg tcctttttta aagtttcaat ctctttggta aagtattggt    41580
tcgttcctta cttttattcc taggctcact aaactgcctt ctgagctttc tcatgccgt     41640 tgagtttttc atgatggcta ttttaattc tttgtcattt ggatcacaat cttccttgac     41700
ttcaagtttg gtcatttct ttttgtgata ctgtgtgact gggttttttc acagtgtttg     41760
atgagttgtt tctctgctgg tgcatttaaa gtaacaagaa agaaaagaaa gaaagaaaga    41820
aagtcgctca gtcgtgtctg actctttgtg accccatgga ctgtagccta ccaggctctt    41880
ctgtccatgg gattttccag gcaagaatac tgaagtgggt tgccatttcc ttctccagga    41940
gatcttccca acccaaggat tgaaacccg tctcccgcat tgtaggcaga tgctttaacc     42000
tctggaaagc ccctggtttg aagtagcaaa cccctttcta atttagatga agttttgttt    42060
acttagattc taacaattca acagattgat aattagaggt cttccttctg ttttttagta    42120
gatggtgcta tagcacaagt tttcaacttt tcttgctgag ctgcctctga caatatttga    42180
gaattggcac tttccaccct tcactgcctt tgccagaggt gtcacaggtg ccctccgtgg    42240
tccctgcttg tgcctctggg ctcattggtg ccctgctgat gttggtgcca ttgctgtcac    42300
tgtcattgct gccaggggaa ctgggatgat gggtgccccg ctgtgtccgg ggtcacttgg    42360
ttagtctcag caggagggt gggtgggaga agctgggtc agacaggtgc ctccaccaca     42420 gctgggggttg tcaggtttgt aggcaccacc atgggcaggg ggatgagggt cacgggcacc   42480
accatggctt gaaggaccgg agtcatgggc cctgccacta ctgctgcctg gttctgccat    42540
gaccaggaag ccatatgcac tgcctccaca gctgctgcct ggctctctgg gactgcaggc    42600
ttagccattt cagaagagaa gcgggggttg taggcactgc cgccactgtt accctagttc    42660
cacctcctct gtgtgttcca aaccacccac cttcaggtat acagatgtgt gggtctctgc    42720
agcatcctgg tagtttgaac agaggcaagt tatgaatgtc ttactagttg gaaattgagg    42780
gggagaaata aagcatctta cactgccatg atgctgatat tcagttcagt cgctcagtcg    42840
tgtccgactc tttgcgaccc catgaatcgc agcacgccag gcctccctgt ccatcactaa    42900
ctcccagagt tcaaccagac tcacgtccat tgagtcagtg atgccatcca gccatctcat    42960
cctctgttgt cccccttctcc tcctgcctcc aatccctccc agcatcagag tcttttccaa    43020
tgagtcaact cttcgcatga ggtggtcaaa gtactggagt ttcagcttta gcatcattcc    43080
ttccaaagaa atcccagggc tgatctcctt cagaatggac tggttggatc tccttgcagt    43140
ccaagggact ctcaagagtc ttctccaaca ccacagttca aaagcatcaa ttctttggcg    43200
ctcagccttc ttcacagtcc aactctcaca tccatacatg accacaggaa aaaccatagc    43260
cttgactaga cgaacctttg ttggcaaagt aatgtctctg cttttgaata tgctatctag    43320
gttggtcata actttccttc caaggagtaa gtgtctttta atttcatggc tgcagtcacc    43380
atctgcagtg attttggagc ccccaaaaat aaagtctgac actgttttcca ctgtttcccc   43440 atctatttcc catgaagtta ctctccagca atttttgaaa tcagaaagtg tgagaactcc    43500
actttgttct tcattttcaa gattactttg ggtatttggg attctttgag attcatgtga    43560
attttaggat gaatttttct atttctgcaa aaacacactg gaatttagag agtaattgca    43620
ttcaatctgt ggatcatttt gggtagtatt gtcatttaa caatcttaaa tctccaatcc     43680
atgaatacat gatgtctttc cattcattta tgttttcttt aatttattgt attgtcttgt    43740
atttaaatta ttgtattgcc ttgtagttta cagtgtacaa gtctttcact ttgttggtta    43800
```

```
aatttatttt attcttttg  aagctattat aaatgaaatt gttttcttaa tttccttttc  43860
agattgttca ttgctagagt atagaaaatc cactgatttt tatgtattga ctttgtatgc  43920
tgaagctttg atgaatttat tagctctaag ttttttttgtg tgaaatcttt agcattttct  43980
tcataaaaaa taatgtcacc tattaacaga aattatttta tttccttcaa gtctggtcgc  44040
ctctcctttt cttgcctaat ttgctttagc tacaacttcc agtaccatgt tgaatattgt  44100
tgttgaagtc gctaagtttt gtccaactct tttgcaactc tatggactat agcccatcag  44160
gatcaattgg cagcccacct gccaaagcag gagacatggg tttgatccct gatctgggaa  44220
gatcccacat gccacagagt aactaagcct atgcaccaca acaattgagc ctgtgctcca  44280
gagcctggga gccacaacta ctgagctcag gtgcttcagt tatagaagcc cgtgtgccac  44340
agagcctgtg ctctgcgaca agagaagctg tggcaatgag aagtccacgt actgcagcta  44400
gagagtagcc cccacttgct acaactagag aaaaagacca ggcatcaagg aaggcccagc  44460
acagccaaaa ataaataaat aaattaatta aattatttttt tttaagttgg tgaaagatga  44520
atatttgaga taaatgaaa  attactaaga tccacatctt cagacatgaa agaaaatatt  44580
tatgaaataa aattatttgt tgtctgaaat ttgtttcaaa gtaatctgtg ggaaagggg   44640 aaaaaagagg agtatcagtg aaatgaaaat tgactaccag ttgagattag catatagtca  44700
ttcatcatac tattctttct acttgtgaaa tgcttggaaa tttctgtgta tgtgtgtgtt  44760
aatcattcag tcatgtccta ctctttgaga ctgtagactt ccaggctcct ctgtccatgg  44820
aattctccag gcaagaatac tggagttggt agccattccc ttctgcaggg gatctttccg  44880
gcccagggat tgaacctggg tctcctacat tgcaggcaga ttctttactg tctgagccac  44940
tacagtggta agaaaagtg  aaaaagatga cagatacatt tgagaatttc tagttttcagc  45000 aatattgcag agttaagagg ccctgaaact attcagctac ataatatcta aaaatgcttg  45060
ataaaatatt aaaaccactc ttatttttta acttaaactt tttattttcc attgaggtat  45120
agccaattaa caatatagtg atagcttcag gtaaacagtg aaaggactca gccatatata  45180
tacatgtatc cattctcccc caaactccct tcccatccag gctgccacat aacactgagc  45240
agagttccat gtgtatatag taggtcgttg ttgaaaatat tgaaaccact cttaattgat  45300
tggatgattc ccactaagat cagaatggag tacagactag gcaggtaaac taaattttag  45360
agccttggat actctgaggc ctacagtatt ctttattgac actctgaact gcattgcaca  45420
gaagggacag aaacaaagcc tgaagtcacg tagaagggaa gcatagtacc tacatctaag  45480
agaggcatac cctcacaacg ggcaaactca aggtgaacca taagaacacg tttccttact  45540
ggactgggct atgaatggaa gttaaaaaaa aaaccaacaa cattttcttt gagaacttttt  45600 tcttctggct agatgtcaca tagtttggga ctcagtccac atattttgcc tgatcccaaa  45660
acacaagcct ataatttaaa gagtagcagg ttaggtacta tccccaggtg cctgagagaa  45720
gtaaaaatag acttttccag atgagcatac cctcaagcag gcctcaaaga attcctggag  45780
acagtcaaca aaaagctcat agtaaaaagt ataaacaaa  aatcaagcaa gccatagata  45840
gcaaacccag aaccatagag agttcaactt ttataattaa ttatcataag taaactaaaa  45900
aaataagtct gcttgaaatg cttttagatt aaaaaaggac tttgaaaaca tgagcaaaaa  45960
taggagacta atgattaggc caatttgaag aagaacaaaa tattactctt agaaattaaa  46020
aaaaatactt actgaaatcc catccaggct gccacataac actgagcaga gttcctggat  46080
tcaaatggat agacagttaa aagaaagatt aatggaaata aagagcaacc caccccagta  46140
```

-continued

```
ttcttgcctg ggaaagccca tgaacagagg agcctggtgg gctatagtcc atggggtctc    46200
aaagagtcgg acatgtactt agctgtactt ttttttttaa ttttgggatt aacatgattt    46260
atttcattat cagtcttaca aattactgag gttgggtaag gccgggattg tagcttgaat    46320 ttcacactt ggttgaggaa cagtctgtta gtgaacagaa ggccgtggag gtgccacagt    46380
tcatccagca gtgttagaga ccttctcaga agcaacaggt gagaccaggc acatcacagt    46440
cagaggtcca ctccagtggc tctcagggtc cactgcctgc cccgccac cctgctttat    46500 ggaggcacgg aggcccctag aggcccagg gagacatgat gggctgaggg gcttcaccat    46560
caggtggtgt gtctctgcct cagcatttcc atccatacca cacatcactt tctcccacta    46620
tctacactct tatttatttt taatactagt gtattttaa aaatatactt ttatttggct    46680
gcgacggtcc tagttgcagc acatgggatc ttcagtcttc attgaggcat gcaggatctt    46740
tagtggtggc atgtgggatc tagttcccca atcagggatc aaacctggac cccctgcatt    46800
ggcactgagt ttttgcacca ccagggaagt cccactccac ccttttataa gtgggcagcc    46860
tcatccctgc ctgggcttca agcagagagc ctggttctgg tccccaactt tttgtcagtg    46920
gagtcccctt tattgcgcca aactccttac caccattacc tgttcctgga ctcaagacct    46980
tcaacccaca agcttggtaa ttctcaccac tttggatttc tttcatggag atattcatct    47040
tggttttgca actgcctgga tttcttgtt tttcttcttt tatttggatc cattgtgact    47100
gagaagggtg aacaaattta ttttactttc tctctccaaa gaaatcttat agcagttttt    47160
gcataatccc actatgcttc agtttcatct tcaagataaa aattttaaca gaacccacct    47220
aaaggcattg ttgtaaagat caaatgagat ttagaaaaaa ctgcacaaaa cctaaaggca    47280
cttagaacac tgcctggcaa gtaccaagta ctcaataaac attagccact actattggta    47340
ctggggaaag attgaggcta ccttatattt tccaaatata cataatttta ttgtctttat    47400
tcaaccccgt ggcataggta ttatcaccct taatttgaag taaagaaatt gaggcaccca    47460
agggtcaaat agcaaaagct gtagagatga gatgaacctt gggtacatct agactggctg    47520
ttgactttgt tataaaatag aataattaat gtatatttct tgctctaata tgggtgatga    47580
catggagaag actaaaatct cattctggat gaagttataa gctttggctc tgttgacatc    47640
atctgttata atagatggca tgacagccag aaatgaaaaa agtctaaggc attatataat    47700
gaatgatgtg tcacttaatg ctcattacac tttaacttca gttgctccca cgaatgaatt    47760
cttgtctcta caggcaataa aatgttatag tagtcagtaa ggtatcatag aaaaagggca    47820
gtctcaataa acccttctcc acttttacaa cattcaggtc agggtggata agcccctgaa    47880
ttacatgaga taaactcact tttattattc agtcaataaa tatttatcaa gtatctgttg    47940
tgttcaaggc tctgagcaag gcaacattta ggaaatacac tgaggtggga gacatacttt    48000
ctactttcgt aattcccttt aatggcccac aagacgttcc agcttctttg tctctcccat    48060
tcaatgtttt atctgttacc aggactgtaa attcttcctt tatggtgttt ctttcctcac    48120 aaatttttt ccaccataaa actctagttc agtctatttt tttcattccc agactgttca    48180
ctgctttccc acatccgcca tccatccat acgtaaacag attactcttc ctaaacacca    48240
ctttgacagt gtcatccctc tacactaaac tttcaatggt ttctcactct caagataaat    48300
ctgcactctt ggtttggcct tagggcctcc acatttggcc ccagaagatt ctcttacatt    48360
tttgttagta tgtttctgag aatacagtga ttgagctact ttttggtgaa gagcttccat    48420
gaacaaatgc tgtatacgtg ttctgcaatg atgaaaccta cttaatcagc ttgttttaat    48480
ctagcatctc ctcgtctttc ttttccccat atcacgtgtt cataaagtct tttgtttaag    48540
```

```
taaactttta aattgcagta taacatacat acagaaaaag caaagaaaat cttaagtaaa    48600
cgatttggtg tatatttaaa aagtgaacat acctgtatat ctgccaccct aacctctttc    48660
tctatctctc tgtctatata tatgtgtata tatactttta tatttgttta ttctcaatat    48720
cccagaagtt tccattatgt tctaccctag ttattgtccc ttccaaagat aactactcat    48780
ctcactttta tcactatata tgagttttgt ttatttggtt ttttttttt tggcttgttt    48840 atttttattg aaatataatt gacatataac aaatacacat acaaatatat atgcatacat    48900
ttgatctgag taacagatat acaagtgtgt ttactttgta aatatacatc aagctgttta    48960
cttagatttt ctgtacattt tctatatgtg tattatactt caattaaaaa gtttaaagac    49020
tttatagata tgtgaaattt agtttggtga actgtcaacg tttaaacttt cagtctattt    49080
ttcaaggaca aatgttacat cttctgcccc actttctaac tctgcagatt aattatctgt    49140
acctaattat atacattttc ccctctacta tgcttatttt ttagggcttg actacctctg    49200
tgaactttac aaccaaatga attatttggt ctcttgtctc ctacataaag aaaattatta    49260
gaatcaaggt gatcgggctt cacatctggc ctcaacacct ccaccacacc ctgctctctc    49320
accactcccc tttccccccc attatgctgt ctctctgtat taatgccagc ctcttttctc    49380
catacccata aaagacattg ataattggtt tttgatattt ctcttctttc caagatggtc    49440
actaccttgg cagagtctgt gtttatttag atgaccaagc catcacccta gcttttgtgt    49500
tctttgatct caacataacc ttcagtgtag gcagaattct aaaaatcccc atctgggaac    49560
tgctctgagg aattctgaag ttgtgactga agttccaaat gaattcaccc caaaatagtg    49620
aaattatcta gatggcctga tgtaatcaca caagcccttt aaaagagggg atataaaatc    49680
cgagagaagt ttgaggatgt gctttgagat gaggagtcac atgagaagga atgtgggcag    49740
cctgaagaag atggttgact gtcagcaagg aaacacagac ctcagtccta aaactacaaa    49800
gaaatggatt ctgccaacaa ttggtcctta gcagattctt cagatggaag tcttcggata    49860
agaatccagc tgaccgactg gattgaatgc atgatagcct aagcagagcc cagcctagcc    49920
cacctagatt cctgacctcc agtgaaataa taaatgagta ttgctttaag atgctaaacc    49980
gatgccaagt tcttactcag cactagaaga cagatatacc tttcttccat ttccgtaatt    50040
caactgtcat gttcaaatca tgagaccttg tcaagcctgg attgctaata ctatattata    50100
tgctaatatt atattatatg ctaatattat tgctaataat ataatattat tatattcagt    50160
gacttcaccc tctggtttca gctcttagc ctccaagtga ccctaattta ggtcccctca    50220
ccacctctgt cttcctgcct tcacttttct gtgatgaatc acttaacctg ctcaaactct    50280
tgctccattt ttctgttgcc ttacccacct agcaaaacca catcctcaaa tttattcagc    50340
cttctaacct gctctagctt tacttctctg tgattgggaa agccatgtcc atttgtaact    50400
ctgatgtcac cacatttata gaatccagtc ttagggtct tggtgctcgg caatctctct    50460
ttaggtccct tggaagaaaa acttttttgtc tacaatttag gtctagtggt gggggggat    50520 gagctgaaag ttaattgaca acagattaaa ggaaaaaaga taaggtcctg gggtttatag    50580
accagtttaa taggggaaag tgggatgggg agaaagggat tctatgggaa aacaaaggac    50640
ttttaagaaa gacaagtagg cgtttaggga aagaagcaaa gatatttctt tcaattttct    50700
ctcttttccc taattaaaac atttatctac acatcttgac tcccttccct ttggtcacaa    50760
cttaaaaaat atataatatt tgcttttctt ttctaattcc tctgaattct agatccattc    50820
tgttttctaa gttacctgat taaccacctt ttcctctttta tggcttgtct tcctggcatg    50880
```

| | |
|---|---|
| cacacctatt ctggcctaat ttaaaccaaa caagaaatat tttctcagag ccccaagata | 50940 |
| ggctttagat atactgcttt ctctcacctt tcttttatag tgagactttt ggaaagtgtt | 51000 |
| gtttataccc tgtttctatt tagagactaa ctgttctctc actgaattga tcgaaggccc | 51060 |
| ctggtagctg ataagcagag ccatggtggg ggtcatggtg catacagcct cttgcactgg | 51120 |
| tttttatttg cttcaactta agtagtagtg aaaataaata tactggaagc caatacagat | 51180 |
| attatattcc caaatgcccc cagggctata ataagccctg cctgacacct gacatctcac | 51240 |
| acgctagtaa agtaatgctc aaaattctcc aagccaggct tcaacaatac gtcaactgtg | 51300 |
| aacttccaga tgttcaagct agttttagaa aaggcagaga aaccagagat caaattgccc | 51360 |
| aacatccatt ggatcatcga aaaagcaaga gagttccaga aaaactgctg ctgctgctgc | 51420 |
| tgctgctgct aagtcgcttc agtcgtgtcc gactctgtgc gacccatag acggcagccc | 51480 |
| accaggctcc gccatccctg ggattctcca ggtgagaaca ctggagtagg ttgccatttc | 51540 |
| cttctccaat gcatgaaagt gaaaagtgaa agtgaagtcg ctcagttgtg tccgactctt | 51600 |
| cgcgatccca tggactgcag cctgccaggc tcctctgtcc ctgggatttt ccaggcaaga | 51660 |
| atactggagt gggttgccat tgccttctct gagaagaaca tctacttctg ctttattgac | 51720 |
| tatgccaaag cctttgactg tgtggatcac aataaactgt ggaaaattct gaaagagatg | 51780 |
| ggaataccag accacctgac ctgcctcttg agaaatctgt atgcaggtca ggaagcaaca | 51840 |
| gttagaactg gacatggaac aacagactgg ttccaaatag gaaaaggagt atgtcaagac | 51900 |
| tgtatattgt caccctgctt atttaactta tatgcagagt acatcatgag aaatgctggg | 51960 |
| ctggatgaag cacaagctga aatcaggatt gctgggagaa atatcaataa cctcagatat | 52020 |
| gcagatgaca ccacccttat ggcagaaagt gaagaactaa agagcctctt aatgaaagtg | 52080 |
| aaggaggaga gtgaaaaaga tggcttaaag ctcagcattc agaaaattaa gatcatggca | 52140 |
| tccagtccca tcacttcatg gcgaatagat ggggaaacag tggaaacagc ggcagacttt | 52200 |
| atttttgtg ggctccaaaa tcactgcaga tggtgactgc agccatgaaa ttaaaagatg | 52260 |
| cttactcctt ggaagaaatg ttatgaccaa cctagactgt gtattaaaaa gcagagacat | 52320 |
| aagcaggagg agcggcgggc aggaggctgc aggatggtga agctgacggc ggagctgatc | 52380 |
| gagcaggcgg cgcagtacac taacgcggtg cgggaccgag agctggacct gcggggggtat | 52440 |
| aaaattcctg tcattgaaaa tctcggtgcc accttagacc aatttgatgc cattgatttt | 52500 |
| tccaacaatg aaatcaggaa actggatggt tttcctttgt tgagaagact aaaaacatta | 52560 |
| ttagtgaaca acaatagaat atgccgtata ggtgaggggc ttgatcaggc tctgccttgt | 52620 |
| ctgacagaac tcattctcac caataacagt cttgtggaac tgggtgatct ggaccctctg | 52680 |
| gcatctctca agtcactgac ttatctgagt attctaagga accctgtaac caataagaag | 52740 |
| cattacagac tctgtgattt ataaagttcc acaagtcaga gtactggatt tccagaaagt | 52800 |
| gaaactaaaa gagcgtcagg aagcagagaa aatgttcaag gcaaacagg gtgcataact | 52860 |
| tgcaaaggat attgccagga gcaaaacttt caatccaggt gctggtttgc cgactgacaa | 52920 |
| aaagaaaggt gggccatccc caggggacgt ggaagccatc aagaatgcta tagcaaatgc | 52980 |
| gtcaactttg gctgaagtgg agcggctgaa gggcttgctg cagtccggtc agacacctgg | 53040 |
| cagagaacgc agagcaggcc ccactgatga tggtgaagag gagatggaag aagacaccgt | 53100 |
| tgcaaatggg tcctgagcag ggcggcctca gcacctcagg atgtgtaaca gtccacctcg | 53160 |
| gacaggtcct gccttgtgtc agcaaagtag agttcatcaa cattgttgaa atgctcaaaa | 53220 |
| ctgctgcttg taattttgta atacagattt tgaaatctaa aacccagttt tctaccagta | 53280 |

```
gtacaaataa aggacactcg ctatgctgcg ggttgtgcgt cactgggcg tgtgcagtga    53340 ggtatggata tggagagttg gaaatgcagc agggcggctc tgtgggcagg cttcacagtc   53400
ctcttgaaat gtttagattt ttaaattcat aataaaactt agattatctg tgtgctgcta   53460
ctggttgtta gaatttgcga tatgggctgc attttttct tcatgaaggc tcacaaacat    53520
cattaaagac agccaggccc cagggctttg caagaaaaaa aaaaaaagca gagacatcac   53580
tttgccaaca aagatccgtc tattttccag tagtcatgta tagatgtgag agttattttc   53640
tttatagaaa gctgagtgct taagaattga tgcttttgaa ctgtggtgtt ggagaagact   53700
cttgagagtc ccttggactt caaggagatc caaccagtcc atcctaaagg agatcagtcc   53760
tgaatgttca ttggaaggac tgatgttgaa gctgaaactc caataccttg gctacctgat   53820
gtgaagaact gacttatttg agaagaccct gatgctggga aagattgaag gtgggaggag   53880
aaggggatga cagaggatga tatggttgga tggcatcact gactcaatgg atatgaattt   53940
gagtaaattc caggagttgg tggtagacag ggaggcctgg tgtgttgcag tccatggggt   54000
aattaagagt cggacaggac tgagcgactg aactgagctg acacctgaat tgctaaggg    54060 ggaattgtgt tcaccactta gagaacacat aaggaatggg ccaagtcctt accacttcct   54120
tgcaattggt agccaggcaa gcagacagag agagctcaag ggggctggga gaggtttgga   54180
ggatattaag aattctatga gaaggatgaa gagagcttct aataggtcca tataagagct   54240
ttgataatag ggttgcctga ttgatggcat tataggccca ggaagcttgt tcctttaatg   54300
agaagacttt gtttttgatt tttactttct tgccattctg tataataaat catacccttt   54360
atactttgtc aacattaagt taatttatta actttattaa taaagtttat caacattaca   54420
tttatcaaca ttaagttgat atcaactcat ctgttgctga cattccatca agcactgata   54480
cccctgtgaa agccatacaa gcaaacaccc ttcactggtg tgatgattgg aaaggagtat   54540
taggctccct ccctgcccc actgcaaaat cttccagtta ttttagagt tttcaaaagg    54600 gtggctcaag tgattttatg aataagacca ttggcttcct tcctgaaggc attttttctg   54660
aaacatctag ctatgcctat gtgcactgcc tacagaaacg catggtgaca cctaggccct   54720
tctagtgctc atttaagatc gccaatgata ccactctaat ggccaaaagc aaagaggaat   54780
taaagagcct cttgatgaag gtgaaagagg agagggaaaa agccggctta aaatttaaaa   54840
ttcaaaaaac taagatcatg gtatccagta ccatcacttc gtggcaaata gattgggaaa   54900
aaatgtaaac cgtgacagat tttatttct tgggctccaa atcattgtg aatggtgact     54960 gcagccatga aattaaaaga aatgtgctcc ttggaagaaa agctatgaca aacctagaca   55020
gcatattaaa aagcagagat atcactttgt gaacaaaggt ccatatagtc aaagctatgg   55080
tttttccaat agtctgatgc tgggaaagat tgagggcagg aggagaaggg ggagacagag   55140
gatgagatgg ctggatggca gcaccgactg agacatgagt ttgggcaaac tccaggagat   55200
agtgaaagac tgggaagcct gatgtgctgt agttgcatag ggatgcaagg agtcagatac   55260
ggcttagcta ctgaacaaca atgatatgtg tatcaaaggt gtgaactcca gttgacctca   55320
tagctttcag ttgggaaatc ttgactttga taagtctatg atttgactgt aaggcatgta   55380
aaacatgact atgacttcaa gggcagaggc aaatgggact gagcacaaag cactcttaaa   55440
ttgttgggag actgaatctg ggaccaactt tttgtgggaa atttagctat atgtattaaa   55500
aacttttaaa tgagcatacc ttttgcctca gcaattccct gtctggaatt tacctgagtg   55560
tgtgtgtaat gacagagctt ataaagatat tttgtgaata ataggaagat tggttaaagt   55620
```

-continued

```
acataacaaa cactgaatac catgtgccca ttaaatataa agttgtagaa agattttgaa   55680
tgacagggaa ccatgttgca aaatagcagt tttacaaaat attaatagta atagctacca   55740
tctagtgtgt gtgcgcgctc agttgtgtct gactctccac aaagcccacc aggcttctct   55800
gttcatagaa ttttctaggc aagagtactg gcatggttg ctgtttccta ctccagggga    55860
gcttgctgaa ccaggggattg aaccttggtc tcttgcctct cctgcattca gttcagtcgc   55920
tcagtcgtgt ccgactcttt gcaacccat ggactgcagc actccaggcc tccctgtcca    55980
tcaccaactc ccggagttta ctcaaactca tgtccattga gttggtgatg ccatccaacc   56040
atcccatcct ctgtcgtccc cttctcctcc caccttcaat ctttcccagc aacagggtct   56100
tttcaaacga gtcagctctt cgtattaggt ggccaaagta ttggagtttc agcttcaaca   56160
tcagtccttc caatgaacac tcaggactga tttcctttag gatggactcc tgcattggcc   56220
agcagattct ttatcactga gctacctagg aagccccagc atctattaag tgctatctaa   56280
tgacattaca tacattatca gtgctttata cacattgtct catttaatgt aactatcctg   56340
agagacccct tccctgatt accgataact acttaaaggc taaggaacta gttcaggtct     56400
ccagggtttg agagagccag aattcagaca cagactatct gactccagag ataatgatgt   56460
ccatccccgt actctgtata caagcccatt tttgtttttt aagaaaatat gtatgcagag   56520
aaagagacta aaagcagatg gtatgtggct ggtgggtata gatgattttc atctatttct   56580
tgatatgtca taagagagga acaaaaagct tagttacatg gaaatgaaaa agtgttagat   56640
taagaacaca tctagggact tccctaattg tttagtggtt aagactccat gctcccactg   56700
caggaagcat tggtttgatc cctgcccgga gctaagatct tcattggctg aaacagtggg   56760
tactgtgggg tcaaagaaaa aagagaacac attcagtagt tgtcccaata accaggcact   56820
ataaatactg ggcagttatt ctgttcaaag agggtgagca gagggcagtg gtctgagaaa   56880
ctgagtcacc catttatcct cctaactttt gaccttgtgc aagatggcct catttggacc   56940
aggtgggtca tcttaaaatt aggaaggtag tctttaggtt cctccctccc taatattcta    57000
ttacctaaaa tacccaaaca ctaaatgaga aaacagggca tttgaaaata gttggttttg   57060
ttcagtcact aagtcgtgtc tgactctttc tgactccatg gactatagcc agccaggctc   57120
ctctgtccat gggattctcc agcaagaaga ctgagtgggt tgctatttcc ttcaccaggg   57180 gctcttttctg acccagggat caaacctgtg cctcctgctt gcaggtggat tctttactac   57240
taagagcagc agcagcagca ggcaaattct ttaccactga gccacctgtg aagcttagcc   57300
caaagtaaaa tgttaactta gaacttaaaa cgactcattt ctataatgca atgcaattat   57360
gaaatgctgg cttcaatctt aaattttcga acagaatttg atggcaatga tccgcttgag   57420
aaagcattag gaagaggtta tgtactcttt tcctgaatct gcacactctt acagcttttc   57480
tacacgatcg gagtattgaa tagatgcatg tatcacagga ttgtgaggaa catatttaaa   57540
ctattcactg aatattttca ttcaaaaagt tttgtttccc cctccgaaca cccttagatt   57600
cagttcctga ttttattggc cctgggaagc agggaccta tttctcagaa gctcattcat    57660
tagagaccgc ctacttgccc cggggtgga caatgtgtgt gacaggaaaa aacctcggtg    57720
ccagggtccc cggtatttta ggggcgtggg acactggcag tggccaaatc cgcccaggtc   57780
agaccaggta ttgatccccc cgggtagcat tttgtggttg gtctccaggg gtactcccca   57840 ctgtctatt catccagcc cgggaagcag gatttgtagc gttgtcgccg caagcccagg     57900
gatatagtca tttccctgac ctcttcccgg cggccgggtg acggtcaggt ccagtacctg   57960
gctgggtcct ctaatgacac ttgcgtgctc tcagcccaga cgccgggcgc ttatcgcagc   58020
```

```
caggcaggca gcgccacgcc tttcacgggc cctcgggcat cgaccctgag ggaacagggg    58080
cgtgagggtg gggccgctgc cgggcgctgt cccggtcagc agtctaaagc ttgcgaagtg    58140
aggctgaagt cggtgctgcc tgcgctcgct cgtcggccct cgaccgccgg ctcgccgccc    58200
gctctctccg acgtgacggt aacccggggc cagtgccttc ccaggtcagc cgctgcgccg    58260
gtgagtgcgg ggtgctaggg gggcgcgtgg gcgcggtggg tgggctgccg ccgggggtcg    58320
tgggcgtcgg tcggggaaag tcgcccccgg ccgggctttg cctccagcgc gggctgtgtc    58380
ctgaatccca cgccgttacc gggcgaatcc cgagcgagcg ggagtttccg gcggtctgat    58440
agggactggg gagacgctgg aaggaggaaa ggagccagag agttttcgta aaagcttttc    58500
atcatttagg aagcactgta cggatgcctg atgtcattgt taagtaggag atgcttccgt    58560
agggtatatt tggaaggtcc agctgactca gcgtttttata taaatgattg ttagtgctct    58620
gcctctgagc acaacagctc ctgagattga agccctcggt taaaactgaa ccgctaactg    58680
tgagtaaatt gtgaaaaccg tttggaatat atggcataaa aggtccgtgg ctattgtgtg    58740
tgcatttggt aggcaataga aaactgtaca attgaaatga ctaggtttta attattccct    58800 ctcagttttta tttgaaagtg agtatgaaac agactgaaaa tttagactcc cctaaatttg    58860
gacctccacc ccgcctccag aaaacagctc cttggtgcaa ccgatttcgt gtctggtagc    58920 atgggtcac acagagtcgg acacgactga agcgacttag cagcagcagc agcagtgtgt    58980
tttagccggt tggtaaaact cttcccttttc cccaaatgta tgatattgga tagataaaag    59040
ttattgagta tggaggtagc agagaaactt gttaatattg gtacctttaa agggattaac    59100
cgatatattc tatgcccatt tcttctccct gggacataaa gtttgtccac aactttggtt    59160
ggtgtgctaa agcattattg agctgccttt tgtaattttt ctgtggatag ttgactcaat    59220
gattaacttc aaaaaattaa ccagcttatt aaaaatactt gttaaaaatg ctactaaagt    59280
tagaatacag aaaaatacat aaccaaaaaa gttagattgt aaatctagca aacagttaaa    59340 aaaaatacccc ataatgttgc tttgtttcat tttctcactc agtggtagaa atataaaagc    59400
tcattccact ttcacgaaaa aaaaaaaaga tttatagtaa caaatgttca ttggtcatct    59460
ttgttctgga ccctgaacat ttagctagag cccccctgagg tgctgttgca tcaaaatgat    59520
attaaaatac acttaccaaa atcaatttct acatttagtt gtgttaagtg ttcatgagct    59580
tttgaggcaa gcctaagtat tacaaatgga aagagaaatg caccaagaaa agagtcactg    59640
tgggggagta catttgaatg tatgtggaca gcaaattaaa gttatatctt ggaagctaga    59700 ataaaatgg accaatcagt cacacaattc agtgaggaca aaggcaggaa atatacatga    59760
gctccttaga gaagcttttc ctggcaccta cttctgagag aaatgtctaa tatcacgaaa    59820
ggctgcagat gagactgaag tatagcggtg gaagagtctc ctgggtgccc acccatagta    59880
catgcggtcg tgcatttctct aggactgctt gctgtagttg tcattctcct taccataagt    59940
attatgagaa acactcgtag gatgctaagc ctctatggtt ccacatgctg tggtttgata    60000
gtttgggaat aaatctggat tttatagagg ggtaggtaga cctcatgttt tcagatactg    60060
tttctctcag gcatttctga cagaagtttg gtgtcagttg aaggttatat caagtgagaa    60120
gttttattct atgttgctta ctggggttag aggttaaggt tgaggctctt ttagtgaaac    60180
ttaaagaacc tgaatgatca tccttgatac agggtatata ggtctgtgct atgctgtgct    60240
tagtcgctca gtcgtgtctg actctttgcg acctcatgga ctgtaggctg ccaggctctt    60300
ctgtccttgg agattcttca ggcaagaata cctgagtggg tttccatgcc ctcctccagg    60360
```

```
gggtcttccc aacccaggat caaaccaatg tctccctctt tgcagttgga ttctttaccg   60420
tctgaaccac cagagaagcc caagaatacc ggagtgggta acctatccct tctctgggaa   60480
ccctattccg acccaggaat caaccagggt ctcctgcatt gcaggtggat tctttaccag   60540
ctgagctacc agggaagccc gtataggtct acagtaagct aaagtttatc cttttaaaaa   60600
atcagttctg agttcagaat gtgaaccaat aatgatggag tatctagatg aatttggctt   60660
tatagttttt ttttcccccc aacattagtt tatgagatct aattcacata tcatacagtt   60720
catgcctatt taaagtgtac agtctctgca gtcttcacat tttcatcatt ctcgcccta    60780 aaaaccagtt aacactcact cctccttctc accataatcc cttaatctct gtagttttt    60840 ggaaaccagt gttctgcttc acaaggagac cattagaaag tggacatcta attttgagc    60900 cacatactta gcttgtttat agaaataagt aaaatattca gagaatcgta acaatgaaag   60960
ttagtggtgt tctgttgttt aaaatgaggt gggtgggtgt gggtgaagca gaagtgctgc   61020
ccacatccca attccagtga agaagttttg ttttggcaa gaagggtaga atgaaatctt    61080
aaaactccat tgaaaatgct gattactagc tcagtccctt tgcagctgaa aagacctgtt   61140
actctttaga gcaatggttg gctgggaatt actgcttaga tggaggtagc agtaggtagt   61200
tctctgtcat ttaacgggat ttaagttctt acctggaagc ataaaaagga aagtctctag   61260
aaagcagcaa gccctgttag ctccctctga aaacacttga gctgagtgtc ttacaaggaa   61320
aaaggaaaga ttgcctgagg ggtacccaaa cttcagatgt tttgcacagg agacctgtct   61380
cttctcttct ggtcctgctg catgggcagt tctacgctga ccacaccctg acttcaccct   61440
gaagtgaagt gaagtgaagt gaagtcactc agttgtgtct gactctttgt gaccccacgg   61500
actgtagcct atcaggttcc tccctccatg ggattctcca ggcaagagta ctggagtggg   61560
ttgccatttc cttctccagg ggatcttccc aacccaggga ttgaacccgg gtctcccgca   61620
ttccaggcag acgctttaac ctctgagcca ccagggaagc cctggacttc acctagagg   61680 agtgaaaaga agggatgcaa aaggtacagg gaacacagga tccttagaaa gggaaaataa   61740
agtatttcat tttacaactt ttcctccacc atcccatatt attttgaaat gccatatgag   61800
agttggacca taaagaagga tgagcgctga agaattgatg ctttcaaact gtggtgttgg   61860
acaagactct tgagagtccc ttggactgca aggagatcaa accagtcaat cctaaaggaa   61920
atcaaccctg catgttcatt ggaaggactg atgccgaagc tgaagttcca attctttggc   61980
cacctgatgt gaagaaccga ctcactggaa aaaaccctga tgctgggaaa gattgaaggc   62040
agcaggagaa ggggacgaca gaggattaga tggttggatg gcatcaccat ctcaatggac   62100
aagagtttga gcaagctctg ggagttggtg atggacaagg aagactgatg tgctacagtc   62160
cattggatca caaagagtca gacatgactg agcaactgaa cagaattgaa attaaaaaaa   62220
ttttgagaag ctgaagcagt agctatattt tccatccaca tttttctcca gtactttggc   62280
cacctgatgt gaagaacgaa ctcactggaa aagaccctga tgctgggaaa gattgagggc   62340
aggaggagaa gggggtgaca gatgagatgg ctggatggca tcatcgattc agtgaatgtg   62400
agtttgagca agttcttgga gacagtgaag gaccaggaag cctggtgggt tgcagcccat   62460
ggggtcacaa agacttggac atgactgtga ctgaacagca acaacaaaga taagatgagc   62520
aggtcttcag aattaataaa cggaaatggc cattaactgg tgaatgcttg ctgtctgcag   62580
gtggttttta tatttattct catttttggg tcacaccaag cctttcaggg aagtattgga   62640
gtttcgtact tacagaggag gaggcagaga attgtacagg gttatttatt gctgggacaa   62700
agtactttat taaagatcac caaccctttc ttttttttttt tttaaacagc ctggtcattt   62760
```

```
gtttcacatt ttctttccat gttcacagag cagctcagtt cattgtaaag gcatgcaggg   62820
acagtgaaaa gagcctgtga gagcagggag gcccagacct acctaacttg ggtctagtca   62880
ctgtgccatg aaatctcttc atctttgtgg accagtttct tcgtgggact aaagaatata   62940
ggaatttgag caagagaggt ctgattttat ttaaggagtc cagaagtaga atatgagtta   63000
gtagaaattg cctgaatagt agtgttaggt atgctgagaa ttcttagtat tcttacctga   63060
tcctacaata aaggattctg caaaccatct actttgattt agaatctttc tgatccattt   63120
ctccttttca taacataggg agactgttac atgtctttct agaatatatc atatgatact   63180
aatagttacc ccaagtaaac atatgtactt gagaaaccta agtagtaggc taactgtag   63240 taaaaaccca atagtatcat ttcagttatc tcttcaatct aatagtactg ttattatcat   63300
gccagaccat tcactgcttc ctctggaatc taagctatga gtataatcca tttgacatgt   63360
gcaatgttgt tttatacccca gctattacta gcaacctagg gccaggtgac tcattacatt   63420
gctacagtgt atgtgctgat tagctctttc ctcgagctac aagctattcc ttgtgttctg   63480
atttcatact tagatatata cctgccctct cccccagtga gatatgttct atctagcctc   63540
ctagaagtac tccttaccca gaagtaaatt caagtggttt aaattttttca acaaaaataa   63600 aattgctatt ctctccctct ataatatgag aaactagaaa aagagctctt tggtgcatta   63660
gtcttcataa aacaatgctt ttccaaatat atacagctgt ggctgggttg catcggtctt   63720
gataaggaag ttttaaagaa caaagatggc agtttaagtt taatattaca ctagcattat   63780
aaacattaaa aaatatgggg gttatttttt tttaattttt aattttgaaa tcattttag   63840 acttacttaa atgttgtaga aaatggtaca gagagttcct ataacatctt atgtaactat   63900
agtaccactg ttaaaactaa actataaact tatttggatt tcatcagctt tccactatct   63960
ttttttctat tcaggatcca gcctcagagc tcacattgca tctgattttt gtatatcctt   64020
aatttccttc aaactatgac agctcttcaa ccttctattg ttttccctga tcttgacact   64080
tataatgaat actgttcagt tattttgtag aatgtcttgc aattaatact ggatatttc   64140 tcatgattag attgaagtta tgcattttag gaagaaattg gagaaggaaa tggcaaccca   64200
ctccagtatt cttgcctgga aaatcccatg gatggagaag cctggcaggc tactgtccat   64260
ggggtggcaa agagtcagac aggactgagc aacttcactt tcactagaag taatcccagt   64320
gcatcatatc aggggtacat gatgtcttat tactgatgta aactgatgta aactttggtt   64380
aagagccgtt tgtcaggtcc ctgatggtta tcattttttc cctttgtatt taatatatat   64440
catgggagag aaacttgggc cttgcaaata ccctgtttct ccttaagtcc ttattcactg   64500
gttttagtcc attggtggaa ctggatgcac atggtactgt gttgttctaa cagtgattta   64560
aagattgttt ctcattactt ctctttatta atgagaattt tataaggaag agctgttcct   64620
tcattttttt attcaactgt atgaatatag actcatggat atttatttta ttgtataggt   64680
tataattgaa tacagtcatt atttaattgc tgatcaaatg gttccaccat tggccactgg   64740
gagctcttct ttcaggttgg ccactgtgcc cttttgatgt accacctccc catcctccct   64800
tttgaaaaag catttccttg ctttctggta tcatgaaatg ctccaggctg attttctat   64860 tttccatgcc ccgacccttg catcaaccat ttttccaagg cactctggtt ccttgtttta   64920
gaggctgtta ttatcagaaa ccaagatctg ggtactaggt gtgttactga agttgctttg   64980
aactttttaa gtttcataga tttgtgacct agcaaatgca tctctatagg aggagtaatg   65040
ccttaaattt caaagactct agagaccata gttgccaatt tgcattcagt ctcttatggg   65100
```

```
aaagaaatac aattggaagg gctagaattt taaaagttcc cagttttcct caaatgaaga  65160
cctgtaagtg tttataaaac aaatagaata aacacattaa tttttattta ctcaggctct  65220
gataagaaat tagcttgtta cttactgaat gtatgtgaag gggagatatg catagatcat  65280
atctttcaga aatgcaaaat gtctttaaat gaattgtgag atcctggcct ctacttcccc  65340
acacaaaaaa gacttctggg taagtctttg agcctacttt ctcattctga aaagaaaggt  65400
tttaggcaag attttcattt ctcttgactc ttagtgggct cagaggaccc tttaatatcc  65460
agaaaatttg dacccttttt ctatatttta ggtataattt agtgtgtgtt tattggttca  65520
ctggttaaaa agattcagtt taatttcata tctaatttat gttaatcatg ccagcttact  65580
tttaacactg aaatttactc agttaaactt tattttaatc taagacagtc cggaccacgt  65640
acagaagtct tttctaagag ttccatttcc acaaaccttc tttaacttc tttttactga  65700 taggttttgt cctatgcttt tcctttctct ctctctagga taaaattact ttcttttccc  65760
tcaacaaatt gtattttcat ttcttatacc ttttttcctt tcatgcaaga tgttttcctt  65820
accaatttta gttgtctcaa ttacatacat taaccagaat tctaactttt taaaaacctc  65880
aatttctagt gaaaactaag aagtatgcag ttataaactg tttttcaatt attattctgt  65940
agattgtcaa aatcacaaat actgtttatg atttctaaaa aatgtgtggt tttttaatga  66000 aaattttttca atgtgatatt tttattagta gacctaaata tcttctctgt aaaaaggcag  66060
cctatgttga gtaattaatg tttcagtatc ttatttta ttgggaatgat ctagatattt  66120 aaacggaaaa gaacatggca acccactcca gtattcttgc ttagagaatc ccatggacag  66180
aggagcctgg tgggctgctg tccatgaggt tgcacagagt cggacacaac tgaagcaact  66240
tagcatgcat gcatgcactg gagaaggaaa tggcaaccca ctccagtgtt cttgcctgga  66300
gaatcccagg gatggaggag cctggtgggc tgctgtctgt ggggtcacac agtcggacac  66360
gattgaagca acttagcagc agcagcagca gatatttcat aatttccatc atttcattta  66420
atttagcaaa actataaata ttaagtcatc taaaatctag agaaattatt tttaagtaga  66480
caaaccgtaa gacataatta ttcttaaaga atttacctca aaattgttac tctgtttata  66540
tctgttgaat tatagttatg tttagattac catgaaaact aatgagacat tacacaaaat  66600
aagccatcat ttcaagattt tttttttttga aaattttata acagagacag tatgaccctat  66660 ttaactttg gtaaacctag gtgcaataaa agtaagaatg gtctgtattc attaaaccaa  66720
caaatttaaa ctttaaaact gattcagttc agttcaattc ggtcgctcag tcgtgtctga  66780
ctctttgtga ccccatgaat cgcagcacgc caggcctccc tgtccatcac caactcccgg  66840
agttcactca gactcatgtc catcgagtca gtcatgccat ccagccatct catcctctgt  66900
cgtccccttc tcctcctgcc cccaatccct ccagcatca gagtctttc cagtgagtca  66960 actcttcaca tgaggtggcc aaagtactgg agtttcagct ttagcatcat tccttccaaa  67020
gaaatcccag gctgattgc cttcagaatg gactggttgg atctccttgc agtccaaggg  67080
actctcaaga gtcttctcca acaccatagt tcaaaaccat caattcttcg gcactcagct  67140
ttcttcacag tccaactctc acatccatac atgaccactg gaaaaactat agccttgact  67200
agacggacct tgttagcaa agtaatgtct ttgcttttca atatgctatc taggttgatc  67260
ataactttgc ttccaaggag taagcatctt ttaattcat ggctgcagtc accatctgca  67320
gtgattttgg agccccaaaa aagaaagcct gacactgttt ccactgtttc cccatctatt  67380
tcccatgaag tgatgggacc agatgccatg atctttgttt tctgaatgtt aagttttaag  67440
tcaactattt cactctcctc tttcaccttc atcaagaggc ttttgagttc ctcttcgctt  67500
```

```
tctgccataa gggtggtgtc atctgcatat ctgagattat tgatatttct cccggcaatc    67560
ttgatcccag cttgtgcttc ttccagccca acatttctca tgatgtactc tgcatataag    67620
ttaaataagc agggtgacaa tgtacagctt tgacgtactc cttttctat ttgaaaccag    67680 tctgttgttc catgtccagt tctaactgtt gcttcctgac ctgcatacac atttctcaag    67740
aggcaaaact gattattagt ataatattga ctatttccca gatcacaaga acttgaaatt    67800
tatttgggtt ggctttcttt taagtaactt aattaaaaaa cttttttttt tttccaagat    67860
tttttatttt taatttttg gccaagccct gcagcatgtg ggatcttaat ttgctgacca    67920
gggatcatcc taggcccctt gtcagtgagc acgtagagtc ctaaccactg gactgccagg    67980
caatttgcag gctagttttt tattatattt ttaaaatatc aatttgtaag tgattacttt    68040
gtcaacaaag gtccgtctag tcaaggctat ggttttttca gtagtcgtgt atggatatga    68100
aagttggact ataaagaaag ctgatcacag aggaattgat gcttttgaac tatggtgttg    68160
gagaagactc ttgagagtcc cttggactgc aagagttcca accagtccat cctaaaggag    68220
atcagtcctg ggtgttcatt ggaaggactg atgctaaagc tgaaacccca atactttggc    68280
cacctgatgc gaagagctga cttgttggaa agacccccct gatgctggga aagattgaag    68340
gtgggaggag aagtggacga cagaggatga gatggttgga tggcatcatg gactcaatgg    68400
acatgagttt ggctaaacta cggaagttgg tgatggacag ggaggcctgg catgctgcgg    68460
tccatggggt tgcaaagagt cagacacgac taagcacatg aactgaactt ttacatcagt    68520
taaatacagc ttttttatat gtgtaatttt gataatatta tctggagtta ggaacatatc    68580
atatgtataa tgtacacata gaaatataaa aagacataac tagagacctc atagcttcat    68640
ttgaaaactt agttatgtat cagttattgc attataaatt tactagttta taaataacaa    68700
tttgaataag ttaaatatat ttgctcagat gactaaagct tttcactgtt tgtgaagaat    68760
attttaaagt ttgtatttgt ccttgataaa tcctgaagga ggctgtgaat tagatatgat    68820
gagggatgct ttctagcagt ttgagttcag aaaagcctgt ttctctctct ttctctcttt    68880
cttttttttt tggtgcaggt tctacctgat tgagctaatt cataagctca gtcttaggtc    68940
cttgtgggat gtacttatgt ttctgatatg tagagatttg taagacaaga cagttgcttt    69000
taattcctca gagaactggt ctgtcaccta tatggtattg aaagattgat ttgcccaact    69060
acattttctt tatttgcttc tttatatcag taaaaagatt tccaactaca gtgaaaatca    69120
agagttatat gttctagaac tttagggttc agtttatcct gctttccaaa cttttgcacaa    69180 gctattcaat aaaggccctc ttttttgagt atacaaatta aacccagagc agttcactct    69240
aggggctaaa agtcttcatt attttttatta actcctgaat attagccccc agttttattt    69300
catattgtgt gggctcaggt aaccctattg attttcctta gtgtgtttaa tcaatgttgc    69360
ctgaggggca gatttataag ccctatctta caccaggcaa gggtgaccta agtttattcc    69420
ataatataat tggcagaaga gatttaacca tcttatataa agcccattta aacataccaa    69480
cttttataaa cattcatctc aattctctca gctcttatat ctgtaatttt aacctccatt    69540
aagtccccat caacctgtct tggtcttaca cagagtccca gaaacgtttc ttttatctc    69600 cctgaccacg ttatctatct ttatataaaa ggctttgggt ttcccagccg aggggttgag    69660
ccaagggact caggcctttc attgatattt taacttgatt aattggccta actgttgccc    69720
caagcaattg aatttctag cagccttttta aatatgtata tgtttgctg tgcttaattt    69780 tgctcagtgt gtctgactct ttgcgacccc atggagtgta gcccaccagg ctcctctggc    69840
```

```
catgggggat tctccaggcc agaatactgg agtgggttgc caggccctcc tccagggtat    69900
cttcctaacc cagggatcga acccaggtct cctgcatcat aggcagattc tttactgtct    69960
gagccaccag ggaagcccaa actggggtaa atagagtgga cttgtttggg gttctttaat    70020
gatggagacc gatagggagt ccctttggcc atccaacctt agcattgtat caaaatgttt    70080
gttttgatac atgtatttat tggtttattt atcccatttc ttaaccatct aaagattttt    70140
actgttttgg aacaagtctc tttaaaattt cttccttgtt gggaagatgt ctctagactt    70200
tctctgcagt ttttcttat tcctgttaat caacctaact taacaatcta atgcttttat    70260
tagcatctgt aagacccgtt gagggaaat tgaccacaaa tttagtttcc caaacttttt    70320
tgttgttgct ttttgttcgt ttaaactaag ggagttatta aggttagcca ttatatttt    70380
ttgtatccac tttctacttt ggtctttca taggtgccag taatccagct gttaatagtg    70440
agagttctct aaaaatttcc cagtttagaa gtttcttcaa ttttaatctc cattgtctgg    70500
ccattgccag agctctcata acacaggag gaaaaaaaag tcttaagatc aggtaaaaca    70560
tttatatctc aaagacacag tgggagaaat gctagttcct cctttgaaaa gttttttgtt    70620
cctttaaggt cagaattccg agaagatgtt ttatcaagct ggcttttct agctgcacac    70680
atgcacacaa aaattaactt tggagtgtta aagaaccca catttggtcc ttttaaggt    70740
gaggtttcct ttaattccca acaaagcagg tacttgtagg aataaattct gttcatacat    70800
aataaagtct tcccagcgtc tctcaactgt ggtaatccag ttttcaactg agcaaaatct    70860
ttcccttgtc agttcatctg ggataaccca ggtacctctt cttgaaatta gttcaagga    70920
aaatctcctc cagcgaggat tttattcacc atcaaataaa actaaggata atcagccaat    70980
agtggagatc caggacccag aagagattta cctaaattca tatggactct gaggaggtgg    71040
ctaggcacaa gaggtctttg ctggtaccaa ggctccagat tcttgtagcg ttcgggtgag    71100
ggagagaagt ctgctctggg tccctttgtt gctaactaaa gcggtcgact gaagaaaaac    71160
gcataaccta aaagttgcaa gttaagtttt atttgaggat cttactgagg actgtggttc    71220
aggagacagc ctctcagatc actctgagga actgctccaa acacaaaaga ataagggagt    71280
agccagggta tttaggaaat tttgctgaaa cgaaaaacaa caacaggaaa aaccaaacca    71340
tgtagtcaaa catcaaagat agtcacaaaa aatagacatt actagttaat gattttagta    71400
cttttctgta tgagaagata caagactctg ggctcattgt aattattcct tagatatgca    71460
tcttaactta tctagggcca gtgcccagaa cacacaatgc ttccttttt tctctatcct    71520
aatttctcct cagctgtacc tggggggttt ggggaatgcg actgcagtgg ctaatggctt    71580
gatccttgtt tactgaaata agaggcaaca ttctttgttt actagaatgg caggcaacat    71640
tccctgtcca cgtccacgtc tgtcagtttc ctcttaaatg taaatgagtg tgaatgtaaa    71700
tgtaaaatga atataaaatg taaatgagtt tccatggacc tgaagctgga ccattactat    71760
acttgccctt gttttcccctt aattgggcaa atttggggga ggttgagagt gagattgctt    71820
tgaaatgggg caaacagtag agagtcatta taaaactccc attggctgtg accttgctgt    71880
gggaataggt gcctttgct tgttggaatg ctggatcttc cttgctctac cagccccact    71940
cttttgtgta taaaggctgc acaccaaggg taaccggcat cctaagatat atatctgaat    72000
acactcttcc ttagaaacca gataatgttt ttacatacag tttcagagtg cttgttttgt    72060
gtctggtgtt gtatttaaga ggcttccctg gtggctcaga tggtaaagaa tatgcctgta    72120
gtgcaggacc tagaggacag tgtccacatc ttggctcttg aatgactaca gtagcctcta    72180
tgtagtctcc ctgctctgct cctgtctcca gcaccccac ccccaccccc aagtcagagt    72240
```

```
gatcttttta aacataatta gattatgtta ttcctccacc gagaagccaa gcaaagttct    72300
tatagtggcc tgaggtatgg acactgccag aattgacctg aacctctgac ttcatatcct    72360
atgctctccc tccctctgct tcagtccctt ggccgtgct cttcctcagg ctagcacttg     72420
atcttggcat cacaactcca gagagccacc ctcaggtttc tgctcaaaga cctcattggg    72480
aaggccttcc ctgacttcat ttcctccttc acttttattt ttttctcttt agcactgctg    72540
actctgacgt ttttcatcaa aaggaaaaag gaataggagt tagggacata ccccatgca    72600 gtcaaaaatc cattataact tttgactcct ccaaaactta acacatattt tatatgttat    72660
atgcatatct acatatattt tatcattgat gacatatcta actttcttgg ttttttttcaa   72720 tatttcaaat tttttcaaat tgttgcaaat cttgaaaaaa aaaatctccc aatatattta    72780
ttgaaaagaa atccacaata aagtggacc tgcacagttc aaatctgttt gttcaaggta     72840
tggccaaacg caagttcata tgctcgacac acagtaaggc caaactgaaa cactggagtt    72900
tggaacagag aaaggtttat tgcaaggacc aaggaaagag aatgggtggc tgtactcaaa    72960
agatgtgaac tccctgatgg ttttcaggaa agtgttttta taggcaaaat ttggggtgag    73020
ggctgcaggg tgtgtgactt ctgattggtt ggtgatgagt tagcatggtg gtgtttcaga    73080
aatcttgtgc tcagcctgaa gttactgttg tccatcctgg tgggggcctt acttcctata    73140
gaaaaactca aagatattgt aatgtatatc ccttgagggg gaaccaggac cctgctcctt    73200
ggctgtccta tagtttcttg actgcctttc cttggtttct gcattccttc actcttctaa    73260
ttagcaacca tttgaatctg ccctttgaaa ctcaggaag gtctgagaaa ctgaaatttt      73320
ttccctgcaa acaagaaatg ggatacagag agacttttgt atgcaagagg gccacacagg    73380
gtcctgccag gtttcaaggg tcagttatag ttgcattagg tacacttgta tctatttaaa    73440
gagaggatta ggattaaatg gagggacctc cctggtggtc aagtgattaa aactctgcct    73500
tctaatgtag ggggtgtgag ttcagtccct ggtcagggaa ctaagaaccc agatgtctca    73560
gggtgcggcc aaaaagtaaa aaaatagtaa taataaaaaa attttttta aagattaaat     73620 taaaaaggg acaggaaaca gatctatggt tgtcatgggc tggggtggga gagggaattt     73680
ctttgggatg atagaaatgg tctttgtcct acttttcatg attacatgtc tgtatacacc    73740
ttcaaagtcc aaaaactgta cttaaagagg atgtttgatg gtctacaaca ctgtttacta    73800
ttgacacgtt ttgaataaac atgacaaaaa acagagatta ggctgaacca tgagtagagt    73860
tggtgttatg ttggaaggaa tgttatatgt accaaaacgt tccccctctt gtttgttatc    73920 tattccttt tcctctgtgt tttgtgtgtg ttagtcactc agttgtgccc gactctttgt     73980
gaccccgtgt actgtagccc accaggctcc tctgtccgtg ggattctcca gacaagacta    74040
tcagagtggg ttgtcatttc ttcactaggg gattttccta acacagggat caaacccggg    74100
tctttaccat ctgagccata agtcaccaat tctccgtgga tccctcactg gtcttactgc    74160
gtatctcctc agtgcaggaa ggacggggat ctgtagaatg agggaggaga tggctgaggg    74220
gacctgtgga gcttccaaag tcaagtctta gctccctaca gggcatacgt cactctctga    74280
tgaactttgc tgcctctcca gcctaatttt cttactgccc ttccccaaa gctgaactt      74340 aatataatga acttaccaac taaaaaaagt cacaacctaa aagttgaggg ttatgctgca    74400
tttggtggga attttagga cttcaggacc gggaggcaac atttcaagta gccttgagag     74460
aactgctctg aggaggcagg gtggaggagt caggttatat agaccttggc aacgaaggac    74520
aggtagtctg aacatcaaaa gtatttttgt gaattaaaga aaaccagcta tctcaagtta    74580
```

```
aggaatttag cacttttctg tatatggcaa gatgcaagcc tctgagctca ctgaagtctt   74640
tcctttccta tgtatctcag ctatctgggg ccagtatctt gtggtttttc acatcctgag   74700
ttctcctggg ctccccatag ggagtggctg cagcctgaag gctgtcagat cttgctggtg   74760
ttcttctcct tcctgggtgc cctggagggc tgggatcact ggtgactgtg acctcattgt   74820
ttactgatat ggcaggaagt actccatttc tcaaacagca tgcatttccc aaagcaatct   74880
ctttcagttt aatgattttg cttccttta ctaggtcaac tttcttttct cttctctcct   74940
tcctatataa ctggttagtc tcctttaata ggccacttct aaccactgtg accccaccc   75000 ccacccgccc tgcccaagc catgtattcc ctgagagatg aatctggtct taatccctca   75060
agtaattttg aagctctagg caaaggggta gggaaggaca ttcctggctg gaaattctgc   75120
tttgaaacag gataattata ttttctctca actccacctg ggttaataca gtgagttttt   75180 aggggggtatt cattaagctt tgtccttacc ttccacaaag tccaggtgaa atctttggtg   75240
gtatttgtgt cctttctaat ttgtacatat agtttactaa tcctggcaga atttaacttc   75300
tgtagatgac ctctctaaat agggtggtta gtgacttcct cttgtttgtg ctcacaatat   75360
ctttatgaag ctactttgct taatacaggg gtgtggcata ttgtaattta gtctttcatt   75420
cagcgggaat aattgagaat atgatatgag tgaccccaaa ggatacaagg gcttccctgg   75480
tggctcagag gttaaagcgt ctgcctggaa tgcagtagac ccgagttcga tacctgggtc   75540
gggaagatcc cctggagaag gaaatggcaa cccactctag tactcttgct tggagaatcc   75600
catggaggga ggagcctggt aggctacagt ccatgaggtc acaaagagtc ggacacaact   75660
gaccaacttc actttactta aaggatacaa aattgatgga cattaggtcc ctgctcttac   75720
aacagacatg tgggcaaatt tttagtttgc aaatgcatat atggctttct gaaatggcag   75780
gtttgcaata aagtccaaag gagataactt taaaatatca tgattttact tataatttgg   75840
gagatagctg aaggccaaaa gggcatgaga agaatgttcc tgcactgtga gctagggcta   75900
gaaaaaacat tttaatgata atttgcttga tgagctgtga tccaaatact ggtcatacat   75960
tgttagataa agctttgtga ctattattag aaagctttgg agggtggctg gaaggtctat   76020
agttcattta aatttattat ttttctttca tcagcccacc ttcagtattt gaaattcgga   76080
ataaagtagt ctgaaattta ccatgaaaat gctatgagat ttgttattgt tagggaacca   76140
ttaattgccc actttggccg ggcatgataa taattgcttg cctgagttgt ctcacaatag   76200
gaggtcctgg taaagaagga ggtactacct ccaaaaagta acaggaaaga gttcagatca   76260
gatcagtcgc tcagtcgtgt ccgactcttt gtgaccccat gaattgcagc acgccaggcc   76320
tccctgtcca tcaccaactc ccggagttca ctcagactca tgtccatcga atcagtgatg   76380
ccatccagcc atctcatcct ctgttgtccc cttctcctct tgcccccaat ccctcccagc   76440
atcagagtct tttccaatga gtcaactctt cacatgaggt ggccaaagta ctggagtttc   76500
agctttagca tcattccttc caagaaatc ctagggctga tctccttag aacagactgg   76560 ttggatcttc ttgcagtcca agggactctc aagagtcttc tccgacacca cagttcaaaa   76620
gcatcagttc ttcggcgctc agccttcttc acagtccaat tctcacatcc atacatgacc   76680
acaggaaaaa ccatagcctt gactagacga acctttgtta gcaaagtaat gtctctgctt   76740
ttgaatatgc tatctaggtt ggtcataact ttccttccaa ggaataagca tctttaatt   76800 tcatggctgc agtcaccatc tgcagtgatt ttggagcgag cccagaaaaa taaaatctga   76860
cactgtttcc actgtttccc cgtctatttc ccatgaagtg atgggaccgg atgccgtgat   76920
cttcgttttc tgaatgttga gctttaagcc aacttttca ctctccactt caccttcagg   76980
```

```
aaagagttca ggaggggcca aaaggagaag ggaggagtca atatatccta tcaacctccc    77040
agaatccttc tcgctgaaat ccatcttggc tgagagatgt atgcaccacc agggaggacc    77100
ctgagtcaga atgattggcc agagacaacc tggaaaccaa ccccattacc ataaacgcgg    77160
agactctgag ccatgtggtg gagcagttct cctgggttcc cttcccctgc tgctctccgc    77220
tgaggcaccc ctctctaata aagtcttttg ctttgtcagt tcgtgtgtct ccttggacca    77280
ttcatttctt agagctcact cttgggccct ataaggggt ccccttcctg tactcagtag    77340
taaaaaatgt tttgataaaa tgtgaattct gtttggggac cagatacttt agggattcat    77400
cttgtttgtt ttacttgagg aaagtgattt aattcaattt agctattgtt caaaagacag    77460
ttctaaaata atggaagcat tgccttttt cagccattgt atatatgatc attttataga    77520
tttgttattc ttaacctgaa acatatagca ctgtcctatt tttgaaataa atatatctct    77580
ttctctctct ttagtcgcta agtcgtgtcc aactcttgag accccatgga ctgtagcctg    77640
ccaggctcct ctgtccatgg gattctccgg gcaataacac tggagtgggt tgccatttcc    77700
ttctctaggg gatcttccca acccaggaat cgaacccagg tctcctgcat tgcaggcaga    77760
gtctttactg actgagctat aaatatagta tagttttatg gtattttgaa atctaagaat    77820
gaatttgata atagcatata gcaagtatta tttttttttt ttttgatgca ggatgaatat    77880
gggagtgctt ggggtgtcct catagtgttc aagtatatgt gtcttttatg gggttataaa    77940
attgactgtt tataaagtaa cccaagaatg agaaaataca ttttttaaaa gtaagcactt    78000
tagacctgtg ttgtcctata tggtaactat taaccacgtg tggctattta agtataagtg    78060
agtaagttaa ataacataaa atattcacca gctatatttc aagtgctgag tagcagccat    78120
atgtgtctgg tggacagcac tattttatta tccctatgcg tattaataaa gaacatggaa    78180
aggagcacag gcacttttcc atctgacctc tgattatctt gaactcaaga gaatcacttc    78240
ttgggcctca tttacagcct ttttacacat aagaaaccag attaccatct atgagatcag    78300
tggttgtgta acttgtgaga atgaagggaa ttggtaattt tattttgtgt gtgtgtgtgg    78360 ggggggggt ggggggcgggg gcctgtgctg ctaagcatga aggatcttaa ttccctaacc    78420
agggattgaa tccatgcctc ctgcagtgga agcacaaagt cctaaccact gtaccatcag    78480
ggaattccag ggagttggta atttttatct tgtcaagtta tatatctctt agctggtgct    78540
ccctaatctc cactatttta aacatatcct cagcactcag tccttgataa atccttctct    78600
tagctataga ggaggggaga aaaagtttt cattaccagg cccattcctg tgtctcactg    78660
ttagcgtgtc tcactgtttt tctgcagtag cctcctaacg cccttgcttc cacacttgtc    78720
tcacagtagc agctacagtg atttttaaaa aacagttaag atcatgagcc tttcctgctt    78780
gaacggcctc agcggcttct cttggactat acagaccttc cgcaatggta tttcttcctg    78840
tctgtctgtc tgacctcgtt cttttgtgccg ccctccccag atcactctgc tgcagcgctg    78900
tgggggcctt gagtgccaga tcgtttcctt gacctgaaga catcagccct ctgactccaa    78960
cgctgcagtg ccgatgtcaa cactggatgt ttgctccagg gtggaactgt tagatgagag    79020
atgatgtgaa aacccattga tggatagagg actctttaaa cttcagggat ttattgtgga    79080
agttacagct cagattttga gttccttttc taacaatgtt caaaactatc cagcttctat    79140
ttctgtttgt tcataagttt tgtagcagtc acctgacagt gacccaagaa gcctaattcc    79200
ttgtcagggt agcgaggtct gggcgtcaca gtaaatagct gaagaaggtg tgtttaccca    79260
gcatgtcctc ttggctatga ggcagagtgt cacttttgct attattatcc ctaggggaaa    79320
```

```
aaaaagtaag aagaaggcct gaactcttga cctgaggctg ctctggcttc taccagcagg    79380
tgcaatattt ccagctatgg acagctgtct ggctgaggac tttagaactg aactctactt    79440
ttattacctg tgtgcaattt ctattgactt atgtactctg tttatagtag actgtctgat    79500
taagagtatg ataaagagta agatagagaa aaatggtatt ttttttttt taagcgagtc     79560 ctatattatt gaattctgca atagggagca gaattatata tggttgagtg tgtgggcttc    79620
aaaggcagca ggcctatttt ggcttttttt ttttcaatta actaatttat tttaattgga    79680
ggataattac tttatagtat tatgatggct tttttcatat atcaacctga atcggctaca    79740
ggtatatgtg tcgcccccat cctgatccct cctcccacct ccctcccac ctatccctc      79800 tgggttgtcc cagagcactg gctttgggtg cctggcttca tgcgttgaac ttgcactggt    79860
catctgtttt acatatggta atgtacttgc ttcaatgcta ttctcttaaa tcatcccact    79920
cttgccttct cccactgagt ctaaaagtcc attcaaaagt ggtagtttta atgcaagtta    79980
tcattcttat aatagatata ccagtgtcta tggaagaaga ctttccaaaa aagtaaaaat    80040
gtacctcatt agttagaaaa caagaagaag agaggaaagg tgacaaaggt agacacaggt    80100
agaaaagaga tagctgggaa gggggaaaga atctcgttat tcaaagccgc tcagtcatgt    80160
atggaagact gttccagctg gtgaaaagat aatcaggccg gttaacaggg caggctggtt    80220
caggcgagtt gtatgaagcc atttggatgc tgcttttatt tttcaagtct ttgaagtggg    80280
tctcagattc agaaaacgat ttagcacatg ctctggaagc tgaactaaac tggaagcaag    80340
gaagcagcaa caaggggga agttgatttt tgtcatagg aaatctagat gtggtgtata      80400
tatatatatc tgtagggaaa gattaatgtt tacttagaga cagttacttt cagtgattcc    80460
tctataaacc caggatactg ggataaaccc agtatctgga taaacccagt atactgtata    80520
cagtataccc aggatactgt ataaactgga gacttgagta cttgaggtta atatggtgct    80580
gagatgtgtg tttttaaaat tttgttatca ttcctataag ttttttgttt catcttagag    80640
taatatattg tttcatattg gtgttagaaa taagtttggt ttttggtata atgtgcttca    80700
gctggatggt gtacttcagt tatgcctgct catctcttga tttgtgacac atgaattact    80760
aagaccctgt actaagcatc tcctattcct aagcacctcc tagcaatgtg aattactaac    80820
ttaatcctat cacagtgaag acgaactcag tatgcacata cttctagaat tgtgattgta    80880
tttatctgtt ctctatcttg gatggatgga tgggtatgga tgatctttct tgggtactat    80940
agttccagtt ggtgccttt attaacagaa aatctcacaa agattttgta ttaatgtttg     81000
tcttgagcca atggcctatt taaatttagg tgggatgtta tttgattctc ttaatgagcc    81060
ttgtggaata ggaaatgaca acccactttg gtattcttga ctggaaaatt ctatgggcag    81120
aggagcctgg caggctacat tccacgggtc gcaaagagtt ggacagactg accacacaca    81180
cacacacaca cacacacaca cacagagcct tgggagattg ttagaaagtg tccttacgca    81240
cacacgcaca cacacacaca gccttgggag agtgttagaa agtgtccttg gagcctgaac    81300
atcaaatggg gaatggcaag agaagcaatt gctcgtgtca ggctagtata gtttggcttt    81360
tgaagacatg ggggatggct taagaagttt acaaagtcga tatgcaaggt ctctatagtt    81420
atttgcacct tgagccttct ctttcactgc tttcagagag tagggcttga gctagttatt    81480
accattcatt gtgctcacag attaaaacta ggctctttta attttctggg tgccagtcta    81540
taagtggttt cctactttg cagtttccaa agtggaatat gttttaaatg tgataacaat     81600
agagcagttt ccggctatag gaagaattac agattatttt gatttggggg aagttctact    81660
atgatatgct caggtgtgtg tggttttctt atgcatatcc tgtcttggtg ttcctggagc    81720
```

```
tccttcagtc tgtggcttga taccttcagt tttggaaaat gtttggccaa tatttcttca   81780
aacactgatt ctgcttcatt tttatttct cttttcagg tctccagtta cttgtatgcc   81840 agatctttt catcacattt catatgtttc ttagctcttt tatgtagtta aaaaaaaaa   81900 agctacttct tcattctctt cagtctgaag ttttttgttt cttttccatg ctgataattt   81960
tcatacactc ttcaatctgg atgttttcca catggaagtc tgtcagttca ctaattcttt   82020
cccagtctgt atctaaactg ctattaaact catctactga tttttaaaa actattgatt   82080 agttctttgg tgatagccta tcttttcatt tattttctta gacatattac tcagttattt   82140
taacgcagat gtctgatgac tccaacgtgc aatacttatg ggtctacttc tattttcttg   82200
ttttggaaca ttaggtctta tttctggcg tgcttggtaa ttttttattg aaaatttgga   82260
tgatgatgac tttggaatag atttaaattt cttttagcaa aatatgagtg gatcacattg   82320
cttgagtaaa ggctggtctg cttctaggtt gctcatattt ccaggtcata gccctactgg   82380
tacgatctca aaaacttggg gttttcaact ggtaaactca cagctccaaa ctttgtctcc   82440
ctgttaatga gctgctactg ctgctaagtc acgtcagttg tgtctgactc tgcgacccca   82500
tagacggcag cccaccaggc tcctccatcc ctgggattct ccaggcaaga acactggagt   82560
gggctgccat ttccttctcc aatgcatgaa agtggaaagt gaaagtgaag tcgctcagtc   82620
gtgtctgact cttagtgatc ccatggactg cagcctacca ggctcctcca tccatgggag   82680
tttccaggca agagtactgg agtgggtggc cagtgccttc tccgcctatt aatgagatgc   82740
tacttaaata tattcattca gcttttgagc agctcttttct gcctggtttt tctgggtttt   82800
gccccatgta tgtgtaattt gcctcaagaa tgctgggcat ggaatgcttc atcttttctc   82860
ttttccagaa ttttagatac ttaagtcctg gctgctttgg ttacacccat cagaaaacat   82920
tcttcaaaga gctgcatctt gtattttgtc tgcttctaca gttgtcctta ggaggatgat   82980
tggtttggac aagctactct acagtagcca gagagaaagt tcttcattga ttactttgat   83040
ttttaagaat taaaccaag tttatggaag tttcattttt caaagctatt gcacaagctg   83100
ttaagttcac cttaagatcc tactctaaat ccttataaag gggccttttc taacttgtta   83160
aatgaaatat tttaaacttc atttataaat ttaatactca cttgttgttt taaattcttt   83220
aactacttaa ctcttggttt gatcttctca atcattttta tacataattc taaaccttcc   83280
tagaatttat atgttgtcca ttaagaaaat gagtttatca ttccaaacaa ttttggagtt   83340
tgtcttctta gttgattaaa ggaacatagc aaccagagat gtaaagtcag gagctttaaa   83400
ttcaaagaaa tgtctcttgt cactgactgc ttggccaccc cccttttgt aatatctatg   83460 tcatacactc aaataagaat ggagtgatgg tgatcatgta gcctgtccct gatcttgagt   83520
catattaata atatattttt taagtcagct ctaactccca tttatctttt gctgtttcat   83580
gagttttgag taattttcat actctcccta tttacttgtt agatgtttaa ttgacatcta   83640
attggagttt atatattcgg agttgtgtct gcctccctaa tgtaggttcc aagcttgtta   83700
ttgttgttgt gatatggcct attcattgga aatggagctg cttattgcat tgaagtttaa   83760
aatggacttg tttaaaatt ttaaaaatac atttaattgt attaaatata gccaaactat   83820
ttttacttaa acatgttatc aatataaaat gaccaataag gcattttaca ttaaactttt   83880
tttgatctct aaaatttta acaaattgaa ataattgaca taataacatt agtttcaggt   83940
gtacaacata atgacataat atttgtatat tttgtgaagt gatcaccaaa ataaacctac   84000
ttaatatcca tcacacacaa aagtcacaca ttttttttctt cttatggtga ggactttaa   84060
```

```
gatctctctt ggctactttc aaatatacaa tacagtatta ttacctatag ttactgtgcc    84120
acacattata tccccaggtc ttatttattt tataactgga agtttgtacc aaagcagttt    84180
tgttttaagt gtattgttaa ctactgttta cagtctcatt tacctggact atcaacttat    84240
tgttgctttt ccctccacag gaaggcggaa atgctcaaaa tgtcttccaa tagttacgag    84300
gtttctatcc caatgtcaaa aaactcaac ggcattccag agacaacctc taaggacctg    84360
cagacattaa ctgaaggagc tgtgttaagt tttcataaca tctgctatcg agtaaaagtg    84420
aagactggct ttctactttg tcggaaaaca attgagaaag aaatactagc aaatatcaag    84480
```

<210> SEQ ID NO 183
<211> LENGTH: 1977
<212> TYPE: DNA
<213> ORGANISM: Bos taurus
<400> SEQUENCE: 183

```
atgctcaaaa tgtcttccaa tagttacgag gtttctatcc caatgtcaaa aaactcaac      60 ggcattccag agacaacctc taaggacctg cagacattaa ctgaaggagc tgtgttaagt     120
tttcataaca tctgctatcg agtaaaagtg aagactggct ttctactttg tcggaaaaca    180
attgagaaag aaatactagc aaatatcaat ggagtcatga aacctggcct caatgccatt    240
ctgggaccca caggtggagg caaatcttcg ttgttagata tcttagctgc aaggaaggat    300
ccacatggat tatctggaga tgttttgatc aatggagcac ctcgacctgc caattttaaa    360
tgtaactcag ttatgtggt acaagatgat gttgtgatgg aactctgac agtgagagaa     420 aacttacagt tctcagcagc ccttcggctt ccaacaacta tgacaagtta cgaaaaaaat    480
gaacggatta acaaggttat tcaagagtta ggtctggata agtggcaga ttccaaggtt    540 ggaactcagt ttatccgtgg tgtgtctgga ggagaaagaa aaaggactag tattgcaatg    600
gagcttatta ctgatccatc catccttgtt ctggatgagc ccacaactgg cttagattca    660
agcacagcaa atgctgtcct tttgctcctg aagaggatgt ctaaacaagg acggacaatc    720
atcttctcca ttcatcagcc tcgttattcc atcttcaagt tgtttgatag cctcaccttg    780
ttggcctcgg gaagactcat gttccacggg cctgctcagg aggccttggg gtactttgga    840
gccataggtt ccgctgtga gccctataat aaccctgcag acttcttcct ggacatcatt    900
aatggagatt cttctgctgt ggtgttaaat agagaagaca taggtgatga agctaacgag    960
accgaagagc cttccaaaaa agatactcca ctcatagaaa aattagctga gtttatgtc    1020 aactcctcct tcttcaagga aacaaaagtt gaattagata aattctcagg ggatcagaga    1080
aggaagaagc ttccatccta caaggaggtc acttatgcca cctccttctg tcatcagctc    1140 aaaatggattt ccaggcgttc attcaaaaat ttactgggta atccccaggc ttctatagct    1200
cagctaattg tgacagtctt cctgggactg gttataggtg ccattttcta tgatctaaaa    1260
aatgatcctg caggaatcca gaacagagcc ggggtgctct tcttcctgac gaccaaccag    1320
tgtttcagca gtgtgtcagc cgtggagctc ctggtggtgg agaagaagct gtttatacat    1380
gaatatatca gtggatacta tagagtgtca tcttacttct ttggaaaact gttatctgat    1440
ttactcccca tgaggatgtt accaagtatt atatttactt gtataacata cttcttgtta    1500
ggactgaagc caaaggtgga ggccttcttc atcatgatgc ttaccctgat gatggtggct    1560
tattcagcta gttccatggc actggctata gcagcaggtc agagtgtggt atctatagca    1620
actctgctca tgaccatctc ttttgtgttt atgatgatat tttcagggct gttggtaaat    1680
ctcaaaaccg tcgtgccttg gttgtcatgg cttcaatact tgagcattcc tcgatacggc    1740
```

```
tatgcggctt tgcagcataa tgaattttg ggacaaaact tctgcccagg actcaatgta    1800
acaacaaaca atacgtgtag ctatgccata tgtactggcg aagaatttct gaccaaccag    1860
ggcatcgata tctcaccttg gggcctgtgg aagaatcacg tagccttggc atgcatgatt    1920
gttatcttcc ttacaattgc ctacctgaaa ttgttattcc ttaaaaaatt ttcttaa       1977

<210> SEQ ID NO 184
<211> LENGTH: 11
<212> TYPE: DNA
<213> ORGANISM: Bos taurus

<400> SEQUENCE: 184
cggctmtgcg g                                                            11

<210> SEQ ID NO 185
<211> LENGTH: 658
<212> TYPE: PRT
<213> ORGANISM: Bos taurus

<400> SEQUENCE: 185
```

Met Leu Lys Met Ser Ser Asn Ser Tyr Glu Val Ser Ile Pro Met Ser
1               5                   10                  15

Lys Lys Leu Asn Gly Ile Pro Glu Thr Thr Ser Lys Asp Leu Gln Thr
            20                  25                  30

Leu Thr Glu Gly Ala Val Leu Ser Phe His Asn Ile Cys Tyr Arg Val
        35                  40                  45

Lys Val Lys Thr Gly Phe Leu Leu Cys Arg Lys Thr Ile Glu Lys Glu
    50                  55                  60

Ile Leu Ala Asn Ile Asn Gly Val Met Lys Pro Gly Leu Asn Ala Ile
65                  70                  75                  80

Leu Gly Pro Thr Gly Gly Gly Lys Ser Ser Leu Leu Asp Ile Leu Ala
                85                  90                  95

Ala Arg Lys Asp Pro His Gly Leu Ser Gly Asp Val Leu Ile Asn Gly
            100                 105                 110

Ala Pro Arg Pro Ala Asn Phe Lys Cys Asn Ser Gly Tyr Val Val Gln
        115                 120                 125

Asp Asp Val Val Met Gly Thr Leu Thr Val Arg Glu Asn Leu Gln Phe
    130                 135                 140

Ser Ala Ala Leu Arg Leu Pro Thr Thr Met Thr Ser Tyr Glu Lys Asn
145                 150                 155                 160

Glu Arg Ile Asn Lys Val Ile Gln Glu Leu Gly Leu Asp Lys Val Ala
                165                 170                 175

Asp Ser Lys Val Gly Thr Gln Phe Ile Arg Gly Val Ser Gly Gly Glu
            180                 185                 190

Arg Lys Arg Thr Ser Ile Ala Met Glu Leu Ile Thr Asp Pro Ser Ile
        195                 200                 205

Leu Phe Leu Asp Glu Pro Thr Thr Gly Leu Asp Ser Ser Thr Ala Asn
    210                 215                 220

Ala Val Leu Leu Leu Lys Arg Met Ser Lys Gln Gly Arg Thr Ile
225                 230                 235                 240

Ile Phe Ser Ile His Gln Pro Arg Tyr Ser Ile Phe Lys Leu Phe Asp
                245                 250                 255

Ser Leu Thr Leu Leu Ala Ser Gly Arg Leu Met Phe His Gly Pro Ala
            260                 265                 270

Gln Glu Ala Leu Gly Tyr Phe Gly Ala Ile Gly Phe Arg Cys Glu Pro

```
                275                 280                 285
Tyr Asn Asn Pro Ala Asp Phe Phe Leu Asp Ile Ile Asn Gly Asp Ser
            290                 295                 300
Ser Ala Val Val Leu Asn Arg Glu Asp Ile Gly Asp Glu Ala Asn Glu
305                 310                 315                 320
Thr Glu Glu Pro Ser Lys Lys Asp Thr Pro Leu Ile Glu Lys Leu Ala
                325                 330                 335
Glu Phe Tyr Val Asn Ser Ser Phe Phe Lys Glu Thr Lys Val Glu Leu
            340                 345                 350
Asp Lys Phe Ser Gly Asp Gln Arg Arg Lys Lys Leu Pro Ser Tyr Lys
            355                 360                 365
Glu Val Thr Tyr Ala Thr Ser Phe Cys His Gln Leu Lys Trp Ile Ser
    370                 375                 380
Arg Arg Ser Phe Lys Asn Leu Leu Gly Asn Pro Gln Ala Ser Ile Ala
385                 390                 395                 400
Gln Leu Ile Val Thr Val Phe Leu Gly Leu Val Ile Gly Ala Ile Phe
                405                 410                 415
Tyr Asp Leu Lys Asn Asp Pro Ala Gly Ile Gln Asn Arg Ala Gly Val
            420                 425                 430
Leu Phe Phe Leu Thr Thr Asn Gln Cys Phe Ser Ser Val Ser Ala Val
            435                 440                 445
Glu Leu Leu Val Val Glu Lys Lys Leu Phe Ile His Glu Tyr Ile Ser
    450                 455                 460
Gly Tyr Tyr Arg Val Ser Ser Tyr Phe Phe Gly Lys Leu Leu Ser Asp
465                 470                 475                 480
Leu Leu Pro Met Arg Met Leu Pro Ser Ile Ile Phe Thr Cys Ile Thr
                485                 490                 495
Tyr Phe Leu Leu Gly Leu Lys Pro Lys Val Glu Ala Phe Phe Ile Met
            500                 505                 510
Met Leu Thr Leu Met Met Val Ala Tyr Ser Ala Ser Met Ala Leu
            515                 520                 525
Ala Ile Ala Ala Gly Gln Ser Val Val Ser Ile Ala Thr Leu Leu Met
530                 535                 540
Thr Ile Ser Phe Val Phe Met Met Ile Phe Ser Gly Leu Leu Val Asn
545                 550                 555                 560
Leu Lys Thr Val Val Pro Trp Leu Ser Trp Leu Gln Tyr Leu Ser Ile
                565                 570                 575
Pro Arg Tyr Gly Tyr Ala Ala Leu Gln His Asn Glu Phe Leu Gly Gln
            580                 585                 590
Asn Phe Cys Pro Gly Leu Asn Val Thr Thr Asn Thr Cys Ser Tyr
            595                 600                 605
Ala Ile Cys Thr Gly Glu Glu Phe Leu Thr Asn Gln Gly Ile Asp Ile
    610                 615                 620
Ser Pro Trp Gly Leu Trp Lys Asn His Val Ala Leu Ala Cys Met Ile
625                 630                 635                 640
Val Ile Phe Leu Thr Ile Ala Tyr Leu Lys Leu Leu Phe Leu Lys Lys
                645                 650                 655
Phe Ser

<210> SEQ ID NO 186
<211> LENGTH: 208
<212> TYPE: DNA
<213> ORGANISM: Bos taurus
```

```
<400> SEQUENCE: 186
cgggtgggct tggcggaact ggcctctaca ccccgacatc ctccatcgac tgccggggc      60 cgactgtttg gaaagaggat ggggctggtg gcggcgggga agcgctcatc tgcccgggaa    120
aatagctgga gaggagtgcg ggattagagc tatgcccctg atagtgtccc cgcaaccagc   180
gagaccctgt agttcctcgg tcctggag                                        208

<210> SEQ ID NO 187
<211> LENGTH: 336
<212> TYPE: DNA
<213> ORGANISM: Bos taurus

<400> SEQUENCE: 187
gtgatggaga aggaactgtg gttaataacc agctaacagt ggagaaaaaa ggaagtcaat     60
tagatatgag aactggacat tttcccaaga ctagcttgtt tggaaagcct cagtcttttct   120 ggtagttgca gggggctgat aaggttcctc tctggtactt tctcttgcgc cttgaaagct    180
ggcaggaagg gaagctcctg gactgttaat agatgcggct cttgcttgaa gtttctatga    240
gaaagccgac aagagtcgaa atcttctctg tatccccact gcctctctac agaggtttgg    300
gctgttttcc ttccaacatc acagatcata actgag                              336

<210> SEQ ID NO 188
<211> LENGTH: 100
<212> TYPE: DNA
<213> ORGANISM: Bos taurus

<400> SEQUENCE: 188
tgcgctcgct cgtcggccct cgaccgccgg ctcgccgccc gctctctccg acgtgacggt     60
aacccggggc cagtgccttc ccaggtcagc cgctgcgccg                           100

<210> SEQ ID NO 189
<211> LENGTH: 1552
<212> TYPE: DNA
<213> ORGANISM: Bos taurus

<400> SEQUENCE: 189
aggagagact ccatcttgaa gcctgtcatc cgtcttaaag acaggatgtg aactgggccg     60
gaaccctgct taagagtgag gaaacagttg ctagtgaaaa ccaggtctcc tggagacttc    120
actccctaca gatggcaaac ggagattgta gttgtggtca ggctgcccct gttagattaa    180
tcatggagac atcctccctt gatgtataat cattgttccc cctccggc cccacctccc      240 ccgttaacct taattgtttg ttctcctagc acctacttgt aaaactcaat catatacaac    300
aaaaagattg ttaacatgta accagtcacg tgtgtgtgtg tgtgtgtgtg tgtgtgtgtg    360
tgtgtaaaac tgggcctctc aaaaacatca gggtccttgt tgggaactga ttccccttgg    420
acctgctggc ataataaact gtactccagt cttgagtgtc ccctgaggtg tgttttgcaa    480
ctcaggattc cacaacattt ccagaaggac atcagtgttg acctagacag gtgaagcaaa    540
aatgtttgga gccaacagag atctaaccag tgaagtcact gaaccttgtt cacaaatcaa    600
gggtagattc tttcaaggac caggtgacta ggaggcaagc gaccaaaggc aggactggtt    660
acatatttcg tgacagtgtt ggtcgctcag tcgtgtccga ctctgtgcaa tcccatgggc    720
tgtagccttt caggctcctc tgtccaaggg attcttcaag caagaatact ggagtggggtt  780 gccatacccct ccgccaggga atcttcccca ccagggact gaacctaggt ctctcgcatt    840
gtaggcagat tctttaccat ctgagtcacc agctgggtcc tgtgcagctg tacaggtcgt    900
```

```
acccccgtat  ccggagggga  aatactttca  aagcaaacgc  ggcaagttaa  tgcagagcac      960
gggaaaaagt  agggcgccca  ttcactgcat  ctcaaggcct  tccagcactg  aacaagtagc     1020
actgtgggtg  gtgcctggcc  ccaggtggtg  actgaggctg  ctgcctcgga  ttccccaacc     1080
aggtacaccc  ggagcagctc  gcatcctggc  ttcataggca  gagacgagaa  tagcggtgtg     1140
gggcgctctg  ctcactctca  ggaagggggc  gagaggctgc  gcccagaccc  tgtaaccccc     1200
gccccgcgcc  cctccatccc  ccgcccggag  ccctgtatc   cccggcccgg  cgcccctccg     1260
gcccctgctc  cactggtcta  gcggctgcgc  ctcgggaggg  cctggcggag  ccccggacct     1320
gcgccagaaa  acggtccgaa  cagctagctg  cccttccggt  cctcctttc   cgctttgttt     1380 cttctcggtt  tccatccacc  ctaagtcctt  ttctcctctc  ctctccccgc  ccgcggtgt      1440 caatctcccc  ggattgacag  agaacgtagc  ctaaatacta  aagctgagag  aatcgcgcgc     1500
ggaggcgctc  gctggtcccg  cctcctgccg  gctttctttt  ctctgtgcgc  cc             1552
```

<210> SEQ ID NO 190
<211> LENGTH: 74
<212> TYPE: PRT
<213> ORGANISM: Bos taurus

<400> SEQUENCE: 190

```
Asn Leu Lys Thr Val Val Pro Trp Leu Ser Trp Leu Gln Tyr Leu Ser
1               5                   10                  15

Ile Pro Arg Tyr Gly Tyr Ala Ala Leu Gln His Asn Glu Phe Leu Gly
            20                  25                  30

Gln Asn Phe Cys Pro Gly Leu Asn Val Thr Thr Asn Thr Cys Ser
        35                  40                  45

Tyr Ala Ile Cys Thr Gly Glu Glu Phe Leu Thr Asn Gln Gly Ile Asp
    50                  55                  60

Ile Ser Pro Trp Gly Leu Trp Lys Asn His
65                  70
```

<210> SEQ ID NO 191
<211> LENGTH: 74
<212> TYPE: PRT
<213> ORGANISM: Canis familiaris

<400> SEQUENCE: 191

```
Asn Phe Lys Thr Val Gly Pro Trp Leu Ser Trp Leu Gln Asn Leu Ser
1               5                   10                  15

Ile Pro Arg Tyr Gly Tyr Gly Ala Leu Gln His Asn Glu Phe Leu Gly
            20                  25                  30

Gln Asn Phe Cys Pro Gly Leu Asn Val Thr Thr Asn Lys Thr Gly Ser
        35                  40                  45

Tyr Ala Ile Cys Thr Gly Glu Glu Phe Leu Thr Asn Gln Gly Ile Asp
    50                  55                  60

Ile Ser Pro Trp Gly Leu Trp Lys Asn His
65                  70
```

<210> SEQ ID NO 192
<211> LENGTH: 74
<212> TYPE: PRT
<213> ORGANISM: Sus scrofa

<400> SEQUENCE: 192

```
Asn Leu Lys Thr Val Val Pro Trp Leu Ser Trp Leu Gln Tyr Phe Ser
1               5                   10                  15
```

```
Ile Pro Arg Tyr Gly Phe Ser Ala Leu Gln Tyr Asn Glu Phe Leu Gly
            20                  25                  30

Gln Asn Phe Cys Pro Gly Leu Asn Val Thr Thr Asn Thr Cys Ser
        35                  40                  45

Phe Ala Ile Cys Thr Gly Ala Glu Tyr Leu Glu Asn Gln Gly Ile Ser
 50                  55                  60

Leu Ser Ala Trp Gly Leu Trp Gln Asn His
 65                  70

<210> SEQ ID NO 193
<211> LENGTH: 74
<212> TYPE: PRT
<213> ORGANISM: Macaca mulatta

<400> SEQUENCE: 193

Asn Leu Thr Thr Ile Ala Ser Trp Leu Ser Trp Leu Gln Tyr Phe Ser
 1               5                  10                  15

Ile Pro Arg Tyr Gly Phe Thr Ala Leu Gln His Asn Glu Phe Leu Gly
            20                  25                  30

Gln Asn Phe Cys Pro Gly Leu Asn Ala Thr Val Asn Thr Cys Asn
        35                  40                  45

Tyr Ala Thr Cys Thr Gly Glu Glu Tyr Leu Ala Lys Gln Gly Ile Asp
 50                  55                  60

Leu Ser Pro Trp Gly Leu Trp Lys Asn His
 65                  70

<210> SEQ ID NO 194
<211> LENGTH: 74
<212> TYPE: PRT
<213> ORGANISM: Pongo pygmaeus

<400> SEQUENCE: 194

Asn Leu Thr Thr Ile Ala Ser Trp Leu Ser Trp Leu Gln Tyr Phe Ser
 1               5                  10                  15

Ile Pro Arg Tyr Gly Phe Thr Ala Leu Gln His Asn Glu Phe Leu Gly
            20                  25                  30

Gln Asn Phe Cys Pro Gly Leu Asn Ala Thr Ala Asn Thr Cys Asn
        35                  40                  45

Tyr Ala Thr Cys Thr Gly Glu Glu Tyr Leu Ala Arg Gln Gly Ile Asp
 50                  55                  60

Leu Ser Pro Trp Gly Leu Trp Lys Asn His
 65                  70

<210> SEQ ID NO 195
<211> LENGTH: 74
<212> TYPE: PRT
<213> ORGANISM: Homo sapiens

<400> SEQUENCE: 195

Asn Leu Thr Thr Ile Ala Ser Trp Leu Ser Trp Leu Gln Tyr Phe Ser
 1               5                  10                  15

Ile Pro Arg Tyr Gly Phe Thr Ala Leu Gln His Asn Glu Phe Leu Gly
            20                  25                  30

Gln Asn Phe Cys Pro Gly Leu Asn Ala Thr Gly Asn Pro Cys Asn
        35                  40                  45

Tyr Ala Thr Cys Thr Gly Glu Glu Tyr Leu Val Lys Gln Gly Ile Asp
 50                  55                  60
```

```
Leu Ser Pro Trp Gly Leu Trp Lys Asn His
 65                  70
```

```
<210> SEQ ID NO 196
<211> LENGTH: 74
<212> TYPE: PRT
<213> ORGANISM: Pan troglodytes

<400> SEQUENCE: 196

Asn Leu Thr Thr Ile Ala Ser Trp Leu Ser Trp Leu Gln Tyr Phe Ser
 1               5                  10                  15

Ile Pro Arg Tyr Gly Phe Thr Ala Leu Gln His Asn Glu Phe Leu Gly
                20                  25                  30

Gln Asn Phe Cys Pro Gly Leu Asn Ala Thr Gly Asn Asn Pro Cys Asn
            35                  40                  45

Tyr Ala Thr Cys Thr Gly Glu Glu Tyr Leu Val Lys Gln Gly Ile Asp
        50                  55                  60

Leu Ser Pro Trp Gly Leu Trp Lys Asn His
 65                  70
```

```
<210> SEQ ID NO 197
<211> LENGTH: 76
<212> TYPE: PRT
<213> ORGANISM: Mus musculus

<400> SEQUENCE: 197

Asn Leu Arg Thr Ile Gly Pro Trp Leu Ser Trp Leu Gln Tyr Phe Ser
 1               5                  10                  15

Ile Pro Arg Tyr Gly Phe Thr Ala Leu Gln His Asn Glu Phe Leu Gly
                20                  25                  30

Gln Glu Phe Cys Pro Gly Leu Asn Val Thr Met Asn Ser Thr Cys Val
            35                  40                  45

Asn Ser Tyr Thr Ile Cys Thr Gly Asn Asp Tyr Leu Ile Asn Gln Gly
        50                  55                  60

Ile Asp Leu Ser Pro Trp Gly Leu Trp Arg Asn His
 65                  70                  75
```

```
<210> SEQ ID NO 198
<211> LENGTH: 76
<212> TYPE: PRT
<213> ORGANISM: Rattus norvegicus

<400> SEQUENCE: 198

Asn Leu Arg Thr Ile Gly Pro Trp Leu Ser Trp Leu Gln Tyr Phe Ser
 1               5                  10                  15

Ile Pro Arg Tyr Gly Phe Thr Ala Leu Gln Tyr Asn Glu Phe Leu Gly
                20                  25                  30

Gln Glu Phe Cys Pro Gly Phe Asn Val Thr Asp Asn Ser Thr Cys Val
            35                  40                  45

Asn Ser Tyr Ala Ile Cys Thr Gly Asn Glu Tyr Leu Ile Asn Gln Gly
        50                  55                  60

Ile Glu Leu Ser Pro Trp Gly Leu Trp Lys Asn His
 65                  70                  75
```